United States Patent [19]
Fujii et al.

[11] Patent Number: 4,831,026
[45] Date of Patent: May 16, 1989

[54] 2-OXA-ISOCEPHEM COMPOUNDS, COMPOSITIONS CONTAINING SAME AND PROCESSES OF USING

[75] Inventors: Setsuro Fujii, Kyoto; Hiroshi Ishikawa, Otsu; Koichi Yasumura, Otsu; Koichiro Jitsukawa, Otsu; Sachio Toyama, Aichi; Hidetsugu Tsubouchi, Toyonaka; Kimio Sudo; Kouichi Tsuji, both of Otsu, all of Japan

[73] Assignee: Otsuka Pharmaceutical Co., Ltd., Tokyo, Japan

[21] Appl. No.: 23,602

[22] Filed: Mar. 9, 1987

Related U.S. Application Data

[63] Continuation-in-part of Ser. No. 905,205, Sep. 9, 1986, abandoned.

[30] Foreign Application Priority Data

| Sep. 9, 1985 | [JP] | Japan | 60-199044 |
|---|---|---|---|
| Dec. 18, 1985 | [JP] | Japan | 60-285031 |
| Feb. 18, 1986 | [JP] | Japan | 61-34412 |
| Apr. 3, 1986 | [JP] | Japan | 61-77229 |
| Jun. 9, 1986 | [JP] | Japan | 61-132976 |
| Jul. 15, 1986 | [JP] | Japan | 61-167134 |

[51] Int. Cl.$^4$ .................. A61K 31/535; C07D 498/04
[52] U.S. Cl. ...................................... 514/210; 540/300
[58] Field of Search ...................... 540/300; 514/210

[56] References Cited

U.S. PATENT DOCUMENTS

| 4,013,648 | 3/1977 | Horning et al. | 540/300 |
|---|---|---|---|
| 4,386,089 | 5/1983 | Konig et al. | 540/301 X |
| 4,476,124 | 10/1984 | Heymes et al. | 514/210 |

*Primary Examiner*—Richard L. Raymond
*Attorney, Agent, or Firm*—Sughrue, Mion, Zinn, Macpeak & Seas

[57] ABSTRACT

A 2-oxa-isocephem compound of the formula (1):

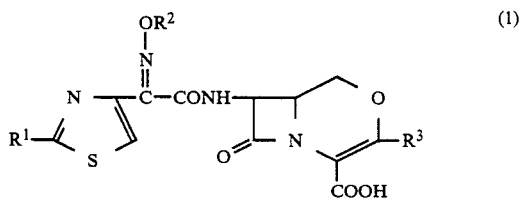

wherein $R^1$, $R^2$ and $R^3$ are as defined, pharmaceutically acceptable salts thereof, esters of the carboxy group in the 4-position thereof and quaternary ammonium salts thereof, composition containing the same and processes for preparing the same are disclosed. The compound is useful as an antimicrobial compound.

49 Claims, No Drawings

2-OXA-ISOCEPHEM COMPOUNDS, COMPOSITIONS CONTAINING SAME AND PROCESSES OF USING

This application is a continuation-in-part application of Ser. No. 905,205, filed Sept. 9, 1986, now abandoned.

FIELD OF THE INVENTION

This invention relates to new 2-oxa-isocephem compounds and pharmaceutically acceptable salts thereof which are useful as antimicrobial compounds, processes for preparing the same, and pharmaceutical compositions containing the 2-oxa-isocephem compounds or salts thereof.

BACKGROUND OF THE INVENTION

Various 2-oxa-isocephem compounds are known which have antimicrobial activity as described in U.S. Pat. No. 4,476,124.

However, the 2-oxa-isocephem compounds of this invention are structurally different from the conventional 2-oxa-isocephem compounds.

SUMMARY OF THE INVENTION

One object of this invention is to provide 2-oxa-isocephem compounds having antimicrobial activity.

Another object of this invention is to provide a pharmaceutical composition containing the 2-oxaisocephem compound in an antimicrobially effective amount.

A further object of this invention is to provide a process for preparing the 2-oxa-isocephem compounds and pharmaceutically acceptable salts thereof.

As a result of extensive research this invention has been accomplished which, in one aspect, provides a 2-oxa-isocephem compound of the following formula (1), pharmaceutically acceptable salts thereof, esters of the carboxy group in the 4-position thereof and quaternary ammonium salts thereof:

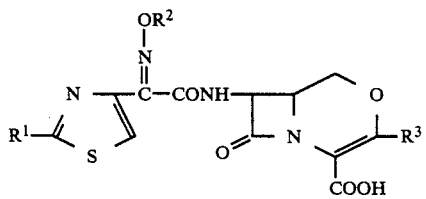

wherein $R^1$ is a hydrogen atom, an amino group, a lower alkanoylamino group, a halogen-substituted lower alkanoylamino group, a phenyl-substituted lower alkylamino group having 1 to 3 phenyl groups, a phenyl-lower alkoxycarbonylamino group or a lower alkoxycarbonylamino group; $R^2$ is a hydrogen atom, a lower alkyl group, a lower alkenyl group, a lower alkynyl group, a cycloalkyl group, a tetrahydropyranyl group or a group of the formula:

—A—$R^4$ (wherein A is a lower alkylene group, $R^4$ is a cyano group, a carboxy group, a lower alkoxycarbonyl group, a halogen-substituted lower alkyl group, a lower alkylthio group, a thiazolyl group, an imidazolyl group, a cycloalkyl group, a phenyl group, a tetrahydrofuranyl group, an oxazolyl group, a 4-lower alkyl-2,3-dioxo-1-piperazinylcarbonyl group, a trityl-substituted or unsubstituted pyrazolyl group or a lower alkyl-substituted or unsubstituted pyridyl group); $R^3$ is a hydrogen atom, a methyl group, a lower alkanoyloxymethyl group, a carbamoyloxymethyl group, a lower alkoxymethyl group, or an unsaturated heterocycle-thiometyhl group containing 1 to 4 hetero atoms selected from the group consisting of nitrogen and sulfur atoms; in which the heterocyclic moiety of said heterocycle-thiomethyl group may optionally have 1 to 3 substituents selected from the group consisting of lower alkyl, lower alkenyl, lower alkoxycarbonyl, carboxy, phenyl-lower alkoxycarbonyl-lower alkyl having 1 to 3 phenyl groups, carboxy-lower alkyl, hydroxy-lower alkyl, hydroxy, oxo, amino, carbamoyl, cyano, lower alkyl-substituted amino-lower alkyl, piperidinyl-lower alkyl, pyrrolidinyl-lower alkyl, carbamoyl-lower alkyl, and cyano-lower alkyl groups, or a 4-lower alkyl-1-piperazinyl-lower alkyl group; provided that when $R^1$ is an amino group, a lower alkanoylamino group, a halogen-substituted lower alkanoylamino group, a phenyl-substituted lower alkyl amino group having 1 to 3 phenyl groups, a phenyl-lower alkoxycarbonylamino group or a lower alkoxycarbonylamino group and $R^3$ is a hydrogen atom, a methyl group or a lower alkanoyloxymethyl group, $R^2$ means a cyclo-lower alkyl group or a tetrahydropyranyl group or $R^4$ means a cyano group, a cycloalkyl group, a tetrahydrofuranyl group or a 4-lower alkyl-2,3-dioxo-1-piperazinylcarbonyl group.

In another aspect, this invention provides an antimicrobial composition containing the compound of the formula (1) or a pharmaceutically acceptable salt thereof in an antimicrobially effective amount.

In a further aspect, this invention provides a process for preparing the compounds of formula (1) and pharmaceutically acceptable salts thereof.

The above compound of general formula (1) according to the present invention has high antimicrobial activity against a broad spectrum of gram-positive and gram-negative bacteria, displaying particularly high activity against Staphylococcus aureus (FDA-209-P), Streptococcus pneumoniae and Corynebacterium diphtheria.

The compound according to the present invention is further characterized by good absorption, long duration of effect, low toxicity and excellent effects on resistant strains and clinically isolated strains of bacteria. Moreover, the compound is highly stable and has a satisfactory pharmacokinetic profile. Thus, the compound shows a high renal excretion and a good transfer into the bile. It is well distributed in various organs including the lungs. The difference between minimal inhibitory concentration and minimal bactericidal concentration is small. Furthermore, the compound has few side effects such as immunosuppression and allergy.

Therefore, the compound according to the present invention is also useful as a therapeutic agent for the diseases caused by various pathogenic bacteria in man, animals and fish or as an external microbicide or disinfectant for medical devices, instruments and so on.

DETAILED DESCRIPTION OF THE INVENTION

The groups given in terms of symbols in the above general formula (1) are respectively described in more detail in the following.

Examples of the lower alkanoylamino group include alkanoylamino groups having 1 to 6 carbon atoms, such as formylamino, acetylamino, propionylamino, butyrylamino, isobutyrylamino, pentanoylamino, hexanoylamino and the like.

Examples of the halogen-substituted lower alkanoylamino group include mono-, di- and trihaloalkanoylamino groups having 2 to 6 carbon atoms, such as monochloroacetylamino, monofluoroacetylamino, monobromoacetylamino, monoiodoacetylamino, dichloroacetylamino, trichloroacetylamino, tribromoacetylamino, 3-chloropropionylamino, 2,3-dichloropropionylamino, 3,3,3-trichloropropionylamino, 4-chlorobutyrylamino, 5-chloropentanoylamino, 6-chlorohexanoylamino, 3-fluoropropionylamino, 4-fluorobutyrylamino and the like.

Examples of the phenyl-lower alkylamino group having 1 to 3 phenyl groups include phenylalkylamino groups containing 1 to 3 phenyl groups and having 1 to 6 carbon atoms in the alkyl moiety thereof, such as benzylamino, α-phenetylamino, β-phenethylamino, 3-phenylpropylamino, benzhydrylamino, tritylamino and the like.

Examples of the phenyl-lower alkoxycarbonylamino group include phenylalkoxycarbonylamino groups whose alkoxy moiety has 1 to 6 carbon atoms, such as 1-phenylethoxycarbonylamino, 2-phenylethoxycarbonylamino, 3-phenylpropoxycarbonylamino, 4-phenylbutoxycarbonylamino, 5-phenylpentyloxycarbonylamino, 6-phenylhexyloxycarbonylamino and the like.

Examples of the lower alkoxycarbonylamino group include alkoxycarbonylamino groups having 1 to 6 carbon atoms in the alkoxy moiety, such as methoxycarbonylamino, ethoxycarbonylamino, propoxycarbonylamino, isopropoxycarbonylamino, butoxycarbonylamino, tertiarybutoxycarbonylamino, pentyloxycarbonylamino, hexyloxycarbonylamino and the like.

Examples of the lower alkyl group include alkyl groups having 1 to 6 carbon atoms, such as methyl, ethyl, propyl, isopropyl, butyl, isobutyl, tertiarybutyl, pentyl, hexyl and the like.

Examples of the lower alkenyl group include alkenyl groups having 2 to 6 carbon atoms, such as vinyl, allyl, crotyl, 2-pentenyl, 3-pentenyl, 2-hexenyl, 1-methylallyl, 1,1-dimethylallyl and the like.

Examples of the lower alkynyl group include alkynyl groups having 2 to 6 carbon atoms, such as ethynyl, 1-propynyl, 2-propynyl, 1-methyl-2-propynyl, 1-butynyl, 2-butynyl, 3-butynyl, 1-methyl-2-butynyl, 1-pentynyl, 2-pentynyl, 4-pentynyl, 1-hexynyl, 3-hexynyl, 5-hexynyl and the like.

Examples of the cycloalkyl group include cycloalkyl groups having 3 to 8 carbon atoms, such as cyclopropyl, cyclobutyl, cyclopentyl, cyclohexyl, cycloheptyl, cyclooctyl and the like.

Examples of the tetrahydropyranyl group include 2-tetrahydropyranyl, 3-tetrahydropyranyl and 4-tetrahydropyranyl.

Examples of the lower alkylene group include methylene, methylmethylene, ethylene, dimethylmethylene, trimethylene, 1-methyltrimethylene, 2-methyltrimethylene, 2,2-dimethyltrimethylene, tetramethylene, pentamethylene, hexamethylene and the like.

Examples of the lower alkoxycarbonyl group include alkoxycarbonyl groups containing 1 to 6 carbon atoms in the alkyl moiety thereof, such as methoxycarbonyl, ethoxycarbony, propoxycarbonyl, isopropoxycarbonyl, butoxycarbonyl, tertiary-butoxycarbonyl, pentyloxycarbonyl, hexyloxycarbonyl and the like.

Examples of the halogen-substituted lower alkyl group include halogen-substituted alkyl groups containing 1 to 3 halogen atoms and 1 to 6 carbon atoms, such as chloromethyl, bromomethyl, iodomethyl, fluoromethyl, dichloromethyl, dibromomethyl, difluoromethyl, trichloromethyl, tribromomethyl, trifluoromethyl, 2-chloroethyl, 2-bromoethyl, 2-fluoroethyl, 1,2-dichloroethyl, 2,2-difluoroethyl, 1-chloro-2-fluoroethyl, 2,2,2-trifluoroethyl, 2,2,2-trichloroethyl, 3-fluoropropyl, 3,3,3-trichloropropyl, 4-chlorobutyl, 5-chloroheptyl, 6-chlorohexyl, 3-chloro-2-methylpropyl and the like.

Examples of the lower alkylthio group include alkylthio groups containing 1 to 6 carbon atoms, such as methylthio, ethylthio, propylthio, isopropylthio, butylthio, isobutylthio, pentylthio, hexylthio and the like.

Examples of the thiazolyl group include 1,3-thiazol-2-yl, 1,3-thiazol-4-yl, 1,3-thiazol-5-yl, 1,2-thiazol-3-yl, 1,2-thiazol-4-yl, 1,2-thiazol-5-yl and the like.

Examples of the tetrahydrofuranyl group include 2-tetrahydrofuranyl and 3-tetrahydrofuranyl.

Examples of the imidazolyl group include 1-imidazolyl, 2-imidazolyl, 4-imidazolyl, 5-imidazolyl and the like.

Examples of the oxazolyl group include 2-oxazolyl, 4-oxazolyl, 5-oxazolyl and the like.

Examples of the 4-lower alkyl-2,3-dioxo-1-piperazinylcarbonyl group include 4-methyl-2,3-dioxo-1-piperazinyl-carbonyl, 4-ethyl-2,3-dioxo-1-piperazinylcarbonyl, 4-propyl-2,3-dioxo-1-piperazinylcarbonyl, 4-isopropyl-2,3-dioxo-1-piperazinylcarbonyl, 4-butyl-2,3-dioxo-1-piperazinylcarbonyl, 4-pentyl-2,3-dioxo-1-piperazinylcarbonyl, 4-hexyl-2,3-dioxo-1-piperazinylcarbonyl and the like.

Examples of the trityl-substituted or unsubstituted pyrazolyl group may be pyrazolyl groups such as, 1-pyrazolyl, 3-pyrazolyl, 4-pyrazolyl, 1-trityl-3-pyrazlyl, 1-trityl-4-pyrazolyl, 4-trityl-3-pyrazolyl, 5-trityl-3-pyrazolyl and the like.

Examples of the lower alkyl-substituted or unsubstituted pyridyl group include pyridyl groups which may optionally have 1 to 5 alkyl groups each of 1 to 6 carbon atoms, such as 2-pyridyl, 3-pyridyl, 4-pyridyl, 2-pyridinio, 3-pyridinio, 4-pyridinio, 4-methyl-2-pyridyl, 4-methyl-3-pyridyl, 2-methyl-3-pyridyl, 2-methyl-4-pyridyl, 2-methyl-5-pyridyl, 2-methyl-6-pyridyl, 3-methyl-2-pyridyl, 3-methyl-4-pyridyl, 3-methyl-5-pyridyl, 3-methyl-6-pyridyl, 1-methyl-4-pyridinio, 1-methyl-3-pyridinio, 1-methyl-2-pyridinio, 2-ethyl-4-pyridyl, 3-ethyl-5-pyridyl, 4-ethyl-2-pyridyl, 1-ethyl-4-pyridinio, 4-propyl-2-pyridyl, 1-propyl-4-pyridinio, 3-butyl-6-pyridyl, 1-butyl-4-pyridinio, 2-pentyl-4-pyridyl, 1-pentyl-4-pyridinio, 3-hexyl-5-pyridyl, 1-hexyl-4-pyridinio, 2,3-dimethyl-6-pyridyl, 2,6-dimethyl-4-pyridyl, 1,3-dimethyl-4-pyridinio, 1,4-dimethyl-3-pyridinio, 2-methyl-6-ethyl-4-pyridyl, 1-methyl-3-ethyl-4-pyridinio, 1-methyl-3-propyl-5-pyridinio, 2,3-diethyl-6-pyridyl, 1,3-diethyl-4-pyridinio, 2,3-dipropyl-5-pyridyl, 1,3-dipropyl-4-pyridinio, 1,4,6-trimethyl-3-pyridinio, 1,2,3,5-tetra-methyl-4-pyridinio, 1,2,3,5,6-pentamethyl-4-pyridinio and the like.

Examples of the lower alkanoyloxymethyl group include alkanoyloxymethyl groups the alkanoyl moiety of which has 1 to 6 carbon atoms, such as formyloxymethyl, acetoxymethyl, propionyloxymethyl, butyryloxymethyl, isobutyryloxymethyl, pentanoyloxymethyl, hexanoyloxymethyl and the like.

Examples of the lower alkoxymethyl group include alkoxy-methyl groups the alkoxy moiety of which has 1 to 6 carbon atoms, such as methoxymethyl, ethoxymethyl, propoxymethyl, isopropoxymethyl, butoxymethyl, tertiary-butoxymethyl, pentyloxymethyl, hexyloxymethyl and the like.

Examples of the heterocyclic moiety of the unsaturated heterocycle-thiomethyl group include, for example, 5- or 6-membered monocyclic heterocyclic group such as 1,3,4-thiadiazolyl, 1,2,3-thiadiazolyl, 1,2,4-thiadiazolyl, 1,2,4-triazolyl, 1,3,4-triazolyl, tetrazolyl, pyridyl, 1,2-thiazolyl, 1,3-thiazolyl, imidazolyl, 1,2,3-triazolyl, 1,2,4-triazinyl and the like, fused heterocyclic groups derived from the above-mentioned heterocycle and a cyclo-lower alkane such as 5,6,7,8-tetrahydroquinolyl, α,β-ethylenepyridyl, 6,7-dihydro-5H-pyrindinyl and the like.

Examples of the lower alkoxycarbonyl moiety having 1 to 3 phenyl groups of the phenyl-substituted lower alkoxycarbonyl-lower alkyl group having 1 to 3 phenyl groups include phenylalkoxycarbonyl groups having 1 to 3 phenyl groups with the alkoxy moiety having 1 to 6 carbon atoms, such as benzyloxycarbonyl, α-phenetyloxycarbonyl, β-phenetyloxycarbonyl, 3-phenylpropoxycarbonyl, benzhydryloxycarbonyl, trityloxycarbonyl and the like. The lower alkyl moiety of the phenyl-substituted lower alkoxy carbonyl-lower alkyl group having 1 to 3 pheny groups can be referred to the above-mentioned lower alkyl groups.

Examples of the carboxy-lower alkyl group include carboxyalkyl groups having 1 to 6 carbon atoms in the alkyl moiety thereof, such as carboxymethyl, 2-carboxyethyl, 3-carboxypropyl, 4-carboxybutyl, 5-carboxypentyl, 6-carboxyhexyl and the like.

Examples of the hydroxy-lower alkyl group include hydroxymethyl, 1-hydroxyethyl, 2-hydroxyethyl, 2-hydroxypropyl, 3-hydroxypropyl, 4-hydroxybutyl, 2-hydroxy-1,1-dimethylethyl, 5-hydroxypentyl, 6-hydroxyhexyl, 1,2-dihydroxyethyl, 2,3-dihydroxypropyl and the like.

Examples of the lower alkyl-substituted amino moiety of the lower alkyl-substituted amino-lower alkyl group include amino groups having 1 or 2 alkyl groups of 1 to 6 carbon atoms, such as methylamino ethylamino, propylamino, isopropylamino, butylamino, isobutylamino, pentylamino, hexylamino, dimethylamino, diethylamino, dipropylamino, diisopropylamino, dibutylamino, dipentylamino, dihexylamino, N-methyl-N-ethlamino, N-methyl-N-propylamino, N-methyl-N-isopropylamino, N-ethyl-N-propylamino, N-propyl-N-hexylamino, etc., and the alkyl moiety may be one of above-mentioned alkyl groups. Preferred examples of the lower alkyl-substituted amino-lower alkyl group include methylaminomethyl, dimethylaminomethyl, ethylaminomethyl, diethylaminomethyl, propylaminomethyl, dipropylaminomethyl, isopropylaminomethyl, diisopropylaminomethyl, butylaminomethyl, dibutylaminomethyl, pentylaminomethyl, dipentylaminomethyl, hexylaminomethyl, dihexylaminomethyl, N-methyl-N-ethylaminomethyl, N-methyl-N-propylaminomethyl, N-ethyl-N-propylaminomethyl, N-propyl-N-hexylaminomethyl, 2-(methylamino)ethyl, 2-(dimethylamino)ethyl, 1-(ethylamino)ethyl, 2-(diethylamino)ethyl, 2-(propylamino)ethyl, 2-(dipropylamino)ethyl, 2-(isopropylamino)ethyl, 2-(diisopropylamino)ethyl, 2-(butylamino)ethyl, 2-(dibutylamino)ethyl, 2-(pentylamino)ethyl, 2-(dipentylamino)ethyl, 2-(hexylamino)ethyl, 2-(dihexylamino)ethyl, 2-(N-methyl-N-ethylamino)ethyl, 2-(N-methyl-N-propylamino)ethyl, 2-(N-ethyl-N-propylamino)ethyl, 2-dimethylamino-1-methylethyl, 2-(N-methyl-N-ethylamino)-1-methylethyl, 3-(methylamino)propyl, 3-(diethylamino)propyl, 2-(ethylamino)propyl, 3-(diethylamino)propyl, 1-(propylamino)propyl, 3-(hexylamino)propyl, 3-(N-methyl-N-ethylamino)propyl, 4-(methylamino)butyl, 3-(dimethylamino)butyl, 2-(ethylamino)butyl, 4-(diethylamino)butyl, 3-(propylamino)butyl, 4-(hexylamino)butyl, 5-(methylamino)pentyl, 5-(dimethylamino)pentyl, 5-(ethylamino)pentyl, 5-(diethylamino)pentyl, 5-(propylamino)pentyl, 5-(hexylamino)pentyl, 6-(methylamino)hexyl, 6-(dimethylamino)hexyl, 6-(ethylamino)hexyl, 4-(diethylamino)hexyl, 3-(propylamino)hexyl, 6-(hexylamino)hexyl and the like.

Examples of the piperidinyl-lower alkyl group include piperidinyl-bearing alkyl groups of 1 to 6 carbon atoms, such as piperidinomethyl, 4-piperidinylmethyl, 3-piperidinylmethyl, 2-piperidinylmethyl, 1-piperidinoethyl, 2-piperidinoethyl, 2-(3-piperidinyl)ethyl, 1-(4-piperidinyl)ethyl, 1-methyl-2-piperidinoethyl, 1-methy-2-(4-piperidinyl)ethyl, 3-piperidinopropyl, 3-(3-piperidinyl)propyl, 2-(4-piperidinyl)propyl, 2-methyl-3-piperidinopropyl, 4-piperidinobutyl, 4-(4-piperidinyl)butyl, 5-piperidinopentyl, 5-(2-piperidinyl)pentyl, 6-piperidinohexyl, 6-(4-piperidinyl)hexyl and the like.

Examples of the pyrrolidinyl-lower alkyl group include by pyrrolidinyl-bearing alkyl groups of 1 to 6 carbon atoms, such as 1-pyrrolidinylmethyl, 2-pyrrolidinylmethyl, 3-pyrrolidinylmethyl, 2-(1-pyrrolidinyl)ethyl, 2-(3-pyrrolidinyl)ethyl, 1-(1-pyrrolidinyl)ethyl, 1-methyl-2-(1-pyrrolidinyl)ethyl, 3-(1-pyrrolidinyl)propyl, 3-(2-pyrrolidinyl)propyl, 2-(1-pyrrolidinyl)propyl, 2-methyl-3-(1-pyrrolidinyl)propyl, 4-(1-pyrrolidinyl)butyl, 4-(2-pyrrolidinyl)butyl, 5-(1-pyrrolidinyl)pentyl, 5-(3-pyrrolidinyl)pentyl, 6-(1-pyrrolidinyl)hexyl, 6-(2-pyrrolidinyl)hexyl and the like.

Examples of the carbamoyl-lower alkyl group include carbamoyl-bearing alkyl groups of 1 to 6 carbon atoms, such as carbamoylmethyl, 1-carbamoylethyl, 2-carbamoylethyl, 1-methyl-2-carbamoylethyl, 3-carbamoylpropyl, 2-carbamoylpropyl, 1-carbamoylpropyl, 2-methyl-3-carbamoylpropyl, 4-carbamoylbutyl, 3-carbamoylbutyl, 5-carbamoylpentyl, 3-carbamoylpentyl, 6-carbamoylhexyl, 4-carbamoylhexyl and the like.

Examples of the cyano-lower alkyl group include cyano-bearing alkyl groups of 1 to 6 carbon atoms such as cyanomethyl, 1-cyanoethyl, 2-cyanoethyl, 1-methyl-2-cyanoethyl, 3-cyanopropyl, 2-cyanopropyl, 1-cyanopropyl, 2-methyl-3-cyanopropyl, 4-cyanobutyl, 3-cyanobutyl, 5-cyanopentyl, 3-cyanopentyl, 6-cyanohexyl, 4-cyanohexyl and the like.

Examples of the 4-lower alkyl-1-piperazinyl-lower alkyl group include by 4-alkyl-1-piperazinylalkyl groups containing 1 to 6 carbon atoms in each alkyl moiety thereof, such as 4-methyl-1-piperazinylmethyl, 2-(4-methyl-1-piperazinyl)ethyl, 3-(4-methyl-1-piperazinyl)propyl, 4-(4-methyl-1-piperazinyl)butyl, 5-(4-methyl-1-piperazinyl)pentyl, 6-(4-methyl-1-piperazinyl)hexyl, 2-(4-ethyl-1-piperazinyl)ethyl, 2-(4-propyl-1-piperazinyl)ethyl, 4-isopropyl-1-piperazinylmethyl, 2-(5-pentyl-1-piperazinyl)ethyl, 2-(6-hexyl-1-piperazinyl)ethyl, 4-(4-butyl-1-piperazinyl)butyl, 2-(4-ethyl-1-piperazinyl)ethyl and the like.

The ester residue of the carboxylic acid ester is exemplified by conventional ester residues, for example, alkyl groups of 1 to 6 carbon atoms such as methyl, ethyl, propyl, isopropyl, butyl, isobutyl, tertiary-butyl, pentyl, hexyl, etc., (mono- or di-)phenyl-lower alkyl groups containing 1 to 6 carbon atoms in the alkyl moiety thereof such as benzyl, benzhydryl, α-phenethyl, β-phenethyl, α,β-diphenylethyl, 3-phenylpropyl, 4-phenylbutyl, 5-phenylpentyl, 6-phenylhexyl, etc., alkenyl groups of 2 to 6 carbon atoms such as vinyl, allyl, crotyl, 2-pentenyl, 2-hexenyl, etc., cycloalkyl groups of 3 to 8 carbon atoms such as cyclopropyl, cyclobutyl, cyclopentyl, cyclohexyl, cycloheptyl, cyclooctyl, etc. and cycloalkyl(lower)alkyl groups containing 3 to 8 carbon atoms in the cycloalkyl moiety and 1 to 6 carbon atoms in the alkyl moiety thereof such as cyclohexylmethyl, 2-cyclohexylethyl, 3-cyclohexylpropyl, 4-cyclohexylbutyl, 5-cyclohexylpentyl, 6-cyclohexylhexyl, cyclopropylmethyl, 2-cyclobutylethyl, cyclopentylmethyl, 2-cycloheptylethyl, cyclooctylmethyl, etc.

Further, the phenyl moiety of the (mono- or di-)phenyl-lower alkyl group as one of the above-mentioned ester residues may optionally have 1 to 3 substituents selected from the group comprising halogen atoms, such as chlorine, bromine, fluorine and iodine atoms; alkyl groups of 1 to 6 carbon atoms such as methyl, ethyl, propyl, isopropyl, butyl, isobutyl, tertiary-butyl, pentyl, hexyl, etc.; alkoxy groups of 1 to 6 carbon atoms such as methoxy, ethoxy, propoxy, isopropoxy, butoxy, tertiary-butoxy, pentyloxy, hexyloxy, etc.; nitro group; carboxy group; cyano group; alkoxycarbonyl groups containing 1 to 6 carbon atoms in the alkoxy moiety thereof such as methoxycarbonyl, ethoxycarbonyl, propoxycarbonyl, isopropoxycarbonyl, butoxycarbonyl, tertiary-butoxycarbonyl, pentyloxycarbonyl, hexyloxycarbonyl, etc.; hydroxy group; and lower alkanoyloxy groups containing 1 to 6 carbon atoms in the alkanoyl moiety thereof such as acetyloxy, propionyloxy, butyryloxy, isobutyryloxy, pentanoyloxy, hexanoyloxy, etc.; or a lower alkylene dioxy group of 1 to 4 carbon atoms such as methylenedioxy, ethylenedioxy, trimethylenedioxy, tetramethylenedioxy, etc.

The lower alkyl group as one of the abovementioned ester residues may optionally be substituted by 1 to 3 halogen atoms mentioned above, a hydroxy group, a mercapt group, the above-mentioned lower alkoxy group, the above-mentioned lower alkanoyloxy group, a carboxy group, a cyano group, a nitro group, an amino group, the above-mentioned lower alkyl group, a (mono- or di-)lower alkylamino group such as methylamino, dimethylamino, ethylamino, diethylamino, propylamino, butylamino, etc., the above-mentioned lower alkanoylamino group or a lower alkylthio group such as methylthio, ethylthio, propylthio, butylthio, etc.

The quaternary ammonium salt according to the present invention can be obtained by reacting the corresponding compound with, for example, a lower alkyl halide, a lower alkenyl halide, a phenyl-substituted lower alkoxycarbonyl-lower alkyl halide, a carboxy-lower alkyl halide, a sulfo-lower alkyl halide, a sulfamoyllower alkyl halide, a lower alkylthio-lower alkyl halide, hydroxy-lower alkyl halide, a cyano-lower alkyl halide, a carbamoyl-lower alkyl halide or the like. The phenyl-substituted lower alkoxycarbonyl-lower alkyl moiety of the above-mentioned phenyl-substituted lower alkoxycarbonyl-lower alkyl halide may be benzyloxycarbonylmethyl, benzhydryloxycarbonylmethyl, trityloxycarbonylmethyl, 2-phenylethoxycarbonylmethyl, 2,2-diphenylethoxycarbonylmethyl, tritylmethoxycarbonylmethyl, 2-(benzhydryloxycarbonyl)ethyl or the like. The carboxy-lower alkyl moiety of the carboxy-lower alkyl halide may be carboxymethyl, 2-carboxyethyl, 2-carboxypropyl, 3-carboxypropyl, 2-carboxy-1-methylethyl, 4-carboxybutyl, 5-carboxypentyl, 6-carboxyhexyl or the like. The sulfo-lower alkyl moiety of the sulfo-lower alkyl halide may be sulfomethyl, 2-sulfoethyl, 2-sulfopropyl, 3-sulfopropyl, 2-sulfo-1-methylethyl, 4-sulfobutyl, 5-sulfopentyl, 6-sulfohexyl or the like. The sulfamoyl-lower alkyl moiety of the sulfamoyl-lower alkyl halide may be sulfamoylmethyl, 2-sulfamoylethyl, 2-sulfamoylpropyl, 3-sulfamoylpropyl, 2-sulfamoyl-1-methylethyl, 4-sulfamoylbutyl, 5-sulfamoylpentyl, 6-sulfamoylhexyl or the like The lower alkylthio-lower alkyl moiety of the lower alkylthio-lower alkyl halide may be methylthiomethyl, ethylthiomethyl, propylthiomethyl, 1-methyl-ethylthiomethyl, butylthiomethyl, pentylthiomethyl, hexylthiomethyl, 2-(methylthio)ethyl, 2-(ethylthio)ethyl, 3-(methylthio)propyl, 4-(propylthio)butyl 5-(methylthio)pentyl, 6-(methylthio)hexyl or the like. The hydroxy-lower alkyl moiety of the hydroxy-lower alkyl halide may be hydroxymethyl, 2-hydroxyethyl, 2-hydroxypropyl, 3-hydroxypropyl, 2-hydroxy-1-methylethyl, 4-hydroxybutyl, 5-hydroxypentyl, 6-hydroxyhexyl or the like. The cyano-lower alkyl moiety of the cyano-lower alkyl halide may be cyanomethyl, 2-cyanoethyl, 2-cyanopropyl, 3-cyanopropyl, 2-cyano-1-methylethyl, 4-cyanobutyl, 5-cyanopentyl, 6-cyanohexyl or the like. The carbamoyl-lower alkyl moiety of the carbamoyl-lower alkyl halide may be carbamoylmethyl, 2-carbamoylethyl, 2-carbamoylpropyl, 3-carbamoylpropyl, 2-carbamoyl-1-methylethyl, 4-carbamoylbutyl, 5-carbamoylpentyl, 6-carbamoylhexyl and the like. The lower alkyl moiety of the lower alkyl halide and the lower alkenyl moiety of the lower alkenyl halide include those groups given above as examples thereof, respectively. The halide moiety of the above-mentioned halide compounds may for example be chloride, bromide or iodide.

Representative examples of the compounds of the present invention which has the general formula (1-a) given below are shown in the following table.

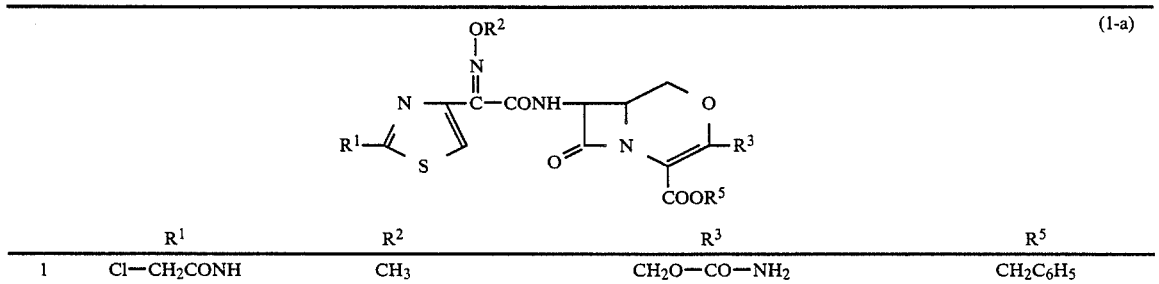

| | $R^1$ | $R^2$ | $R^3$ | $R^5$ |
|---|---|---|---|---|
| 1 | Cl—CH$_2$CONH | CH$_3$ | CH$_2$O—CO—NH$_2$ | CH$_2$C$_6$H$_5$ |

-continued

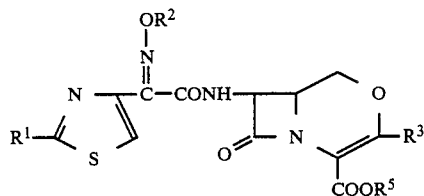

(1-a)

| | R¹ | R² | R³ | R⁵ |
|---|---|---|---|---|
| 2 | H₂N | " | | " |
| 3 | " | " | | H |
| 4 | Cl—CH₂CONH | " | CH₂-S-(1,3,4-thiadiazole) | CH₂C₆H₅ |
| 5 | H₂N | " | " | " |
| 6 | " | " | " | H |
| 7 | " | " | " | CH(CH₃)—O—CO—CH₃ |
| 8 | Cl—CH₂CONH | CH₂CH=CH₂ | " | CH₂C₆H₅ |
| 9 | " | " | " | H |
| 10 | H₂N | " | " | H |
| 11 | Cl—CH₂CONH | CH₂CN | " | CH₂C₆H₅ |
| 12 | " | " | " | H |
| 13 | H₂N | " | " | H |
| 14 | Cl—CH₂CONH | CH₂-imidazole | " | CH₂C₆H₅ |
| 15 | " | " | " | H |
| 16 | H₂N | " | " | H |
| 17 | Cl—CH₂CONH | CH₃ | CH₂-S-(triazine dione) | CH₂C₆H₅ |
| 18 | " | " | " | H |
| 19 | H₂N | " | " | H |
| 20 | Cl—CH₂CONH | " | CH₂-S-(tetrazole-CH₂CH₂-N-methylpiperazine) | CH₂C₆H₅ |
| 21 | " | " | " | H |
| 22 | " | " | CH₂—O—CH₃ | " |
| 23 | H₂N | " | " | " |
| 24 | Cl—CH₂CONH | CH₂CH=CH₂ | " | " |
| 25 | H₂N | " | " | " |
| 26 | Cl—CH₂CONH | CH₂CN | " | " |
| 27 | H₂N | " | " | " |
| 28 | Cl—CH₂CONH | CH₂-imidazole | " | " |
| 29 | H₂N | " | " | " |
| 30 | Trityl-NH | H | " | " |
| 31 | H₂N | H | CH₂—O—CH₃ | H |
| 32 | Cl—CH₂CONH | CH₂COO—t-Butyl | " | " |
| 33 | H₂N | " | " | " |
| 34 | " | CH₂COOH | " | " |

-continued (1-a)

| | R¹ | R² | R³ | R⁵ |
|---|---|---|---|---|
| 35 | Cl—CH₂CONH | CH₃—C(CH₃)—COO—t-Butyl | " | " |
| 36 | H₂N | CH₃—C(CH₃)—COOH | " | " |
| 37 | Cl—CH₂CONH | CH₃—C(CH₃)—COO—t-Butyl | t-Butyl-OOC, OH on isothiazole (CH₂—S-) | " |
| 38 | H₂N | CH₃—C(CH₃)—COOH | " | " |
| 39 | " | " | HOOC, OH on isothiazole (CH₂—S-) | " |
| 40 | H | CH₂—COOH | H | " |
| 41 | H | CH(CH₃)—COOH | H | H |
| 42 | " | CH₃—C(CH₃)—COOH | " | " |
| 43 | " | CH₂—COOH | CH₂—O—CH₃ | " |
| 44 | H₂N | " | CH₂—S—(pyridinium N—CH₃) | ⊖ |
| 45 | Cl—CH₂CONH | CH₃ | CH₂—S—(pyridine) | CH₂C₆H₅ |
| 46 | " | " | " | H |
| 47 | H₂N | " | " | " |
| 48 | Cl—CH₂CONH | CH₂COO—t-Butyl | " | CH₂C₆H₅ |
| 49 | " | CH₂—COOH | " | H |
| 50 | " | " | CH₂—S—(pyridinium N—CH₂COO⊖) | " |
| 51 | H₂N | CH₃—C(CH₃)—COO—t-Butyl | CH₂—S—(pyridinium N—CH₃) | ⊖ |

-continued

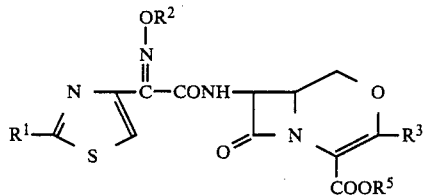
(1-a)

| | $R^1$ | $R^2$ | $R^3$ | $R^5$ |
|---|---|---|---|---|
| 52 | HCONH | $CH_3$ | ![N-N/CH2-S-/S] | H |
| 53 | $CH_3$CONH | " | " | " |
| 54 | Cl—$CH_2$CONH | cyclopentyl | " | " |
| 55 | $H_2N$ | cyclopentyl | " | " |
| 56 | Cl—$CH_2$CONH | cyclopropyl | " | " |
| 57 | $H_2N$ | cyclopropyl | " | " |
| 58 | " | $CH_2$-(4-methylthiazole) | " | " |
| 59 | Cl—$CH_2$CONH | $CH_2$—S—$CH_3$ | " | " |
| 60 | $H_2N$ | " | " | " |
| 61 | Cl—$CH_2$CONH | $CH_2$—$CF_3$ | " | " |
| 62 | $H_2N$ | " | " | " |
| 63 | H | $CH_2$COOH | $CH_2$O—CO—$CH_3$ | " |
| 64 | " | C($CH_3$)—COOH | " | " |
| 65 | " | $\begin{array}{c}CH_3\\|\\C-COOH\\|\\CH_3\end{array}$ | " | " |
| 66 | $(C_6H_5)_3$CNH | $CH_3$ | ![tetrazole $CH_2$-S-, N-$CH_3$] | $CH(C_6H_5)_2$ |
| 67 | $H_2N$ | " | " | " |
| 68 | " | " | " | H |
| 69 | $(C_6H_5)_3$CNH | " | ![$CH_2$-S-thiadiazole] | $CH(C_6H_5)_2$ |
| 70 | $H_2N$ | " | " | " |
| 71 | " | " | " | H |
| 72 | $(C_6H_5)_3$CNH | " | ![$CH_2$-S-isothiazole] | $CH(C_6H_5)_2$ |

-continued (1-a)

Structure: Thiazole-R¹ with =N-OR² oxime, -CONH- linked to β-lactam fused with oxazine bearing R³ and COOR⁵.

| | R¹ | R² | R³ | R⁵ |
|---|---|---|---|---|
| 73 | H₂N | CH₃ | CH₂-S-(isothiazole) | CH(C₆H₅)₂ |
| 74 | " | " | " | H |
| 75 | (C₆H₅)₃CNH | " | CH₂-S-(4-HOOC-3-OH-isothiazole) | CH(C₆H₅)₂ |
| 76 | H₂N | " | " | " |
| 77 | " | " | " | H |
| 78 | (C₆H₅)₃CNH | " | CH₂-S-(4-methyl-thiazol-5-yl)-CH₂COOH | CH(C₆H₅)₂ |
| 79 | H₂N | " | " | " |
| 80 | " | " | " | H |
| 81 | (C₆H₅)₃CNH | CH₃ | CH₂-S-(1-(CH₂CH₂OH)-tetrazol-5-yl) | CH(C₆H₅)₂ |
| 82 | H₂N | " | " | " |
| 83 | " | " | " | H |
| 84 | (C₆H₅)₃CNH | " | CH₂-S-(1-(CH₂CH=CH₂)-tetrazol-5-yl) | CH(C₆H₅)₂ |
| 85 | H₂N | " | " | " |
| 86 | " | " | " | H |
| 87 | (C₆H₅)₃CNH | CH₂-(tetrahydrofuran-2-yl) | CH₂-S-(1,3,4-thiadiazol-2-yl) | CH(C₆H₅)₂ |
| 88 | H₂N | CH₂-(tetrahydrofuran-2-yl) | CH₂-S-(1,3,4-thiadiazol-2-yl) | CH(C₆H₅)₂ |
| 89 | " | " | " | H |
| 90 | (C₆H₅)₃CNH | CH₂-(oxazol-4-yl) | " | CH(C₆H₅)₂ |
| 91 | H₂N | " | " | " |
| 92 | " | " | " | H |
| 93 | (C₆H₅)₃CNH | CH₂-(N-CH₂CN, N-C₂H₅ dioxopiperazinyl) | " | CH(C₆H₅)₂ |

-continued
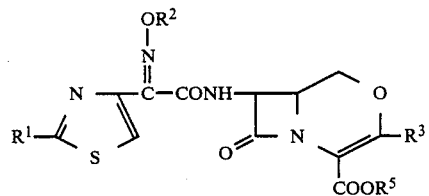
(1-a)
| | R¹ | R² | R³ | R⁵ |
|---|---|---|---|---|
| 94 | H₂N | " | " | " |
| 95 | " | " | " | H |
| 96 | (C₆H₅)₃CNH | CH₃ | CH₂—S—(4-pyridyl) | CH(C₆H₅)₂ |
| 97 | H₂N | " | " | " |
| 98 | " | " | CH₂—S—(N-methyl-4-pyridinium) I⁻ | CH(C₆H₅)₂ |
| 99 | " | " | CH₂—S—(N-methyl-4-pyridinium) | ⊖ |
| 100 | " | " | CH₂—S—(N-allyl-4-pyridinium) Br⁻ | CH(C₆H₅)₂ |
| 101 | " | " | CH₂—S—(N-allyl-4-pyridinium) | ⊖ |
| 102 | (C₆H₅)₃CNH | " | CH₂—S—(2-pyridyl) | CH(C₆H₅)₂ |
| 103 | H₂N | CH₃ | CH₂—S—(2-pyridyl) | CH(C₆H₅)₂ |
| 104 | " | " | " | H |
| 105 | " | " | CH₂—S—(N-methyl-2-pyridinium) I⁻ | CH(C₆H₅)₂ |
| 106 | " | " | CH₂—S—(N-methyl-2-pyridinium) | ⊖ |

-continued (1-a)

[Structure: thiazole-R¹, with N-OR² oxime, C-CONH linked to β-lactam fused ring with O, =C-R³, COOR⁵]

| | R¹ | R² | R³ | R⁵ |
|---|---|---|---|---|
| 107 | " | " | [2-(CH₂S-)pyridinium N-CH₂CH=CH₂, Br⁻] | CH(C₆H₅)₂ |
| 108 | " | " | [2-(CH₂S-)pyridinium N-CH₂CH=CH₂] | ⊖ |
| 109 | H₂N | CH₃ | [2-(CH₂S-)pyridinium N-CH₂COOH(C₆H₅)₂, Cl⁻] | CH(C₆H₅)₂ |
| 110 | " | " | [2-(CH₂S-)pyridinium N-CH₂COOH] | ⊖ |
| 111 | " | " | [4-(CH₂S-)pyridinium N⊕CH₂COOCH(C₆H₅)₂, Cl⁻] | CH(C₆H₅)₂ |
| 112 | " | " | [4-(CH₂S-)pyridinium N⊕CH₂COOH] | ⊖ |
| 113 | (C₆H₅)₃CNH | " | [CH₂-S- 6,7-dihydro-5H-cyclopenta[b]pyridin-4-yl] | CH(C₆H₅)₂ |
| 114 | H₂N | " | " | " |
| 115 | H₂N | CH₃ | [CH₂-S- 6,7-dihydro-5H-cyclopenta[b]pyridin-4-yl] | H |

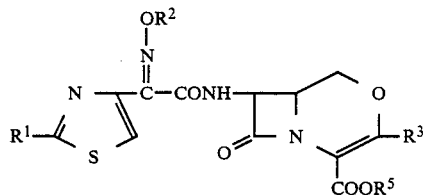

(1-a)

| | R¹ | R² | R³ | R⁵ |
|---|---|---|---|---|
| 116 | " | " | (cyclopenta-pyridinium CH₂S, N⁺CH₃ I⁻) | CH(C₆H₅)₂ |
| 117 | " | " | (cyclopenta-pyridinium CH₂S, N⁺CH₃) | ⊖ |
| 118 | " | " | (cyclopenta-pyridinium CH₂S, N⁺CH₂CH=CH₂, Br⁻) | CH(C₆H₅)₂ |
| 119 | " | " | (cyclopenta-pyridinium CH₂S, N⁺CH₂CH=CH₂) | ⊖ |
| 120 | HCNH (O=) | CH₂COO—t-Butyl | (cyclopenta-pyridinium CH₂S, N⁺CH₃ I⁻) | CH(C₆H₅)₂ |
| 121 | " | CH₂COOH | (cyclopenta-pyridinium CH₂S, N⁺CH₃) | ⊖ |
| 122 | H₂N | " | " | ⊖ |
| 123 | HCNH (O=) | C(CH₃)₂COO—t-Butyl | (cyclopenta-pyridinium CH₂S, N⁺CH₃ I⁻) | CH(C₆H₅)₂ |

-continued

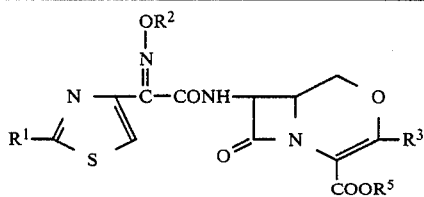
(1-a)

| | R¹ | R² | R³ | R⁵ |
|---|---|---|---|---|
| 124 | " | CH₃-C(COOH)-CH₃ | CH₂-S-[cyclopenta-fused pyridinium N⁺CH₃] | ⊖ |
| 125 | H₂N | CH₃-C(COOH)-CH₃ | CH₂-S-[cyclopenta-fused pyridinium N⁺CH₃] | ⊖ |
| 126 | " | C₂H₅ | CH₂-S-[pyridinium N⊕CH₂COOH] | ⊖ |
| 127 | " | " | CH₂-S-[cyclopenta-fused pyridinium N⊕CH₂COOH] | ⊖ |
| 128 | " | CH₂-△ | CH₂-S-[pyridinium N⊕CH₂COOH] | ⊖ |
| 129 | " | CH₂-△ | CH₂-S-[cyclopenta-fused pyridinium N⊕CH₂COOH] | ⊖ |
| 130 | H₂N | CH₃ | CH₂-S-[1,2,4-triazole-NH] | H |
| 131 | " | " | CH₂-S-[tetrazole-N-CH₂COOH] | " |
| 132 | " | " | CH₂-S-[tetrazole-N-CH₂CH₂N(piperazine)NCH₃] | " |

-continued

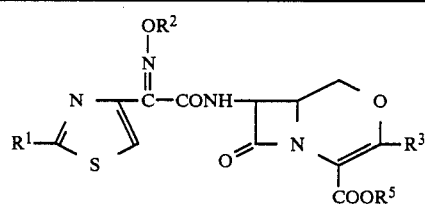
(1-a)

| | R¹ | R² | R³ | R⁵ |
|---|---|---|---|---|
| 133 | " | cyclopentyl | $CH_2-S-\underset{S}{\underset{|}{C}}=\underset{N}{\overset{N}{\|}}$ (1,2,4-thiadiazol-5-yl) | " |
| 134 | " | " | $CH_2-S-$ (4-thiomethyl-cyclopenta-fused pyridinium-N-CH$_2$COOH) $CF_3COO^\ominus$ | " |
| 135 | " | $CH_2CN$ | $CH_2-S-$ (4-thiomethyl-cyclopenta-fused pyridinium-N-CH$_2$COOH) $CF_3COO^\ominus$ | " |
| 136 | $H_2N$ | cyclopentyl | $CH_2-S-$ (4-thiomethyl-cyclopenta-fused pyridinium-N-CH$_3$) | $\ominus$ |
| 137 | " | " | $CH_2-S-$ (pyridinium-N-CH$_3$) | $\ominus$ |
| 138 | " | " | $CH_2-S-\underset{S}{\underset{|}{C}}=\underset{N-N}{\|}$ (1,3,4-thiadiazol-2-yl) | H |
| 139 | " | " | $CH_2-S-$ (thiazol-2-yl) | H |
| 140 | $H_2N$ | cyclopentyl | $CH_2-S-$ (1,2,3-thiadiazol-5-yl) | H |
| 141 | " | " | $CH_2-S-$ (5-methyl-1,3,4-thiadiazol-2-yl) | " |
| 142 | " | cyclohexyl | $CH_2-S-$ (1,3,4-thiadiazol-2-yl) | " |

-continued
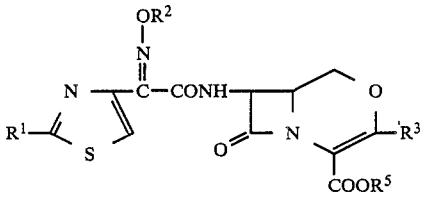
(1-a)
| | R¹ | R² | R³ | R⁵ |
|---|---|---|---|---|
| 143 | " |  | 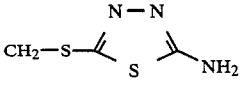 | " |
| 144 | H₂N | 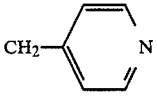 | $CH_2OCH_3$ | H |
| 145 | " |  | " | ⊖ |
| 146 | " | 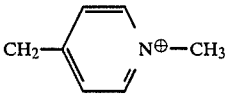 | $CH_2O-CO-NH_2$ | H |
| 147 | " | 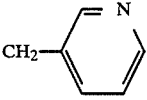 | " | ⊖ |
| 148 | " | 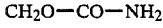 | 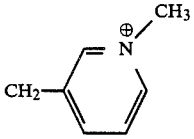 | H |
| 149 | H₂N | 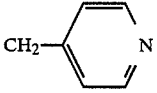 | 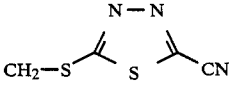 | ⊖ |
| 150 | " | 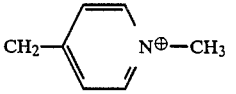 | 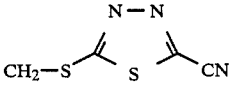 | H |
| 151 | " | 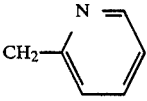 | " | ⊖ |
| 152 | " | 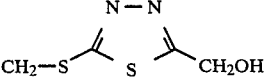 | 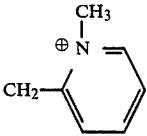 | H |
| 153 | " | 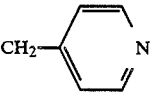 | " | ⊖ |

-continued
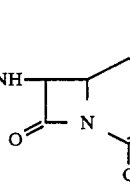
(1-a)
| | R¹ | R² | R³ | R⁵ |
|---|---|---|---|---|
| 154 | H₂N | 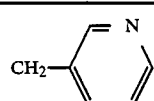 | 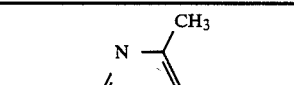 | H |
| 155 | " | 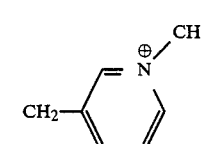 | " | ⊖ |
| 156 | (C₆H₅)₃CNH | 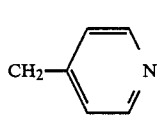 | 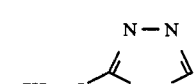 | CH(C₆H₅)₂ |
| 157 | H₂N | " | " | H |
| 158 | " | 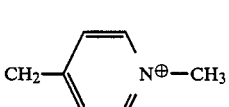 | " | ⊖ |
| 159 | (C₆H₅)₃CNH | 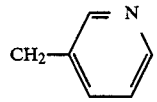 | 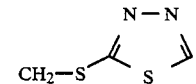 | CH₂C₆H₅ |
| 160 | H₂N | " | " | " |
| 161 | Cl—CH₂CONH | 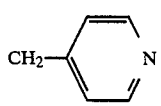 | 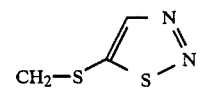 | " |
| 162 | " | " | " | H |
| 163 | CF₃CONH | 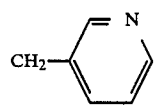 | 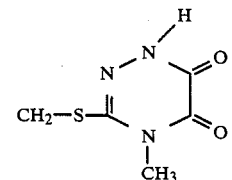 | " |
| 164 | CF₃CONH | 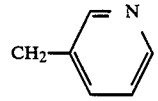 | 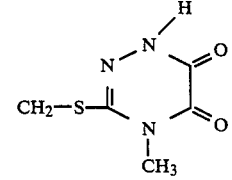 | CH(CH₃)—OCOCH₃ |
| 165 | C₆H₅—CH₂OCONH | " | 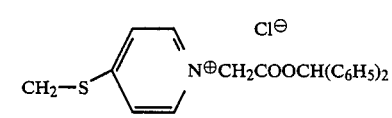 | CH(C₆H₅)₂ |

-continued (1-a)

$$\text{R}^1\text{-thiazole-C(=NOR}^2\text{)-CONH-[azetidinone-CH}_2\text{O-C(=)-R}^3\text{]-COOR}^5$$

| | R¹ | R² | R³ | R⁵ |
|---|---|---|---|---|
| 166 | " | " | CH₂-S-(pyridinium-N⊕CH₂COOH) | ⊖ |
| 167 | H₂N | " | CH₂-S-(1,3,4-thiadiazole) | H |
| 168 | HCO—NH | CH₂-(4-pyridyl) | CH₂-S-(pyridinium-N⊕CH₃) | ⊖ |
| 169 | (C₆H₅)₃CNH | CH₂-(3-pyridyl) | CH₂-S-(pyridinium-N⊕CH₃) I⊖ | CH(C₆H₅)₂ |
| 170 | H | CH₂-(4-pyridyl) | CH₂-S-(4-pyridyl) | CH₂C₆H₅ |
| 171 | Cl₂C—CONH | CH₂-(2-pyridyl) | CH₂OCONH₂ | CH(CH₃)—OCOCH₃ |
| 172 | H₂N | CH₂-(3-pyridyl) | CH₂-S-(4-methyl-1,2,4-triazole, CH₃) | CH₂C₆H₅ |
| 173 | CF₃CONH | CH₂-(2-pyridyl) | CH₂-S-(tetrazole-CH₂CH=CH₂) | H |
| 174 | C₆H₅—CH₂OCONH | CH₂-(3-pyridyl) | CH₂-S-(thiazole with CH₃, CH₂COOH) | H |
| 175 | Cl—CH₂CONH | CH₂-(4-pyridyl) | CH₂-S-(1,3,4-thiadiazole) | CH(C₆H₅)₂ |
| 176 | H₂N | " | CH₂-S-(tetrazole-CH₃) | H |

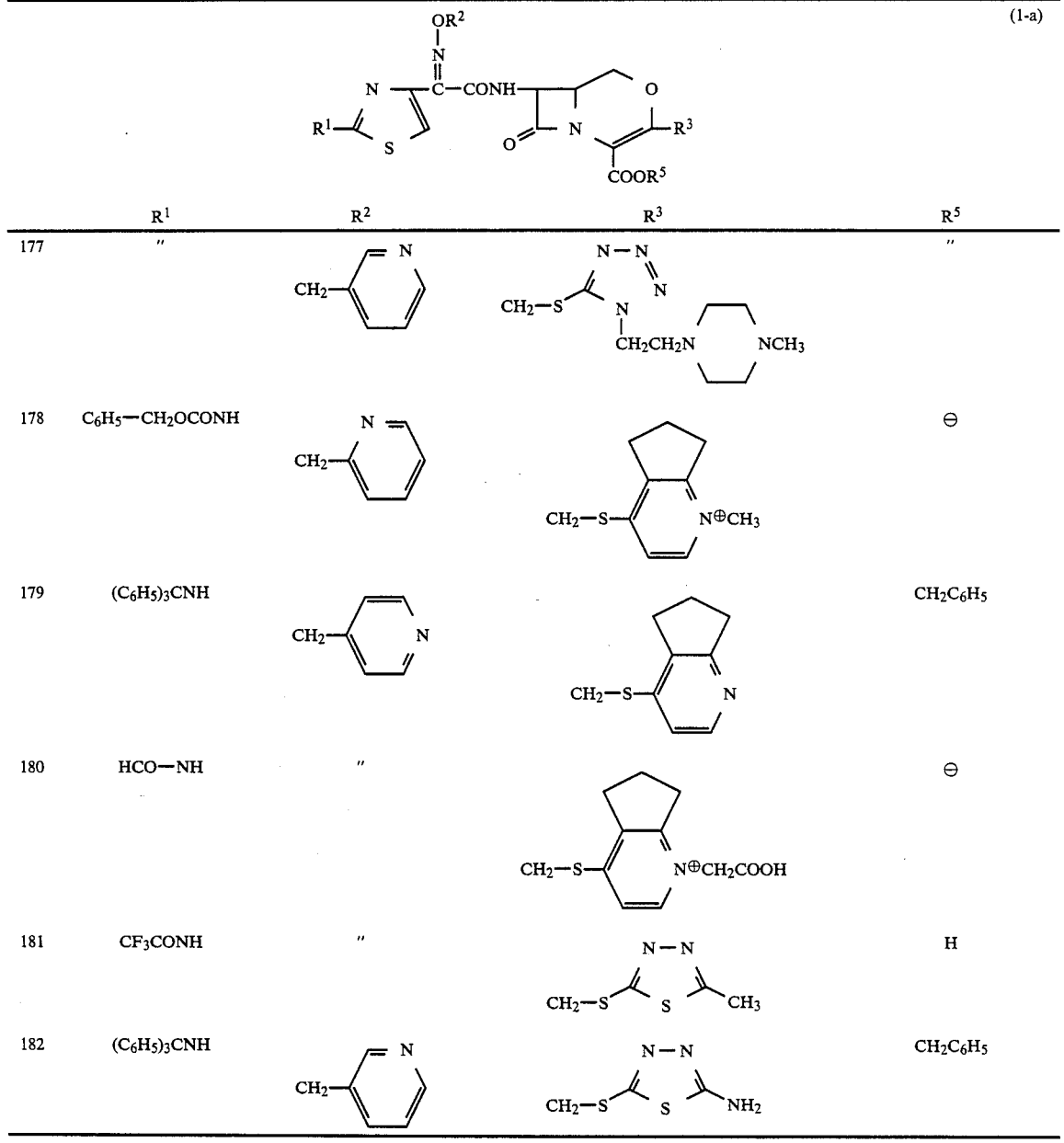
The compounds of the present invention can be produced by various processes, and the processes represented by the reaction scheme-1 to reaction scheme-6 may be mentioned by way of example.
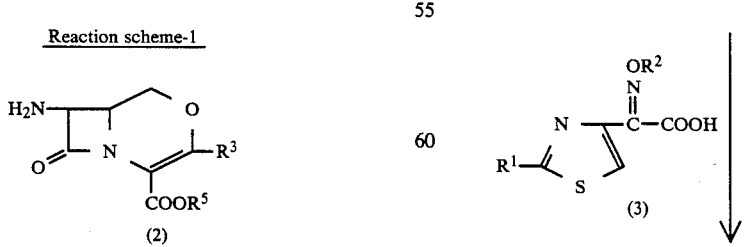

-continued
Reaction scheme-1

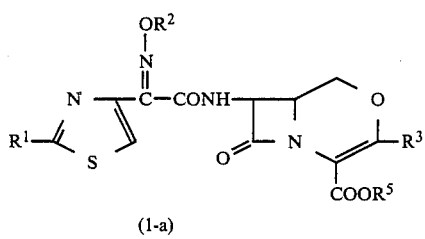

(1-a)

wherein $R^1$, $R^2$ and $R^3$ have the same meanings as defined above; and $R^5$ means a hydrogen atom or an ester residue.

Referring to the above reaction scheme-1, the compound of formula (1-a) can be produced by reacting an amine compound of formula (2) with a carboxylic acid compound of formula (3) or an active ester of the carboxy group thereof by a conventional amide bond-forming reaction. This amide bond-forming reaction can be carried out by any of the methods known in the art, e.g.

(a) The method involving the use of a condensing agent, wherein the carboxylic acid compound (3) is reacted with the amine compound (2) in the presence of a condensing agent.

(b) The mixed acid anhydride method, wherein the carboxylic acid compound (3) is reacted with an alkyl halocarboxylate to give a mixed acid anhydride, which is then reacted with the amine compound (2).

(c) The active ester method, wherein the carboxylic acid compound (3) is esterified into an active ester such as p-nitrophenyl ester, N-hydroxysuccinimide ester, 1-hydroxybenzotriazole ester or the like, which is then reacted with the amine compound (2).

(d) The method in which the carboxylic acid compound (3) is treated with a dehydrating agent such as acetic anhydride to give a carboxylic acid anhydride, which is then reacted with the amine compound (2).

(e) The method in which a lower alcohol ester of the carboxylic acid compound (3) is reacted with the amine compound (2) at elevated temperature and pressure.

(f) The method in which the carboxylic acid compound (3) is converted to an acid halide, i.e. a carboxylic acid halide, which is then reacted with the amine compound (2).

An example of the amide bond-forming reaction is specifically described below.

The compound (1-a) according to the present invention can be obtained by reacting an amine compound of formula (2) with a carboxylic acid compound of formula (3) in the presence of a condensing agent, either in the absence of a solvent or in the presence of an inert solvent.

The condensing agent that can be employed in this reaction includes, for example, thionyl chloride, phosphorus oxychloride, phosphorus pentachloride, Vilsmeier reagent, for example, (chloromethylene)dimethylammonium chloride produced by reaction of dimethylformamide with thionyl chloride, phosgen or phosphorous oxychloride, dicyclohexylcarbodiimide (DCC), 2,2'-pyridinyl disulfide-triphenlphosphine, and so on.

As examples of the solvent, there may be mentioned any solvent which does not adversely influence the reaction, for example, ethers such as diethyl ether, tetrahydrofuran, dioxane, etc., halogenated hydrocarbons such as dichloromethane, dichloroethane, chloroform, carbon tetrachloride, etc., aromatic hydrocarbons such as benzene, toluene, xylene, etc., amines such as pyridine, piperidine, triethylamine, etc., aliphatic hydrocarbons such as hexane, heptane, etc., alcohols such as methanol, ethanol, propanol, etc., aprotoic polar solvents such as diemthylformamide (DMF), hexamethylphosphoric triamide (HMPA), dimethyl sulfoxide (DMSO), etc., and carbon disulfide.

The above reaction is preferably carried out in the presence of a basic compound. As examples of such basic compound, there may be mentioned trialkylamines such as triethylamine, tributylamine, etc., such other organic bases as pyridine, picoline, 1,5-diazabicyclo[4,3,0]nonene-5, 1,4-diazabicyclo[2,2,2]octane, 1,8-diazabicyclo[5,4,0]undecene-7, etc., monotrimethylsilylacetamide, and inorganic bases such as alkali metal hydroxides, e.g. sodium hydroxide, potassium hydroxide, etc., alkali metal hydrogen carbonates such as sodium hydrogen carbonate, potassium hydrogen carbonate, and so on.

In the above reaction, the carboxylic acid compound of formula (3) and the amine compound of formula (2) are present in a molar ratio of 1:1 to 10:1 and preferably 1:1 to 3:1. The basic compound and the amine compound of formula (2) are present in a molar ratio of 1:1 to 40:1 and preferably 5:1 to 20:1.

The above reaction is conducted at about $-20°$ to about 100° C., preferably about $-20°$ to 50° C., for about 30 minutes to about 24 hours, preferably about 30 minutes to about 10 hours.

The above procedure gives the compound (1-a) according to the present invention.

Referring to the above reaction between the amine compound of formula (2) and the carboxylic acid compound of formula (3), when the group $R^5$ is a hydrogen atom, there may be obtained, in certain cases, a compound such that the carboxy group of the product compound of formula (1-a) is condensed with the carboxy group of the amine compound of formula (2). In such cases, the compound (1-a) can be produced by hydrolyzing the condensation product compound in the presence of an acid catalyst such as an inorganic or organic acid, e.g. hydrochloric acid, hydrobromic acid, trifluoroacetic acid or the like.

Reaction scheme-2

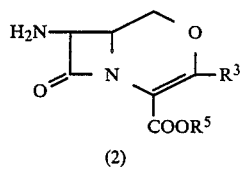

(2)

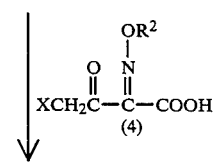

(4)

-continued
Reaction scheme-2

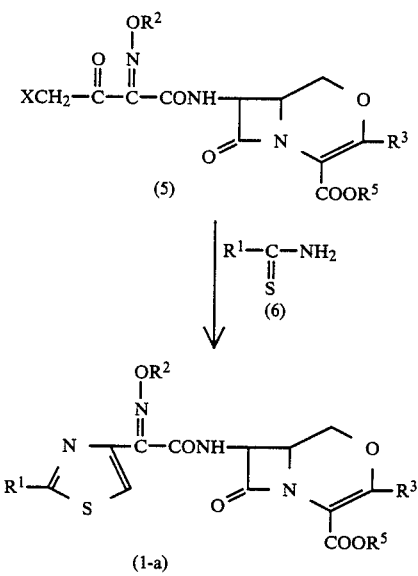

wherein $R^1$, $R^2$, $R^3$ and $R^5$ have the same meanings as defined above; and X means a halogen atom.

Referring to the above reaction formula, the compound of formula (5) can be obtained by reacting an amine compound of formula (2) with a carboxylic acid compound of formula (4). This reaction can be conducted in the same manner as the amide bond-forming reaction between the amine compound of formula (2) and the carboxylic acid compound of formula (3) in accordance with the reaction scheme-1.

The compound (1-a) according to the present invention can be obtained by reacting a compound of formula (5) with a thioacetamide compound of formula (6) in the presence of a suitable solvent or in the absence of a solvent.

Many different types of solvents can be used in this reaction, and the same solvent as used according to the above-mentioned reaction scheme-1 can be employed.

In this reaction, the thioacetamide compound of formula (6) and the compound of formula (5) are present in a molar ratio of 1:1 to 10:1 and preferably 1:1 to 5:1. This reaction is conducted at $-10°$ C. to $100°$ C., preferably $-10°$ C. to $50°$ C., and completed generally in 1 to 50 hours, preferably in 1 to 10 hours.

Reaction scheme-3

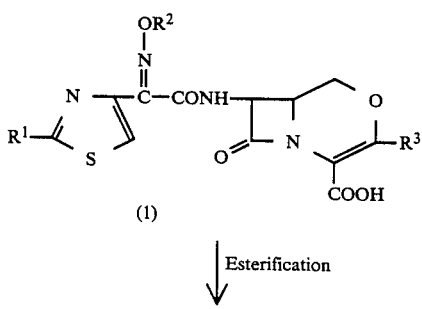

-continued
Reaction scheme-3

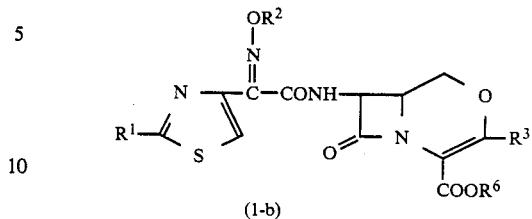

wherein $R^1$, $R^2$ and $R^3$ have the same meanings as defined above; and $R^6$ means an ester residue.

The ester compound of formula (1-b) can be obtained by subjecting a compound of formula (1) to a conventional esterification reaction.

By way of example, the above-mentioned esterification reaction is conducted in the presence of a catalyst, which may be one of the common esterification catalysts. Examples of such catalyst are inorganic acids such as hydrogen chloride gas, concentrated sulfuric acid, phosphoric acid, polyphosphoric acid, boron trifluoride, perchloric acid, etc., organic acids such as trifluoroacetic acid, trichloromethanesulfonic acid, naphthalenesulfonic acid, p-toluenesulfonic acid, benzenesulfonic acid, ethanesulfonic acid, etc.; acid anhydrides such as trichloromethanesulfonic anhydride, trifluoromethanesulfonic anhydride, etc., thionyl chloride, dimethylacetal, and so on. Cation exchange resins (acid form) can also be employed.

The above-mentioned esterification reaction can be conducted in the absence of a solvent or in the presence of a suitable solvent. The solvent mentioned just above may be any of the solvents used in esterification reactions in general, being thus exemplified by aromatic hydrocarbons such as benzene, toluene, xylene, etc., halogenated hydrocarbons such as dichloromethane, dichloroethane, chloroform, carbon tetrachloride, etc., and ethers such as diethyl ether, tetrahydrofuran, dioxane, and so on.

The acid and the compound of formula (1) are present in a molar ratio of 1:1 to 100:1 and preferably 10:1 to 30:1. The reaction temperature is $-20°$ C. to $200°$ C. and preferably 0 to $150°$ C.

The compound (1-b) according to the present invention can also be produced by the following methods. For example:

(1) Condensation with salt elimination

This method comprises reacting an alkali (e.g. sodium, potassium) salt of the compound of formula (1) with a halide compound corresponding to $R^6$ and this reaction can be conducted in any type of solvent that does not interfere with the reaction, e.g. ethers such as dimethyl ether, diethyl ether, tetrahydrofuran, dioxane, etc., alcohols such as methanol, ethanol, etc., and aprotic polar solvents such as dimethylformamide (DMF), dimethyl sulfoxide (DMSO), hexamethylphosphoric triamide (HMPA), and so on. The halide compound and the alkali metal salt of the compound (1) are present in a molar ratio of 1:1 at least and preferably 1:1 to about 3:1. This reaction is conducted at $-10°$ C. to $100°$ C. and preferably $0°$ C. to room temperature for about 1 to 12 hours.

(2) Diazotization

This method comprises reacting a compound of formula (1) with a diazo compound corresponding to $R^6$, for example diazomethane, phenyldiazomethane, diphenyldiazomethane, etc., in the presence of an inert solvent. As the inert solvent, there may be mentioned halogenated hydrocarbons such as dichloromethane, dichloroethane, chloroform, carbon tetrachloride, etc., ethers such as dimethyl ether, diethyl ether, tetrahydrofuran, dioxane, etc., nitro compounds such as nitromethane, nitrobenzene, etc., alcohols such as methanol, ethanol, etc., acetic acid esters such as methyl acetate, ethyl acetate, etc., alphatic hydrocarbons such as hexane, heptane, octane, etc., aprotic polar solvents such as dimethylformamide (DMF), dimethyl sulfoxide (DMSO) and hexamethylphosphoric triamide (HMPA), carbon disulfide, and so on.

The diazo compound should advisably be used in an amount of at least 1 mole, preferably about 1 to 3 moles, per mole of the compound of formula (1). The reaction proceeds smoothly at −10° C. to room temperature and generally is completed in about 10 minutes to about 6 hours.

Reaction scheme-4

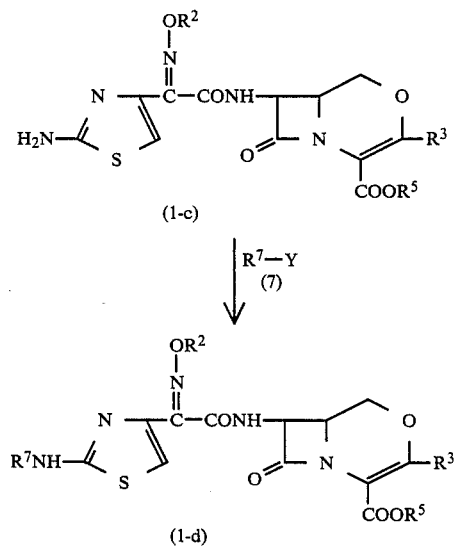

wherein $R^2$, $R^3$, $R^5$ and X have the same meanings as defined above; $R^7$ means a lower alkanoyl group, a halogen-substituted lower alkanoyl group, a phenyl-substituted lower alkyl group having 1 to 3 phenyl groups, a phenyl-lower alkoxycarbonyl group or a lower alkoxycarbonyl group; and Y means a halogen atom or a hydroxyl group; provided that when $R^7$ is a phenyl-substituted lower alkyl group having 1 to 3 phenyl groups, Y is a halogen atom.

The compound of formula (1-d) can be obtained by reacting a compound of formula (1-c) with a compound of formula (7).

This reaction is carried out by reacting the compound of formula (1-c) with the compound of formula (7) in the presence of a basic compound and in the absence or presence of an inert solvent. It can be carried out in substantially the same manner as in the above-mentioned amide bond formation reaction according to reaction scheme-1. Therefore, the reaction mode and reaction conditions (e.g. basic compound, solvent, reaction temperature, reaction time) for this reaction may be the same as those as explained in the reaction scheme-1 mentioned before.

Reaction scheme-5

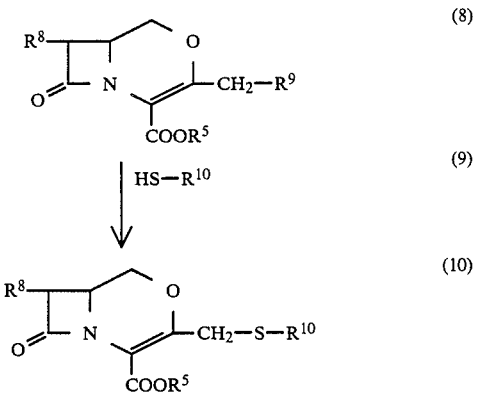

wherein $R^5$ has the same meaning as defined above; $R^8$ means an azido group, an amino group, a phthalimido group, a phenylacetamido group or a group of the formula:

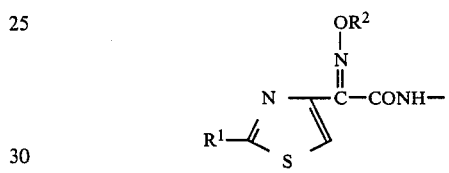

(in which $R^1$ and $R^2$ have the same meanings as defined above); $R^9$ means a halogen atom, a lower alkanesulfonyloxy group or an arylsulfonyloxy group; and $R^{10}$ means an unsaturated heterocyclic group containing 1 to 4 hetero atoms selected from the group consisting of nitrogen and sulfur atoms; in which the heterocyclic group may optionally have 1 to 3 substituens selected from the group consisting of lower alkyl, lower alkenyl, lower alkoxycarbonyl, carboxy, phenyl-lower alkoxycarbonyl-lower alkyl having 1 to 3 phenyl, carboxy-lower alkyl, hydroxy-lower alkyl, hydroxyl, oxo, amino, carbamoyl, cyano, lower alkyl-subsituted amino-lower alkyl, piperidinyl-lower alkyl, pyrrolidinyl-lower alkyl, carbamoyl-lower alkyl and cyano-lower alkyl, or a 4-lower alkyl-1-piperazinyl-lower alkyl group.

The heterocycle-containing thiomethyl groups can be introduced into the isocephem skeleton at the 3-position thereof by a variety of methods to give the 3-heterocycle-thiomethyl-substituted compounds of this invention. The above reaction scheme-5 exemplified one 20 method suited for that purpose.

Thus, reacting a compound of formula (8) with a thiol compound of formula (9) in a suitable inert solvent in the presence of a basic compound yields heterocycle-containing thiomethyl compound of formula (10) which comprises a portion of the compound of the present invention.

Referring to $R^9$ in the compound of formula (8), the halogen atom means chlorine, bromine, iodine or fluorine, for instance, and the lower alkanesulfonyloxy group may for example be methanesulfonyloxy, ethanesulfonyloxy, propanesulfonyloxy, etc., and the arylsulfonyloxy group may for example be benzenesulfonyloxy, toluenesulfonyloxy, p-chlorobenzenesulfonyloxy, p-nitrobenzenesulfonyloxy, etc.

The basic compound used in the above reaction is exemplified by organic basic compounds such as tertiary amines, e.g. triethylamine, pyridine, etc., and inorganic basic compounds such as sodium carbonate, potassium carbonate and so on.

As the inert solvent, the solvents that may be used in the reaction according to the reaction scheme-1 given hereinbefore can be used.

The compound of formula (9) and the compound of formula (8) are present in a molar ratio of 1:1 at least and preferably 1:1 to 2:1. The basic compound and the compound of formula (9) are present in a molar ratio of 1:1 at least and preferably 1:1 to 2:1. The reaction temperature is $-10°$ C. to 100° C. and preferably 0° to 50° C.

The above reaction yields a heterocycle-containing thiomethyl compound of formula (10).

When, in the compound according to the present invention, at least one of $R^1$, $R^2$, $R^3$ and $-COOR^5$ represents an amino group having a protective group or an ester group which is a carboxy-protecting group or has an ester group which is a carboxy-protecting group, the compound can be subjected to the deprotecting reaction shown below to give a compound of the present invention with the elimination of 1 or more protective groups.

Reaction scheme-6

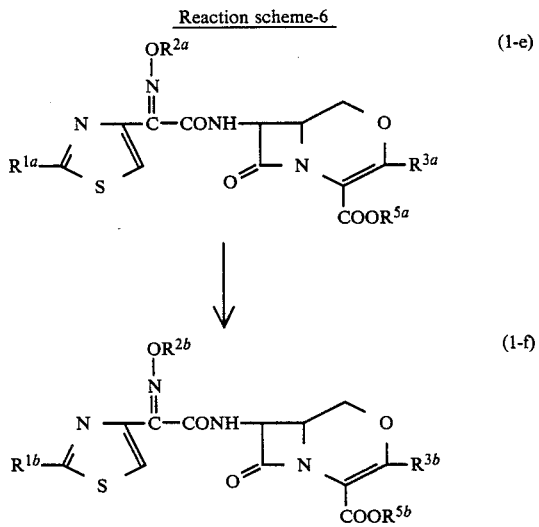

wherein $R^{1a}$, $R^{2a}$, $R^{3a}$ and $R^{5a}$ have the same meanings as $R^1$, $R^2$, $R^3$ and $R^5$, respectively; provided that at least one of $R^{1a}$, $R^{2a}$, $R^{3a}$ and $R^{5a}$ is a protected amino group or an ester residue or has an esterified carboxy group, and $R^{1b}$, $R^{2b}$, $R^{3b}$ and $R^{5b}$ have the same meanings as $R^1$, $R^2$, $R^3$ and $R^5$ respectively; provided that at least one of $R^{1b}$, $R^{2b}$, $R^{3b}$ and $R^{5b}$ means an amino group or a hydrogen atom, or has a carboxy group.

The above reaction is conducted in the absence of a solvent or in the presence of an inert solvent by the method of reacting a compound of formula (1-e) with an acidic compound or a basic compound or by subjecting the compound of formula (1-e) to catalytic reduction.

As examples of the inert solvent used in the above reaction, there may be mentioned halogenated hydrocarbons such as dichloromethane, dichloroethane, chloroform, carbon tetrachloride, etc., ethers such as dimethyl ether, diethyl ether, tetrahydrofuran, dioxane, anisole, etc.; nitro compounds such as nitromethane, nitrobenzene, etc.; alcohols such as methanol, ethanol, etc., acetic acid esters such as ethyl acetate, methyl acetate, etc.; aliphatic hydrocarbons such as hexane, heptane, octane, etc.; aromatic hydrocarbons such as benzene, toluene, xylene, etc.; amines such as pyridine, piperidine, etc.; aprotic polar solvents such as dimethylformamide (DMF), hexamethylphosphoric triamide (HMPA), dimethyl sulfoxide (DMSO), etc.; carbon disulfide, water; and mixtures of water and the above-mentioned organic solvents.

As examples of the acid compound, there may be mentioned Lewis acids such as anhydrous aluminum chloride, stannic chloride, titanium tetrachloride, boron trichloride, boron trifluoride-ethyl ether complex, zinc chloride, etc., inorganic acids such as hydrochloric acid, nitric acid, sulfuric acid, etc., organic acids such as trichloroacetic acid, trifluoroacetic acid, methanesulfonic acid, acetic acid, etc., and acid-form ion exchange resins. The basic compound mentioned above is exemplified by organic bases such as trialkylamines, e.g. triethylamine, tributylamine, etc., pyridine, picoline, 1,5-diazabicyclo [4,3,0]nonene-5, 1,4-diazabicyclo [2,2,2]octane, 1,8-diazabicyclo [5,4,0]undecene-7, etc., and inorganic bases such as alkali metal hydroxides, e.g. sodium hydroxide, potassium hydroxide, etc., alkali metal carbonates, e.g. sodium carbonate, potassium carbonate, etc., and alkali metal hydrogen carbonates, e.g. sodium hydrogen carbonate, potassium hydrogen carbonate, and so on.

When the above reaction is carried out by the catalytic reduction method, the catalyst may for example be a platinum catalyst (for example, platinum oxide, platinum black, platinum wire, platinum plate, platinum sponge, colloidal platinum, etc.), a palladium catalyst (for example, palladium black, palladium chloride, palladium oxide, palladium-on-carbon, palladium-on-barium sulfate, palladium-on-barium carbonate, palladium sponge, etc.), a nickel catalyst (for example, reduced nickel, nickel oxide, Raney nickel, etc.), a cobalt catalyst (for example, reduced cobalt, Raney cobalt, etc.), an iron catalyst (for example, reduced iron, Raney iron, etc.), or a copper catalyst (for example, reduced copper, Raney copper, etc.).

When the acid compound or the basic compound is used in the above reaction, the acid or basic compound and the compound of formula (1-e) are present in a molar ratio of 1:1 to 100:1 and preferably 1:1 to 20:1. This reaction is conducted at $-20°$ C. to 80° C., preferably $-10°$ C. to 50° C., and completed generally in 30 minutes to 48 hours, preferably in about 1 to 24 hours.

When the catalytic reduction method is used, the catalyst and the compound of formula (1-e) are present in a molar ratio of 0.1:1 to 10:1 and preferably 0.1:1 to 1:1. This reaction is conducted at 0° to 200° C. and preferably 0° to 100° C., and is complete in about 30 minutes to 48 hours and preferably in about 30 minutes to 6 hours.

The reaction according to the above reaction scheme-6 may be more specifically illustrated by way of the following reaction schemes-6a through 6d.

Reaction scheme-6a

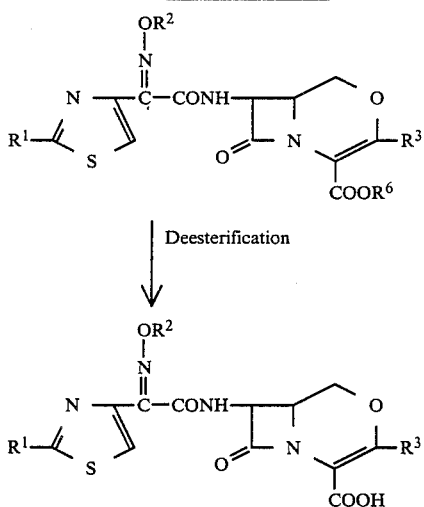

wherein $R^1$, $R^2$, $R^3$ and $R^6$ have the same meanings as defined above.

The carboxylic acid derivative of formula (1) can be produced by subjecting a compound of formula (1-b), an ester derivative in 4-position of the isocephem ring, to deesterification.

This deesterification reaction is conducted either without a solvent or in a suitable solvent, in the presence of a hydrolysis catalyst. The inert solvent and hydrolysis catalyst that are used in this reaction may be exemplified by the inert solvents and acid and basic compounds as explained in the reaction scheme-6.

This deesterification reaction can be carried out by the catalytic reduction method when the ester residue $R^6$ is a residue that can be easily cleaved thereby, for example a benzyl group: The catalyst used in this catalytic reduction is exemplified by the catalysts as explained in the reaction scheme-6.

When an acid or a base is used in the above reaction, the acid or base and the compound of formula (1-b) are present in a molar ratio of 1:1 to 100:1 and preferably 1:1 to 20:1. This reaction is conducted at $-20°$ C. to $80°$ C., preferably at $-10°$ C. to $50°$ C., and can be carried to completion in 30 minutes to 48 hours, preferably in 1 to 24 hours.

When the catalytic reduction method is employed, the catalytic reduction catalyst and the compound of formula (1-b) are present in a molar ratio of 0.1:1 to 10:1 and preferably 0.1:1 to 1:1. This reaction is conducted at $0°$ to $200°$ C., preferably 0 to $100°$ C. and may be carried to completion in 30 minutes to 48 hours, preferably 30 minutes to about 6 hours.

Reaction scheme-6b

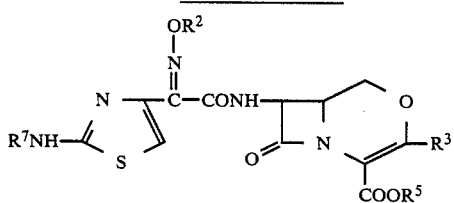

-continued
Reaction scheme-6b

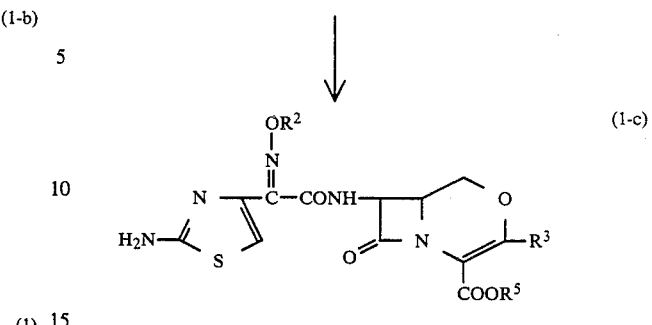

wherein $R^2$, $R^3$, $R^5$ and $R^7$ have the same meanings as defined above.

The compound (1-c) according to the present invention wherein the substituent in 2-position of the thiazolyl group is an amino group can be produced by subjecting a compound (1-d) of the present invention wherein the substituent in 2-position of the thiazolyl group is a substituted amino group to a reaction which is substantially similar to the deesterification reaction according to the aforementioned reaction scheme-6a. Thus, for example, an acid compound or a basic compound may be permitted to act on the starting compound or the starting compound is subjected to catalytic reduction, either in the absence of a solvent or in the presence of a suitable solvent.

Many different types of solvents can be used in this reaction and the solvents exemplified in the reaction scheme-6 can be employed for the purposes of this reaction.

The acid compound mentioned just above may be selected from among the acid compounds exemplified in the reaction scheme-6 but preferably be an inorganic acid such as hydrochloric acid, hydrobromic acid, sulfuric acid, nitric acid, etc., an organic acid such as trifluoroacetic acid, acetic acid, formic acid, etc., or an ion exchange resin of the acid-form. Of these acid compounds, those which are liquid can be utilized as the reaction solvent as well.

As examples of the basic compounds, there may be mentioned organic bases such as trialkylamines, e.g. triethylamine, tributylamine, etc., pyridine, picoline, 1,5-diazabicyclo [4,3,0]nonene-5, 1,4-diazabicyclo [2,2,2]octane, 1,8-diazabicyclo [5,4,0] undecene-7, etc., inorganic bases such as alkali metal hydroxides, e.g. sodium hydroxide, potassium hydroxide, etc., alkali metal carbonates, e.g. sodium carbonate, potassium carbonate, etc., and alkali metal hydrogen carbonates, e.g. sodium hydrogen carbonate, potassium hydrogen carbonate, etc., and urea compounds such as thiourea and urea.

When water is added to the reaction system, its proportion relative to the acid or basic compound is preferably in the range of 10 to 80 v/v percent and it is advantageous to add a further amount, 10 to 20 volumes, of water at completion of the reaction.

The acid or basic compound and the compound (1-d) according to the present invention are present in a molar ratio of 1:1 to 100:1 and preferably 2:1 to 10:1. The reaction temperature is $-20°$ C. to $80°$ C. and preferably $-10°$ C. to $50°$ C. The reaction time is about 1 to 24 hours.

When the reaction according to the reaction scheme-6b is carried out by the catalytic reduction method, the conditions (for example, the type and amount of catalytic reduction catalyst, solvent, reaction temperature and time) may be the same as those of catalytic reduction mentioned hereinbefore in the reaction scheme-6a.

The above procedure yields an amine compound of formula (1-c) which is one of the compounds according to the present invention.

Reaction scheme-6c

Reaction scheme-6d

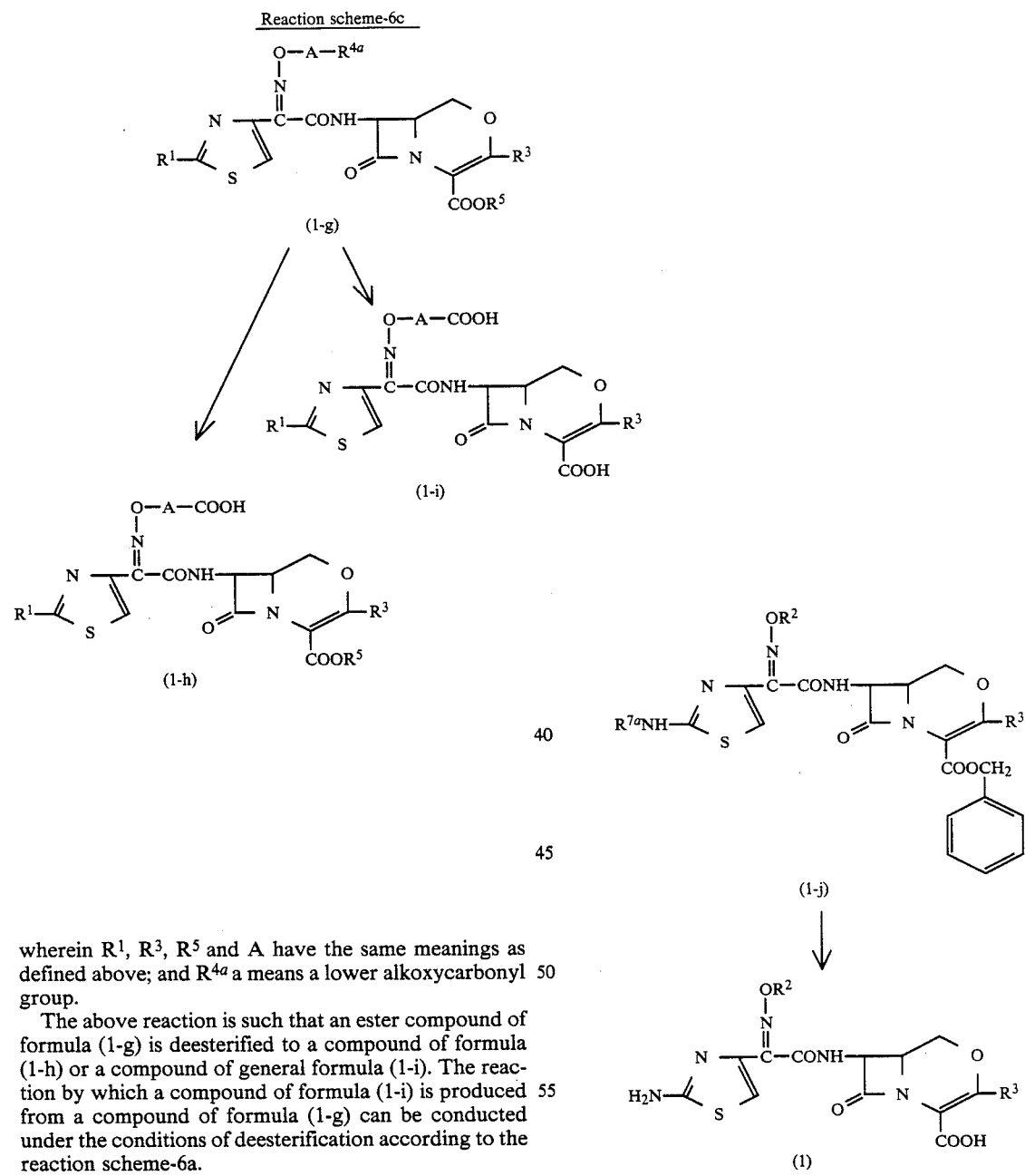

wherein $R^1$, $R^3$, $R^5$ and A have the same meanings as defined above; and $R^{4a}$ means a lower alkoxycarbonyl group.

The above reaction is such that an ester compound of formula (1-g) is deesterified to a compound of formula (1-h) or a compound of general formula (1-i). The reaction by which a compound of formula (1-i) is produced from a compound of formula (1-g) can be conducted under the conditions of deesterification according to the reaction scheme-6a.

The conditions of deesterification according to the reaction scheme-6a can be applied also to the reaction by which a compound of formula (1-h) is produced from a compound of formula (1-g). In this case, however, the ester residue $R^5$ should be selected according to the conditions of deesterification reaction. Thus, for example, when the deesterification reaction is conducted by alkali hydrolysis, the group which is not deesterified by alkali hydrolysis, for example a t-butyl group, is selected as $R^5$.

wherein $R^2$ and $R^3$ have the same meanings as defined above; and $R^{7a}$ means the phenyl-lower alkoxycarbonyl group.

In this reaction, deesterification of the 4-position of a compound of formula (1-j) and elimination of the phenyl-lower alkoxycarbonyl group $R^{7a}$ from the protected amino group thereof are simultaneously accomplished to give a compound of formula (1). This reaction can be conducted under substantially the same conditions as the reaction according to the reaction scheme-6a or 6b but it is preferable to use an acid as the hydrolysis catalyst. More desirably, Lewis acids such as aluminum chloride, zinc chloride, iron chloride, tin chloride and boron trifluoride may be employed.

Referring to the reaction schemes 1 to 6 mentioned above, the starting compounds of formula (2) and formula (8) include novel compounds and can be produced by the following reaction processes.

Reaction scheme-7

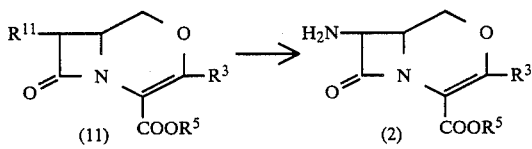

Wherein $R^3$ and $R^5$ have the same meanings as defined above; and $R^{11}$ means an azido group, a phenylacetamido group or a phthalimido group.

According to this reaction scheme-7, a compound of formula (11) is subjected to reduction, hydrolysis or hydrazinolysis according to the nature of substituent $R^{11}$ to give a compound of formula (2) which covers novel compounds.

Referring to the above reaction scheme-7, when the group $R^{11}$ is an azido group, an amine compound of formula (2) is produced by permitting a reducing agent to act on a compound of formula (11) in the absence of a solvent or in the presence of a suitable inert solvent.

The solvent to be used in this reaction is exemplified by halogenated hydrocarbons such as dichloromethane, dichloroethane, chloroform, carbon tetrachloride, etc., aromatic hydrocarbons such as benzene, toluene, xylene, etc., ethers such as diethyl ether, tetrahydrofuran, dioxane, etc., and amines such as triethylamine, pyridine, etc.

The reducing agent may for example be hydrogen sulfide. When hydrogen sulfide, for instance, is employed, it is preferable to add an amine such as triethylamine, pyridine or the like.

The reducing agent and the compound of formula (11) are present in a molar ratio of 1:1 to 100:1 and preferably 3:1 to 50:1. This reaction is conducted generally at −30° C. to 50° C. and preferably at −10° C. to 10° C., and completed in about 30 minutes to 10 hours.

When the group $R^{11}$ is a phenylacetamido group, an amine compound of formula (2) can be produced by subjecting a compound of general formula (11) to hydrolysis in the absence of a solvent or in the presence of an inert solvent.

This reaction can be carried out substantially in the same manner as the reaction according to the reaction scheme-6b. Thus, the reaction procedure and conditions (for example, the hydrolysis, catalyst, solvent, reaction temperature, reaction time, etc.) for this reaction may be the same as those as explained in the reaction scheme-6b.

When the group $R^{11}$ is a phthalimido group, an amine compound of formula (2) can be produced by subjecting a compound of formula (11) to hydrazinolysis, i.e. reaction with hydrazine or a hydrazine derivative, in the absence of a solvent or in the presence of an inert solvent.

The inert solvent to be used in this reaction include halogenated hydrocarbons such as dichloromethane, dichloroethane, chloroform, carbon tetrachloride, etc., and alcohols such as methanol, ethanol, etc. The hydrazine derivative is exemplified by lower alkyl-substituted hydrazine such as methylhydrazine, ethylhydrazine, etc., and aryl-substituted hydrazine such as phenylhydrazine, etc.

The hydrazine or hydrazine derivative and the compound of formula (11) are present in a molar ratio of 1:1 at least and preferably 1:1 to 2:1. This reaction is conducted generally at 0° to 100° C. and preferably at 0° to 80° C., and completed in about 1 to about 40 hours.

When, in the compound of formula (2) obtained by the above reaction, the group $R^5$ is an ester residue, the compound can be deesterified in substantially the same manner as the deesterification reaction according to the reaction scheme-6a to give a compound in which $R^5$ is a hydrogen atom. When the group $R^5$ is a hydrogen atom, the compound of formula (2) can be esterified in substantially the same manner as the esterification reaction according to the reaction scheme-3 given hereinbefore to give a compound wherein $R^5$ is an ester residue.

Reaction scheme-8

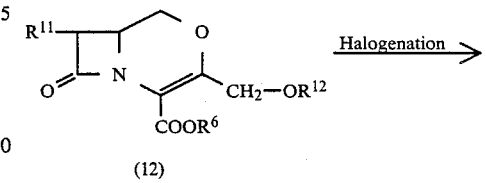

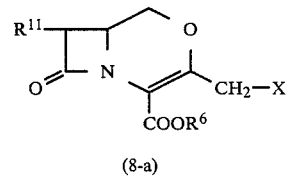

wherein $R^6$, $R^{11}$ and X have the same meanings as defined above; and $R^{12}$ means a hydrogen atom or a lower alkanoyl group.

This reaction is a halogenation reaction which substitutes the alcoholic hydroxy group or lower alkanoyloxy group of a compound of formula (12) with a halogen atom and can be conducted under the various halogenating conditions commonly adopted.

By way of illustration, when the group $R^{12}$ means a hydrogen atom, a compound of formula (12) can be reacted with a thionyl halide such as thionyl chloride, thionyl bromide, thionyl iodide or the like in the presence or absence of a solvent to give a compound of formula (8-a). As the solvent, any solvent that does not interfere with the reaction can be employed. For example, halogenated hydrocarbons such as dichloromethane, dichloroethane, chloroform, carbon tetrachloride, etc., ethers such as dimethyl ether, diethyl ether, tetrahydrofuran, dioxane, etc., nitro compounds such as nitromethane, nitrobenzene, etc., acetic acid esters such as ethyl acetate, methyl acetate, etc., aliphatic hydrocarbons such as hexane, heptane, octane, etc., aprotic polar solvents such as dimethyl-formamide (DMF), dimethyl sulfoxide (DMSO), hexamethylphosphoric triamide (HMPA), etc., and carbon disulfide may be mentioned. The thionyl halide and the compound of formula (12) are present in a molar ratio of 1:1 at least and preferably 1:1 to 2:1. This reaction is conducted at −10° C. to room temperature and preferably under ice-cooling, and completed in about 5 minutes to 1 hour.

In conducting this reaction, a basic compound such as pyridine, dimethylaniline, triethylamine or the like is preferably added as an acid acceptor to the reaction system.

When the group $R^{12}$ is a lower alkanoyl group, a compound of formula (12) can be reacted with a tri(-lower alkyl)silyl halide in the absence of a solvent or in the presence of an inert solvent to give a compound of formula (8-a).

The inert solvent to be used in this reaction is the same as exemplified above. The tri(lower alkyl)silyl halide includes trimethylsilyl chloride and triethylsilyl chloride, for instance.

The tri(lower alkyl)silyl halide and the compound of formula (12) are present in a molar ratio of 1:1 at least and preferably 1:1 to 2:1. This reaction is conducted at −20° C. to 50° C., preferably at room temperature, and is complete in about 30 minutes to 5 hours.

Among the compounds of general formula (1), optically active compounds can be produced from optically active starting materials in accordance with the reaction schemes 1 to 6, and the product compounds have steric configurations corresponding to those of the starting compounds.

The following is an exemplary process for the production of an optically active starting compound. The steric configuration illustrated by the following reaction scheme is only an example and when a cis-or trans-isomer is used, for instance, there can be obtained a product compound having the corresponding configuration.

Reaction scheme-9

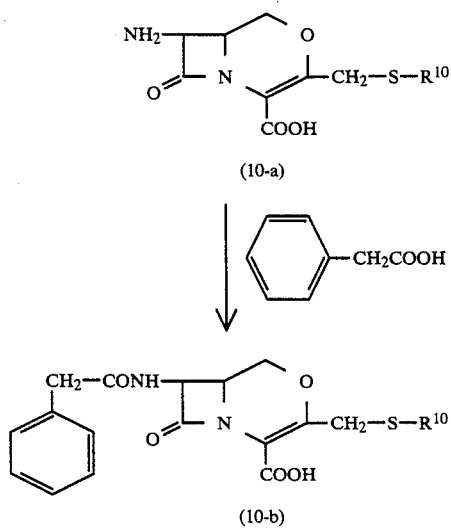

(10-a)

(10-b)

-continued
Reaction scheme-9

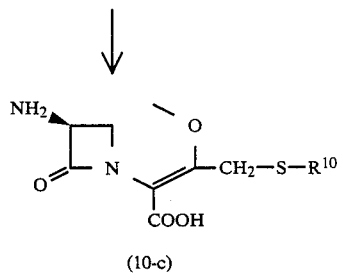

(10-c)

wherein $R^{10}$ has the same meaning as defined above.

Referring to the above reaction scheme, the reaction by which a compound of formula (10-b) is produced from a compound at formula (10-a) is carried out by reacting the compound (10-a) with phenylacetic acid or a reactive derivative at the carboxy group thereof. This reaction can be conducted in substantially the same manner as the reaction according to the aforementioned reaction scheme-1. Therefore, the acylation conditions (for example, the reactive derivative, solvent, reaction temperature, reaction time, etc.) for this reaction may be the same as those as exemplified in the reaction scheme-1.

The reaction by which a compound of formula (10-c) is produced from a compound of formula (10-b) is such that the phenylacetamido group in the 7-position of the compound of formula (10-b) is selectively hydrolyzed by means of an enzyme to give the compound of formula (10-c).

This reaction is conducted in water or an aqueous solvent in the presence of an enzyme. The enzyme used in this reaction may be any enzyme that will selectively hydrolyze the amido group, being thus exemplified by penicillin G amidase, etc.

The proportion of the enzyme relative to the compound of formula (10-b) is generally about 0.5 to 2 gram equivalents. As the reaction system is rendered acidic by the byproduct acid with the progress of the reaction, a basic compound is preferably added to the reaction system so as to maintain the system at the optimal pH for the enzyme. The basic compound is exemplified by, for example, aqueous ammonia, alkali metal hydroxides such as sodium hydroxide, potassium hydroxide, etc., alkali metal carbonates or alkali metal hydrogen carbonates such as sodium carbonate, potassium carbonate, sodium hydrogen carbonate, etc. This reaction is preferably conducted at the optimal temperature for the enzyme used, and is carried to completion in 1 to 10 hours and preferably in about 1 to about 5 hours.

Reaction scheme-10

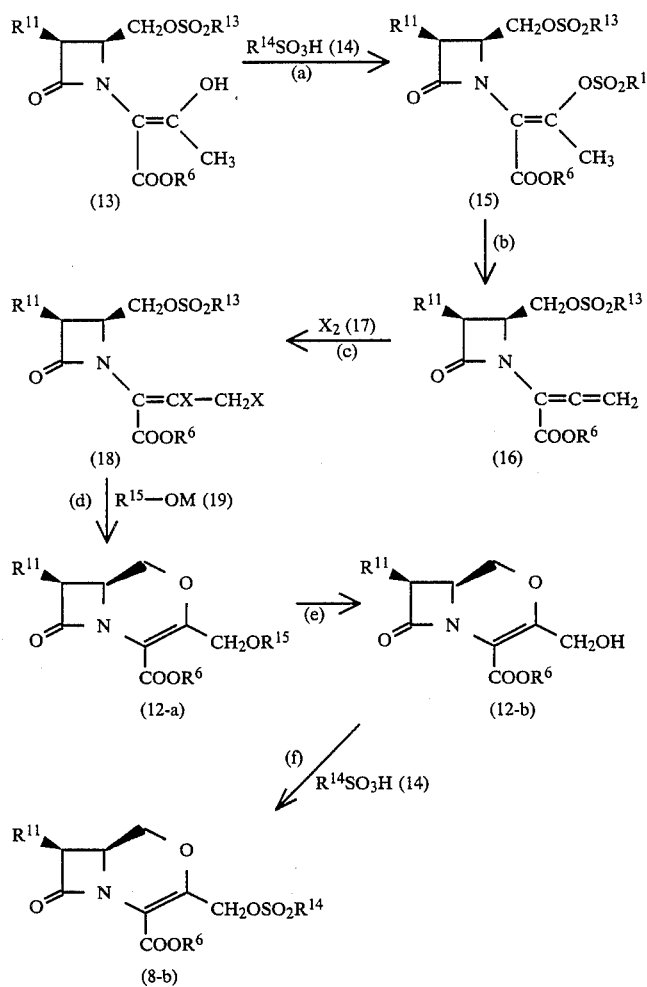

wherein $R^6$, $R^{11}$ and X have the same meanings as defined above; $R^{13}$ and $R^{14}$ each means a lower alkyl group which may optionally be substituted with halogen or an aryl group which may optionally be substituted with lower alkyl, halogen and/or nitro; and $R^{15}$ is a lower alkanoyl group; and M means an alkali metal.

Referring to the above reaction scheme, the reaction (a) by which a compoound of formula (15) is produced from a compound of formula (13) is carried out by reacting the compound of formula (13) with a sulfonic acid of formula (14) or a reactive derivative at the sulfo group thereof in the presence of an inert solvent or in the absence of a solvent.

The inert solvent is exemplified by halogenated hydrocarbons such as dichloromethane, dichloroethane, chloroform, carbon tetrachloride, etc., ethers such as dimethyl ether, diethyl ether, etc., and aliphatic hydrocarbons such as hexane, heptane, octane, etc.

The sulfonic acid represented by the formula (14) is exemplified by lower alkanesulfonic acids such as methanesulfonic acid, ethanesulfonic acid, propanesulfonic acid, etc., halogen-substituted lower alkanesulfonic acids such as trifluoromethanesulfonic acid, 2-trifluoroethanesulfonic acid, etc., and arylsulfonic acids which may optionally be substituted with lower alkyl, halogen and/or nitro, such as benzenesulfonic acid, toluenesulfonic acid, p-chlorobenzenesulfonic acid, p-nitrobenzenesulfonic acid, etc. The reactive derivative at the sulfo group of the sulfonic acid is exemplified by sulfonic acid halides such as sulfonyl chloride, sulfonyl bromide, etc., and sulfonic anhydride.

The sulfonic acid or the reactive derivative at the sulfo group thereof and the compound of formula (13) are present in a molar ratio of 1:1 at least and preferably 1:1 to 1.5:1. This reaction is conducted at −50° C. to ice-cooling conditions and completed in about 1 to 50 minutes. This reaction can be carried out in the presence of an acid acceptor such as pyridine, triethylamine, etc., but it is preferable to add the acid acceptor at completion of the above reaction and continue the reaction further for about 30 minutes to 3 hours, preferably for about 1 hour. The acid acceptor and the reactive derivative of sulfonic acid are present in a molar ratio of 1:1 at least and preferably 1:1 to about 1.5:1.

The reaction (b) which converts a compound of formula (15) to a compound of formula (16) is carried out by reacting the compound (15) with a basic compound such as triethylamine, pyridine, piperidine or the like in the presence of an inert solvent or in the absence of a solvent. The inert solvent may be one that is used in the above reaction step(a). The basic compound and the compound of formula (15) are present in a molar ratio of 1:1 at least and preferably 1:1 to about 1.5:1. This reaction is carried out under ice-cooling to room temperature conditions and carried to completion in about 10 minutes to about 2 hours, preferably in about 1 hour.

The reaction (c) which converts a compound of formula (16) to a compound of formula (18) is such that a halogen molecule represented by formula (17) is added to the compound of formula (16). The halogen molecule and the compound of formula (16) are present in a molar ratio of 1:1 at least and preferably 1:1 to 1.2:1. The halogen molecule is preferably iodine molecule. This reaction is conducted under ice-cooling to room temperature conditions and carried to completion in about 1 to 5 hours, preferably in about 3 hours.

The reaction (d) by which a compound of formula (12-a) is produced from a compound of formula (18) is carried out by reacting the compound of formula (18) with a lower alkanoic acid alkali metal salt of formula (19) such as sodium formate, potassium formate, sodium acetate, potassium acetate, sodium propionate or the like, in a mixture of water with an organic solvent exemplified in the above reaction step (a).

The proportion of water in the mixed solvent is about 0.1 to about 1 vol% based on the organic solvent. The lower alkanoic acid alkali metal salt of formula (19) and the compound of formula (18) are present in a molar ratio of 1:1 to 6:1 and preferably 4:1 to 5:1. This reaction is conducted at room temperature and completed in about 6 to 24 hours.

The reaction (e) by which a compound of formula (12-b) is produced from a compound of formula (12-a) is carried out by reacting the compound of formula (12-a) with a mineral acid such as hydrochloric acid, nitric acid, sulfuric acid or the like. The inert solvent to be used in the reaction is exemplified by water, ketones such as acetone, diethyl ketone, acetophenone, etc., ethers such as diethyl ether, tetrahydrofuran, dioxane, etc., halogenated hydrocarbons such as dichloromethane, dichloroethane, chloroform, carbon tetrachloride, etc., aromatic hydrocarbons such as benzene, toluene, xylene, etc., amines such as triethylamine, pyridine, piperidine, etc., aliphatic hydrocarbons such as hexane, heptane, etc., alcohols such as methanol, ethanol, propanol, etc., aprotic polar solvents such as dimethylformamide (DMF), dimethyl sulfoxide (DMSO), hexamethylphosphoric triamide (HMPA), etc., and carbon disulfide. The mineral acid and the compound of formula (12-a) are present in a molar ratio of about 3:1. This reaction is conducted at room temperature and completed in about 1 to about 10 hours.

The reaction (f) by which a compound of formula (8-b) is produced from a compound of formula (12-b) is carried out by reacting a compound of formula (12-b) with a sulfonic acid of formula (14) or a reactive derivative at the sulfo group thereof in the presence of a basic compound such as pyridine, triethylamine or the like. This reaction can be conducted in the same manner as the aforesaid reaction step (a).

The use of a compound of formula (13) in which the 3- and 4-positions of the azetidinone ring are (R, R), (R, S) and (S, R) give the compounds of formula (8-b) having the corresponding steric configurations.

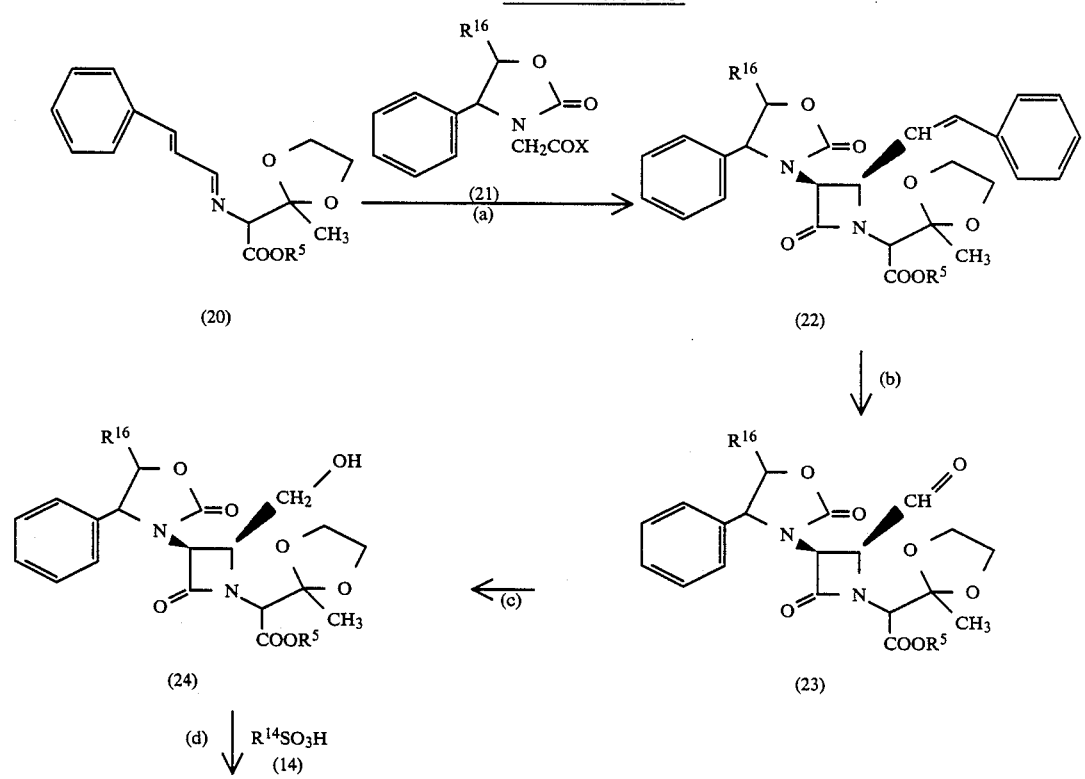

-continued
Reaction scheme-11

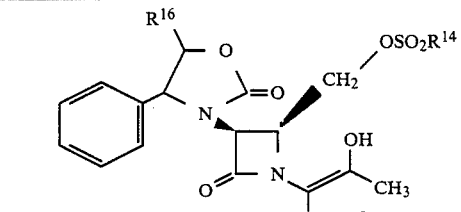
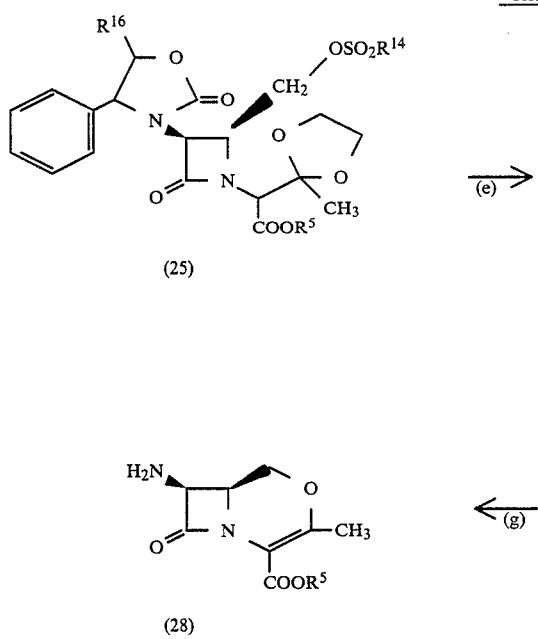

wherein R⁵, R¹⁴ and X have the same meanings as defined above; and $R^{16}$ means a hydrogen atom or a phenyl group.

Referring to the above reaction scheme, the reaction (a) by which a compound of formula (22) is produced from a compound of formula (20) is carried out by reacting the compound of formula (20) with a compound of formula (21) in the presence or absence of a basic compound. The basic compound to be used includes inorganic bases, e.g. alkali metal hydroxides such as sodium hydroxide, potassium hydroxide, etc., alkali metal carbonates or alkali metal hydrogen carbonates such as sodium carbonate, potassium carbonate, sodium hydrogen carbonate, etc., organic bases, e.g. triethylamine, pyridine, N,N-dimethylaniline, etc. The reaction is usually conducted in an organic solvent. Examples of the solvent to be used are aromatic hydrocarbons such as benzene, toluene, etc., ethers such as diethyl ether, tetrahydrofuran, etc., and halogenated hydrocarbons such as methylene chloride, chloroform, etc. Halogenated hydrocarbons are preferred. The compound of formula (21) and the compound of formula (20) are present in a molar ratio of 1:1 at least and preferably 1:1 to about 1.5:1. This reaction is conducted at −70° C. to 0° C., preferably −40° to −20° C. and carried to completion in about 1 to about 10 hours, preferably in about 1 to about 5 hours.

The reaction (b) by which a compound of formula (23) is produced from a compound of formula (22) is carried out by permitting ozone to act on the compound of formula (22) in the presence of an inert solvent to thereby oxidize the compound (22). Examples of the inert solvent are halogenated hydrocarbons such as methylene chloride, dichloroethane, chloroform, etc., and alcohols such as methanol, ethanol, etc. The ozone and the compound of formula (22) are present in a molar ratio of 1:1 at least and generally an excess. This reaction is conducted at −100° C. to 0° C. and preferably at −50° C. to −30° C. While the reaction time varies with the feeding rate of ozone, reaction temperature, etc., the reaction is generally continued until an excess of ozone is detected in the reaction system (for example, the blue color of ozone is detected). After the reaction, an inert gas such as nitrogen gas is optionally introduced to remove the excess ozone and an after-treatment with a reducing agent is preferably carried out. Examples of the reducing agent are dimethyl sulfide, sodium borohydride, sodium sulfite and so on. This after-treatment is generally carried out under cooling to at room temperature.

The reaction (c) by which a compound of formula (24) is produced from the compound of formula (23) prepared as above is a reaction that reduces the aldehyde group of the compound (23) to a hydroxy group, and any of the known procedures for reducing an aldehyde group to a hydroxy group can be utilized. By way of example, this reaction is carried out by reacting the compound of formula (23) with a reducing agent in the presence of a solvent. Examples of the solvent to be used in this reaction include ethers such as diethyl ether, tetrhydrofuran, dioxane, etc., and alcohols such as methanol, ethanol, etc. Examples of the reducing agent include borohydride compounds (e.g. sodium borohydride, lithium borohydride, sodium cyanoborohydride, tetramethylammonium borohydride, diborane, etc.), and aluminum hydride compounds (e.g. lithium aluminum hydride, sodium aluminum hydride, aluminum hydride, lithium trimethoxyaluminum hydride, lithium tri-t-butoxyaluminum hydride, etc.). This reaction is conducted at −60° C. to room temperature, preferably at −30° C. to −10° C. and carried to completion in about 1 to about 10 hours, preferably in about 1 to about 5 hours.

The reaction (d) by which a compound of formula (25) is produced from a compound of formula (24) is carried out by reacting the compound of formula (24) with a sulfonic acid of formula (14) or a reactive derivative at the sulfo group thereof in the presence of a solvent. Examples of the solvent to be used in this reaction include aromatic hydrocarbons such as benzene, toluene, etc., ethers such as diethyl ether, tetrahydrofuran, etc., halogenated hydrocarbons such as methylene chloride, chloroform, dichloroform, etc., aprotic polar solvents such as dimethylformamide, dimethyl sulfoxide, hexamethylphosphoric triamide, etc., and acetonitrile. The aforesaid sulfonic acid of formula (14) and the reactive derivative at the sulfo group thereof are exemplified by the sulfonic acid compounds and reactive derivatives mentioned hereinbefore in the reaction scheme-10 step (a). The sulfonic acid or its reactive derivative and the compound of formula (24) are present in a molar ratio of 1:1 at least and preferably 1:1 to about 1.5:1. This reaction is preferably carried out in the presence of a base. The base is exemplified by the organic or inorganic basic compounds mentioned in the reaction step (a) described above, although the use of an organic base is preferred. This reaction is conducted generally at −10° C. to 100° C., preferably at 0° C. to room temperature, and carried to completion in about 1 to about 20 hours, preferably in about 1 to about 10 hours.

The reaction (e) by which a compound of formula (26) is produced from a compound of formula (25) is carried out by reacting the compound of formula (25) with an acid compound in the presence or absence of a solvent. Examples of the acid to be used include mineral acids such as hydrochloric acid, sulfuric acid, nitric acid, etc., organic acids such as acetic acid, trifluoroacetic acid, p-toluenesulfonic acid, methanesulfonic acid, etc., Lewis acids such as aluminum chloride, titanium tetrachloride, tin tetrachloride, zinc chloride, etc., and compounds containing phenolic hydroxy groups such as phenol, cresol, etc. The proportion of the acid compound relative to the compound of formula (25) is generally a stoichiometric excess. The solvent that can be used is exemplified by organic acids such as acetic acid, etc., alcohols such as methanol, ethanol, etc., aprotic polar solvents such as dimethylformamide, dimethyl sulfoxide, hexamethylphosphoric triamide, etc., and acetonitrile. When the above acid compound is a liquid, it can be utilized as the reaction solvent as well. This reaction is conducted at about −20° C. to about 80° C., preferably at about 0° C. to room temperature, and is carried to completion in about 1 to about 10 hours, preferably in about 1 to about 5 hours.

The reaction (f) by which a compound of formula (27) is produced from a compound of formula (26) is carried out by reacting the compound of formula (26) with a basic compound in the presence or absence of a solvent. Examples of the solvent to be used in this reaction include aromatic hydrocarbons such as benzene, toluene, etc., ethers such as ethyl ether, tetrahydrofuran, etc., halogenated hydrocarbons such as methylene chloride, chloroform, dichloroethane, etc., alcohols such as methanol, ethanol, etc., ketones such as acetone, methyl ethyl ketone, etc., aprotic polar solvents such as dimethylformamide, dimethyl sulfoxide, hexamethylphosphoric triamide, etc., and acetonitrile. Examples of the basic compound to be used include inorganic bases such as alkali metal hydroxides, e.g. sodium hydroxide, potassium hydroxide, etc., alkali metal carbonates or alkali metal hydrogen carbonates, e.g. sodium carbonate, potassium carbonate, sodium hydrogen carbonate, etc., and organic bases such as triethylamine, pyridine, N,N-dimethylaniline, DUB, etc. Particularly preferred are organic bases. The basic compound and the compound of formula (26) are present in a molar ratio of 1:1 at least and generally the basic compound is used a slight excess. This reaction is conducted at 0° to 100° C., preferably at about 20° C. to about 80° C., and is carried to completion in about 1 to about 20 hours, preferably in about 1 to about 10 hours.

The reaction (g) by which a compound of formula (28) is produced from a compound of formula (27) is carried out by reducing the compound of formula (27). This reduction reaction can be conducted by the catalytic reduction method, reduction utilizing molten metals such as the Birch's reduction, for instance.

The catalytic reduction method can be carried out in substantially the same manner as the catalytic reduction according to the reaction scheme-6a. Therefore the conditions of this reaction (for example, catalyst, solvent, reaction temperature, reaction time, etc.) may be the same as those as exemplified in the reaction scheme-6a mentioned above.

The reduction using a molten metal can for example be carried out in a solution of an alkali metal such as sodium or potassium in liquid ammonia, methylamine, ethylamine or the like. The alkali metal and the compound of formula (27) are present in a molar ratio of about 10:1 and preferably about 1:1 to about 5:1. In conducting this reaction, it is preferably to add a small amount of alcohol to the reaction system and this alcohol is preferably t-butanol. The reaction is conducted at about −50° C. to room temperature and preferably at about −30° C. to about 0° C. The reaction time is about 1 to about 10 hours and preferably about 1 to about 3 hours.

Referring, further, to the reaction scheme-11, when the group $R^5$ in the products of reaction steps (a) to (g), i.e. compounds (22), (23), (24), (25), (26), (27) and (28), means an ester residue, each of these compounds can be deesterified in substantially the same manner as the deesterification reaction according to the reaction scheme-6a to give the corresponding compound wherein $R^5$ is a hydrogen atom. On the other hand, when the group $R^5$ means a hydrogen atom, each of the various compounds can be esterified in substantially the same manner as the esterification reaction according to the reaction scheme-3 to give the corresponding compound wherein $R^5$ is an ester residue.

4,831,026
Reaction scheme-12
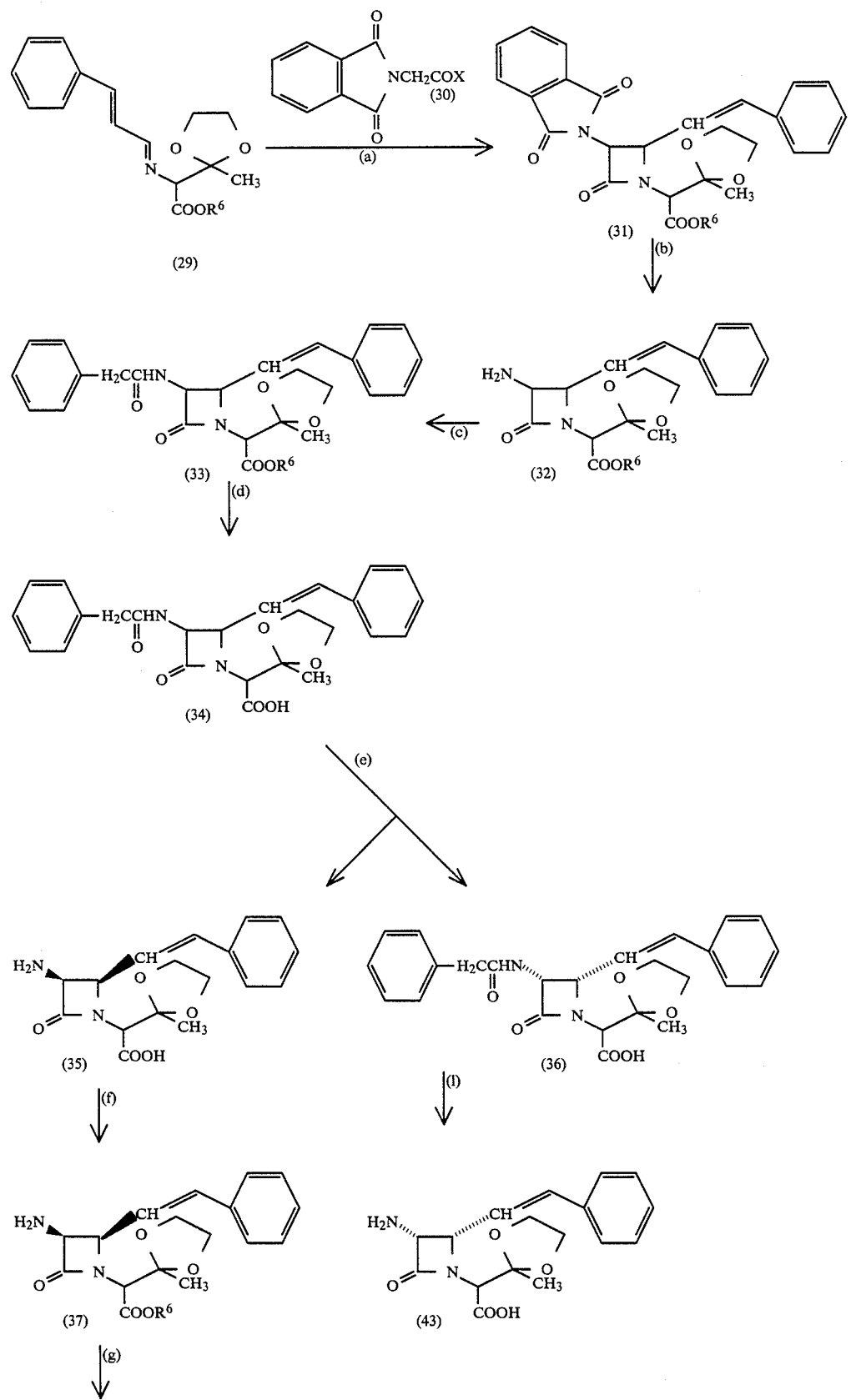

Reaction scheme-12 -continued

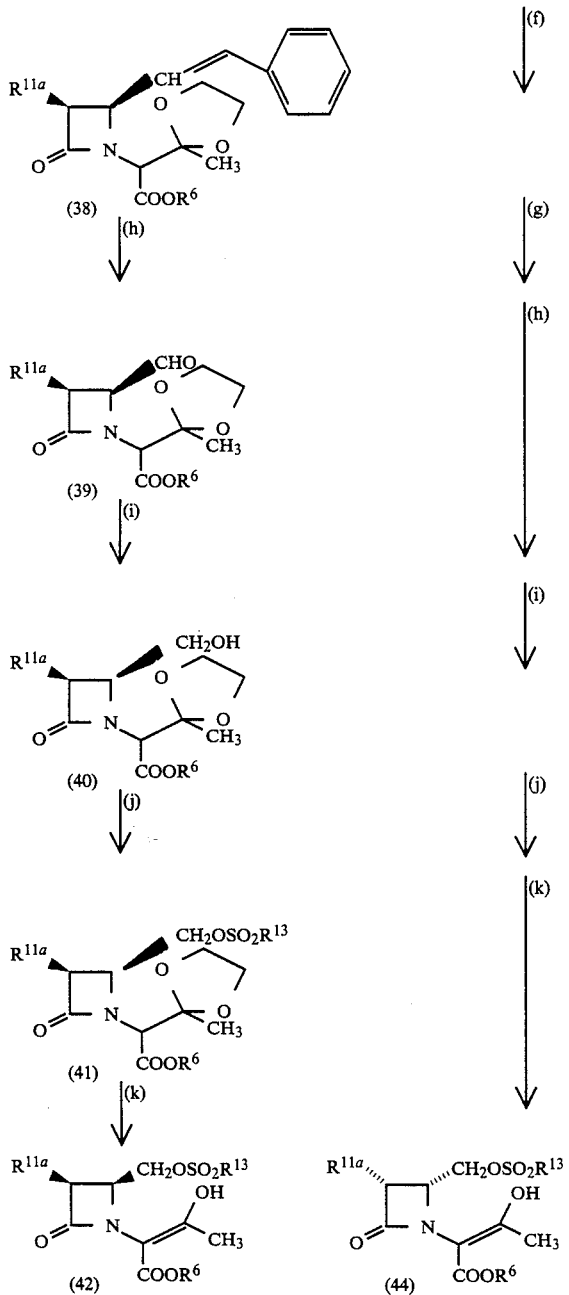

wherein $R^6$, $R^{13}$ and $X$ have the same meanings as defined above; and $R^{11a}$ means a phthalimido group or a phenylacetamido group.

Referring to the above reaction scheme, the reaction (a) by which a compound of formula (31) is produced from a compound of formula (29) is carried out by reacting the compound of formula (29) with a compound of formula (30) in the absence on presence of a basic compound. Examples of the basic compound to be used include inorganic bases such as alkali metal hydroxide, e.g. sodium hydroxide, potassium hydroxide, etc., and alkali metal carbonates or alkali metal hydrogen carbonates, e.g. sodium carbonate, potassium carbonate, sodium hydrogen carbonate, etc., and organic bases such as triethylamine, pyridine, N,N-dimethylaniline, etc. The reaction is usually conducted in an organic solvent. Examples of the solvent to be used include aromatic hydrocarbons such as benzene, toluene, xylene, etc., ethers such as diethyl ether, tetrahydrofuran, etc., and halogenated hydrocarbons such as methylene chloride, dichloroethane, chloroform, etc. The compound of formula (30) and the compound of formula (29) are present in a molar ratio of 1:1 at least and preferably 1:1 to about 2:1. This reaction is conducted at about $-50°$ C. to room temperature, preferably at about $-30°$ C. to about $0°$ C., for about 1 to about 10 hours, preferably about 30 minutes to about 6 hours.

The reaction (b) by which a compound of formula (32) is produced from a compound of formula (31) is carried out by reacting the compound of formula (31) with hydrazine or a derivative thereof. This reaction can be carried out in substantially the same manner as the hydrazinolsis according to the reaction scheme-7 described above. Therefore, reaction conditions (for example, the reactants, solvent, reaction temperature and time, etc.) for this reaction may be the same as those as exemplified in the above-mentioned reaction scheme-7.

The reaction (c) by which a compound of formula (33) is produced from a compound of formula (32) is carried out by reacting the compound of formula (32) with phenylacetic acid or a reactive derivative at the carboxy group thereof. This reaction is carried out in substantially the same manner as the reaction scheme-1 given hereinbefore. Therefore, reaction procedures (for example, the method using a condensing agent, the mixed acid anhydride method, the active ester method, etc.) and reaction conditions (for example, the basic compound, solvent, reaction temperature, reaction time, etc.) for this reaction may be the same as those as exemplified in the reaction scheme-1.

The reaction (d) by which a compound of formula (34) is produced from a compound of formula (33) is carried out by subjecting the compound of formula (33) to deesterification in the presence of a basic compound and an inert solvent.

Examples of the inert solvent to be used in the above reaction include water, alcohols such as methanol, ethanol, propanol, isopropanol, etc., and ethers such as diethyl ether, dioxane, tetrahydrofuran, etc. Examples of the basic compound include alkali metal hydroxides such as sodium hydroxide, potassium hydroxide, etc., alkali metal carbonates such as sodium carbonate, potassium carbonate, etc., and alkali metal alkoxides such as sodium methoxide, sodium ethoxide, potassium ethoxide, etc. This reaction is conducted at about 0° C. to 100° C., preferably about 0° C. to room temperature, and completed in about 1 to about 10 hours.

The reaction (e) which yields a compound of formula (35) and a compound of formula (36) from a compound of formula (34) is carried out by permitting an enzyme capable of cleaving an amido linkage to act upon the compound of formula (34). This reaction is carried out in substantially the same manner as the reaction of converting a compound of formula (10-b) to a compound of formula (10-c) in accordance with the reaction scheme-9. Therefore, reaction conditions (for example, the enzyme, solvent, pH of reaction system, reaction temperature, reaction time, etc.) for this reaction may be the same as those as exemplified in the reaction scheme-9. After this reaction, the compound from which the amido linkage has been cleaved enzymatically and the compound whose amido linkage remains intact are separated from each other to give a compound of formula (35) and a compound of formula (36), respectively.

The reaction step (f) by which a compound of formula (37) is produced from a compound of formula (35) is carried out by esterifying the compound of formula (35). This reaction is conducted in substantially the same manner as the esterification according to the reaction scheme-3 Therefore, reaction conditions (for example, the acid catalyst, solvent, reaction temperature, reaction time, etc.) for this reaction may be the same as those as exemplified in the reaction scheme-3.

The reaction (g) by which a compound of formula (38) is produced from a compound of formula (37) is carried out by reacting the compound of formula (37) with phenylacetic acid or a reactive derivative at the carboxy group thereof or with phthalic acid or a reactive derivative thereof.

The reaction between the compound of formula (37) and phenylacetic acid or a reactive derivative at the carboxy group thereof is conducted in substantially the same manner as the aforementioned reaction according to the reaction scheme-1. Therefore, reaction procedures (for example, the method using a condensing agent, the mixed acid anhydride method, the active ester method, etc.) and reaction conditions (for example, the basic compound, solvent, reaction temperature, reaction time, etc.) for this reaction may be the same as those as exemplified in the reaction scheme-1.

The reaction between the compound of formula (37) and phthalic acid or a reactive derivative thereof is generaly conducted in a solvent. The reactive derivative of the phthalic acid is exemplified by phthalic anhydride, N-(esterified carboxy)phthalimides such as N-methoxycarbonylphthalimide, N-ethoxycarbonylphthalimide, N-phenoxycarbonylphthalimide, etc., and 2-(esterified carboxy)benzoyl halides such as 2-methoxycarbonylbenzoyl chloride, 2-ethoxycarbonylbenzoyl chloride, 2-phenoxycarbonylbenzoyl chloride, etc.

When phthalic acid is used in the above reaction, the reaction can be conducted in substantially the same manner as the reaction according to the aforementioned reaction scheme-1. Therefore, reaction procedures (for example, the method using a condensing agent, the mixed acid anhydride method, the active ester method, etc.) and reaction conditions (for example, the solvent, reaction temperature, reaction time, etc.) for this reaction may be the same as those as exemplified in the reaction scheme-1.

When phthalic anhydride is used, the reaction is conducted in an inert solvent. Examples of the inert solvent include halogenated hydrocarbons such as dichloromethane, dichloroethane, chloroform, carbon tetrachloride, etc., ethers such as dimethyl ether, diethyl ether, dioxane, tetrahydrofuran, etc., aromatic hydrocarbons such as benzene, toluene, xylene, etc., and aliphatic hydrocarbons such as hexane, heptane, octane, etc. In this reaction, the phthalic anhydride and the compound of formula (37) are present in a molar ratio of 1:1 at least and preferably 1:1 to 2:1. The reaction is conducted at room temperature to 100° C., preferably at about 40° to about 80° C.

When an N-(esterified carboxy)phthalimide is employed, the reaction is conducted in an inert solvent in the presence of a basic compound.

Examples of the inert solvent to be used in this reaction include water, alcohols such as methanol, ethanol, propanol, etc., and ethers such as dimethyl ether, diethyl ether, dioxane, tetrahydrofuran, etc. Examples of the basic compound include inorganic bases such as alkali metal hydroxides, e.g. sodium hydroxide, potassium hydroxide, etc., and alkali metal carbonates or alkali metal hydrogen carbonates such as sodium carbonate, potassium carbonate, sodium hydrogen carbonate, etc., and organic bases such as triethylamine, pyridine, N,N-dimethylaniline, etc.

The N-(esterified carboxy)phthalimide and the compound of the formula (37) are present in a molar ratio of 1:1 at least and preferably 1:1 to 2:1. The basic compound and the compound of formula (37) are present in a molar ratio of 1:1 to 10:1. This reaction is conducted at 0° to 50° C., preferably at room temperature, and completed in about 1 to about 5 hours.

When a 2-(esterified carboxy)benzoyl halide is employed, the reaction is conducted in an inert solvent in the presence of a basic compound.

Examples of the inert solvent to be used in this reaction include halogenated hydrocarbons such as dichloromethane, dichloroethane, chloroform, carbon tetrachloride, etc., ethers such as dimethyl ether, diethyl ether, dioxane, tetrahydrofuran, etc., aromatic hydrocarbons such as benzene, toluene, xylene, etc., and aliphatic hydrocarbons such as hexane, heptane, octane, etc. Examples of the basic compound include organic bases such as alkali metal hydroxides, e.g. sodium hydroxide, potassium hydroxide, etc., and alkali metal carbonates and alkali metal hydrogen carbonates such as sodium carbonate, potassium carbonate, sodium hydrogen carbonate, etc., and organic bases such as triethylamine, pyridine, N,N-dimethylaniline, etc.

The 2-(esterified carboxy)benzoyl halide and the compound of formula (37) are present in a molar ratio of 1:1 at least and preferably 1:1 to 2:1. This reaction is conducted at 0° C. to room temperature and completed in about 1 to about 5 hours.

The order of the reactions (f) and (g) may be reversed. Thus, it is possible to first subject the compound of formula (35) to this reaction and, then, carry out the aforesaid esterification to give a compound of formula (38).

The reaction (h) by which a compound of formula (39) is produced from a compound of formula (38) is carried out by oxidizing the compound of formula (38) with ozone. This reaction is conducted in substantially the same manner as the reaction according to the aforementioned reaction scheme-11 step (b). Therefore, reaction conditions (for example, the solvent, reaction temperature, etc.) for this reaction may be the same as those as exemplified in the reaction scheme-11 step (b).

The reaction (i) by which a compound of formula (40) is produced from a compound of formula (39) is carried out by reducing the compound of formula (39). This reduction reaction is conducted in substantially the same manner as the aforementioned reaction scheme 11 step (c). Therefore, reaction procedures and conditions (for example, the reducing agent, solvent, reaction temperature, reaction time, etc.) for this reaction may be the same as those as exemplified in the reaction scheme-11 step (c).

The reaction (j) by which a compound of formula (41) is produced from a compound of formula (40) is conducted by reacting the compound of formula (40) with a sulfonic acid compound or a reactive derivative at the sulfo group thereof. This reaction is carried out in substantially the same manner as the reaction according to the reaction scheme-11 step (d). Therefore, reaction procedures and conditions (for example, the solvent, reaction time, etc.) for this reaction may be the same as those as exemplified in the reaction scheme-11 step (d).

The reaction (k) by which a compound of formula (42) is produced from a compound of formula (41) is carried out by reacting the compound of formula (41) with an acid. This reaction is conducted in substantially the same manner as the reaction according to the reaction scheme-11 step (e). Therefore, reaction procedures and conditions (for example, the acid, solvent, reaction temperature, reaction time, etc.) for this reaction may be the same as those as exemplified in the reaction scheme-11 step (e).

The reaction (l) by which a compound of formula (43) is produced from a compound of formula (36) is carried out by subjecting the compound of formula (36) to a reaction causing elimination of the phenylacetyl group. This reaction can be conducted in substantially the same manner as the reaction according to the reaction scheme-6b. Therefore, reaction procedures and conditions (for example, the acid compound, solvent, reaction temperature, reaction time, etc.) for this reaction may be the same as those as exemplified in the reaction scheme-6b.

The reaction by which a compound of formula (44) is produced from a compound of formula (43) is carried out by subjecting the compound of formula (43) to the aforementioned reactions (f), (g), (h), (i), (j) and (k), subsequently, and reference may be made to the description of reaction precedures and conditions given hereinbefore in connection with the respective reaction steps.

The compound of formula (21) which is a starting material for the aforementioned reaction scheme-11 step (a) includes novel compounds and these compounds can be produced by the following process.

Reaction scheme-13

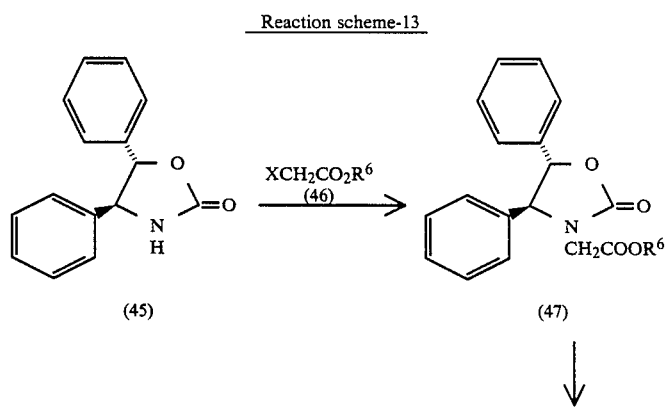

Reaction scheme-13

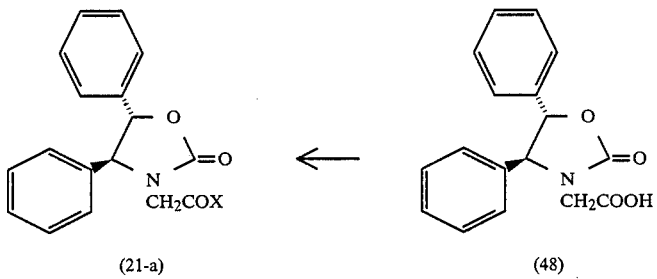

(21-a)                    (48)

wherein R⁶ and X have the same meanings as defined above.

Referring to the above reaction scheme, the reaction by which a compound of formula (47) is produced from a compound of formula (45) is carried out by reacting the compound of formula (45) with a compound of formula (46) in the presence of a solvent Examples of the solvent to be used in this reaction include aromatic hydrocarbons such as benzene, toluene, etc., ethers such as diethyl ether, tetrahydrofuran, etc., halogenated hydrocarbons such as methylene chloride, chloroform, dichloroethane, etc., alcohols such as methanol, ethanol, etc., acetonitrile and pyrrolidone. Ethers are preferred. The compound cf formula (46) and the compound of formula (45) are present in a molar ratio of 1:1 at least and preferably 1:1 to 1.2:1. This reaction is preferably conducted in the presence of a basic compound which is exemplified by the compounds mentioned in the reaction scheme-1 The basic compound and the compound of formula (45) are present in a molar ratio of 1:1 to 5:1 and preferably 1:1 to about 1.2:1. The reaction temperature may range from 0° C. to 100° C. and preferably from about 0° C. to room temperature. The reaction time is about 1 to about 10 hours, preferably about 1 to 5 hours.

The reaction by which a compound of formula (48) is produced from a compound of formula (47) obtained as above is carried out by subjecting the compound of formula (47) to deesterification. This reaction is carried out in substantially the same manner as the hydrolysis reaction using an acid or a base in the deesterification step according to the reaction scheme-6a. Therefore, reaction conditions (for example, the acid compound, basic compound, solvent, reaction temperature, reaction time, etc.) for this reaction may be the same as those as exemplified in the reaction scheme-6a.

The reaction by which a compound of formula (21-a) is produced form a compound of formula (48) is carried out by reacting the compound of formula (48) with a halogenating agent in the presence or absence of a solvent to give an acid halide represented by the formula (21-a). This reaction can be conducted by any of the known methods of converting a carboxy group to a halocarbonyl group. Examples of the halogenating agent include thionyl chloride, phosphorus trichloride, phosphorus tribromide, phosphorus pentachloride, triphenylphosphine dibromide, triphenylphosphine dichloride, oxalyl chloride, benzoyl chloride, etc. The halogenating agent and the compound of formula (48) are present in a molar ration of 1:1 at least and preferably the halogenating agent is used an excess. The reaction is generally conducted in an inert solvent and examples of the solvent include aromatic hydrocarbons such as benzene, toluene, etc., and halogenated hydrocarbons such as methylene chloride, chloroform, dichloroethane, carbon tetrachloride, etc. When the halogenating agent is a liquid, it can be used as the solvent as well. The reaction temperature may range from −20° C. to 150° C. and preferably from about 0° C. to about 100° C., and the reaction completed in about 1 to about 20 hours, preferably in about 1 to about 5 hours.

Among the compounds of general formula (1) according to the present invention, compounds having basic groups can be easily converted to salts by permitting a pharmacentically acceptable acid to act thereon, while compounds having acidic groups can be easily converted to salts by reacting them with a pharmacentically acceptable basic compound. The acid is exemplified by inorganic acids such as hydrochloric acid, sulfuric acid, phosphoric acid, hydrobromic acid, etc., and organic acids such as oxalic acid, maleic acid, fumaric acid, malic acid, tartaric acid, citric acid, benzoic acid, acetic acid, p-toluenesulfonic acid, ethanesulfonic acid, etc. The basic compound is exemplified by metal hydroxides such as sodium hydroxide, potassium hydroxide, calcium hydroxide, etc., and alkali metal carbonates or alkali metal hydrogen carbonates such as sodium carbonate, sodium hydrogen carbonate, potassium hydrogen carbonate, etc. The salts of the compound of the invention naturally include inner salts and quaternally ammonium salts as well. The quaternary ammonium salts can be obtained by reacting the corresponding compound with the abovementioned halide compound, such as the lower alkyl halide, lower alkenyl halide, phenyl-substituted lower alkoxycarbonyl-lower alkyl halide, carboxy-lower alkyl halide, sulfo-lower alkyl halide, sulfamoyl-lower alkyl halide, lower alkylthio-lower alkyl halide, hydroxylower alkyl halide, cyanolower alkyl halide, carbamoyllower alkyl halide, etc., in the presence of an inert solvent. Examples of the inert solvent include halogenated hydrocarbons such as dichloromethane, dichloroethane, chloroform, carbon tetrachloride, etc., aromatic hydrocarbons such as benzene, toluene, xylene, etc., and ethers such as diethyl ether, tetrahydrofuran, dioxane, etc. The reaction is carried out at room temperature to about 100° C., preferably at about 50 to about 80° C. and is completed in about 2 to about 8 hours. The above-mentioned halide compound is preferably used in an amount of about 1 to 1.5 moles per mole of the corresponding compound.

After the reaction, the halide ion may be eliminated to give an inner salt by purification by column chromatography using Diaion HP-20 (Mitsubishi Chemical Industies), Amberlite XAD-2 (Rohm and Haas), etc.

The thus-produced compound of this invention can be isolated and purified without difficulty by conventional means of separation. Employable as the conventional means of separation are, for instance, solvent extraction, dilution, recrystallization, column chromatography and preparative thin layer chromatography.

The compound of the invention as represented by general formula (1) naturally includes optical isomers as well as syn and anti isomers. These isomers can be separated from each other by a conventional resolution method, for example by using an optical resolution agent or an enzyme.

The using the compounds of this invention as therapeutic agents, these compounds can be formulated into pharmaceutical compositions together with ordinary pharmaceutically acceptable carriers. Suitable carriers which can be used are, for example, solvents, wetting agents, disintegrants, surface active agents and lubricants which are usually employed to prepare such drugs depending on the type of dosage form.

Various dosage forms of the therapeutic agents can be selected according to the purpose of the therapy. Typical dosage forms which can be used are tablets, pills, powders, liquid preparations, suspensions, emulsions, granules, capsules, suppositories, and injectable preparations (solutions, suspensions, etc.).

In molding a pharmaceutical composition into a tablet form, a wide range of carriers known in the art can be used. Examples of suitable carriers include excipients such as lactose, white sugar, sodium chloride, glucose, urea, starch, calcium carbonate, kaolin, crystalline cellulose and silicic acid, binders such as water, ethanol, propanol, simple syrup, glucose solution, starch solution, gelatin solution, carboxymethyl cellulose, shellac, methyl cellulose, potassium phosphate and polyvinyl pyrrolidone, disintegrants such as dired starch, sodium alginate, agar powder, laminaria powder, sodium hydrogencarbonate, calcium carbonate, polyoxyethylenesorbitan fatty acid esters, sodium laurylsulfate, stearic acid monoglyceride, starch, and lactose, disintegration inhibitors such as white sugar, stearic acid glyceryl ester, cacao butter and hydrogenated oils, absorption promotors such as quaternary ammonium bases and sodium laurylsulfate, humectants such as glycerol and starch, adsorbents such as starch, lactose, kaolin, bentonite and colloidal silicic acid, and lubricants such as purified talc, stearic acid salts, boric acid powder, polyethylene glycol.

The tablets, if desired, can be coated, and made into sugar-coated tablets, gelatin-coated tablets, enteric-coated tablets, film-coated tablets, or tablets comprising two or more layers.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, esters of higher alcohols, gelatin, and semisynthetic glycerides.

When the pharmaceutical composition is formulated into an injectable preparation, the resulting solution and suspension are preferably sterilized, and are isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and polyoxyethylenesorbitan fatty acid esters. Sodium chloride, glucose or glycerol may be incorporated into a pharmaceutical composition, in an amount sufficient to prepare isotonic solutions. The pharmaceutical composition may further contain ordinary dissolving aids, buffers, painalleviating agents, and preservatives, and optionally coloring agents, perfumes, flavors, sweeteners, and other drugs.

In molding a pharmaceutical composition into an ointment form, a cream form and a gel form, a wide range of diluents known in the arts can be used. Examples of suitable diluents include white petrolatum, paraffin, glycerin, cellulose derivatives, polyethylene glycol, silicones, and bentonite.

The amount of the compound of the formula (1) and the pharmaceutically acceptable salts thereof of this invention as an active ingredient to be incorporated into a pharmaceutical composition is not particularly limited, and can vary over a wide range. A suitable therapeutically effective amount of the compound of the general formula (1) and the pharmaceutically acceptable salts thereof of this invention is usually about 1 to about 70% by weight, preferably 1 to 30% by weight, based on the entire composition.

The administration method of the pharmaceutical composition according to the invention is not particularly limited and can be adequately selected according to the form of the preparation, age and sex of the patient, and symptom of disease. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the injectable preparations can be singly administered intramuscularly, intracutaneously, subcutaneously, or intraperitoneally. The suppository is administered intrarectally.

The dosage of the pharmaceutical composition is suitably selected according to the purpose of use, age and sex of the patient, and the symptoms of disease, etc. Usually, a preferred dosage of the compound of this invention is about 1 to 100 mg/kg, preferably 5 to 20 mg/kg weight per day, and the pharmaceutical composition may be administered 2 to 4 times per day.

Hereinafter, this invention will be described in greater detail with reference to Reference Examples, Examples and Pharmaceutical Examples.

EXAMPLES

Reference Example 1

Benzyl 7-azido-3-[(1,4,5,6-tetrahydro-4-methyl-5,6-dioxo-1,2,4-triazin-3-yl)thiomethyl]-$\Delta^3$-O-2isocephem-4-carboxylate In methylene chloride was dissolved benzyl 7-azido-3-methanesulfonyloxymethyl-$\Delta^3$-O-2-isocephem-4-carboxylate (1.23 g, 3 mmol), followed by a (1,4,5,6-tetrahydro-4-methyl-5,6-dioxo-1,2,4,-triazin3-yl)thiol (0.57 g, 3.6 mmol). The solution was cooled to 0° to 2° C. and triethylamine (0.5 ml, 3.6 mmol) was added dropwise. The reaction was conducted at the same temperature for 30 minutes and, then, at room temperature for 3 hours. Thereafter, the reaction mixture was washed twice with water and once with a saturated solution of sodium chloride in water, dried over anhydrous sodium sulfate, and filtered. The filtrate was concentrated under reduced pressure and the residue was purified by silica gel chromatogrpahy to give the title compound (0.95 g).

NMR (CDCl$_3$) δ: 3.41 (3H, s), 3.65-4.16 (2H, m), 4.17 (1H, d), 4.46 (1H, d), 5.22 (1H, d), 5.26 (2H, s), 7.30-7.45 (5H, m).

Reference Example 2

Benzyl 7-amino-3-[(1,4,5,6-tetrahydro-4-methyl5,6-dioxo-1,2,4-triazin-3-yl)thiomethyl]-Δ$^3$-O-2- isocephem-4-carboxylate Benzyl 7-azido-3-[(1,4,5,6-tetrahydro-4-methyl5,6-dioxo-1,2,4-triazin-3-yl)thiomethyl]-Δ$^4$-O-2- isocephem-4-carboxylate (400 mg, 0.85 mmol) was dissolved in dichloromethane (80 ml) and after addition of triethylamine (0.12 ml, 0.85 mmol), hydrogen sulfide was introduced to saturation at 0 to 2° C. The reaction was continued for 1 hour after the saturation. Thereafter, the reaction mixture was washed twice with a 5% aqueous solution of sodium hydrogen carbonate and once with a saturated solution of sodium chloride in water, dried over anhydrous sodium sulfate, and filtered. The filtrate was concentrated under reduced pressure to give the title compound (370 mg).

NMR (DMSO-d6-CDCl$_3$) δ: 3.39 (3H, s), 3.55-4.17 (2H, m), 4.20 (1H, d), 4.41 (1H, d), 4.45-4.72 (1H, m), 4.79 (1H, d), 5.23 (2H, s), 7.20-7.48 (5H, m).

Reference Example 3

Benzhydryl 7-amino-3-[(1,2,3-thiadiazol-5-yl) thiomethyl]-Δ$^3$-O-2-isocephem-4-carboxylate In a manner analogous to Reference Example 2, the title compound was produced from the corresponding starting compound.

NMR (CDCl$_3$)δ: 3.53-4.01 (2H, m), 4.20 (1H, d, J=15 Hz), 4.40 (1H, d, J=15 Hz), 4.65 (1H, q, J=3 Hz, 10 Hz), 4.86 (1H, d, J=5 Hz), 6.90 (1H, s), 7.14–7.70 (10H, m), 8.51 (1H, s)

Reference Example 4

7-Azido-3-[(1,2,3-thiadiazol-5-yl)thiomethyl]-Δ$^3$-O-2-isocephem-4-carboxlic acid Benzyl 7-azido-3-[(1,2,3-thiadiazol-5-yl) thiomethyl]-Δ$^3$-O-2-isocephem-4-carboxylate (5.17 g, 12 mmol) was dissolved in methylene chloride (360 ml), followed by addition of nitromethane (60 ml). A solution of anhydrous aluminum chloride (8.00 g, 60 mmol) in nitromethane (60 ml) was added dropwise at room temperature and the reaction was continued for 1 hour after completion of the dropwise addition. The reaction mixture was then poured into ice-water, whereupon small amounts of crystals separated out. The crystals were dissolved by addition of tetrahydrofuran. The organic layer was separated and the water layer was extracted once with tetrahydrofuran-ethyl acetate (1:1) mixture. The organic layers were combined, washed three times with saturated aqueous sodium chloride, dried over anhydrous sodium sulfate and filtered. The filtrate was concentrated under reduced pressure to give crude crystals, which were washed with methylene chloride to obtain the title compound (3.60 g).

Light brown powder
mp: 148° C. (discoloration),183° C. (decomposition).
NMR (DMSO-d6) δ: 3.73-4.11 (2H, m), 4.41 (2H, s), 4.64–4.92 (1H, m), 5.76 (1H, d, J=5 Hz), 8.93 (1H, s).

Reference Example 5

(6S,7S)-7-Azido-3-[(1,3,4-thiadiazol-2-yl)thiomethyl]-Δ$^3$-O-2-isocephem-4-carboxylic acid In a manner analogous to Reference Example 4, the title compound was produced from the corresponding starting compound.

NMR (DMSO-d6) δ: 3.75–3.90 (2H, m), 4.53 (2H, dd), 4.74 (1H, d), 5.69 (1H, d), 9.49 (1H, s).

Reference Example 6

(6S,7S)-7-Azido-3-[(1,2,3-thiadiazol-5-yl)thiomethyl]-Δ$^3$-O-2-isocephem-4-carboxylic acid In a manner analogous to Reference Example 4, the title compound was produced from the corresponding starting compound.

NMR (DMSO-d6) δ: 3.75–3.90 (2H, m), 4.36 (2H, s ), 4.74 (1H, d), 5.71 (1H, d), 8.85 (1H, s).

Reference Example 7

Benzhydryl 7-azido-3-[(1,2,3-thiadiazol-5-yl)thiomethyl]-Δ$^3$-O-2-isocephem-4-carboxylate 7-Azido-3-[(1,2,3-thiadiazol-5-yl)thiomethyl]-Δ$^3$-O-2-isocephem-4-carboxylic acid (3.60 g, 10.6 mmol) was suspended in a mixture of methanol (50 ml) and tetrahydrofuran (50 ml). Then, diphenyldiazomethane (4.12 g, 21.2 mmol) was added to the above suspension at room temperature. The reaction was conducted for 30 minutes and the reaction mixture was concentrated under reduced pressure. A small amount of methanol was added to the residue to give crystals, which were collected by filtration to obtain the title compound (4.40 g) as pale yellow powder.

mp: 203° C.-205° C. (decomposition).
NMR (DMSO-d6) δ: 3.77-4.15 (2H, m), 4.30 (1H, d, J=15 Hz), 4.48 (1H, d, J=15 Hz), 4.65-4.96 (1H, m ), 5.85 (1H, d, J=5 Hz), 6.86 (1H, s), 7.14-7.73 (10H, m), 8.88 (1H, s).

Reference Example 8

Benzhydryl (6S,7S)-7-azido-3-[(1,2,3-thiadiazol-5yl)thiomethyl]-Δ$^3$-O-2-isocephem-4-carboxylate In a manner analogous to Reference Example 7, the title compound was produced from the corresponding starting compound.

mp: 190° C. (discoloration), 194° C. (decomposition).
[α]$_D^{22}$ = −126° (C=1, in chloroform)
NMR (CDCl$_3$) δ: 3.78 (1H, m), 3.98 (1H, dd, J=11.3 Hz, 9.5 Hz), 4.16 (1H, d, J=13.8 Hz), 4.39 (1H, d, J=13.8 Hz), 4.59 (1H, dd, J=11.3 Hz, 4.0 Hz), 5.25 (1H, d, J=5.2 Hz), 6.86 (1H, s), 7.3–7.6 (10H, m), 8.49 (1H, s).

Reference Example 9

Benzhydryl (6S,7S)-7-azido-3-[(1,3,4-thiadiazol-5-yl)thiomethyl]-Δ$^3$-O-2-isocephem-4-carboxylate In a manner analogous to Reference Example 7, the title compound was produced from the corresponding starting compound.

Yellow powder
mp: 193° C.-194° C.
[α]$_D^{20}$= −128° (C=1, in chloroform).

NMR (CDCl$_3$) δ: 3.78 (1H, m), 3.98 (1H, dd, J=11.3 Hz, 9.5 Hz), 4.48 (1H, d, J=13.8 Hz), 4.59 (1H, dd, J=11.3 Hz, 4.00 Hz), 4.76 (1H, d, J=13.8 Hz), 5.25 (1H, d, J=5.2 Hz), 6.88 (1H, s), 7.28 (2H, tt, J=8.5 Hz, 1.8 Hz), 7.34 (2H, t, J=8.5 Hz), 7.35 (2H, t, J=8.5 Hz), 7.42 (2H, dd, J=8.5 Hz, 1.8 Hz), 7.56 (1H, dd, J=8.5 Hz, 1.8 Hz), 8.95 (1H, s).

Reference Example 10

Benzyl 7-azido-3-chloromethyl-Δ$^3$-O-2-isocephem-4-carboxylate

Benzyl 7-azido-3-hydroxymethyl-Δ$^3$-O-2-isocephem-4carboxylate (330 mg, 1 mmol) was dissolved in methylene chloride (10 ml). Under ice-cooling, triethylamine (0.28 ml, 2 mmol) was added to the above solution, followed by dropwise addition of thionyl chloride (0.11 ml, 1.5 mmol). After the reaction was conducted for 15 minutes, ice-water was added thereto. The methylene chloride layer was taken, washed twice with ice-water and then once with saturated aqueous sodium chloride, dried over anhydrous sodium sulfate and filtered. The filtrate was concentrated under reduced pressure and the residue was purified by silica gel column chromatography [eluent: methylene chloride-ethyl acetate (20:1)]to give the title compound (300 mg).

Light yellow powder
mp: 57°-58° C.
NMR (CDCl$_3$) δ: 3.64–4.12 (2H, m), 4.64 (1H, q, J=3 Hz, 10 Hz), 4.93 (1H, d, J=14 Hz), 5.13 (1H, d, J=14 Hz), 5.24 (1H, d, J=5 Hz), 5.30 (2H, s), 7.20–7.62 (5H, m).

Reference Example 11

Benzyl 7-azido-3-[(1,2,3-thiadiazol-5-yl)thiomethyl ]-Δ$^3$-O-2-isocephem-4-carboxylate Benzyl 7-azido-3-hydroxymethyl-Δ$^3$-O-2-isocephem4-carboxylate (6.61 g, 20 mmol) was dissolved in methylene chloride (100 ml). Under ice-cooling, triethylamine (5.59 ml, 40 mmol) was added to the above solution, followed by dropwise addition of thionyl chloride (2.13 ml, 30 mmol). After the reaction was conducted for 20 minutes, ice-water was added thereto. The methylene chloride layer was taken, washed twice with water and then once with saturated aqueous sodium chloride, dried over anhydrous sodium sulfate and filtered. The filtrate was concentrated under reduced pressure to give crude benzyl 7-azido-3-chloromethyl-Δ$^3$-O-2-isocephem-4-carboxylate, which was dissolved in dimethylformamide (100 ml), followed by addition of sodium 1,2,3-thiadiazol-5-thiolate (20% hydrate) (5.26 g, 30 mmol). The reaction was conducted for 1 hour and 30 minutes. Thereafter, the reaction mixture was concentrated under reduced pressure. Ethyl acetate was added to the residue for dissolution and the solution was washed three times with water and then once with saturated aqueous sodium chloride and dried over anhydrous sodium sulfate. After filtration, the filtrate was concentrated under reduced pressure, and the residue was purified by silica gel column chromatography [eluent: methylene chloride-ethyl acetate (10:1)]to give the title compound (4.02 g).

Benzyl 7-azido-3-hydroxymethyl-Δ$^3$-O-2-isocephem-4carboxylate (3.41 g) was also recovered.

Light yellow powder
mp: 119–120° C.
NMR (CDCl$_3$) δ: 3.60–4.12 (2H, m), 4.17 (1H, d, J=13 Hz), 4.34 (1H, d, J=13 Hz), 4.61 (1H, q, J=3 Hz, 10 Hz), 5.19 (1H, d, J=9 Hz), 5.25 (2H, s), 7.23–7.54 (5H, m), 8.52 (1H, s).

Reference Example 12

(3S,4S)-N-(α-Benzyloxycarbonyl-β-trifluoromethanesulfonyloxy-α,β-propenyl)-3-azido-4-methanesulfonyloxymethyl-2-azetidinone (3S,4S)-N-(α-Benzyloxycarbonyl-β-hydroxy-α,β-propenyl)-3-azido-4-methanesulfonyloxymethyl-2azetidinone (26.3 g, 64 mmol) was dissolved in dry methyele chloride (300 ml). The solution was cooled to −30° C. in a dry ice-acetone bath, followed by addition of anhydrous trifluoromethanesulfonic acid (21.7 g, 77 mmol). A solution of triethylamine (12.5 ml, 90 mmol) in dry methylene chloride (110 ml) was added dropwise to the above-obtained solution over 40 minutes. After completion of dropwise addition, the mixture was stirred at the same temperature for 20 minutes and, after addition of a 10-fold dilution of conc. hydrochloric acid, the mixture was washed twice with water and the organic layer was dried over anhydrous magnesium sulfate. The solvent was then distilled off under reduced pressure to give the title compound (31.3 g) as dark red oil.

[α]$_D^{20}$= −52.9° (C=3.48, in chloroform).
NMR (CDCl$_3$) δ: 2.27 (3H, s), 2.86 (3H, s), 4.18–4.64 (3H, m), 4.95 (1H, d, J=5 Hz), 5.27 (2H, s), 7.38 (5H, s).

Reference Example 13

Benzyl (6S,7S)-7-azido-3-hydroxymethyl-Δ$^3$-O-2-isocephem-4-carboxylate (A) (3S,4S)-N-(α-benzyloxycarbonyl-β-trifluoromethanesulfonyl-α, β-propenyl)-3-azido-4-methanesulfonyloxymethyl-2-azetidinone (30.3 g, 56 mmol) was dissolved in methylene chloride (300 ml) and the solution was cooled to 0° C. To the solution was added dropwise a solution of triethylamine (9.37 ml, 67 mmol) in methylene chloride (94 ml). After completion of dropwise addition, the mixture was stirred at room temperature for 40 minutes. Thereafter, a 0.1M methylene chloride solution of iodine (672 ml, 67 mmol) was added dropwise over 1.5 hours. After 1 hour of stirring, the reaction mixture was washed twice with water and dried over anhydrous magnesium sulfate, followed by removal of the solvent, whereby there was obtained crude (3S,4S)-N-(α-benzyloxycarbonyl-βγ-diiodo-α,β-propenyl)-3-azido-4-methanesulfonyloxymethyl-2-azetidinone (42.0 g).

The thus-obtained crude product was directly subjected to the next reaction procedure without purification.

(B) The crude iodide compound (42.0 g) obtained by the above procedure was dissolved in dimethylformamide (600 ml), followed by addition of water (0.6 ml). Thereafter, potassium formate (18.8 g, 224 mmol) was added under ice-cooling. The mixture was stirred at room temperature for 12 hours, poured into ice-water (1 l) and extracted five times with methylene chloride. The extract was washed four times with water and dried over anhydrous magnesium sulfate. The solvent was then removed to give crude benzyl (6S,7S)-7-azido-3-formyloxymethyl-Δ$^3$-O-2-isocephem-4-carboxylate (24.7 g) as brown oil.

(C) The crude formate compound (24.7 g) obtained by the above procedure was dissolved in a mixture of acetone (200 ml) and water (100 ml) and, after addition of 12M hydrochloric acid (12 ml), the mixture was warmed to 28° C. and stirred at the same temperature for 6 hours. The reaction mixture was poured into water and extracted five times with methylene chloride and the extract was washed three times with water and dried over anhydrous magnesium sulfate. The solvent was then removed under reduced pressure to give crude benzyl (6S,7S)-7-azido-3-hydroxymethyl-$\Delta^3$-O-2-isocephem-4-carboxylate, which was purified by silica gel column chromatography [eluent: methylene chloride-methyl acetate (15:1)] to obtain the title compound (31.5 g) as orange oil.

$[\alpha]_D^{22} = -29°$ (C=0.62, in chloroform).

NMR (CDCl$_3$) δ: 3.60-3.90 (1H, m), 3.94 (1H, d, J=10 Hz), 4.27 (1H, d, J=14 Hz), 4.51 (1H, d, J=14 Hz), 4.61 (1H, dd, J=10 Hz, 3 Hz), 5.20 (1H, d, J=5 Hz), 5.29 (2H, s), 7.00-7.73 (5H, m).

Reference Example 14

Benzyl (6S,7S)-7-azido-3-[(1,3,4-thiadiazol-2-yl)thiomethyl]-$\Delta^3$-O-2-isocephem-4-carboxylate (A) Benzyl (6S,7S)-7-azido-3-hydroxymethyl-$\Delta^3$-O-2-isocephem-4-carboxylate (3.15 g, 9.54 mmol) was dissolved in methylene chloride (100 ml) and the solution was cooled in an ice-methanol bath. To the solution was added triethylamine (2.13 ml, 15.6 mmol), followed by dropwise addition of methanesulfonyl chloride (0.96 ml, 12.40 mmol). After 40 minutes of stirring, the reaction mixture was washed twice with water and once with saturated aqueous sodium chloride. After drying over anhydrous sodium sulfate, the solvent was removed to give crude benzyl (6S,7S)-7-azido-3-methanesulfonyloxymethyl-$\Delta^3$-O-2-isocephem-4-carboxylate (4.82 g), which was subjected directly to the next reaction procedure.

(B) The crude mesylate compound (4.82 g) obtained by the above procedure was dissolved methylene chloride (100 ml) and, followed by addition of 1,3,4-thiadiazole-2-thiol (1.35 g, 11.45 mmol) and triethylamine (1.6 ml, 11.45 mmol). The mixture was stirred at room temperature for 1.5 hours and washed with a 5% aqueous solution of sodium hydrogen carbonate and then twice with water. The solvent was then removed under reduced pressure to give a red-brown oily substance, which was purified by silica gel column chromatography [eluent: ethyl acetate-hexane (1:1)] to give the title compound (3.03 g) as light brown powder.

$[\alpha]_D^{20} = -147.68°$ (C=1, in chloroform).

NMR (CDCl$_3$) δ: 3.53-4.08 (2H, m), 4.40 (1H, d, J=14 Hz), 4.55 (1H, dd, J=11 Hz, 3 Hz), 4.77 (1H, d, J=14 Hz), 5.17 (1H, d, J=5 Hz), 5.24 (2H, s), 6.88-7.53 (5H, m), 8.92 (1H, s).

Reference Example 15

Benzyl (6S,7S)-7-azido-3-[(1,2,3-thiadiazol-5-yl)thiomethyl]-$\Delta^3$-O-2-isocephem-4-carboxylate (A) Benzyl (6S,7S)-7-azido-3-hydroxymethyl-$\Delta^3$-O-2-isocephem-4-carboxylate (3.32 g, 10.05 mmol) was dissolved in methylene chloride (100 ml) and, under ice-cooling, triethylamine (2.81 ml, 20.10 mmol) was added, followed by dropwise addition of thionyl chloride (1.07 ml, 15.08 mmol). The reaction was conducted for 20 minutes, after which ice-water was added. The methylene chloride layer was taken, washed twice with water and once with saturated aqueous sodium chloride and dried over anhydrous sodium sulfate. The solvent was then removed to give crude benzyl (6S,7S)-7-azido-3-chloromethyl-$\Delta^3$-O-2-isocephem-4-carboxylate.

(B) The crude chloride compound obtained by the above procedure was dissolved in dimethylformamide (50 ml), followed by addition of sodium 1,2,3-thiadiazole-5-thiolate (20% hydrate) (2.64 g, 15.08 mmol). The reaction was conducted for 1 hour and 30 minutes and the reaction mixture was concentrated under reduced pressure. Ethyl acetate was added for dissolution of the residue and the solution was washed three times with water and once with saturated aqueous sodium chloride and dried over anhydrous sodium sulfate. The solvent was then removed under reduced pressure and the residue was purified by silica gel column chromatography [eluent: methylene chloride-ethyl acetate (10:1)] to give the title compound (1.27 g) as light yellow powder.

Benzyl (6S,7S)-7-azido-3-hydroxymethyl-$\Delta^3$-O-2-carboxylate (1.13 g) was also recovered.

Pale yellow powder
mp: 114.5°-115° C.
$[\alpha]_D^{21} = -133°$ (C=1, in chloroform).

NMR (CDCl$_3$) δ: 3.60-4.12 (2H, m), 4.17 (1H, d, J=13 Hz), 4.34 (1H, d, J=13 Hz), 4.61 (1H, q, J=3 Hz, 10 Hz), 5.19 (1H, d, J=9 Hz), 5.25 (2H, s), 7.23-7.54 (5H, m), 8.52 (1H, s).

Reference Example 16

7-Azido-3-[(1,3,4-thiadiazol-2-yl)thiomethyl]-$\Delta^3$-O-2-isocephem-4-carboxylic acid Benzyl 7-azido-3-acetoxymethyl-$\Delta^3$-O-2-isocephem-4-carboxylate (16.76 g, 45 mmol) was dissolved in methylene chloride (230 ml) under a nitrogen gas stream, followed by addition of iodotrimethylsilane (14.08 ml, 99 mmol) at room temperature. The reaction was conducted for 2 hours. Thereafter, 2-mercapto- 1,3,4-thiadiazole (11.7 g, 99 mmol) and triethylamine (13.9 ml, 0.1 mol) in methylene chloride (50 ml) were added dropwise. After 1 hour of stirring, saturated aqueous sodium hydrogen carbonate was added and the mixture was extracted. The aqueous layer was adjusted to pH 1 with a 10-fold dilution of concentrated hydrochloric acid to give a precipitate, which was collected by filtration, washed with water and dried to give the title compound (11.6 g).

Light orange powder
mp: 178°-182° C. (decomposition).

Reference Example 17

7-Phenylacetamido-3-[(1,3,4-thiadiazol-2-yl)thiomethyl]-$\Delta^3$-O-2-isocephem-4-carboxylic acid 7-Azido-3-(1,3,4-thiadiazol-2-yl)thiomethyl-$\Delta^3$-O-2-isocephem-4-carboxylic acid (10.7 g, 32 mmol) was suspended in methylene chloride (320 ml), followed by addition of triethylamine (8.9 ml, 64 mmol) to give a homogeneous solution. Then, hydrogen sulfide gas was bubbled into the solution under ice-cooling. The reaction was conducted for 1.5 hours, after which the reaction mixture was concentrated under reduced pressure. To the crude product were added water (100 ml) and acetone (100 ml) and the mixture was cooled to −7° C. Thereafter, a solution of phenylacetyl chloride (8.2 ml, 64 mmol) in acetone (30 ml) was added dropwise, during which time the reaction was conducted with the pH 8 to 7.5 with 1N aqueous sodium hydroxide. After completion of dropwise addition, the reaction temperature was increased to 0° C. over 1 hour. The reaction mixture was washed with ethyl acetate (200 ml). The aqueous layer was separated, adjusted to pH 1 with a 10-fold dilution of concentrated hydrochloric acid and extracted three times with ethyl acetatetetrahydrofuran (1:1) mixture (300 ml). The organic layer was washed with saturated aqueous sodium chloride, dried over anhydrous magnesium sulfate, filtered and concentrated under reduced pressure. Diethyl ether was added to the residue to give the title compound as powder (13.18 g).

Pale yellow powder mp: 112° C. (discoloration), 158° C. (decomposition).

Reference Example 18

(6S,7S)-7-Amino-3-[(1,3,4-thiadiazol-2-yl)thiomethyl]-$\Delta^3$-O-2-isocephem-4-carboxylic acid 7-Phenylacetamido-3-(1,3,4-thiadiazol-2-yl)thiomethyl-$\Delta^3$-O-2-isocephem-4-carboxylic acid (11.24 g, 26 mmol) was dissolved in a solution of sodium hydrogen carbonate (2.18 g, 26 mmol) in water (50 ml). Thereafter, penicillin G amidase (5 g, Boehringer-Mannheim) was added and the mixture was stirred. The pH was adjusted to 7.5-8 with dilute aqueous ammonia as it decreased as the reaction proceeded. After 1 hour of reaction, the reaction mixture was filtered and the filtrate was taken, adjusted to pH 1.9 with phosphoric acid and extracted twice with ethyl acetate-tetrahydrofuran (1:1) mixture (300 ml). The aqueous layer was adjusted to pH 3.8 with concentrated aqueous ammonia and then ice-cooled. The precipitate was filtered off, washed with water and dried under reduced pressure to give the title compound (2.42 g).

Pale yellow powder mp: 140° C. (discoloration).

$[\alpha]_D^{20} = -51°$ (C=1, dimethyl sulfoxide).

Reference Example 19

Ethyl (4,5-cis-diphenyl-2-oxo-3-oxazolidinyl)acetate 4,5-cis-Diphenyl-2-oxooxazolidine (48.6 g, 203 mmol) was suspended in tetrahydrofuran (330 ml) and, under ice-cooling, sodium hydride (8.12 g, 203 mmol) was added carefully. Thereafter, ethyl bromoacetate (33.9 g, 203 mmol) was added dropwise. The mixture was stirred at room temperature for 4 hours, poured into a mixture of a 10-fold dilution of conc. hydrochloric acid (60 ml) and ice-water (50 ml) and extracted twice with ethyl acetate. The extract was washed with saturated aqueous sodium chloride and dried over sodium sulfate. After filtration, the filtrate was concentrated and the residue was purified by silica gel column chromatography [eluent: n-hexane-ethyl acetate (4:1)] to give the title compound (40.6 g) as yellow oil.

Mass spectrum: m/e=326.

NMR (CDCl$_3$) δ: 1.26 (3H, t), 3.4 (1H, d), 4.29 (2H, q), 4.48 (1H, d), 5.34 (1H, d), 5.92 (1H, d), 6.80-7.20 (10H, m).

Reference Example 20

(4,5-cis-Diphenyl-2-oxo-3-oxazolidinyl)acetic acid

Ethyl (4,5-cis-diphenyl-2-oxo-3-oxazolidinyl)acetate (40.6 g, 125 mmol) was dissolved in tetrahydrofuran (100 ml) and a solution of sodium hydroxide (6 g, 150 mmol) in water (40 ml) was added thereto. The mixture was stirred at room temperature for 15 minutes. To the homogeneous solution was added water (150 ml) and the mixture was washed twice with diisopropyl ether (20 ml). The aqueous layer was adjusted to pH 2 with a 10-fold dilution of concentrated hydrochloric acid and extracted with ethyl acetate. The extract was dried over magnesium sulfate and filtered. The filtrate was concentratred and the residue was recrystallized from methylenechloride-n-hexane mixture to give the title compound (29.1 g) as white crystals.

mp 161°-163° C.

NMR (CDCl$_3$) δ: 3.49 (1H, d), 4.56 (1H, d), 5.35 (1H, d), 5.95 (1H, d), 7.07 (10H, br), 8.01 (1H, br).

Reference Example 21

(4,5-cis-Diphenyl-2-oxo-3-oxazolidinyl)acetyl chloride

A suspension composed of (4,5-cis-diphenyl-2-oxo-3-oxazolidinyl)acetic acid (29.1 g, 97.9 mmol), oxalyl chloride (18.6 g, 147 mmol) and benzene (120 ml) was refluxed for 2 hours. When the suspension became homogeneous, the solvent was distilled off. By the above procedure there was obtained the title compound (30.9 g) as light brown oil.

Mass spectrum: m/e=253 (M+−63).

NMR (CDCl$_3$) δ: 3.81 (1H, d), 4.88 (1H, d), 5.25 (1H, d), 5.94 (1H, d), 6.70-7.20 (10H, m).

Reference Example 22

3,4-cis-3-(4,5-cis-Diphenyl-2-oxo-3-oxazolidinyl)-1-(2,2-ethyleneketal-1-ethoxycarbonylpropyl)-4-styrylaztidin-2-one Ethyl 2-[(3-phenylallylidene)amino]-3,3-ethylenedioxybutyrate (35.6 g, 117 mmol) was dissolved in methylene chloride (250 ml), followed by addition of triethylamine (15.7 g, 155 mmol) at −50° C. To the solution was added dropwise a solution of (4,5-diphenyl-2-oxo-3-oxazolidinyl)acetyl chloride (30.9 g, 97.9 mmol) in methylene chloride (80 ml) at −60° C. and the mixture was stirred at −50° C. for 2 hours. The reaction mixture was washed with water, a 10-fold dilution of concentrated hydrochloric acid and saturated aqueous sodium chloride in that order, dried over magnesium sulfate and filtered. The filtrate was concentrated and the residue was treated with diethyl ether to give light brown crystals, which were recrystallized from methylene chloride-n-hexane mixture to obtain a diastereomer mixture of the title compound (32.2 g) as white crystals.

mp: 196°-198° C.

NMR (CDCl$_3$) δ: 1.20 (3H, t), 1.37 (3H, t), 1.45 (3H, s), 1.48 (3H, s), 3.78 (4H, s), 3.92 (4H, s), 4.07 (4H, q), 4.16 (4H, q), 4.40-4.90 (6H, m), 5.02 (1H, d), 5.74 (1H, d), 6.27-6.55 (4H, m), 6.97 (10H, br), 7.01 (10H, br), 7.30 (10H, br)

IR (CHCl$_3$) ν: 1750 cm$^{-1}$.

| Elemental analysis: | C | H | N |
|---|---|---|---|
| Calcd. | 70.09 | 5.88 | 4.81 |
| Found | 70.17 | 6.18 | 4.57 |

Reference Example 23

(3S,4R)-3-[(4S)-Phenyl-2-oxo-3-oxazolidinyl]-1-(2,2-ethyleneketal-1-ethoxycarbonylpropyl)-4-styrylazetidin-2-one

[(4S)-Phenyl-2-oxo-3-oxazolidinyl]acetyl chloride (608.9 g, 2.54 mol) was dissolved in methylene chloride (8 l), and triethylamine (560 ml, 4.02 mol) was added dropwise at −35° to −40° C. over 30 minutes. Thereafter, at −40° to −45° C., a solution of ethyl 2-[(3- phenylallylidene)amino]-3,3-ethylenedioxybutyrate (930 g, 3.07 mol) in methylene chloride (2 l) was added dropwise over a period of 6 hours. After completion of addition, the mixture was stirred at the same temperature for 6 hours. The reaction temperature was returned to room temperature and the reaction mixture was washed successively with a 10-fold dilution of concentrated hydrochloric acid (3 l) and saturated aqueous sodium chloride (3 l) and dried over magnesium sulfate. After filtration, the filtrate was concentrated and the residue was washed with diethyl ether and recrystallized from benzene-n-hexane mixture to give the title compound (955 g) as white crystals.

mp: 183°–185° C.

NMR (CDCl$_3$) δ: 1.27 (3H, t), 1.40 (3H, s), 3.87 (4H, d), 4.0–5.0 (8H, m), 6.0–6.7 (2H, m), 7.25 (5H, d), 7.30 (5H, s).

IR (CHCl$_3$) ν: 1760cm$^1$.

| Elemental analysis: | C | H | N |
|---|---|---|---|
| Calcd. | 66.39 | 5.97 | 5.53 |
| Found | 66.54 | 5.86 | 5.39 |

$[\alpha]_D^{20} = +66.4°$ (c=1.1 in chloroform).

Reference Example 24

(3S,4R)-3-[(4S)-Phenyl-2-oxo-3-oxazolidinyl]-1-(2,2-ethyleneketal-1-benzyloxycarbonylpropyl)-4-styrylazetidin-2-one (3S,4R)-3-[(4S)-Phenyl-2-oxo-3-oxazolidinyl]-1(2,2-ethyleneketal-1-carboxypropyl)-4-styrylazetidin-2-one (1.78 g, 3.7 mmol) was dissolved in methylene chloride (10 ml), and triethylamine (1.07 g, 10.6 mmol) was added to the solution, followed by dropwise addition of carbobenzoxy chloride (1.06 g, 6.2 mmol) under ice-cooling. The mixture was stirred at the same temperature for 30 minutes and, then, refluxed for 15 minutes and then washed successively with water, a 10-fold dilution of concentrated hydrochloric acid and saturated aqueous sodium chloride and dried over magnesium sulfate. After filtration, the filtrate was concentrated and the residue was separated and purified by silica gel column chromatography [eluent: n-hexane-ethyl acetate (1:1)]. Two compounds (diastereomers) were identified by the thin layer chromatography. Their physicochemical data are shown in the following.

| Yield: | diastereomer-A | 900 mg | Yellow prisms |
|---|---|---|---|
|  | diastereomer-B | 500 mg | White Needls | diastereomer-A $[\alpha]_D^{20} = +45.8°$ (C=0.52, in chloroform).

mp: 134°–137° C.

NMR (CDCl$_3$) δ: 1.47 (3H, s), 3.74 (4H, br), 4.0–5.1 (8H, m), 5.97–6.6 (2H, m), 7.22 (10H, s), 7.3 (5H, s).

IR (CHCl$_3$) ν: 1750, 1760 cm$^{-1}$.

diastereomer-B mp: 130°–133° C.

$[\alpha]_D^{20} = +69.2°$ (C=0.51, in chloroform).

NMR (CDCl$_3$) δ: 1.5 (3H, s), 3.84 (4H, d), 3.96–4.97 (8H, m), 5.7–6.35 (2H, m), 7.17 (15H, s).

IR (CHCl$_3$) ν: 1750 cm$^{-1}$.

Reference Example 25

(3S,4R)-3-[(4S)-Phenyl-2-oxo-3-oxazolidinyl]-1-(2,2-ethyleneketal-1-benzyloxycarbonylpropyl)-4-styrylazetidin-2-one (3S,4R)-3-[(4S)-Phenyl-2-oxo-3-oxazolidinyl]-1-(2,2-ethyleneketal-1-carboxypropyl)-4-styrylazetidin-2-one (57.2 g, 120 mmol) was dissolved in dimethylformamid (150 ml), and dicyclohexylamine (26.0 g, 144 mmol) was added to the solution, followed by dropwise addition of benzyl bromide (24.5 g, 144 mmol). The mixture was stirred at room temperature for 12 hours, diluted with water and extracted with ethyl acetate. The extract was washed successively with water, a 10-fold dilution of concentrated hydrochloric acid and saturated aqueous sodium chloride and dried over magnesium sulfate. After filtration, the filtrate was concentrated and the residue was purified by silica gel column chromatography [eluent: n-hexane-ethyl acetate (1:1)] to give a mixture of the diastereomers of the title compound.

Yield: 57.6 g.

Reference Example 26

3,4-cis-3-(4,5-cis-Diphenyl-2-oxo-3-oxazolidinyl)-1-(2,2-ethyleneketal-1-ethoxycarbonylpropyl)-4-formylazetidin-2-one 3,4-cis-3-(4,5-cis-Diphenyl-2-oxo-3-oxazolidinyl)-1-(2,2-ethyleneketal-1-ethoxycarbonylpropyl)-4-styrylazetidin-2-one (25 g, 42.9 mmol) was dissolved in methylene chloride (150 ml) and, at the internal temperature of −50° C., the solution was oxidized with ozone. Thereafter, nitrogen gas was introduced at the same temperature for 30 minutes, followed by addition of dimethyl sulfide (12.5 ml). The reaction temperature was gradually returned to room temperature. The reaction mixture was washed three times with a 1% aqueous solution of sodium hydrogen carbonate (50 ml) and then saturated aqueous sodium chloride (50 ml) and dried over magnesium sulfate. After filtration, the filtrate was concentrated and the residue was washed thoroughly with n-hexane and treated with diisopropyl ether to give the title compound (17.3 g) as red-yellow powder.

mp: 143°–146° C.

NMR (CDCl$_3$) δ: 1.33 (3H, t), 1.40 (3H, t), 1.57 (3H, s), 1.63 (3H, s), 3.90 (4H, br), 3.94 (4H, br), 4.00–4.76 (10H, m), 5.07 (1H, d), 5.16 (1H, d), 5.82 (2H, d), 6.67–7.20 (20H, br), 10.00 (1H, d), 10.16 (1H, d),

IR (CHCl$_3$) ν: 1780, 1750, 1720 cm$^{-1}$.

Reference Example 27

(3S,4S)-3-[(4S)-Phenyl-2-oxo-3-oxazolidinyl]-1-(2,2-ethyleneketal-1-ethoxycarbonylpropyl)-4-formylazetidin-2-one (3S,4R)-3-[(4S)-Phenyl-2-oxo-3-oxazolidinyl]-1-(2,2-ethyleneketal-1-ethoxycarbonylprpoyl)-4-styrylazetidin-2-one (50 g, 98.7 mmol) was dissolved in methylene chloride (50 ml) and the ozonolysis was conducted at −50° C. After completion of the reaction, nitrogen gas was bubbled into the solution at the same temperature for 30 minutes and, after addition of dimethyl sulfide (14.4 ml), the reaction temperature was gradually returned to room temperature. The mixture was washed successively with a 1% aqueous solution of sodium hydrogen carbonate, water and saturated aqueous sodium chloride and dried over magnesium sulfate. After filtration, the filtrate was concentrated and the residue was treated with n-hexane and dried. By the above procedure there was obtained the title compound (41.6 g) as orange oil.

NMR (CDCl$_3$) δ: 1.33 (3H, t), 1.60 (3H, s), 3.90 (4H, br), 4.0–5.0 (8H, m), 7.35 (5H, s), 9.7 (1H, d).

Reference Example 28

(3S,4S)-3-[(4S)-Phenyl-2-oxo-3-oxazolidinyl]-1-(2,2-ethyleneketal-1-benzyloxycarbonylpropyl)-4-formylazetidin-2-one In a manner analogous to Reference Example 27, the title compound (17.3 g) was produced from (3S,4R)-3-[(4S)-phenyl-2-oxo-3-oxazolidinyl]-1-(2,2-ethyleneketal-1-benzyloxycarbonylpropyl)-4-styrylazetidin-2-one (20 g, 35.2 mmol).

NMR (CDCl$_3$) δ: 1.56 (3H, s), 3.80 (4H, br), 4.1–5.08 (8H, m), 7.2 (5H, s), 7.26 (5H, s), 9.8 (1H, d).

Reference Example 29

(3S,4S)-3-[(4S)-Phenyl-2-oxo-3-oxazolidinyl]-1-(2,2-ethyleneketal-1-ethoxycarbonylpropyl)-4-hydroxymethyl-azetidin-2-one (3S,4S)-3-[(4S)-Phenyl-2-oxo-3-oxazolidinyl]-1-(2,2-ethyleneketal-1-ethoxycarbonylpropyl)-4-formylazetidin-2-one (41.6 g, 96.2 mmol) was dissolved in tetrahydrofuran (350 ml) and, at −60° C., sodium borohydride (2 g, 52.9 mmol) was added gradually to the solution. The mixture was stirred at a temperature not exceeding −30° C. for 2.5 hours, poured into cold saturated aqueous sodium chloride and extracted with ethyl acetate. The extract was washed with water and dried over anhydrous magnesium sulfate. After filtration, the filtrate was concentrated and the residue was purified by silica gel column chromatography [eluent: n-hexane-ethyl acetate (1:5)] to give the title compound (25.2 g) as white powder.

mp: 42°–44° C.

[α]$_D^{20}$ = +83.5° (C=1.32, in chloroform)

NMR (CDCl$_3$) δ: 1.25 (3H, t), 1.32 (3H, s), 3.60 (2H, m), 3.92 (4H, br), 4.05–5.00 (8H, m), 7.32 (5H, s).

Reference Example 30

(3S,4S)-3-[(4S)-Phenyl-2-oxo-3-oxazolidinyl]-1-(2,2-ethyleneketal-1-benzyloxycarbonylpropyl)-4-hydroxymethylazetidin-2-one In a manner analogous to Reference Example 29, the title compound (1.69 g) was obtained from (3S,4S)-3-[(4S)-phenyl-2-oxo-3-oxazolidinyl]-1-(2,2-ethyleneketal-1-benzyloxycarbonylpropyl)-4-formyl azetidin-2-one (4 g, 8.1 mmol) as white powder.

mp: 48°–50° C.

[α]$_D^{20}$ = +61.8° (C=1.65, in chloroform).

NMR (CDCl$_3$) δ: 1.50 (3H, s), 3.60 (2H, t), 3.77 (4H, br), 4.0–5.1 (10H, m), 7.25–7.35 (10H, d).

Reference Example 31

3,4-cis-3-(4,5-cis-Diphenyl-2-oxo-3-oxazolidinyl)-1-(2,2-ethyleneketal-1-ethoxycarbonylpropyl)-4-hydroxymethylazetidin-2-one 3,4-cis-3-(4,5-cis-Diphenyl-2-oxo-3-oxazolidinyl)-1-(2,2-ethyleneketal-1-ethoxycarbonylpropyl)-4-formylazetidin-2-one (12 g, 23.6 mmol) was dissolved in tetrahydrofuran (120 ml) and, at −50° C., sodium borohydride (496 mg, 13.1 mmol) was carefully added thereto. The mixture was stirred at the same temperature for 2 hours. Then, a saturated aqueous solution of sodium chloride (120 ml) was added and the mixture was extracted twice with diethyl ether (250 ml). The ether layer was washed with saturated aqueous sodium chloride (120 ml) and dried over anhydrous magnesium sulfate. After filtration, the filtrate was concentrated and the residue was purified by silica gel column chromatography [eluent: ethyl acetate-n-hexane (2:1)] to give the title compound (5.2 g) as white solid.

mp: 185°–187° C.

NMR (CDCl$_3$) δ: 1.25 (3H, t), 1.36 (3H, t), 1.48 (3H, s), 1.60 (3H, s), 3.92 (4H, br), 3.98 (4H, br), 4.0–4.78 (14H, m), 5.12 (2H, d), 5.88 (2H, d), 6.80–7.20 (20H, m).

IR (CHCl$_3$) ν: 1770, 1760, 1730, 3450 cm$^{-1}$.

Reference Example 32

(3S,4S)-3-[(4S)-Phenyl-2-oxo-3-oxazolidinyl]-1-(2,2-ethyleneketal-1-ethoxycarbonylpropyl)-4-methanesulfonyloxymethylazetidin-2-one (3S,4S)-3-[(4S)-Phenyl-2-oxo-3-oxazolidinyl]-1-(2,2-ethyleneketal-1-ethoxycarbonylpropyl)-4-hydroxymethyl-azetidin-2-one (35 g, 80.6 mmol) and triethylamine (16.3 g, 161.2 mmol) were dissolved in methylene chloride (300 ml) and, at 0° C., a solution of methanesulfonyl chloride (13.8 g, 120.9 mmol) in methylene chloride (30 ml) was added dropwise to the solution. The mixture was stirred at the same temperature for 2 hours, washed succesively with water and saturated aqueous sodium chloride and dried over magnesium sulfate. After filtration, the filtrate was concentrated to give the title compound (40.4 g) as red-yellow powder.

mp: 52°–55° C.

[α]$_D^{20}$ = +53.7° (C=0.43, in chloroform).

NMR (CDCl$_3$) δ: 1.26 (3H, t), 1.41 (3H, s), 3.06 (3H, s), 3.37 (5H, s), 3.91 (4H, br), 4.02–5.03 (10H, m).

Reference Example 33

(3S,4S)-3-[(4S)-Phenyl-2-oxo-3-oxazolidinyl]-1-(2,2-ethyleneketal-1-benzyloxycarbonylpropyl)-4-methanesulfonyloxymethylazetidin-2-one In a manner analogous to Reference Example 32, the title compound (6.7 g) was produced from (3S,4S)-3-(4S)-phenyl-2-oxo-3-oxazolidinyl]-1-(2,2-ethyleneketal-1-benzyloxycarbonylpropyl)-4-hydroxymethylazetidin-2-one (6 g, 12.1 mmol) as white powder.

mp: 56°–58° C.

[α]$_D^{20}$ = +49.1° (C=0.57, in chloroform).

NMR (CDCl$_3$) δ: 1.50 (3H, s), 3.03 (3H, s), 3.55 (2H, br), 3.83 (4H, br), 4.10–5.26 (8H, m), 7.24 (5H, s), 7.34 (5H, s).

Reference Example 34

3,4-cis-3-(4,5-cis-Diphenyl-2-oxo-3-oxazolidinyl)-(2,2-ethyleneketal-1-ethoxycarbonylpropyl)-4-methanesulfonyloxymethylazetidin-2-one 3,4-cis-3-(4,5-cis-Diphenyl-2-oxo-3-oxazolidinyl)-1-(2,2-ethyleneketal-1-ethoxycarbonylpropyl)-4-hydroxymethylazetidin-2-one (4.7 g, 9.21 mmol) and triethylamine (1.86 g, 18.42 mmol) were dissolved in methylene chloride (63 ml). A solution of methanesulfonyl chloride (1.58 g, 13.82 mmol) in methylene chloride (12 ml) was added dropwise to the above solution at −10° C. to −20° C. and the mixture was stirred at the same temperature for 1.5 hours. The reaction mixture was then washed three times with water (100 ml) and dried over anhydrous magnesium sulfate. After filtration, the filtrate was concentrated and the residual yellow oily substance was treated with diisopropyl ether to give the title compound (5.31 g) as white solid.

mp: 148°–150° C.

NMR(CDCl$_3$) δ: 1.25 (3H, t), 1.30 (3H, t), 1.50 (3H, s), 1.55 (3H, s), 3.10 (6H, s), 3.93 (8H, br), 4.05–5.00 (14H, m), 5.10 (2H, d), 5.95 (1H, d), 5.98 (1H, d), 6.80–7.15 (20H, br)

IR (CHCl$_3$) ν: 1775, 1750, 1365 cm$^{-1}$.

Reference Example 35

3,4-cis-3-(4,5-cis-Diphenyl-2-oxo-3-oxazolidinyl)-1-(1-ethoxycarbonyl-2-hydroxy-1-propenyl)-4-methanesulfonyloxymethylazetidin-2-one 3,4-cis-3-(4,5-cis-Diphenyl-2-oxo-3-oxazolidinyl)-1-(2,2-ethyleneketal-1-ethoxycarbonylpropyl)-4-methanesulfonyloxymethyl-azetidine-2-one (5 g, 8.5 mmol) was suspended in methylene chloride (30 ml) and, under ice-cooling, 95% trifluoroacetic acid (24 ml) was added thereto. The mixture was stirred at room temperature for 1.5 hours, diluted with saturated aqueous sodium chloride (120 ml) and extracted twice with methylene chloride (100 ml). The organic layer was washed twice with saturated aqueous sodium chloride (100 ml) and then with saturated sodium hydrogen carbonate (100 ml) and dried over magnesium sulfate. After filtration, the filtrate was concentrated and the residue was washed with n-hexane and dried under reduced pressure. By the above procedure there was obtained the title compound (4.4 g) as white crystals.

mp: 159°–162° C.

NMR (CDCl$_3$) δ: 1.23 (3H, t), 2.20 (3H, s), 3.07 (3H, s), 4.03–4.90 (6H, m), 5.15 (1H, d), 5.88 (1H, d), 6.80–7.20 (10H, m), 12.48 (1H, s).

IR (CHCl$_3$) ν: 3500, 1780, 1750, 1370 cm$^{-1}$.

Reference Example 36

(3S,4S)-3-[(4S)-Phenyl-2-oxo-3-oxazolidinyl]-1-(1-ethoxycarbonyl-2-hydroxy-1-propenyl)-4-methanesulfonyloxymethylazetidin-2-one (3S,4S)-3-[(4S)-Phenyl-2-oxo-3-oxazolidinyl]-1-(2,2-ethyleneketal-1-ethoxycarbonylpropyl)-4-methanesulfonyloxymethylazetidin-2-one (20 g, 39 mmole) and 95% trifluoroacetic acid (100 ml) were mixed under ice-cooling and the mixture was stirred at room temperature for 1.5 hours, diluted with saturated aqueous sodium chloride and extracted with methylene chloride. The extract was washed with saturated aqueous sodium chloride and dried over anhydrous sodium sulfate. After filtration, the filtrate was concentrated to give the title compound (14.5 g) as white crystals.

mp: 164°–166° C.

$[\alpha]_D^{20}$ = +34.4° (C=0.64, in chloroform).

NMR (CDCl$_3$) δ: 1.26 (3H, t), 2.04 (3H, s), 3.02 (3H, s), 4.07–5.06 (9H, m), 7.38 (5H, s), 12.2 (1H, s)

Reference Example 37

(3S,4S)-3-[(4S)-Phenyl-2-oxo-3-oxazolidinyl]-1-(1-benzyloxycarbonyl-2-hydroxy-1-propenyl)-4-methanesulfonyloxymethylazetidin-2-one In a manner analogous to Reference Example 36, the title compound (6.5 g) was produced from (3S,4S)-3-[(4S)-phenyl-2-oxo-3-oxazolidinyl]-1-(2,2-ethyleneketal-1-benzyloxycarbonylpropyl)-4-methanesulfonyloxymethylazetidin-2-one (7.6 g, 13.2 mmol) as white crystals.

mp: 120°–122° C.

$[\alpha]_D^{20}$ = +48.2° (C=0.83, in chloroform).

NMR (CDCl$_3$) δ: 2.03 (3H, s), 2.96 (3H, s), 4.05–5.20 (9H, m), 7.30 (5H, s), 7.37 (5H, s).

Reference Example 38

Ethyl (6S,7S)-7-[(4S)-phenyl-2-oxo-3-oxazolidinyl]-3-methyl-Δ$^3$-O-2-isocephem-4-carboxylate (3S,4S)-3-[(4S)-Phenyl-2-oxo-3-oxazolidinyl]-1-(1-ethoxycarbonyl-2-hydroxy-1-propenyl)-4-methanesulfonyloxymethylazetidin-2-one (7 g, 14.9 mmol) and triethylamine (1.5 g, 14.9 mmol) were refluxed in methylene chloride (70 ml) for 2 hours. The reaction mixture was washed successively with water, a 10-fold dilution of concentrated hydrochloric acid and saturated aqueous sodium chloride and dried over magnesium sulfate. After filtration, the filtrate was concentrated and the residue was recrystallized from methylene chloride-diethyl ether mixture to give the title compound (5.05 g) as white crystals.

mp: 196°–198° C.

$[\alpha]_D^{20}$ = +244° (C=0.5, in chloroform).

NMR (CDCl$_3$) δ: 1.30 (3H, t), 2.15 (3H, s), 3.36–3.55 (3H, m), 4.08–5.05 (6H, m), 7.33 (5H, s).

Reference Example 39

Benzyl (6S,7S)-7-[(4S)-phenyl-2-oxo-3-oxazolidinyl]-3-methyl-Δ$^3$-O-2-isocephem-4-carboxylate In a manner analogous to Reference Example 38, the title compound (4.8 g) was produced from (3S,4S)-3-[(4S)-phenyl-2-oxo-3-oxazolidinyl]-1-(1-benzyloxy carbonyl-2-hydroxy-1-propenyl)-4-methanesulfonyloxymethylazetidin-2-one (6.2 g, 11.7 mmol) as yellowish-white powder.

mp: 66°–68° C.

$[\alpha]_D^{20}$ = +138.6° (C=0.7, in chloroform).

NMR (CDCl$_3$) δ: 2.17 (3H, s), 3.4–3.8 (3H, m), 4.08–5.18 (6H, m), 7.30 (5H, s), 7.34 (5H, s).

Reference Example 40

Ethyl (6,7-cis)-7-[4,5-cis-diphenyl-2-oxo-3-oxazolidinyl]-3-methyl-Δ$^3$-O-2-isocephem-4-carboxylate 3,4-cis-3-(4,5-cis-Diphenyl-2-oxo-3-oxazolidinyl)-1-(1-ethoxycarbonyl-2-hydroxy-1-propenyl)-4-methane sulfonyloxymethylazetidin-2-one (4.1 g, 7.5 mmol) and triethylamine (762 mg, 7.5 mmol) were dissolved in methylene chloride (37 ml) and the solution was refluxed for 2 hours. The reaction mixture was diluted with methylene chloride (63 ml), washed successively with water, a 10-fold dilution of concentrated hydrochloric acid and saturated aqueous sodium chloride and dried over anhydrous magnesium sulfate. After filtration, the filtrate was concentrated and the residue was treated with n-hexane to give the title compound (3.13 g) as white crystals.

NMR (CDCl$_3$) δ: 1.30 (3H, t), 2.29 (3H, s), 3.60–4.50 (5H, m), 5.03 (1H, d), 5.12 (1H, d), 6.92 (1H, d), 6.80–7.20 (10H, m).

Reference Example 41

(6S,7S)-7-[(4S)-Phenyl-2-oxo-3-oxazolidinyl]-3-methyl-Δ$^3$-O-2-isocephem-4-carboxylic acid Benzyl (6S,7S)-7-[(4S)-phenyl-2-oxo-3-oxazolidinyl]-3-methyl-Δ$^3$-O-2-isocephem-4-carboxylate (2 g, 4.6 mmol) and nitromethane (5 ml) were dissolved in methylene chloride (50 ml) and, under ice-cooling, a solution of aluminum chloride (4.9 g, 36.7 mmol) in nitromethane (5 ml) was added thereto. The mixture was stirred at room temperature for 1.5 hours, poured into an ice-water and extracted with ethyl acetate. The organic layer was separated and extracted with saturated aqueous sodium hydrogen carbonate. The aqueous layer was adjusted to pH 2 with a 10-fold dilution of conc. hydrochloric acid extracted with ethyl acetate and dried over anhydrous sodium sulfate. After filtration, the filtrate was concentrated to give the title compound (520 mg) as yellow crystals.

mp: 204°–208° C.

$[\alpha]_D^{20} = +163°$ (C=0.68, in methanol).

NMR (CDCl$_3$-DMSO-d6) δ: 2.19 (3H, s), 3.5–5.05 (7H, m), 7.24 (5H, s).

Reference Example 42

Ethyl (6S,7S)-7-amino-3-methyl-Δ$^3$-O-2-isocephem-4-carboxylate

Ammonia was introduced into a dry ice-acetone bath (−78° C.) to prepare liquid ammonia (30 ml), followed by addition of lithium metal (0.42 g, 60 mmol). Thereafter, a solution of ethyl (6S,7S)-7-[(4S)-phenyl-3-oxazolidinyl]-3-methyl-Δ$^3$-O-2-isocephem-4-carboxylate (3.72 g, 10 mmol) in tetrahydrofuran (10 ml)-t-butanol (1 ml) was added dropwise. Five minutes after completion of addition, ammonium chloride (3.2 g, 60 mmol) was added and the temperature of the reaction mixture was returned to room temperature to remove the ammonia, followed by addition of water (10 ml). The mixture was adjusted to pH 3 with a 10-fold dilution of concentrated hydrochloric acid and made alkaline with saturated aqueous sodium carbonate. The aqueous solution was extracted twice with 10% isopropanol-methylene chloride mixture (50 ml). The extract was dried over anhydrous sodium sulfate and concentrated and the residue was separated and purified by silica gel column chromatography [eluent: chloroform-methanol (50:1)] to give the title compound (0.23 g).

Yellow oil

NMR (CDCl$_3$) δ: 1.28 (3H, t, J=7 Hz), 2.25 (3H, s), 3.10 (2H, s), 3.50–4.65 (4H, m), 4.22 (2H, q, J=7 Hz).

Reference Example 43

(3S,4R)-3-[(4S)-phenyl-2-oxo-3-oxazolidinyl]-1-(2,2-ethyleneketal-1-carboxypropyl)-4-styrylazetidin-2-one (3S,4R)-3-[(4S)-phenyl-2-oxo-3-oxazolidinyl]-1-(2,2-ethyleneketal-1-ethoxycarbonylpropyl)-4-styrylazetidin-2-one (20.24 g, 40 mmol) was dissolved in tetrahydrofuran (160 ml), and 1N sodium hydroxide (80 ml) was added dropwise thereto. The mixture was warmed at 36° C. for 1.5 hours and washed twice with diisopropyl ether (30 ml). The aqueous layer was adjusted to pH 2 with a 10-fold dilution of concentrated hydrochloric acid and extracted twice with methylene chloride (150 ml). The extract was washed with saturated aqueous sodium chloride and dried over anhydrous magnesium sulfate. After filtration, the filtrate was concentrated and the residue was treated with diisopropyl ether to give the title compound (16.6 g) as yellow powder.

mp: 91°–93° C.

$[\alpha]_D^{20} = +72.3°$ (C=1.18, in methanol).

NMR(CDCl$_3$)δ: 1.45 (3H, s), 3.95 (4H, br), 4.05–5.0 (6H, m), 6.05–7.6 (2H, m), 7.26 (5H, s).

Reference Example 44

Benzhydryl 7-azido-3-[(1,3,4-thiadiazol-2-yl)thiomethyl]-Δ$^3$-O-2-isocephem-4-carboxylate 7-Azido-3-[(1,3,4-thiadiazol-2-yl)thiomethyl]-Δ$^3$-O-2-isocephem-4-carboxylic acid (3.6 g, 10.6 mmol) was suspended in a mixture of ethanol (50 ml) and tetrahydrofuran (50 ml) and, at room temperature, diphenyldiazomethane (4.12 g, 21.2 mmol) was added thereto. The reaction was conducted for 30 minutes and the reaction mixture was concentrated under reduced pressure. After addition of a small amount of methanol to achieve complete crystallization, the crystals were collected by filtration to give the title compound (4.2 g).

mp: 169°–172° C.

NMR (CDCl$_3$) δ: 3.78 (1H, m), 3.98 (1H, dd, J=11.3 Hz, 9.5 Hz), 4.48 (1H, d, J=13.8 Hz), 4.59 (1H, m), 4.76 (1H, d, J=13.8 Hz), 5.25 (1H, d, J=5.2 Hz), 6.88 (1H, s), 7.2–7.4 (6H, m), 7.42 (2H, dd, J=8.5 Hz, 1.8 Hz), 7.56 (2H, dd, J=8.5 Hz, 1.8 Hz), 8.95 (1H, s).

REFERENCE EXAMPLE 45

3,4-cis-3-Phthalimido-1-(2,2-ethyleneketal-1-ethoxycarbonylpropyl)-4-styrylazetidin-2-one In methylene chloride (200 ml) was dissolved ethyl 1-(3-phenylallylidene)amino-2, 2-ethyleneketalbutyrate (30.3 g, 0.1 mol), and after addition of triethylamine (21 ml, 0.15 mol), the solution was cooled to −30° C. Then, a solution of 2-phthalimidoacetyl chloride (24.6 g, 0.11 mol) in methylene chloride (200 ml) was added dropwise and the mixture was stirred for 1 hour. After completion of the reaction, the reaction mixture was washed with a 10-fold dilution of concentrated hydrochloric acid (200 ml). The organic layer was washed twice with water (200 ml), dried over anhydrous magnesium sulfate, and filtered. The filtrate was concentrated and the residue was purified by silica gel column chromatography [eluent: methylene chloride-ethyl acetate(10:1)]to give the title compound (36.8 g).

mp: 143°–144° C.

| Elemental analysis | C | H | N |
|---|---|---|---|
| Calcd. | 66.11 | 5.34 | 5.71 |
| Found | 65.92 | 5.51 | 5.74 |

REFERENCE EXAMPLE 46

3,4-cis-3-Phenylacetamido-1-(2,2-ethyleneketal-1-ethoxycarbonylpropyl)-4-styrylazetidin-2-one In ethanol (300 ml) was suspended 3,4-cis-3-phthalimido-1-(2,2-ethyleneketal-1-ethoxycarbonylpropyl)-4-styrylazetidin-2-one (49 g, 0.1 mol), followed by addition of 1M hydrazine hydrate in ethanol (100 ml). The mixture was refluxed for 2 hours, at the end of which time the precipitate was filtered off and the filtrate concentrated under reduced pressure. To the residue was added methylene chloride (300 ml) and the resulting crystals were filtered off. To the filtrate was added triethylamine (16.7 ml, 0.12 mol), and under cooling at 0° C., phenylacetyl chloride (15.4 g, 0.1 mol) was added dropwise. After completion of the dropwise addition, the reaction was continued at the same temperature for 2 hours. The reaction mixture was washed by addition of a 10-fold dilution of conc. hydrochloric acid (200 ml). The organic layer was washed with a saturated solution of sodium chloride in water and dried over anhydrous magnesium sulfate. It was then filtered and the filtrate was concentrated and recrystallized from benzene to give the title compound (40.5 g).
mp: 111°–112° C.

| Elemental analysis | C | H | N |
|---|---|---|---|
| Calcd. | 67.77 | 6.32 | 5.85 |
| Found | 67.92 | 6.18 | 5.79 |

REFERENCE EXAMPLE 47

3,4-cis-3-Phenylacetamido-1-(2,2-ethyleneketal-1-carboxypropyl)-4-styrylazetidin-2-one In tetrahydrofuran (150 ml) was dissolved 3,4-cis-3-phenylacetamido-1-[2,2-ethyleneketal-1-ethoxycarbonylpropyl]-4-styrylazetidin-2-one (47.9 g, 0.1 mol), followed by addition of water (100 ml). Then, 1N aqueous sodium hydroxide (110 ml) was added dropwise at room temperature and the reaction was conducted at the same temperature for 3 hours. After completion of the reaction, the reaction mixture was adjusted to pH 2 with concentrated hydrochloric acid and extracted twice with ethyl acetate (250 ml). The extract was washed with a saturated solution of sodium chloride in water, dried over anhydrous sodium sulfate, and filtered. The filtrate was concentrated and the residue was recrystallized from ethyl acetate to give the title compound (38.5 g)
mp: 165°–167° C.

| Elemental analysis | C | H | N |
|---|---|---|---|
| Calcd. | 66.66 | 5.82 | 6.22 |
| Found | 66.48 | 5.92 | 6.35 |

REFERENCE EXAMPLE 48

(3S,4R)-3-Amino-1-(2,2-ethyleneketal-1-carboxypropyl)-4-styrylazetidin-2-one and (3R,4S)-3-phenylacetamido-1-(2,2-ethyleneketal-1-carboxypropyl)-4-styrylazetidin-2-one In water (740 ml) was suspended 3,4-cis-3-phenylacetamido-1-(2,2-ethyleneketal-1-carboxypropyl)4-styrylazetidin-2-one (66.4 g, 0.147 mol), followed by addition of 1N aqueous sodium hydroxide (147 ml). After the mixture was adjusted to pH 8 or less, penicillin G amidase (13.3 g) was added. The mixture was stirred at room temperature for 4 hours while it was adjusted to pH 8 with a saturated solution of sodium hydrogen carbonate in water. After completion of the reaction, the penicillin G amidase was filtered off and the filtrate was adjusted to pH 2. The filtrate was then washed twice with ethyl acetate-tetrahydrofuran (1:1) and the organic layer was extracted three times with 0.1 N hydrochloric acid. The water layers were pooled, adjusted to pH 7 and concentrated to about 300 ml. Then, the solution was adjusted to pH 3 with 10-fold dilution of conc. hydrochloric acid. The resulting white crystals were recovered by filtration, washed 3 times with ice-water, and dried to give (3S,4R)-3-amino-1-(2,2-ethylene-ketal-1-carboxypropyl)-4-styrylazetidin-2-one (8.9 g) as white crystals.
mp: 129°–131° C.
$[\alpha]_D^{\cong} = -102.8°$ (C=0.924, in ethanol).

| Elemental analysis | C | H | N |
|---|---|---|---|
| Calcd. | 61.44 | 6.07 | 8.42 |
| Found | 61.59 | 5.92 | 8.56 |

Further, the remaining ethyl acetate-tetrahydrofuran washings were evaporated in vacuo and the residue was purified by silica gel column chromatography to give (3R,4S)-3-phenylacetamido-1-(2,2-ethyleneketal-1-carboxypropyl)-4-styrylazetidin-2-one as white sharppointed needles.
mp: 166°–167° C.
$[\alpha]_D^{23} = -2.9°$ (C=1.05, in chloroform-dimethylformamide)

REFERENCE EXAMPLE 49

(3S,4R)-3-Phthalimido-1-(2,2-ethyleneketal-1-benzyloxycarbonylpropyl)-4-styrylazetidin-2-one In a mixture of water (100 ml) and acetone (100 ml) was dissolved (3S,4R)-3-amino-1-(2,2-ethyleneketal-1-carboxypropyl)-4-styrylazetidin-2-one (16.6 g, 0.05 mol). After addition of 1N aqueous sodium hydroxide (55 ml), the solution was cooled to −20° C. To this was added dropwise a solution of o-methoxycarbonylbenzoyl chloride (11 g, 0.055 mol) in acetone (30 ml). After completion of the dropwise addition, the mixture was stirred at the same temperature for 1 hour, at the end of which time it was adjusted to pH 1 with 10-fold dilution of conc. hydrochloric acid. The mixture was extracted with ethyl acetate (200 ml) and the extract was washed with a saturated solution of sodium chloride in water, dried over anhydrous magnesium sulfate, and filtered. The filtrate was concentrated under reduced pressure. To the residue were added dimethylformamide (50 ml) and cesium carbonate (19 g, 0.06 mol), followed by addition of benzyl bromide (10.3 g, 0.06 mol). The reaction was conducted at room temperature for 3 hours. Thereafter, water (300 ml) was added thereto and the mixture was extracted twice with ethyl acetate (200 ml). The extract was washed with a saturated solution of sodium chloride in water, dried over anhydrous sodium sulfate, and filtered. The filtrate was concentrated and the residue was purified by silica gel column chromatography [eluent:n-hexane-ethyl acetate(3:2)]to give the title compound (17.7 g) as white powder.
mp: 57°–61° C.
$[\alpha]_D^{23} = -50.0°$ (C=1.02, in chloroform).

| Elemental analysis | C | H | N |
|---|---|---|---|
| Calcd. | 69.56 | 5.11 | 5.07 |
| Found | 69.77 | 5.39 | 5.21 |

REFERENCE EXAMPLE 50

(3S,4S)-3-Phthalimido-1-(2,2-ethyleneketal-1-benzyloxycarbonylpropyl)-4-formylazetidin-2-one In methylene chloride (150 ml) was dissolved (3S,4R)-3-phthalimido-1-(2,2-ethyleneketal-1-benzyloxycarbonylpropyl)-4-styrylazetidin-2-one (26.56 g, 48.1 mmol). After cooling to -50° C., ozone was bubbled into the solution. When the reaction mixture turned light blue, the introduction of ozone was discontinued and nitrogen gas was introduced instead until nitrogen purging was complete. Then, after addition of dimethyl sulfide (7.3 ml), the temperature was gradually returned to room temperature over 2.5 hours. Thereafter, the reaction mixture was washed with a 5% aqueous solution of sodium hydrogen carbonate (150 ml) and washed twice with water (150 ml). The solution was dried over anhydrous sodium sulfate and filtered and the filtrate was concentrated. The residue was washed twice with n-hexane and re-washed with a mixture of diethyl ether (50 ml) and n-hexane (50 ml). The residue was sufficiently dried under reduced pressure to give the title compound (23.28 g) as white powder.
mp: 38°–42° C.
$[\alpha]_D^{23} = -60.2°$ (C=1.245, in chloroform).

| Elemental analysis | C | H | N |
|---|---|---|---|
| Calcd. | 55.91 | 4.69 | 5.02 |
| Found | 55.72 | 4.73 | 5.29 |

REFERENCE EXAMPLE 51

(3S,4S)-1-(1-benzyloxycarbonyl-2,2-ethyleneketalpropyl)-3-phthalimido-4-hydroxymethylazetidin-2one In a mixture of tetrahydrofuran (40 ml) and water (10 ml) was dissolved (3S,4S)-1-(1-benzyloxycarbonyl-2,2-ethyleneketalpropyl)-3-phthalimido-4-formylazetidin-2-one (8.65 g, 18 mmol) and while the solution was stirred at room temperature, sodium cyanoborohydride was added. The reaction was conducted for 3 hours, with the mixture being adjusted to the range of pH 3 to pH 4 with a 10-fold dilution of concentrated hydrochloric acid. After addition of a saturated aqueous solution of sodium chloride (40 ml), the reaction mixture was extracted twice with ethyl acetate (40 ml). The ethyl acetate layers were pooled and washed twice with a saturated aqueous solution of sodium chloride (80 ml). The solution was dried by addition of anhydrous sodium sulfate and filtered, and the filtrate was concentrated under reduced pressure to give the title compound (7.80 g) as pale yellow powder.
mp: 37°–44° C.
$[\alpha]_D^{23} = +10.3°$ (C=1.07, in chloroform).

| Elemental analysis | C | H | N |
|---|---|---|---|
| Calcd. | 62.50 | 5.03 | 5.83 |
| Found | 62.38 | 5.24 | 6.02 |

REFERENCE EXAMPLE 52

(3S,4S)-1-(1-benzyloxycarbonyl-2,2-ethyleneketalpropyl)-3-phthalimido-4-mesyloxymethylazetidin-2one In methylene chloride (90 ml) was dissolved (3S,4S)-1-(1-benzyloxycarbonyl-2,2-ethyleneketalpropyl)-3-phthalimido-4-hydroxymethylazetidin-2one (8.65 g, 18 mmol) and after the solution was cooled to 3° C., triethylamine (3.0 ml) and mesyl chloride (1.5 ml) were added. The mixture was stirred for 1 hour The reaction mixture was washed with a 5-fold dilution of concentrated hydrochloric acid (90 ml) and, then, washed 3 times with water (90 ml). The solution was dried over anhydrous sodium sulfate and filtered, and the filtrate was concentrated under reduced pressure to give the title compound (9.80 g) as pale yellow powder.
mp: 43°–47° C.
$[\alpha]_D^{\leqq} = -18.6°$ (C=1.02, in chloroform).

| Elemental analysis | C | H | N |
|---|---|---|---|
| Calcd. | 62.76 | 4.63 | 5.85 |
| Found | 63.03 | 4.75 | 6.09 |

REFERENCE EXAMPLE 53

(3S,4S)-1-(1-Benzyloxycarbonyl-2-hydroxy-1-propenyl)-3-phthalimido-4-mesyloxymethylazetidin-2-one (3S,4S)-1-(1-benzyloxycarbonyl-2,2-ethyleneketalpropyl)-3-phthalimido-4-mesyloxymethylazetidin-2-one (8.94 g, 16 mmol) was dissolved by addition of 5% trifluoroacetic acid (32 ml). After 30 minutes' stirring, the solution was concentrated under reduced pressure. The residue was diluted with water (100 ml) and extracted twice with methylene chloride (50 ml). The methylene chloride layers were pooled, washed 4 times with water (100 ml), dried over anhydrous sodium sulfate, and filtered. The filtrate was concentrated under reduced pressure and the residue was purified by silica gel column chromatography [eluent:methylene chloride-ethyl acetate(20:1)]to give the title compound (6.41 g) as white powder.
mp: 61°–65° C.
$[\alpha]_D^{\leqq} = -34.10°$ (C=0.85, in chloroform).

| Elemental analysis | C | H | N |
|---|---|---|---|
| Calcd. | 56.03 | 4.31 | 5.44 |
| Found | 56.12 | 4.37 | 5.17 |

REFERENCE EXAMPLE 54

(3S,4S)-1-(1-Benzyloxycarbonyl-2-trifluoromethanesulfonyloxy-1-propenyl)-3-phthalimido-4-mesyloxymethylazetidin-2-one In methylene chloride (40 ml) was dissolved (3S,4S)-1-(1-benzyloxycarbonyl-2-hydroxyl-1-propenyl)-3-phthalimido-4-mesyloxymethylazetidin-2-one (5.15 g, 10 mmol). The solution was cooled to −30° C. and, then, trifluoromethanesulfonic anhydride was added. Thereafter, a solution of triethylamine (1.9 ml) in methylene chloride (20 ml) was added in portions over a period of 10 minutes. After completion of the dropwise addition, the reaction mixture was stirred for 50 minutes. Then, it was made weakly acidic with a 10-fold dilution of concentrated hydrochloric acid and the temperature was returned to room temperature. The reaction mixture was washed 3 times with water (100 ml each), dried by addition of anhydrous sodium sulfate, and filtered. The filtrate was concentrated to give the title compound (6.21 g) as white powder.
mp: 51°–55° C.
$[\alpha]_D^{23} = +40.8°$ (C=1.03, in chloroform).

| Elemental analysis | C | H | N |
|---|---|---|---|
| Calcd. | 46.44 | 3.27 | 4.33 |
| Found | 46.70 | 3.09 | 4.61 |

REFERENCE EXAMPLE 55

Benzyl (6S,7S)-7-phthalimido-3-acetoxymethyl-$\Delta^3$-O-2-isocephem-4-carboxylate In methylene chloride (15 ml) was dissolved (3S,4S)-1-(1-benzyloxycarbonyl-2-trifluoromethanesulfonyloxy-1-propenyl)-3-phthalimido-4-mesyloxymethylazetidin-2-one (1.94 g, 3 mmol). Then, triethylamine (0.42 ml) was added under ice-cooling and the mixture was stirred at room temperature for 35 minutes. To this was added dropwise a solution of bromine (0.15 ml) in methylene chloride (15 ml) over a period of 5 minutes, after which the mixture was stirred for 15 minutes. The reaction mixture was washed 3 times with water (30 ml), dried by addition of anhydrous sodium sulfate, and filtered. The filtrate was concentrated under reduced pressure. The residue was dissolved by addition of dimethylformamide (15 ml), followed by addition of potassium acetate (1.18 g) and water (0.15 ml). The mixture was stirred for 5 hours. Thereafter, water (150 ml) was added and the mixture was extracted 3 times with ethyl acetate (50 ml). The ethyl acetate layers were pooled, washed 3 times with water (100 ml) and washed occe with saturated aqueous sodium chloride (100 ml). The solution was dried by addition of anhydrous sodium sulfate and filtered, and the filtrate was concentrated under reduced pressure. Finally, the residue was purified by silica gel column chromatography [eluent-:hexane-ethyl acetate(7:4)] to give the title compound (0.92 g) as light yellow powder.

mp: 80°-83° C.
$[\alpha]_D^{23} = +11.4°$ (C=2.016, in chloroform).

| Elemental analysis | C | H | N |
|---|---|---|---|
| Calcd. | 63.02 | 4.23 | 5.88 |
| Found | 63.21 | 4.34 | 5.71 |

REFERENCE EXAMPLE 56

Benzyl (6S,7S)-7-phthalimido-3-formyloxymethyl-$\Delta^3$-O-2-isocephem-4-carboxylate In a manner analogous to Reference example 55, the title compound (0.8 g) was produced from (3S,4S)-1-benzyloxycarbonyl-2-trifluoromethanesulfonyloxy-1-propenyl)-3-phthalimido-4-mesyloxymethylazetidin-2-one (1.94 g, 3 mmol), triethylamine (0.42 ml), bromine (0.15 ml) and sodium formate (1.01 g), as light yellow powder.

mp: 83°-85° C.
$[\alpha]_D^{23} = +23°$ (C=0.95, in chloroform).

| Elemental analysis: | C | H | N |
|---|---|---|---|
| Calcd. | 62.34 | 3.92 | 6.06 |
| Found | 62.29 | 3.78 | 5.92 |

REFERENCE EXAMPLE 57

Benzyl (6S,7S)-7-phthalimido-3-hydroxymethyl-$\Delta^3$-O-2-isocephem-4-carboxylate To a solution of benzyl (6S,7S)-7-phthalimido-3-formyloxymethyl-$\Delta^3$-O-2-isocephem-4-carboxylate (460 mg, 1 mmol) in a mixture of acetone (5 ml) and water (2 ml) was added conc. hydrochloric acid (0.25 ml), and the mixture was stirred overnight. After completion of reaction, precipitated crystals were filtered, washed with water and dried to give the title compound (320 mg) as sharp-pointed needles.

mp: 193°-194° C.
$[\alpha]_D^{\cong} = +51.5°$ (C=1.3; in chloroform).

| Elemental analysis: | C | H | N |
|---|---|---|---|
| Calcd. | 63.59 | 4.18 | 6.45 |
| Found | 63.37 | 4.27 | 6.53 |

EXAMPLE 1

Benzyl 7-[2-(2-chloroacetamidothiazol-4-yl)-2-methoxyiminoacetamido]-3-[(carbamoyloxy)methyl]-$\Delta^3$-O-2-isocephem-4-carboxylate (sym-isomer)

Vilsmeier reagent (540 mg, 2.4 mmol) was suspended in ethyl acetate (20 ml) and, under ice-cooling, 2-(2-chloroacetamidothiazol-4-yl)-2-methoxyiminoacetic acid (syn-isomer) (610 mg, 2.2 mmol) was added thereto. The reaction was conducted for 1 hour to give a homogeneous solution (hereinafter referred to as solution A).

On the other hand, benzyl 7-amino-3-[(carbamoyloxy)methyl]-$\Delta^3$-O-2-isocephem-4-carboxylate (740 mg, 2 mmol) was added to ethyl acetate (20 ml), followed by addition of monotrimethylsilylacetamide (1.6 g). The mixture was cooled in an ice-methanol bath. To the reaction mixture was added the above-mentioned solution A and the reaction was conducted for 2 hours. Thereafter, water (10 ml) was added to terminate the reaction, and the mixture was washed with 5% aqueous sodium hydrogen carbonate and then with saturated aqueous sodium chloride in that order. The ethyl acetate layer was separated, dried over anhydrous sodium sulfate, filtered and concentrated. Diethyl ether was added to the residue to give the title compound (780 mg).

Light yellow powder
mp: 161° C. (discoloration), >300° C.
NMR (DMSO-d6+CDCl₃) δ: 3.95 (3H, s), 3.68–4.13 (2H, m), 4.23 (2H, s), 4.70 (2H, s), 5.22 (2H, s), 5.68 (1H, dd), 5.97 (2H, bs), 7.30 (5H, s), 7.67 (1H, s), 9.25 (1H, d).

EXAMPLE 2

Benzyl 7-[2-(2-chloroacetamidothiazol-4-yl)-2-(tert-butoxycarbonylmethoxyimino)acetamido]-3-[(1,3,4-thiadiazol-2-yl)thiomethyl]-$\Delta^3$-O-2-isocephem-4carboxylate (syn-isomer)

Benzyl 7-amino-3-[(1,3,4-thiadiazol-2-yl)thiomethyl]-$\Delta^3$-O-2-isocephem-4-carboxylate (1.02 g, 2.4 mmol) was dissolved in methylene chloride (30 ml), followed by addition of 2-(2-chloroacetamidothiazol-4-yl)-2-(tert-butoxycarbonylmethoxyimino)acetic acid (syn-isomer) (1.10 g, 2.9 mmol) and, then, dicyclohexylcarbodiimide (DCC) (0.60 g, 2.9 mmol). The reaction was conducted at room temperature for 3 hours. Thereafter, the resulting crystalline precipitate was filtered off and the filtrate was washed with a 5% aqueous solution of sodium hydrogen carbonate and water in that order, dried over anhydrous magnesium sulfate and filtered. The filtrate was concentrated and diethyl ether was added to the residue to give the title compound (0.97 g) as powder.

NMR (CDCl$_3$) δ: 1.43 (9H, s), 3.60–4.10 (2H, m), 4.29 (2H, s), 5.28 (2H, s), 5.68 (1H, dd), 7.33 (5H, m), 7.42 (1H, s), 8.99 (1H, s).

EXAMPLE 3

Benzyl 7-[2-(2-aminothiazol-4-yl)-2-methoxyiminoacetamido]-3-[(carbamoyloxy)methyl]-Δ$^3$-O-2-isocephem-4-carboxylate (syn-isomer)

2-(2-Aminothiazol-4-yl)-2-methoxyiminoacetic acid (syn-isomer) (240 mg) was suspended in tetrahydrofuran (3 ml) and, at 5° C., phosphorus oxychloride (0.14 ml) was added. The mixture was stirred for 10 minutes, followed by addition of monotrimethylsilylacetamide (240 ml). The mixture was stirred for 10 minutes, followed by addition of phosphorus oxychloride (0.17 ml). The mixture was further stirred for 10 minutes and dimethylformamide (0.1 ml) was added. The reaction was conducted at the same temperature for 1 hour (referred to as solution A).

On the other hand, benzyl 7-amino-3-[(carbamoyloxy)methyl]-Δ$^3$-O-2-isocephem-4-carboxylate (190 mg, 0.51 mmol) was added to ethyl acetate (20 ml), followed by addition of monotrimethylsilylacetamide (920 mg). The mixture was cooled in an ice-methanol bath. To the reaction mixture was added the above-mentioned solution A and the reaction was conducted for 2 hours. Thereafter, water (10 ml) was added to the reaction mixture to terminate the reaction. The ethyl acetate layer was separated, washed with a 10-fold dilution of concentrated hydrochloric acid, 5% aqueous sodium hydrogen carbonate and saturated aqueous sodium chloride in that order. The ethyl acetate layer was separated, dried over anhydrous sodium sulfate, filtered and concentrated. Diethyl ether was added to the residue to give the title compound (340 mg) as powder.

Light yellow powder mp: 141° C. (discoloration), >300° C.

NMR (CDCl$_3$) δ: 4.02 (3H, s), 4.37°–4.79 (2H, m), 5.01 (2H, s), 5.24 (2H, s), 5.68 (1H, dd), 5.97 (2H, bs), 6.82 (1H, s), 7.15–7.50 (5H, m), 9.31 (1H, d).

EXAMPLE 4

Benzyl 7-[2-(2-trifluoroacetamidothiazol-4-yl)-2-methoxyiminoacetamido]-3-[(carbamoyloxy)methyl]-Δ$^3$-O-2-isocephem-4-carboxylate (syn-isomer)

Vilsmeier reagent (270 mg, 1.2 mmol) was suspended in ethyl acetate (10 ml) and, under ice-cooling, 2-(2-trifluoroacetamidothiazol-4-yl)-2-methoxyiminoacetic acid (syn-isomer) (350 mg, 1 mmol) was added thereto. The reaction was conducted for 1 hour (referred to as solution A).

On the other hand, benzyl 7-amino-3-[(carbamoyloxy)methyl]-Δ$^3$-O-2-isocephem-4-carboxylate (350 mg, 1 mmol) was added to ethyl acetate (10 ml), followed by addition of monotrimethylsilylacetamide (790 mg, 6 mmol). The mixture was cooled in an ice-methanol bath. To the reaction mixture was added the above-mentioned solution A and the reaction was conducted for 2 hours. Thereafter, water (5 ml) was added to the reaction mixture to terminate the reaction, and the mixture was washed with 5% aqueous sodium hydrogen carbonate and then with saturated aqueous sodium chloride in that order. The ethyl acetate layer was separated, dried over anhydrous sodium sulfate, filtered and concentrated. Diethyl ether was added to the residue to give the title compound (600 mg) as powder.

NMR (DMSO-d6+CDCl$_3$) δ: 3.98 (3H, s), 3.70–4.08 (2H, m), 4.51–4.74 (1H, m), 4.99 (2H, s), 5.23 (2H, s), 5.72 (1H, dd), 6.08 (2H, bs), 7.33 (1H, s), 7.37 (5H, s), 9.28 (1H, d).

EXAMPLE 5

Benzyl 7-[2-(2-trichloroacetamidothiazol-4-yl)-2-methoxyiminoacetamido]-3-[(carbamoyloxy)methyl]-Δ$^3$-O-2-isocephem-4-carboxylate (syn-isomer)

Using Vilsmeier reagent (270 mg, 1.2 mmol), 2-(2-trichloroacetamidothiazol-4-yl)-2-methoxyiminoacetic acid (syn-isomer) (340 mg, 1.2 mmol), benzyl 7-amino-3-[(carbamoyloxy)methyl]-Δ$^3$-O-2-isocephem-4-carboxylate (347 mg, 1 mmol), monotrimethylsilylacetamide (790 mg, 6 mmol) and ethyl acetate (20 ml), the title compound (670 mg) was produced in a manner analogous to Example 4.

NMR (CDCl$_3$+DMSO-d6) δ: 3.99 (3H, s), 4.47–4.76 (2H, m), 4.99 (2H, s), 5.24 (2H, s), 5.72 (1H, dd), 6.01 (2H, bs), 7.04–7.5 (5H, m), 7.42 (1H, s).

EXAMPLE 6

7-[2-(2-Trifluoroacetamidothiazol-4-yl)-2-methoxyiminoacetamido]-3-[(carbamoyloxy)methyl]-Δ$^3$-O-2-isocephem-4-carboxylic acid (syn-isomer)

To benzyl 7-[2-(2-trifluoroacetamidothiazol-4-yl)-2-methoxyiminoacetamido]-3-[(carbamoyloxy)methyl]-Δ$^3$-O-2-isocephem-4-carboxylate (syn-isomer) (650 mg, 1 mmol) were added methylene chloride (60 ml) and nitromethane (10 ml) to give a suspension and a solution of anhydrous aluminum chloride (1.73 g, 13 mmol) in nitromethane (10 ml) was added dropwise thereto, whereupon the color of the mixture changed from yellow to dark brown. After 1 hour of reaction, the reaction mixture was poured into water (50 ml), followed by addition of a 10-fold dilution of concentrated hydrochloric acid (20 ml). The mixture was extracted with ethyl acetate (100 ml). The ethyl acetate layer was extracted three times with a 5% aqueous solution of sodium hydrogen carbonate (60 ml in total). The extract was adjusted to pH 2 with a 10-fold dilution of concentrated hydrochloric acid and extracted with 100 ml of ethyl acetate (100 ml). The ethyl acetate extract was washed with saturated aqueous sodium chloride, dried over anhydrous magnesium sulfate, filtered and concentrated to give the title compound (300 mg).

Light orange powder mp: >300° C.; discoloration and decomposition begin at 162° C.

NMR (DMSO-d6+CDCl$_3$) δ: 3.98 (3H, s), 4.33–4.73 (2H, m), 4.97 (2H, s), 5.35–5.55 (1H, dd), 5.70 (1H, dd), 6.24 (2H, bs), 7.51 (1H, s), 9.33 (1H, d).

EXAMPLE 7

7-[2-(2-Trichloroacetamidothiazol-4-yl)-2-methoxyiminoacetamido]-3-[(carbamoyloxy)methyl]-Δ$^3$-O-2-isocephem-4-carboxylic acid (syn-isomer)

Using benzyl 7-[2-(2-trichloroacetamidothiazol-4-yl)-2-methoxyiminoacetamido-3-[(carbamoyloxy)methyl]-Δ$^3$-O-2-isocephem-4-carboxylate (syn-isomer) (650 mg), anhydrous aluminum chloride (1.74 g, 13 mmol), methylene chloride (60 ml) and nitromethane (20 ml), the title compound (500 mg) was produced in a manner analogous to Example 6.

Light yellow powder mp: >300° C.; discoloration and decomposition begin at 160° C.

NMR (DMSO-d6+CDCl3) δ: 3.97 (3H, s), 3.73–4.17 (2H, m), 4.44–4.73 (1H, m), 4.97 (2H, s), 5.68 (1H, dd), 6.15 (2H, bs), 7.40 (1H, s), 9.32 (1H, d).

EXAMPLE 8

7-[2-(2-Chloroacetamidothiazol-4-yl)-2-methoxyiminoacetamido]-3-[(carbamoyloxy)methyl]-$\Delta^3$-O-2-isocephem-4-carboxylic acid (syn-isomer)

Using benzyl 7-[2-(2-chloroacetamidothiazol-4-yl)-2-methoxyiminoacetamido-3-[(carbamoyloxy)methyl]-$\Delta^3$-O-2-isocephem-4-carboxylate (syn-isomer) (560 mg, 0.94 mmol), anhydrous aluminum chloride (1.9 g, 14.3 mmol), methylene chloride (80 ml) and nitromethane (22 ml), the title compound (330 mg) was produced in a manner analogous to Example 6.

Colorless powder
mp: >300° C.

NMR (DMSO-d6+CDCl3) δ: 3.97 (3H, s), 3.70–4.15 (2H, m), 4.24 (2H, s), 5.04 (2H, s), 6.69 (1H, dd), 6.81 (2H, bs), 7.31 (1H, s), 9.22 (1H, d).

EXAMPLE 9

7-[2-(2-Aminothiazol-4-yl)-2-methoxyiminoacetamido]-3-[(carbamoyloxy)methyl]-$\Delta^3$-O-2-isocephem-4-carboxylic acid (syn-isomer)

Thiourea (160 mg, 2.17 mmol) and sodium acetate (180 mg, 2.17 mmol) were dissolved in water (10 ml), followed by addition of 7-[2-(2-chloroacetamidothiazol4-yl)-2-methoxyiminoacetamido]-3-[(carbamoyloxy)methyl]- $\Delta^3$-O-2-isocephem-4-carboxylic acid (syn-isomer) (350 mg, 0.72 mmol) to give a suspension. The reaction was conducted at room temperature for 24 hours, at the end of which time the nonionic adsorbent resin Diaion HP-20 (manufactured by Mitsubishi Chemical) (7 g) was added. The mixture was adjusted to pH 3.5 with a 10-fold dilution of concentrated hydrochloric acid and a 5% aqueous solution of sodium hydrogen carbonate. The resin was taken, washed with water and eluted with 5%, 10%, 15% and 20% aqueous solutions of isopropyl alcohol. The eluates were combined and concentrated under reduced pressure to give the title compound (150 mg).

Pale yellow powder
mp: 170° C. (discoloration), >300° C.

NMR (DMSO-d6) δ: 3.86 (3H, s), 3.55–4.00 (2H, m), 5.02 (2H, s), 5.52 (1H, dd), 6.48 (2H, bs), 6.75 (1H, s), 7.16 (2H, bs), 9.12 (1H, d).

EXAMPLE 10

Benzyl 7-[2-(2-chloroacetamidothiazol-4-yl)-2-methoxyiminoacetamido]-3-[(1,3,4-thiadiazol-2-yl)thiomethyl]-$\Delta^3$-O-2-isocephem-4-carboxylate (syn-isomer)

To Vilsmeier reagent (1.20 g, 4.3 mmol) was added ethyl acetate (35 ml) to make a suspension, followed by addition of 2-(2-chloroacetamidothiazol-4-yl)-2methoxyiminoacetic acid (syn-isomer) (1.2 g, 4.3 mmol). The reaction was conducted for 40 minutes to make a solution (referred to as solution A).

On the other hand, ethyl acetate (35 ml) was added to benzyl 7-amino-3-[(1,3,4-thiadiazol-2-yl)thiomethyl]-$\Delta^3$-O-2-isocephem-4-carboxylate (1.46 g, 3.6 mmol), followed by addition of trimethylsilylacetamide (2.84 g, 21.7 mmol). The mixture was cooled to −15° C., followed by dropwise addition of the above-mentioned solution A. After completion of addition, the reaction temperature was returned gradually to room temperature over a period of 1 hour. Thereafter, the reaction mixture was poured into water. The ethyl acetate layer was taken, washed with water, 5% aqueous sodium hydrogen carbonate, water and saturated aqueous sodium chloride in that order, dried over anhydrous sodium sulfate, and filtered. The filtrate was concentrated under reduced pressure and the residue was purified by silica gel column chromatography to give the title compound (1.37 g).

Colorless powder
mp: 142° C. (decomposition).

NMR (DMSO-d6) δ: 3.80–4.20 (2H, m), 3.90 (3H, s), 4.37 (2H, s), 5.21 (2H, s), 5.75 (1H, dd), 7.36 (5H, m), 7.44 (1H, s), 9.30 (1H, d), 9.47 (1H, s).

EXAMPLE 11

7-[2-(2-Chloroacetamidothiazol-4-yl)-2-methoxyiminoacetamido]-3-[(1,3,4-thiadiazol-2-yl)thiomethyl]-$\Delta^3$-O-2-isocephem-4-carboxylic acid (syn-isomer)

To benzyl 7-[2-(2-chloroacetamidothiazol-4-yl)-2methoxyiminoacetamido]-3-[(1,3,4-thiadiazol-2-yl)-thiomethyl]-$\Delta^3$-O-2-isocephem-4-carboxylate (syn-isomer) (660 mg, 1 mmol) were added methylene chloride (80 ml) and nitromethane (20 ml) to give a suspension, followed by dropwise addition of a solution of anhydrous aluminum chloride (1.33 g, 10 mmol) in nitromethane (20 ml). After completion of addition, the reaction was conducted for 4 hours. The reaction mixture was poured into ice-water and, after addition of an adequate amount of a 10-fold dilution of conc.hydrochloric acid, extracted three times with ethyl acetate. The ethyl acetate layers were combined, washed with saturated aqueous sodium chloride, dried over anhydrous sodium sulfate, filtered and concentrated under reduced pressure. The residue was washed with diethyl ether to give the title compound (380 mg).

Light orange powder
mp: 174° C. (discoloration), >300° C.

NMR (DMSO-d6) δ: 3.53–4.12 (2H, m), 3.87 (3H, s), 4.34 (2H, s), 5.71 (1H, dd), 7.43 (1H, s), 9.26 (1H, d), 9.47 (1H, s), 12.48 (1H, bs).

EXAMPLE 12

7-[2-(2-Aminothiazol-4-yl)-2-methoxyiminoacetamido]-3-[(1,3,4-thiadiazol-2-yl)thiomethyl]-$\Delta^3$-O-2-isocephem-4-carboxylic acid (syn-isomer)

Thiourea (150 mg, 2 mmol) and sodium acetate (160 mg, 2 mmol) were dissolved in water (6.6 ml), followed by addition of 7-[2-(2-chloroacetamidothiazol-4-yl)-2methoxyiminoacetamido]-3-[(1,3,4-thiadiazol-2-yl)thiomethyl]-$\Delta^3$-O-2-isocephem-4-carboxylic acid (syn-isomer) (380 mg, 0.66 mmol) to give a suspension. The reaction was conducted for 1 day and the nonionic adsorbent resin Diaion HP-20 (7 g) was added thereto. The mixture was adjusted to pH 3.5 with a 10-fold dilution of concentrated hydrochloric acid and a 5% aqueous solution of sodium hydrogen carbonate. The Diaion HP-20 was filtered off and washed with water, followed by successive elution with 5%, 10% and 20% aqueous solutions of isopropyl alcohol. The eluates were combined and concentrated under reduced pressure to give the title compound (160 mg).

Light yellow powder.
mp: 146° C. (discoloration), 158° C. (decomposition).

NMR (DMSO-d6) δ: 3.60–4.13 (2H, m), 3.83 (3H, s), 5.67 (1H, dd), 6.75 (1H, s), 7.13 (2H, bs), 9.13 (1H, d), 9.49 (1H, s)

EXAMPLE 13

1-Acetoxyethyl 7-[2-(2-aminothiazol-4-yl)-2-methoxyiminoacetamido]-3-[(1,3,4-thiadiazol-2-yl)thiomethyl]-$\Delta^3$-O-2-isocephem-4-carboxylate (syn-isomer)

7-[2-(2-Aminothiazol-4-yl)-2-methoxyiminoacetamido]3-[(1,3,4-thiadiazol-2-yl)thiomethyl]-$\Delta^3$-O-2-isocephem-4-carboxylic acid (syn-isomer) (200 mg, 0.4 mmol) was dissolved in an equimolar amount of aqueous sodium hydrogen carbonate and the solution was lyophilized to give a sodium salt. Thereafter, the sodium salt was dissolved in dimethylformamide (DMF) (5 ml) and, under ice-cooling, 1-acetoxybromoethane was added dropwise thereto. After completion of addition, the reaction was conducted for 3 hours. The reaction mixture was poured into water, followed by addition of ethyl acetate. The ethyl acetate layer was taken, washed with water, 5% aqueous sodium hydrogen carbonate and saturated aqueous sodium chloride in that order, dried over anhydrous sodium sulfate, and filtered. The filtrate was concentrated under reduced pressure to give the title compound (50 mg).

Colorless powder
mp: 146° C. (discoloration), 158° C. (decomposition).
NMR (DMSO-d6) δ: 1.46 (3H, d), 2.02 and 2.03 (3H, s), 3.84 (3H, s), 3.90–4.27 (2H, m), 6.78 (1H, s), 6.75–6.97 (1H, m), 9.15 (1H, d), 9.50 (1H, s)

EXAMPLE 14

Benzyl 7-[2-(2-chloroacetamidothiazol-4-yl)-2allyloxyiminoacetamido]-3-[(1,3,4-thiadiazol-2-yl)thiomethyl]-$\Delta^3$-O-2-isocephem-4-carboxylate (syn-isomer)

To Vilsmeier reagent (1.09 g, 4.8 mmol) was added ethyl acetate (40 ml) to make a suspension, followed by addition of 2-(2-chloroacetamidothiazol-4-yl)-2allyloxyiminoacetic acid (syn-isomer) (1.46 g, 4.8 mmol). The reaction was conducted for 30 minutes to make a solution (referred to as solution A).

On the other hand, ethyl acetate (40 ml) was added to benzyl 7-amino-3-[(1,3,4-thiadiazol-2-yl)thiomethyl]-$\Delta^3$-O-2-isocephem-4-carboxylate (1.62 g, 4 mmol), followed by addition of N-trimethylsilylacetamide (3.15 g, 24 mmol). The mixture was cooled to −15° C., followed by dropwise addition of the above-mentioned solution A. After completion of addition, the reaction temperature was returned gradually to room temperature over a period of 1 hour. Thereafter, water was added thereto and the ethyl acetate layer was taken, washed with 5% aqueous sodium hydrogen carbonate, water and saturated aqueous sodium chloride in that order, dried over anhydrous sodium sulfate and filtered. The filtrate was concentrated under reduced pressure to recover a light yellow powder, which was separated and purified by silica gel column chromatography to give the title compound (2.28 g).

Colorless powder
mp: 100° C.–105° C.
NMR (CDCl3) δ: 3.73–4.10 (4H, m), 4.26 (2H, s), 4.63–4.93 (3H, m), 5.28 (2H, s), 5.16–5.60 (3H, m), 5.74–6.20 (1H, m), 7.33 (1H, s), 7.35 (5H, m), 8.99 (1H, s).

EXAMPLE 15

7-[2-(2-Chloroacetamidothiazol-4-yl)-2-allyloxyiminoacetamido]-3-[(1,3,4-thiadiazol-2-yl)thiomethyl]-$\Delta^3$-O-2-isocephem-4-carboxylic acid (syn-isomer)

To benzyl 7-[2-(2-chloroacetamidothiazol-4-yl)-2-allyloxyiminoacetamido]-3-[(1,3,4-thiadiazol-2-yl)thiomethyl]-$\Delta^3$-O-2-isocephem-4-carboxylate (syn-isomer) (2.06 g, 3.3 mmol) was added methylene chloride (240 ml) to give a solution, followed by addition of nitromethane (30 ml) and then by dropwise addition of a solution of anhydrous aluminum chloride (4 g, 30 mmol) in nitromethane (30 ml). After completion of addition, the reaction was conducted for 2.5 hours. The reaction mixture was poured into ice-water and, after addition of an adequate amount of a 10-fold dilution of concentrated hydrochloric acid, extracted twice with ethyl acetate. The oily substance remaining in the aqueous layer was extracted with tetrahydrofuran-ethyl acetate mixture. The extracts were combined, washed with saturated aqueous sodium chloride, dried over anhydrous sodium sulfate, filtered and concentrated under reduced pressure. The residue was washed with diethyl ether to give the title compound (1.1 g).

Light orange powder
mp: 170° C. (discoloration), >250° C.
NMR (DMSO-d6) δ: 3.70–4.13 (4H, m), 4.37 (2H, s), 4.54 (2H, s), 4.58–4.85 (2H, m), 5.09–5.48 (2H, m), 5.73 (1H, dd), 5.70–6.25 (1H, m), 7.45 (1H, s), 9.32 (1H, d), 9.52 (1H, s), 12.83 (1H, s).

EXAMPLE 16

7-[2-(2-Aminothiazol-4-yl)-2-allyloxyiminoacetamido]-3-[(1,3,4-thiadiazol-2-yl)thiomethyl]-$\Delta^3$-O-2-isocephem-4-carboxylic acid (syn-isomer)

Thiourea (250 mg, 3 mmol) and sodium acetate (230 mg, 3 mmol) were dissolved in water (10 ml), followed by addition of 7-[2-(2-chloroacetamidothiazol-4-yl)-2allyloxyiminoacetamido]-3-[(1,3,4-thiadiazol-2-yl)thiomethyl]-$\Delta^3$-O-2-isocephem-4-carboxylic acid (syn-isomer) (600 mg, 1 mmol) to give a suspension. The reaction was conducted overnight and the reaction mixture was filtered. To the filtrate was added the nonionic adsorbent resin Diaion HP-20 (12 g) and the mixture was adjusted to pH 4 with a 10-fold dilution of concentrated hydrochloric acid and a 5% aqueous solution of sodium hydrogen carbonate. The Diaion HP-20 was filtered and washed with water, followed by successive elution with 5%, 10%, 15% and 20% aqueous solutions of isopropyl alcohol. The eluates were combined and concentrated under reduced pressure to give the title compound (70 mg).

Light yellow powder
mp: 160° C. (discoloration), >250° C.
NMR (DMSO-d6) δ: 3.70–4.10 (4H, m), 4.53 (2H, s), 5.17–5.50 (2H, m), 5.68 (1H, dd), 5.70–6.20 (1H, m), 6.76 (1H, s), 7.16 (2H, bs), 9.17 (1H, d), 9.50 (1H, s).

EXAMPLE 17

7-[2-(2-Chloroacetamidothiazol-4-yl)-2-methoxyiminoacetamido]-3-[(1,4,5,6-tetrahydro-4-methyl-5,6-dioxo-1,2,4-triazin-3-yl)thiomethyl]-$\Delta^3$-O-2-isocephem-4-carboxylic acid (syn-isomer)

Benzyl 7-amino-3-[(1,4,5,6-tetrahydro-4-methyl-5,6-dioxo-1,2,4-triazin-3-yl)thiomethyl]-$\Delta^3$-O-2-isocephem-4-carboxylate (0.90 g, 2 mmol) was dissolved in N,N- dimethylformamide (20 ml), followed by addition of 2-(2-chloroacetamidothiazol-4-yl)-2-methoxyiminoacetic acid (syn-isomer) (610 mg, 2.2 mmol) to make a solution. Thereafter, methylene chloride (200 ml) was added, followed by addition of dicyclohexylcarbodiimide (DCC) (450 mg, 2.2 mmol). The reaction was conducted at room temperature for 7 hours and the reaction mixture was concentrated under reduced pressure. To the residue were added methylene chloride (160 ml) and nitromethane (20 ml), followed by addition of a solution of anhydrous aluminum chloride (2.67 g, 20 mmol) in nitromethane (20 ml). The reaction was conducted at room temperature for 1.5 days. Thereafter, the reaction mixture was poured into water and extracted three times with tetrahydrofuran-ethyl acetate mixture. This extract was further extracted with three portions of 5% a aqueous solution of sodium hydrogen carbonate. To the extract was added a 10-fold dilution of concentrated hydrochloric acid to make pH 2 and the mixture was extracted three times with tetrahydrofuranethyl acetate mixture. The extracts were combined, washed twice with saturated aqueous sodium chloride, dried over anhydrous sodium sulfate and filtered. The filtrate was concentrated under reduced pressure to give the title compound (460 mg).

Light orange powder mp: 167° C. (discoloration), >300° C.

NMR (DMSO-d6) δ: 3.32 (3H, s), 3.35–3.75 (2H, m), 3.91 (3H, s), 4.66 (2H, s), 5.73 (1H, dd), 7.47 (1H, s), 9.30 (1H, d), 12.42 (1H, bs).

EXAMPLE 18

7-[2-(2-Aminothiazol-4-yl)-2-methoxyiminoacetamido]-3-[(1,4,5,6-tetrahydro-4-methyl-5,6-dioxo-1,2,4-triazin-3-yl)thiomethyl]-Δ$^3$-O-2-isocephem-4-carboxylic acid (syn-isomer)

Thiourea (130 mg, 1.5 mmol) and sodium acetate (120 mg, 1.5 mmol) were dissolved in water (5 ml), followed by addition of 7-[2-(2-chloroacetamidothiazol-4-yl)-2-methoxyiminoacetamido]-3-[(1,4,5,6-tetrahydro-4-methyl-5,6-dioxo-1,2,4-triazin-3-yl)thiomethyl] Δ$^3$-O-2-isocephem-4-carboxylic acid (syn-isomer) (310 mg, 0.5 mmol) to give a suspension. The reaction was conducted overnight and the reaction mixture was filtered. To the filtrate was added the nonionic absorbent resin Diaion HP-20 (6 g) and the mixture was adjusted to pH 3 with a 10-fold dilution of concentrated hydrochloric acid. The diaion HP-20 was filtered, followed by successive elution with 0 to 30% aqueous solution of isopropanol. The eluates were lyophilized to give the title compound (70 mg).

Light orange-red powder mp: 190° C. (discoloration), >300° C.

NMR (DMSO-d6) δ: 3.16 (3H, s), 3.85 (3H, s), 380–(2H, m), 5.70 (1H, dd), 6.77 (1H, s), 7.16 (2H, bs), 9.17 (1H, d), 12.43 (1H, bs).

EXAMPLE 19

7-2-(Thiazol-4-yl)-2-tert-butoxycarbonylmethoxyiminoacetamido]-Δ$^3$-O-2-isocephem-4-carboxylic acid (syn-isomer)

Benzyl 7-azido-Δ$^3$-O-2-isocephem-4-carboxylate (1.20 g, 4.00 mmol) was suspended in ethanol (150 ml), followed by addition of palladium chloride (0.35 g, 2.00 mmol). Catalytic reduction was conducted at room temperature and a hydrogen pressure of 3 kg/cm$^2$. After 1 hour, the catalyst was filtered off and the filtrate was concentrated to dryness. The residue was suspended in ethyl acetate (20 ml), followed by addition of monotrimethylsilylacetamide (3.67 g, 28.00 mmol). The mixture was stirred at 35° to 40° C. for 30 minutes to give a homogeneous solution (referred to as solution A).

On the other hand, 2-(thiazol-4-yl)-2-tert-butocycaronylmethoyiminoacetic acid (syn-isomer) (1.26 g, 4.40 mmol) was added to a solution of Vilsmeier reagent (1.09 g, 4.84 mmol) in ethyl acetate (20 ml) and the mixture was stirred under ice-cooling for 20 minutes to give a homogeneous solution. This solution was added to the above-mentioneed solution A and the reaction was allowed to proceed at −10° C. for 3 hours and then at room temperature for 12 hours. To the reaction mixture was added water, and the organic layer was separated and extracted with a 5% aqueous solution of sodium hydrogen carbonate. The aqueous layer was adjusted to pH 2 with a 10-fold dilution of concentrated hydrochloric acid and extracted with ethyl acetate. The ethyl acetate extract was washed with saturated aqueous sodium chloride and dried over anhydrous magnesium sulfate. The magnesium sulfate was filtered off and the solvent was distilled off. The residue was recrystalized from ethyl acetate-hexane mixture to give the title compound (0.42 g).

White powder mp: 178° C. (decomposition).

NMR (CDCl$_3$) δ: 1.46 (9H, s), 3.8–4.1 (2H, m), 4.5–4.8 (3H, m), 5.75 (1H, dd), 7.42 (1H, s), 7.84 (1H, d), 8.55 (1H, d), 8.88 (1H, d).

EXAMPLE 20

7-[2-(Thiazol-4-yl)-2-carboxymethoxyiminoacetamido]-Δ$^3$-O-2-isocephem-4-carboxylic acid (syn-isomer)

7-[2-(Thiazol-4-yl)-2-tert-butoxycarbonylmethoxyiminoacetamido]-Δ$^3$-O-2-isocephem-4-carboxylic acid (syn-isomer) (0.68 g, 1.50 mmol) was dissolved in methylene chloride (100 ml)-nitromethane (20 ml) mixture, followed by addition of anhydrous aluminum chloride (0.80 g, 6.02 mmol). After 2 minutes of stirring, the mixture was poured into ice-water, followed by addition of a 10-fold dilution of concentrated hydrocloric acid. To the aqueous layer was added the nonionic absorbent resin Diaion HP-20 (30 g), and the mixture was adjusted to pH 1.8 with saturated aqueous sodium hydrogen carbonate. The resin was filtered off, washed with dilute hydrochloric acid (pH 1.8) and packed into a column, and programmed elution was carried out using water (200 ml) and a 30% aqueous solution of isopropyl alcohol. The eluate was monitored by liquid chromathography. The desired fractions were combined and concentrated to about 5 ml. The resulting crystalline precipitate was collected by filtration and washed with cold water and then with ethanol to give the title compound (0.38 g).

mp: 197°–200° C. (decomposition).

NMR (DMSO-d6) δ: 3.7–4.1 (2H, m), 4.4–4.9 (3H, m), 5.78 (1H, dd), 7.38 (1H, s), 8.02 (1H, d), 9.17 (1H, d), 9.39 (1H, d).

EXAMPLE 21

Benzhydryl 7-[2-(2-tritylaminothiazol-4-yl)-2-propargyloxyiminoacetamido]-3-[(1,3,4-thiadiazol-2-yl)thiomethyl]-Δ$^3$-O-2-isocephem-4-carboxylate (syn-isomer)

Benzhydryl 7-amino-3-[(1,3,4-thiadiazol-2-yl)thiomethyl]-Δ$^3$-O-2-isocephem-4-carboxylate (1.21 g, 2.52 mmol), 2-(2-tritylaminothiazol-4-yl)-2-propargyloxyiminoacetic acid (syn-isomer) (1.40 g, 3.00 ml) and 1-hydroxybenztriazole (0.41 g, 3.00 mmol) were dissolved in methylene chloride (100 ml)-dimethylformamide (DMF, 10 ml) mixture and, under ice-cooling, dicyclohexylcarbodiimide (DCC) (0.62 g, 3.00 mmol) was added. The mixture was stirred at the same temperature for 2 hours and then at room temperature for 15 hours and filtered. The filtrate was washed successively with a 5% aqueous solution of sodium hydrogen carbonate, 0.5 M citric acid and saturated aqueous sodium chloride and dried over anhydrous sodium sulfate. The solvent was then distilled off and the residue was subjected to silica gel column chromatography [eluent: chloroform-hexane (3:1)] for separation and purification, followed by recrystallization from ethyl acetate-diethyl ether mixture to give the title compound (1.24 g).

mp: 186° C. (decomposition).

NMR (CDCl$_3$) δ: 2.54 (1H, m), 3.96 (2H, m), 4.4–4.9 (5H, m), 5.51 (1H, dd), 6.64 (1H, s), 6.89 (1H, s), 7.15–7.6 (25H, m), 8.87 (1H, s).

EXAMPLE 22

7-[2-(2-Aminothiazol-4-yl)-2-propargyloxyiminoacetamido]-3-[1,3,4-thiadiazol-2-yl)thiomethyl]-Δ$^3$-O-2-isocephem-4-carboxylic acid trifluoroacetate (syn-isomer)

In the presence of anisole (0.2 ml), benzhydryl 7-[2-(2-tritylaminothiazol-4-yl)-2-propargyloxyiminoacetamido]-3-[(1,3,4-thiadiazol-2-yl)thiomethyl]-Δ$^3$-O-2-isocephem-4-carboxylate (syn-isomer) (0.20 g, 0.22 mmol) was treated with trifluoroacetic acid under ice-cooling for 10 minutes and diethyl ether was added thereto. The resulting powder was filtered off and washed thoroughly with diethyl ether to give the title compound (0.08 g).

mp: 127° C. (coloration), 137°–141° C. (decomposition).

NMR (DMSO-d6) δ: 3.49 (1H, m), 3.7–4.1 (2H, m), 4.3–4.9 (5H, m), 5.69 (1H, dd), 6.84 (1H, s), 9.27 (1H, d), 9.52 (1H, s).

EXAMPLE 23

Benzhydryl 7-[2-(2-tritylaminothiazol-4-yl)-2-[(1-tritylpyrazol-3-yl)methoxyiminoacetamido]-3-[(1,3,4-thiadiazol-2-yl)thiomethyl]-Δ$^3$-O-2-isocephem-4-carboxylate (syn-isomer)

Benzhydryl 7-amino-3-[(1,3,4-thiadiazol-2-yl)thiomethyl]-Δ$^3$-O-2-isocephem-4-carboxylate (1.41 g, 2.93 mmol), 2-(2-tritylaminothiazol-4-yl)-2-(1-tritylpyrazol-3-yl)methoxyiminoacetic acid (syn-isomer) (1.77 g, 2.35 mmol) and 1-hydroxybenztriazole (0.32 g, 2.35 mmol) were dissolved in methylene chloride (100 ml) and, under ice-cooling, dicyclohexylcarbodiimide (DCC) (0.48 g, 2.35 mmol) was added. The mixture was stirred for 2 hours and then at room temperature for 16 hours and filtered. The filtrate was washed with 0.5 M citric acid, 5% aqueous sodium hydrogen carbonate and saturated aqueous sodium chloride and dried over anhydrous sodium sulfate. The solvent was then distilled off and the residue was subjected to silica gel column chromatography [eluent: chloroform-hexane (2:1)] for separation and purification and reprecipitated from ethyl acetate-hexane mixture to give the title compound (1.21 g).

Light yellow powder mp: 135°–138° C. NMR (CDCl$_3$) δ: 3.5–3.9 (2H, m), 4.1–4.35 (2H, m), 4.65–4.9 (2H, m), 5.41 (2H, s), 6.16 (1H, d), 6.61 (1H, s), 6.88 (1H, s), 6.9–7.6 (41H, m), 8.87 (1H, s).

EXAMPLE 24

7-[2-(2-Aminothiazol-4-yl)-2-[(pyrazol-3-yl)methoxyiminoacetamido]-3-[(1,3,4-thiadiazol-2-yl)thiomethyl]-Δ$^3$-O-2-isocephem-4-carboxylic acid dihydrochloride (syn-isomer)

In the presence of anisole (0.25 ml), benzhydryl 7-[2-(2-tritylaminothiazol-4-yl)-2-[(1-tritylpyrazol-3-yl)methoxyiminoacetamido]-3-[(1,3,4-thiadiazol-2-yl)thiomethyl]-Δ$^3$-O-2-isocephem-4-carboxylate (syn-isomer) (0.25 g, 0.21 mmol) was treated with trifluoroacetic acid (2.5 ml) under ice-cooling for 10 minutes. To the reaction mixture was added 4 N solution of hydrogen chloride in ethyl acetate (0.51 ml, 2.06 mmol), followed by addition of diethyl ether. The resulting powder was collected by filtration and washed thoroughly with acetone to give the title compound (0.10 g).

mp: 140° C. (coloration), >300° C.

NMR (DMSO-d6) δ: 3.86 (2H, m), 4.2–4.7 (3H, m), 5.20 (2H, s), 5.71 (1H, dd), 6.41 (1H, d), 6.97 (1H, s), 7.65 (1H, d), 9.49 (1H, d), 9.54 (1H, s).

EXAMPLE 25

Benzyl 7-[2-(2-chloroacetamidothiazol-4-yl)-2-cyclopentyloxyiminoacetamido]-3-[(1,3,4-thiadiazol-2-yl)thiomethyl]-Δ$^3$-O-2-isocephem-4-carboxylate (syn-isomer)

A solution of benzyl 7-amino-3-[(1,3,4-thiadiazol-2-yl)thiomethyl]-Δ$^3$-O-2-isocephem-4-carboxylate (0.86 g, 2.1 mmol) and 2-(2-chloroacetamidothiazol-4-yl)-2-cyclopentyloxyiminoacetic acid (syn-isomer) (0.85 g, 2.6 mmol) in a mixture of methylene chloride (15 ml) and dimethylformamide (3 ml) was stirred under ice-cooling. To this solution was added dicyclohexylcarbodiimide (DCC) (0.53 g, 2.6 mmol) all at once and the reaction was allowed to proceed overnight. The precipitate was filtered off and the filtrate was washed with water and dried over anhydrous magnesium sulfate. After removal of the magnesium sulfate by filtration, the filtrate was concentrated and the residue was purified by silica gel column chromatography [eluent: hexane-ethyl acetate (1:1)] to give the title compound (0.84 g).

NMR (CDCl3) δ: 1.54–1.88 (8H, m), 3.91–4.15 (2H, m), 4.22 (2H, s), 4.54 (1H, d), 4.66 (1H, d), 4.39–4.83 (1H, m), 5.26 (2H, s), 5.46 (1H, dd), 7.37 (1H, s), 7.38 (5H, bs), 7.64 (1H, d), 9.00 (1H, s).

EXAMPLE 26

7-[2-(2-Chloroacetamidothiazol-4-yl)-2-cyclopentyloxyiminoacetamido]-3-[(1,3,4-thiadiazol-2-yl)thiomethyl]-Δ$^3$-O-2-isocephem-4-carboxylic acid (syn-isomer)

To a solution of benzyl 7-[2-(2-chloroacetamidothiazol-4-yl)-2-cyclopentyloxyiminoacetamido]-3-[(1,3,4-thiadiazol-2-yl)thiomethyl]-Δ$^3$-O-2-isocephem-4-carboxylate (syn-isomer) (0.83 g, 1.2 mmol) in nitromethane (10 ml)-methylene chloride (80 ml) mixture was added dropwise at room temperature a solution of anhydrous aluminum chloride (1.5 g) in nitromethane (10 ml) and the reaction was allowed to proceed overnight. The mixuure was poured into ice-water and, after addition of a 10-fold dilution of concentrated hydrochloric acid, extraction was carried out with ethyl acetatetetrahydrofuran mixture. The organic layer was washed with saturated aqueous sodium chloride, dried over anhydrous magnesium sulfate and filtered. The filtrate was concentrated and the residue was crystallized with diethyl ether to give the title compound (0.63 g).

Light yellow powder

NMR (DMSO-d6) δ: 1.50–1.82 (8H, m), 4.37 (2H, s), 4.54 (2H, s), 3.93–4.72 (4H, m), 5.70 (1H, dd), 7.44 (1H, s), 9.27 (1H, d), 9.56 (1H, s), 12.84 (1H, s).

EXAMPLE 27

Benzyl 7-[2-(2-chloroacetamidothiazol-4-yl)-2-ethoxyiminoacetamido]-3-[(1,3,4-thiadiazol-2-yl)thiomethyl]-$\Delta^3$-O-2-isocephem-4-carboxylate (syn-isomer)

Under ice-cooling, dicyclohexylcarbodiimide (DCC) (0.89 g, 4.31 mmol) was added all at once to a solution composed of benzyl 7-amino-3-[(1,3,4-thiadiazol-2-yl)thiomethyl]-$\Delta^3$-O-2-isocephem-4-carboxylate (1.40 g, 3.47 mmol), 2-(2-chloroacetamidothiazol-4-yl)-2-ethoxyiminoacetic acid (syn-isomer) (1.24 g, 4.25 mmol), N,N-dimethylformamide (6 ml) and methylene chloride (60 ml) and the reaction was conducted overnight. Thereafter, the mixture was treated in a manner analogous to Example 25, whereby the title compound (0.96 g) was obtained.

NMR (CDCl3) δ: 1.25 (3H, t), 4.05 (2H, s), 3.84–4.51 (5H, m), 4.45 (1H, d), 4.71 (1H, d), 5.27 (2H, s), 5.44 (1H, dd), 7.25–7.45 (7H, m), 9.00 (1H, s).

EXAMPLE 28

7-[2-(2-Chloroacetamidothiazol-4-yl)-2-ethoxyiminoacetamido]-3-[(1,3,4-thiadiazol-2-yl)thiomethyl-]-$\Delta^3$-O-2-isocephem-4-carboxylic acid (syn-isomer)

To a solution of benzyl 7-[2-(2-chloroacetamidothiazol-4-yl)-2-ethoxyiminoacetamido]-3-[(1,3,4-thiadiazol-2-yl)thiomethyl]-$\Delta^3$-O-2-isocephem-4-carboxylate (syn-isomer) (0.96 g, 1.42 mmol) in nitromethane (10 ml)-methylene chloride (80 ml) mixture was added dropwise at room temperature a solution of anhydrous aluminum chloride (1.70 g) in nitromethane and the reaction was conducted overnight. Thereafter, the mixture was treated in a manner analogous to Example 26, whereby the title compound (0.74 g) was obtained.

Yellow solid

NMR (DMSO-d6) δ: 1.25 (3H, t), 3.83–4.64 (5H, m), 4.12 (2H, s), 4.53 (2H, s), 5.63 (1H, dd), 7.46 (1H, s), 8.95 (1H, d), 9.56 (1H, s).

EXAMPLE 29

7-[2-(2-Aminothiazol-4-yl)-2-ethoxyiminoacetamido]-3-[(1,3,4-thiadiazol-2-yl)thiomethyl]-$\Delta^3$-O-2-isocephem-4-carboxylic acid (syn-isomer)

7-[2-(2-Chloroacetamidothiazol-4-yl)-2-ethoxyiminoacetamido]-3-[(1,3,4-thiadiazol-2-yl)thiomethyl]-$\Delta^3$-2-isocephem-4-carboxylic acid (syn-isomer) (0.40 g, 0.68 mmol) was dissolved in N,N-dimethylacetamide (DMA) (6 ml) and, at room temperature, thiourea (0.13 g, 1.71 mmol) was added thereto. The reaction was conducted overnight. The mixture was poured into ice-water and the insoluble matter was filtered off. The insoluble matter was washed with aqueous sodium hydrogen carbonate. The aqueous layer was adjusted to pH 4 and adsorbed on the nonionic adsorbent resin Diaion HP-20. The adsorbent resin was washed with water and elution was carried out with water-isopropyl alcohol (9:1) mixture. The eluate was lyophilized to give the title compound (20 mg).

Light pink powder

NMR (DMSO-d6) δ: 1.20 (3H, t), 3.84–4.60 (3H, m), 4.10 (2H, q), 4.54 (2H, s), 5.69 (1H, dd), 6.78 (1H, s), 7.31 (2H, bs), 9.16 (1H, d), 9.57 (1H, s).

EXAMPLE 30

Benzhydryl 7-[2-(2-formamidothiazol-4-yl)-2-ethoxyiminoacetamido]-3-[(1,3,4-thiadiazol-2-yl)thiomethyl]-$\Delta^3$-O-2-isocephem-4-carboxylate (syn-isomer)

To a solution composed of benzhydryl 7-amino-3-[(1,3,4-thiadiazol-2-yl)thiomethyl]-$\Delta^3$-O-2-isooephem-4-carboxylate (1.55 g, 3.23 mmol), 1-hydroxybenztriazole (HOBT) (0.15 g, 1.12 mmol) and methylene chloride (100 ml) were added 2-(2-formamidothiazol-4-yl)-2-ethoxyiminoacetic acid (syn-isomer) (0.80 g, 3.29 mmol) and N,N-dimethylformamide (DMF) (2 ml) and the mixture was stirred under ice-cooing. To the mixture was added all at once dicyclohexylcarbodiimide (DCC) (0.68 g, 3.30 mmol) and the reaction was allowed to proceed overnight. The precipitate was filtered off and the filtrate was washed with water, aqueous sodium hydrogen carbonate, dilute hydrochloric acid, aqueous sodium hydrogen carbonate and saturated aqueous sodium chloride in that order and dried over anhydrous magnesium sulfate. After removal of the magnesium sulfate by filtration, the filtrate was concentrated and the residue was subjected to silica gel column chromatography [eluent: ethanol-chloroform (2:98)] for separation and purification to give the title compound (1.87 g).

Light yellow amorphous powder

NMR (CDCl3) δ: 1.25 (3H, t), 3.97–4.08 (2H, m), 4.17 (2H, q), 4.52–4.73 (3H, m), 5.63 (1H, dd), 6.91 (1H, s), 7.27–7.66 (12H, m), 8.50 (1H, s), 8.97 (1H, s).

EXAMPLE 31

7-[2-(2-Formamidothiazol-4-yl)-2-ethoxyiminoacetamido]-3-[(1,3,4-thiadiazol-2-yl)thiomethyl-]-$\Delta^3$-O-2-isocephem-4-carboxylic acid (syn-isomer)

Benzhydryl 7-[2-(2-formamidothiazol-4-yl)-2-ethoxyiminoacetamido-]-3-[(1,3,4-thiadiazol-2-yl)thiomethyl]-$\Delta^3$-O-2-isocephem-4-carboxylate (syn-isomer) (0.70 g, 0.99 mmol) was suspended in anisole (0.70 ml) and, under ice-cooling, trifluoroacetic acid (TFA) (7.0 ml) was added. The reaction was conducted for 10 minutes, followed by addition of diethyl ether (25 ml) to give crystals, which were collected by filtration, washed with diethyl ether and dried under reduced pressure to give the title compound (0.46 g).

Light yellowish white powder mp: 135°–137° C. (decomposition).

NMR (DMSO-d6) δ: 1.22 (3H, t), 3.85–4.03 (2H, m), 4.15 (2H, q), 4.48–4.72 (1H, m), 4.54 (2H, s), 5.75 (1H, dd), 7.45 (1H, s), 8.51 (1H, s), 9.30 (1H, d), 9.56 (1H, s), 12.55 (1H, s)

EXAMPLE 32

Benzhydryl 7-[2-(2-formamidothiazol-4-yl)-2-(2-chloroethoxy)iminoacetamido-]-3-[(1,3,4-thiadiazol-2-yl)thiomethyl]-$\Delta^3$-O-2-isocephem-4-carboxylate (syn-isomer)

In a manner analogous to Example 30 except that benzhydryl 7-amino-3-[(1,3,4-thiadiazol-2-yl)thiomethyl]-$\Delta^3$-O-2-isocephem-4-carboxylate (1.18 g, 2.46 mmol), 1-hydroxybenzotriazole (HOBT) (0.15 g, 1.12 mmol), 2-(2-formamidothiazol-4-yl)-2-(2-chloroethoxy)iminoacetic acid (syn-isomer) (0.69 g, 2.48 mmol), dicyclohexylcarbodiimide (DCC) (0.52 g, 2.52 mmol), dimethylformamide (DMF) (2 ml) and methylene chloride (75 ml) were used, there was obtained the title compound (1.33 g).

Light yellow amorphous powder

NMR (CDCl$_3$) δ: 3.68 (2H, t), 3.83–4.16 (2H, m), 4.36 (2H, t), 4.32–4.71 (3H, m), 5.56 (1H, dd), 6.89 (1H, s), 7.29–7.68 (12H, m), 8.53 (1H, s), 8.97 (1H, s), 10.71 (1H, bs).

EXAMPLE 33

7-[2-(2-Formamidothiazol-4-yl)-2-(2-chloroethoxy)iminoacetamido]-3-[(1,3,4-thiadiazol-2-yl)thiomethyl]-$\Delta^3$-O-2-isocephem-4-carboxylic acid (syn-isomer)

In a manner analogous to Example 31 except that benzhydryl 7-[2-(2-formamidothiazol-4-yl)-2-(2-chloroethoxy)iminoacetamido]-3-[(1,3,4-thiadiazol-2-yl)thiomethyl]-$\Delta^3$-O-2-isocephem-4-carboxylate (syn-isomer) (0.50 g, 0.68 mmol), anisole (0.50 ml) and trifluoroacetic acid (5.0 ml) were used, there was obtained the title compound (0.35 g).

Light yellowish white powder mp: 133°–136° C. (decomposition).

NMR (DMSO-d6) δ: 3.72–4.10 (2H, m), 3.82 (2H, t), 4.38 (2H, t), 4.50–4.71 (1H, m), 4.54 (2H, s), 5.74 (1H, dd), 7.51 (1H, s), 8.52 (1H, s), 9.35 (1H, d), 9.56 (1H, s), 12.56 (1H, s).

EXAMPLE 34

7-[2-(2-Aminothiazol-4-yl)-2-(2-chloroethoxy)iminoacetamido]-3-[(1,3,4-thiadiazol-2-yl)thiomethyl]-$\Delta^3$-O-2-isocephem-4-carboxylic acid (syn-isomer)

Under ice-cooling, a mixture of concentrated hydrochloric acid (0.30 ml) and methanol (1 ml) was added dropwise to a solution composed of 7-[2-(2-formamidothiazol-4-yl)-2-(2-chloroethoxy)iminoactamido]-3-[(1,3,4-thiadiazol-2-yl)thiomethyl]-$\Delta^3$-O-2-isocephem-4-carboxylic acid (syn-isomer) (0.33 g, 0.57 mmol), methanol (4 ml) and tetrahydrofuran (1 ml) and the reaction was allowed to proceed for 2 hours. The solvent was then distilled off under reduced pressure and the residue was dissolved by addition of a 5% aqueous solution of sodium hydrogen carbonate (30 ml). The solution was washed with ethyl acetate (50 ml). The aqueous layer was taken and the insoluble matter was filtered off, after which the pH was adjusted to 3 with a 10-fold dilution of concentrated hydrochloric acid to give a precipitate. The precipitate was collected by filtration, washed with water and dried under reduced pressre to give the title compound (0.20 g).

Light yellow powder mp: 125° C. (decoloration), >150° C. (decomposition).

NMR (DMSO-d6) δ: 3.71–4.13 (2H, m), 3.79 (2H, t), 4.30 (2H, t), 4.45–4.65 (1H, m), 4.54 (2H, s), 5.71 (1H, dd), 6.83 (1H, s), 7.31 (2H, bs), 9.25 (1H, d), 9.56 (1H, s).

EXAMPLE 35

Benzhydryl 7-[2-(2-tritylaminothiazol-4-yl)-2-cyclopropylmethyloxyiminoacetamido-]-3-(1,3,4-thiadiazol-2-yl)thiomethyl]-$\Delta^3$-O-2-isocephem-4-carboxylate (syn-isomer)

Benzhydryl 7-amino-3-[(1,3,4-thiadiazol-2-yl)thiomethyl]-$\Delta^3$-O-2-isocephem-4-carboxylate (1.44 g, 3 mmol) and 2-(2-tritylaminothiazol-4-yl)-2-cyclopropylmethyloxyiminoacetic acid (syn-isomer) (1.60 g, 3.3 mmol) were dissolved in methylene chloride (90 ml). Under ice-cooling, dicyclohexylcarbodiimide (DCC) (680 mg, 3.3 mmol) was added to the solution, and the reaction was allowed to proceed at room temperature overnight. The reaction mixture was filtered and the filtrate was concentrated under reduced pressure. Separation and purification of the residue by silica gel column chromatography (eluent: methylene chloride) gave the title compound (1.95 g).

Light yellow powder mp: 124°–127° C.

NMR (CDCl$_3$) δ: 0.14–0.69 (4H, m), 0.90–1.32 (1H, m), 3.94–4.13 (4H, m), 4.36–4.92 (1H, m), 4.52 (1H, d), 4.69 (1H, d), 5.49 (1H, dd), 6.68 (1H, s), 6.90 (1H, s), 7.28 (15H, s), 7.14–7.61 (10H, m), 8.88 (1H, s).

EXAMPLE 36

7-[2-(2-Aminothiazol-4-yl)-2-cyclopropylmethyloxyiminoacetamido]-3-[(1,3,4-thiadiazol-2-yl)thiomethyl]-$\Delta^3$-O-2-isocephem-4-carboxylic acid trifluoroacetate (syn-isomer)

To benzhydryl 7-[2-(2-tritylaminothiazol-4-yl)-2-cyclopropylmethyloxyiminoacetamido]-3-[(1,3,4,-thiadiazol-2-yl)thiomethyl]-$\Delta^3$-O-2-isocephem-4-carboxylate (syn-isomer) (550 mg, 0.6 mmol) was added anisole (0.55 ml) and, under ice-cooling, trifluoroacetic acid (5.5. ml) was added thereto. The mixture was stirred for 10 minutes, followed by addition of diethyl ether (40 ml) to give crystals, which were collected by filtration to obtain the title compound (210 mg).

Pale yellow powder mp: 125°–142° C. (decomposition); discoloration begins at 125° C.

NMR (DMSO-d6) δ: 0.14–0.69 (4H, m), 0.85–1.36 (1H, m), 3.71–4.26 (2H, m), 3.92 (2H, d), 4.33–4.75 (1H, m), 4.54 (2H, s), 5.78 (1H, dd), 6.81 (1H, s), 9.25 (1H, d), 9.51 (1H, s).

EXAMPLE 37

Benzhydryl 7-[2-(2-tritylaminothiazol-4-yl)-2-[(2-butenyl)oxyimino]acetamido]-3-[(1,3,4-thiadiazol-2-yl)thiomethyl]-$\Delta^3$-O-2-isocephem-4-carboxylate (syn-isomer)

Benzhydryl 7-amino-3-[(1,3,4-thiadiazol-2-yl)thiomethyl]-$\Delta^3$-O-2-isocephem-4-carboxylate (1.44 g, 3 mmol) and 2-(2-tritylaminothiazol-4-yl)-2-[(2-butenyl)oxyimino]acetic acid (syn-isomer) (1.60 g, 3.3 mmol) were dissolved in methylene chloride (90 ml). Dicyclohexylcarbodiimide (DCC) (680 mg, 3.3 mmol) was added to the solution under ice-cooling and the reaction was conducted at room temperature overnight. The mixture was filtered and the filtrate was concentrated under reduced pressure. The residue was subjected to silica gel column chromatography (eluent: methylene chloride) for separation and purification to give the title compound (1.86 g).
Light yellow powder
mp: 118°–124° C.
NMR (CDCl$_3$) δ: 1.60–1.75 (3H, m), 3.70–4.06 (2H, m), 4.49–4.79 (3H, m), 4.53 (1H, d), 4.72 (1H, d), 5.50 (1H, dd), 5.58–5.78 (2H, m), 6.63 (1H, s), 6.88 (1H, s), 7.26 (15H, s), 7.16–7.58 (10H, m), 8.85 (1H, s).

EXAMPLE 38

7-[2-(2-Aminothiazol-4-yl)-2-[(2-butenyl)oxyimino]acetamido]-3-[(1,3,4-thiadiazol-2-yl)thiomethyl]-Δ$^3$-O-2-isocephem-4-carboxylic acid trifluoroacetate (syn-isomer)

To benzhydryl 7-[2-(2-tritylaminothiazol-4-yl)-2-[(2-butenyl)oxyimino]acetamido]-3-[(1,3,4-thiadiazol-2-yl)thiomethyl]-Δ$^3$-O-2-isocephem-4-carboxylate (syn-isomer) (550 mg, 0.6 mmol) was added anisole (0.55 ml) and, under ice-cooling, trifluoroacetic acid (5.5 ml) was added thereto. The mixture was stirred for 10 minutes, followed by addition of diethyl ether (40 ml) to give crystals, which were collected by filtration to obtain the title compound (230 mg).
Pale yellow powder
mp: 123°–127° C. (decomposition); Discoloration begins at 123° C.
NMR (DMSO-d6) δ: 1.44–1.89 (3H, m), 3.63–4.17 (2H, m), 4.54 (2H, s), 4.47–5.00 (3H, m), 5.43–5.93 (2H, m), 5.69 (1H, dd), 6.81 (1H, s), 9.19 (1H, d), 9.51 (1H, s).

EXAMPLE 39

Benzhydryl 7-[2-(2-tritylaminothiazol-4-yl)-2-[(3-butenyl)oxyimino]acetamido]-3-[(1,3,4-thiadiazol-2-yl)thiomethyl]-Δ$^3$-O-2-isocephem-4-carboxylate (syn-isomer)

Benzhydryl 7-amino-3-[(1,3,4-thiadiazol-2-yl)thiomethyl]-Δ$^3$-O-2-isocephem-4-carboxylate (970 mg, 2 mmol) and 2-(2-tritylaminothiazol-4-yl)-2-[(3-butenyl)oxyimino]acetic acid (syn-isomer) (1.16 g, 2.4 mmol) were dissolved in methylene chloride (60 ml). Under ice-cooling, dicyclohexylcarbodiimide (DCC) (500 mg (2.4 mmol) was added to the solution and the reaction was allowed to proceed at room temperature overnight. The mixture was filtered and the filtrate was concentrated under reduced pressure. The residue was subjected to silica gel column chromatography [eluent: methylene chloride-ethyl acetate (20:1)] for separation and purification to give the title compound (1.32 g).
Light yellow powder
mp: 117°–124° C.
NMR (CDCl$_3$) δ: 2.45 (2H, q), 4.33 (2H, t), 4.49 (1H, d), 4.69 (1H, d), 4.92–5.22 (2H, m), 5.45 (1H, dd), 5.53–6.03 (1H, m), 6.69 (1H, s) 6.88 (1H, s), 7.27 (15H, s), 7.01–7.62 (10H, m), 8.58 (1H, s).

EXAMPLE 40

7-[2-(2-Aminothiazol-4-yl)-2-[(3-butenyl)oxyimino]acetamido]-3-[(1,3,4-thiadiazol-2-yl)thiomethyl]-Δ$^3$-O-2-isocephem-4-carboxylic acid trifluoroacetate (syn-isomer)

To benzhydryl 7-[2-(2-tritylaminothiazol-4-yl)-2-[(3-butenyl)oxyimino]acetamido]-3-[(1,3,4-thiadiazol-2-yl)thiomethyl]-Δ$^3$-O-2-isocephem-4-carboxylate (syn-isomer) (550 mg, 0.6 mmol) was added anisole (0.55 ml) and, under ice-cooling, trifluoroacetic acid (5.5 ml) was added thereto. The mixture was stirred for 10 minutes, followed by addition of diethyl ether (40 ml) to give crystals, which were collected by filtration to obtain the title compound (220 mg).
Pale yellow powder
mp: 118°–130° C. (decomposition); Discoloration begins at 118° C.
NMR (DMSO-d6) δ: 2.25–2.69 (2H, m), 3.51–4.14 (2H, m), 4.13 (2H, t), 4.33–4.75 (1H, m), 4.54 (2H, s), 4.92–5.27 (2H, m), 5.66–6.10 (1H, m), 5.70 (1H, dd), 6.85 (1H, s), 9.27 (1H, d), 9.56 (1H, s).

EXAMPLE 41

Benzhydryl 7-[2-(2-tritylaminothiazol-4-yl)-2cyanomethyloxyiminoacetamido-]-3-[(1,3,4-thiadiazol-2-yl)thiomethyl]-Δ$^3$-O-2-isocephem-4-carboxylate (syn-isomer)

Benzhydryl 7-amino-3-[(1,3,4-thiadiazol-2-yl)thiomethyl]-Δ$^3$-O-2-isocephem-4-carboxylate (1.16 g, 2.4 mmol) was dissolved in methylene chloride (100 ml). 2-(2-Tritylaminothiazol-4-yl)-2-cyanomethyloxyiminoacetic acid (syn-isomer) (1.31 g, 2.8 mmol) was added to the solution to make a suspension and dimethylformamide (10 ml) was added thereto to give a homogeneous solution. Under ice-cooling, dicyclohexylcarbodiimide (DCC) (0.57 g, 2.7 mmol) was added to the mixture and the reaction was allowed to proceed at room temperature overnight. The mixture was filtered and the filtrate was washed four times with saturated aqueous sodium chloride and dried over anhydrous magnesium sulfate. The magnesium sulfate was filtered off and the filtrate was concentrated under reduced pressure. The residue was subjected to silica gel column chromatography [eluent: methylene chloride-ethyl acetate (10:1)] for separation and purification to give the title compound (1.25 g).
Light yellow powder
mp: 134°–135° C.
NMR (CDCl$_3$) δ: 3.86–4.02 (2H, m), 4.35–4.80 (1H, m), 4.55 (2H, s), 4.89 (2H, s), 5.47 (1H, dd), 6.77 (1H, s), 6.89 (1H, s), 6.95–7.59 (10H, m), 7.30 (15H, s), 8.88 (1H, s).

EXAMPLE 42

7-[2-(2-Aminothiazol-4-yl)-2-cyanomethyloxyiminoacetamido]-3-[(1,3,4-thiadiazol-2-yl)thiomethyl-]-Δ$^3$-O-2-isocephem-4-carboxylic acid trifluoroacetate (syn-isomer)

To benzhydryl 7-[2-(2-tritylaminothiazol-4-yl)-2-cyanomethyloxyiminoacetamido]-3-[(1,3,4-thiadiazol-2-yl)thiomethyl]-Δ$^3$-O-2-isocephem-4-carboxylate (syn-isomer) (600 mg, 0.64 mmol) was added anisole (0.6 ml) and, under ice-cooling, trifluoroacetic acid (6 ml) was added thereto. The mixture was stirred for 10 minutes, followed by addition of diethyl ether (40 ml) to give crystals, which were collected by filtration to obtain the title compound (250 mg).
Pale yellow powder
mp: 145° C. (decomposition).
NMR (DMSO-d6) δ: 3.57–4.20 (2H, m), 4.32–4.84 (1H, m), 4.56 (2H, s), 5.05 (2H, s), 5.75 (1H, dd), 6.95 (1H, s), 9.44 (1H, d), 9.56 (1H, s).

EXAMPLE 43

Benzhydryl 7-[2-(2-tritylaminothiazol-4-yl)-2-allyloxyiminoacetamido]-3-[(1,3,4-thiadiazol-2-yl)thiomethyl]-$\Delta^3$-O-2-isocephem-4-carboxylate (syn-isomer)

Benzhydryl 7-amino-3-[(1,3,4-thiadiazol-2-yl)thiomethyl]-$\Delta^3$-O-2-isocephem-4-carboxylate (1 g, 2.15 mmol) and 2-(2-tritylaminothiazol-4-yl)-2-allyloxyiminoacetic acid (syn-isomer) (1.1 g, 2.35 mmol) were dissolved in methylene chloride (100 ml)-dimethylformamide (10 ml) mixture. Dicyclohexylcarbodiimide (DCC) (0.48 g, 2.33 mmol) was added to the mixture under ice-cooling and the reaction was allowed to proceed at the same temperature overnight. Thereafter, the mixture was filtered off and the filtrate was concentrated under reduced pressure. The residue was subjected to silica gel column chromatography [eluent: methylene chloride-ethyl acetate (10:1)]for separation and purification to give the title compound (1.24 g).

Light yellow powder
mp: 125°–128° C.
NMR (CDCl$_3$) δ: 3.96 (2H, m), 4.50–4.80 (5H, m), 5.10–5.50 (2H, m), 6.63 (1H, s), 6.86 (1H, s), 6.80–6.90 (2H, m), 7.10–7.40 (25H, m), 8.85 (1H, s).

EXAMPLE 44

Benzhydryl 7-[2-(2-formamidothiazol-4-yl)-2-methylthiomethoxyiminoacetamido]-3-[(1,3,4-thiadiazol-2-yl)thiomethyl]-$\Delta^3$-O-2-isocephem-4-carboxylate (syn-isomer)

Benzhydryl 7-amino-3-[(1,3,4-thiadiazol-2-yl)thiomethyl]-$\Delta^3$-O-2-isocephem-4-carboxylate (1.4 g, 3 mmol) and 2-(2-formamidothiazol-4-yl)-2-methylthiomethoxyiminoacetic acid (syn-isomer) (800 mg, 3.3 mmol) were dissolved in methylene chloride (100 ml)dimethylformamide (10 ml) mixture, followed by addition of dicyclohexylcarbodiimide (DCC) (680 mg, 3.3 mmol). The reaction was allowed to proceed at room temperature for 12 hours. Thereafter, the insoluble matter was filtered off and the filtrate was washed with a 10 -fold dilution of concentrated aqueous solution of hydrochloric acid and saturated aqueous sodium chloride. The methylene chloride layer was dried over anhydrous magnesium sulfate and filtered. The filtrate was concentrated under reduced pressure. The residue was subjected to silica gel column chromatography [eluent: methylene chloride-ethyl acetate (5:4)] for separation and purification to give the title compound (860 mg).

Pale pink powder
mp: 172°–176° C. (decomposition).
NMR (DMSO-d6) δ: 2.20 (3H, s), 3.90–4.20 (2H, m), 4.40–4.80 (3H, m), 5.28 (2H, s), 5.78 (1H, dd), 6.85 (1H, s), 7.10–7.70 (10H, m), 7.51 (1H, s), 8.50 (1H, s), 9.40 (1H, d), 9.48 (1H, s), 12.58 (1H, s).

EXAMPLE 45

7-[2-(2-Formamidothiazol-4-yl)-2-methylthiomethoxyiminoacetamido]-3-[(1,3,4-thiadiazol-2-yl)thiomethyl]-$\Delta^3$-O-2-isocephem-4-carboxylic acid (syn-isomer)

To benzhydryl 7-[2-(2-formamidothiazol-4-yl)-2-methylthiomethoxyiminoacetamido]-3-[(1,3,4-thiadiazol-2-yl)thiomethyl]-$\Delta^3$-O-2-isocephem-4-carboxylate (syn-isomer) (700 mg, 0.98 mmol) was added anisole (0.7 ml) and, under ice-cooling, trifluoroacetic acid (7 ml) was added thereto. The mixture was stirred at the same temperature for 10 minutes. Thereafter, diethyl ether (40 ml) was added to the reaction mixture and the precipitate was collected by filtration, washed with diethyl ether and dried to give the title compound (520 mg).

Pale yellow powder
mp: 132° C. (discoloration begins), 145°–147° C. (decomposition).
NMR (DMSO-d6) δ: 2.20 (3H, s), 3.80–4.20 (2H, m), 4.50–4.80 (3H, m), 5.29 (2H, s), 5.78 (1H, dd), 7.50 (1H, s), 8.51 (1H, s), 9.38 (1H, d), 9.52 (1H, s), 12.52 (1H, s).

EXAMPLE 46

7-[2-(2-Aminothiazol-4-yl)-2-methylthiomethoxyiminoacetamido]-3-[(1,3,4-thiadiazol-2-yl)thiomethyl]-$\Delta^3$-O-2-isocephem-4-carboxylic acid (syn-isomer)

7-[2-(2-Formamidothiazol-4-yl)-2-methylthiomethoxyiminoacetamido]-3-[(1,3,4-thiadiazol-2-yl)thiomethyl]-$\Delta^3$-O-2-isocephem-4-carboxylic acid trifluoroacetate (syn-isomer) (400 mg, 0.73 mmol) was dissolved in methanol (4 ml)-tetrahydrofuran (3 ml) mixture, followed by addition of concentrated hydrochloric acid (0.25 ml). The reaction was conducted at room temperature for 2 hours and the solvent was distilled off under reduced pressure. The residue was dissolved by addition of a 5% aqueous solution of sodium hydrogen carbonate (30 ml). The solution was washed with ethyl acetate (50 ml) and the aqueous layer was taken. The insoluble matter was filtered off and the filtrate was adjusted to pH 3 with a 10-fold dilution of concentrated hydrochloric acid. The precipitate was collected by filtration, washed with water and dried under reduced pressure to give the title compound (270 mg).

Pale yellow powder
mp: >300° C. (130° C., discoloration).
NMR (DMSO-d6) δ: 2.20 (3H, s), 3.60–4.10 (2H, m), 4.40–4.70 (3H, m), 5.20 (2H, s), 5.74 (1H, dd), 6.82 (1H, s), 7.30 (2H, bs), 9.25 (1H, d), 9.51 (1H, s).

EXAMPLE 47

Benzhydryl 7-[2-(2-tritylaminothiazol-4-yl)-2-benzyloxyiminoacetamido]-3-[(1,3,4-thiadiazol-2-yl)thiomethyl]-$\Delta^3$-O-2-isocephem-4-carboxylate (syn-isomer)

In a manner analogous to Example 21, the title compound was produced from the corresponding starting compound.

Light yellowish white powder
mp: 122°–124° C.
NMR (CDCl$_3$) δ: 3.34–4.25 (3H, m), 4.43 (1H, d, J=15 Hz), 4.71 (1H, d, J=15 Hz), 5.25 (2H, s), 5.45 (1H, dd, J=7 Hz, 4 Hz), 6.47 (1H, d, J=7 Hz), 6.68 (1H, s), 6.89 (1H, s), 7.30 (30H, bs), 8.91 (1H, s).

EXAMPLE 48

Benzhydryl 7-[2-(2-tritylaminothiazol-4-yl)-2-(2fluoroethoxy)iminoacetamido-]-3-[(1,3,4-thiadiazol-2-yl)thiomethyl]-$\Delta^3$-O-2-isocephem-4-carboxylate (syn-isomer)

In a manner analogous to Example 25, the title compound was produced from the corresponding starting compound.

Light yellowish white powder
mp: 113°–115° C.
NMR (CDCl$_3$) δ: 3.88–4.95 (9H, m), 5.52 (1H, dd, J=7 Hz, 4 Hz), 6.68 (1H, s), 6.90 (1H, s), 7.30 (16H, bs), 8.91 (1H, s).

EXAMPLE 49

7-[2-(2-Aminothiazol-4-yl)-2-(2-fluoroethoxy)iminoacetamido]-3-[(1,3,4-thiadiazol-2-yl)thiomethyl]-Δ$^3$-O-2-isocephem-4-carboxylic acid trifluoroacetate (syn-isomer)

In a manner analogous to Example 31, the title compound was produced from the corresponding starting compound.

Light yellowish white powder.

mp: 128° C. (discoloration begins gradually), 148° C. (discoloration).

NMR (DMSO-d6) δ: 4.53 (2H, s), 3.88–4.94 (7H, m), 5.71 (1H, dd, J=9 Hz, 4 Hz), 6.84 (1H, s), 7.24–7.41 (2H, m), 9.28 (1H, d, J=9 Hz), 9.56 (1H, s).

EXAMPLE 50

7-[2-(2-Aminothiazol-4-yl)-2-benzyloxyiminoacetamido]-3-[(1,3,4-thiadiazol-2-yl)thiomethyl]-Δ$^3$-O-2-isocephem-4-carboxylic acid trifluoroacetate (syn-isomer)

In a manner analogous to Example 31, the title compound was produced from the corresponding starting compound.

Light yellowish white powder mp: 137° C. (discoloration begins gradually).

NMR (DMSO-d6) δ: 3.71–4.55 (3H, m), 4.53 (2H, bs), 5.14 (2H, s), 5.69 (1H, dd, J=9 Hz, 4 Hz), 6.82 (1H, s), 7.33 (7H, bs), 7.27 (1H, d, J=9 Hz), 9.57 (1H, s).

EXAMPLE 51

Benzhydryl 7-[2-(2-tritylaminothiazol-4-yl)-2-methoxyiminoacetamido]-3-[(1,2,3-thiadiazol-5-yl)thiomethyl]-Δ$^3$-O-2-isocephem-4-carboxylate (syn-isomer)

Benzhydryl 7-amino-3-[(1,2,3-thiadiazol-5-yl)-thiomethyl]-Δ$^3$-O-2-isocephem-4-carboxylate (0.96 g, 2 mmol) was dissolved in methylene chloride (60 ml), followed by addition of 2-(2-tritylaminothiazol-4-yl)-2-methoxyiminoacetic acid (syn-isomer) (0.98 g, 2.2 mmol). Dicyclohexylcarbodiimide (0.45 g, 2.2 mmol) was added to the mixture under ice-cooling, and the reaction mixture was returned to room temperature. The reaction was then conducted overnight and the reaction mixture was concentrated under reduced pressure. To the residue was added a small amount of methylene chloride and the mixture was filtered. The filtrate was subjected to silica gel column chromatography [eluent: methylene chloride-ethyl acetate (10:1)] for separation and purification to give the title compound (0.68 g)

Light yellow powder mp: 127°–130° C.

NMR (CDCl3) δ: 3.67–4.00 (2H, m), 4.07 (2H, s), 4.20 (1H, d, J=14 Hz), 4.37 (1H, d, J=14 Hz), 4.66 (1H, d, J=7 Hz), 5.48 (1H, q, J=6 Hz, 4 Hz), 6.89 (1H, s), 6.90 (1H, s), 7.33 & 7.24–7.65 (25H, m+s), 8.49 (1H, s).

EXAMPLE 52

Benzhydryl 7-[2-(2-tritylaminothiazol-4-yl)-2-cyanomethyloxyiminoacetamido]-3-[(1,2,3-thiadiazol-5-yl)thiomethyl]-Δ$^3$-O-2-isocephem-4-carboxylate (syn-isomer)

In a manner analogous to Example 51, the title compound was produced from the corresponding starting compound.

Yellow powder mp: 133°–137° C.

NMR (CDCl3) δ: 3.69–4.05 (2H, m), 4.18 (1H, d, J=13 Hz), 4.37 (1H, d, J=13 Hz), 4.53–4.66 (1H, m), 4.85 (2H, s), 5.51 (1H, q, J=5 Hz, 3 Hz), 6.76 (1H, s), 6.87 (1H, s), 7.28 (15H, s), 7.21–7.60 (10H, s), 8.44 (1H, s).

EXAMPLE 53

Benzhydryl 7-[2-(2-tritylaminothiazol-4-yl)-2-cyclopropylmethyloxyiminoacetamido]-3-[(1,2,3-thiadiazol-5-yl)thiomethyl]-Δ$^3$-O-2-isocephem-4-carboxylate (syn-isomer)

In a manner analogous to Example 51, the title compound was produced from the corresponding starting compound.

Yellow powder mp: 119°–121° C.

NMR (CDCl3) δ: 0.11–0.70 (4H, m), 0.90–1.32 (1H, m), 3.87–4.20 (4H, m), 4.29 (2H, s), 4.65–4.81 (1H, m), 5.52 (1H, q, J=4 Hz, 3 Hz), 6.72 (1H, s), 6.92 (1H, s), 7.34 (2.5H, s), 7.25–7.65 (2.5H, m), 8.49 (1H, s).

EXAMPLE 54

7-[2-(2-Aminothiazol-4-yl)-2-methoxyiminoacetamido]-3-[(1,2,3-thiadiazol-5-yl)thiomethyl]-Δ$^3$-O-2-isocephem-4-carboxylic acid trifluoroacetate (syn-isomer)

To benzhydryl 7-[2-(2-tritylaminothiazol-4-yl)-2methoxyiminoacetamido-]-3-[(1,2,3-thiadiazol-5-yl)thiomethyl]-Δ$^3$-O-2-isocephem-4-carboxylate (syn-isomer) (540 mg) was added anisole (0.54 ml). Under ice-cooling, trifluoroacetic acid (5.4 ml) was added to the mixture and the reaction was allowed to proceed for 10 minutes. Diethyl ether was added to the reaction mixture to give crystals, which were collected by filtration to obtain the title compound (230 mg).

Light brown powder mp: 117° C.–121° C. (decomposition).

NMR (DMSO-d6) δ: 3.87 (3H, s), 3.69–4.13 (2H, m), 4.30–4.50 (1H, m), 4.58 (1H, bs), 5.72 (1H, q, J=8 Hz, 4 Hz), 6.83 (1H, s), 7.30 (2H, bs), 8.88 (1H, s), 9.23 (1H, d, J=8 Hz).

EXAMPLE 55

7-[2-(2-Aminothiazol-4-yl)-2-cyanomethyloxyiminoacetamido]-3-[(1,2,3-thiadiazol-5-yl)thiomethyl]-Δ$^3$-O-2-isocephem-4-carboxylic acid trifluoroacetate (syn-isomer)

In a manner analogous to Example 54, the title compound was produced from the corresponding starting compound.

NMR (CDCl3) δ: 3.75–4.15 (2H, m), 4.29 (1H, d, J=14 Hz), 4.49 (1H, d, J=14 Hz), 4.55–4.79 (1H, m), 5.06 (2H, s), 5.75 (1H, q, J=8 Hz, 4 Hz), 6.95 (1H, s), 7.31 (2H, bs), 8.87 (1H, s), 9.39 (1H, d, J=8 Hz).

EXAMPLE 56

Benzhydryl 7-[2-(2-aminothiazol-4-yl)-2-cyclopropylmethyloxyiminoacetamido]-3-[(1,2,3-thiadiazol-5-yl)thiomethyl]-Δ$^3$-O-2-isocephem-4-carboxylate (syn-isomer)

Benzhydryl 7-[2-(2-tritylaminothiazol-4-yl)-2-cyclopropylmethyloxyiminoacetamido]-3-[(1,2,3-thiadiazol-5-yl)thiomethyl]-Δ$^3$-O-2-isocephem-4-carboxylate (syn-isomer) (540 mg) was dissolved in acetic acid (15 ml), followed by addition of water (2 ml). The reaction was conducted at 40° C. for 3 hours. To the reaction mixture was added water, followed by addition of ethyl acetate. The ethyl acetate layer was taken, washed succesively twice with water, twice with 5% aqueous sodium hydrogen carbonate and twice with saturated aqueous sodium chloride, dried over anhydrous sodium sulfate and filtered. The filtrate was concentrated under reduced pressure. To the residue was added diethyl ether to give crystals, which were collected by filtration to obtain the title compound (260 mg).

Light yellow powder
mp: 135°–137° C.
NMR (CDCl$_3$) δ: 0.15–0.70 (4H, m), 0.96–1.31 (1H, m), 3.80–4.08 (2H, m), 4.08 (2H, d, J=8 Hz), 4.28 (2H, s), 4.58–4.86 (1H, m), 5.59 (1H, q, J=6 Hz, 4 Hz), 7.11 (1H, d, J=6 Hz), 7.18–7.57 (10H, m), 8.42 (1H, s).

EXAMPLE 57

7-[2-(2-Aminothiazol-4-yl)-2-cyclopropylmethyloxyiminoacetamido]-3-[(1,2,3-thiadiazol-5-yl)thiomethyl]-Δ$^3$-O-2-isocephem-4-carboxylic acid (syn-isomer)

To benzhydryl 7-[2-(2-aminothiazol-4-yl)-2-cyclopropylmethyloxyminoacetamido]-3-[(1,2,3-thiadiazol-5-yl)thiomethyl]-Δ$^3$-O-2-isocephem-4-carboxylate (syn-isomer) (260 mg) was added anisole (0.52 ml). Under ice-cooling, trifluoroacetic acid (2.6 ml) was added to the mixture and the reaction was conducted for 10 minutes. Diethyl ether was added to the reaction mixture to give crystals, which were collected by filtration and dissolved in a 5% aqueous solution of sodium hydrogen carbonate. The insoluble matter was filtered off. To the filtrate was added the nonionic adsorbent resin Diaion HP-20 (70 g) and the mixture was adjusted to pH 3.25 with a 10-fold dilution of concentrated hydrochloric acid. The resin was packed into a column and elution was carried out with water to 50% aqueous isopropyl alcohol. The fractions containing the desired compound were combined, concentrated under reduced pressure and lyophilized to give the title compound (80 mg).

mp: 140° C. (coloration), 280° C. (decomposition).
NMR (DMSO-d6) δ: 0.15–0.67 (4H, m), 0.92–1.26 (1H, m), 3.63–4.08 (2H, m), 3.92 (2H, s), 4.25 (1H, d, J=14 Hz), 4.53 (1H, d, J=14 Hz), 4.52–4.69 (1H, m), 5.67 (1H, q, J=8 Hz, 4 Hz), 6.75 (1H, s), 7.17 (2H, bs), 8.85 (1H, s), 9.18 (1H, d, J=8 Hz).

EXAMPLE 58

Benzhydryl (6S,7S)-7-[2-(2-tritylaminothiazol-4-yl)-2-methoxyiminoacetamido]-3-[(1,3,4-thiadiazol-2-yl)thiomethyl]-Δ$^3$-O-2-isocephem-4-carboxylate (syn-isomer)

Benzhydryl (6S,7S)-7-azido-3-[(1,3,4-thiadiazol-2-yl)thiomethyl]-Δ$^3$-O-2-isocephem-4-carboxylate (800 mg, 1.62 mmol) and triethylamine (197 mg, 1.94 mmol) were dissolved in methylene chloride (64 ml). Under ice-cooling, hydrogen sulfide gas was introduced to the solution for 2 hours. The mixture was then washed with 5 aqueous sodium hydrogen carbonate and saturated aqueous sodium chloride in that order and dried over anhydrous sodium sulfate. The solvent was then concentrated under reduced pressure and the residue was dissolved in methylene chloride (90 ml), followed by addition of 2-(2-tritylaminothiazol-4-yl)-2-methoxyiminoacetic acid (syn-isomer) (1.08 g, 2.43 mmol). Dicyclohexylcarbodiimide (DCC) (501 mg, 2.43 mmol) was added to the mixture under ice-cooling and the reaction was allowed to proceed at room temperature overnight. The reaction mixture was filtered and the filtrate was concentrated under reduced pressure. The residue was subjected to silica gel column chromatography [eluent: ethyl acetate-n-hexane (2:1)] for separation and purification to give the title compound (780 mg).

Light yellow powder
mp: 110°–112° C.
$[\alpha]_D^{20}$ = −4.5° (C=5,28, in chloroform).
NMR (CDCl$_3$) δ: 3.80–4.0 (2H, m), 4.00 (3H, s), 4.56 (1H, d), 5.40–5.54 (3H, m), 6.55 (1H, s), 6.87 (1H, s), 7.23 (15H, s), 7.08–7.57 (10H, m), 8.83 (1H, s).

EXAMPLE 59

Benzhydryl (6S,7S)-7-[2-(2-aminothiazol-4-yl)-2-methoxyiminoacetamido]-3-[(1,3,4-thiadiazol-2-yl)thiomethyl]-Δ$^3$-O-2-isocephem-4-carboxylate (syn-isomer)

Benzhydryl (6S,7S)-7-[2-(2-tritylaminothiazol-4-yl)-2-methoxyiminoacetamido]-3-[(1,3,4-thiadiazol-2-yl)thiomethyl]-Δ$^3$-O-2-isocephem-4-carboxylate (syn-isomer) (100 mg, 0.11 mmol) was dissolved in acetic acid (3 ml)-water (0.41 ml) mixture. The mixture was warmed at 40° C. for 3 hours, poured into water (40 ml) and extracted with ethyl acetate. The extract was washed with water, a 5% aqueous solution of sodium hydrogen carbonate in that order and dried over anhydrous sodium sulfate. The solvent was concentrated under reduced pressure and the resulting crystals were washed with diethyl ether to give the title compound (34 mg).

Light yellow powder
mp: 108°–109° C.
$[\alpha]_D^{20}$ = 16.7° (C=0.84, in chloroform).
NMR (CDCl$_3$) δ: 3.90–4.13 (2H, m), 3.91 (3H, s), 4.47–4.52 (1H, d), 5.58 (1H, dd), 5.63–5.83 (2H, m), 6.70 (1H, s), 6.87 (1H, s), 7.13–7.57 (10H, m), 8.12 (1H, d), 8.85 (1H, s).

EXAMPLE 60

(6S,7S)-7-[2-(2-Aminothiazol-4yl)-2-methoxyiminoacetamido]-3-[(1,3,4-thiadiazol-2-yl)thiomethyl]-Δ$^3$-O-2-isocephem-4-carboxylic acid trifluoroacetate (syn-isomer)

Benzhydryl (6S,7S)-7-[2-(2-aminothiazol-4-yl)-2-methoxyiminoacetamido]-3-[(1,3,4-thiadiazol-2-yl)thiomethyl]-Δ$^3$-O-2-isocephem-4-carboxylate (syn-isomer) (34 mg, 0.05 mmol) and anisole (0.02 ml) were dissolved in methylene chloride (1 ml). Under ice-cooling, trifluoroacetic acid (0.2 ml) was added to the mixture and the mixture was stirred for 10 minutes. Diethyl ether was added to the reaction mixture to give crystals, which were washed thoroughly with diethyl ether to obtain the title compound (22 mg).

White crystals
mp: 145°–147° C. (decomposition).
$[\alpha]_D^{20}$ = −14.1° (C=0.71, in methanol).
NMR (DMSO-d6) δ: 3.83 (3H, s), 3.83–4.06 (2H, m), 4.45–4.60 (1H, m), 5.61 (1H, dd), 5.63–5.77 (2H, m), 6.77 (1H, s), 9.15 (1H, d), 9.48 (1H, s).

EXAMPLE 61

Benzhydryl (6S,7S)-7-[2-(2-tritylaminothiazol-4-yl)-2-cyanomethoxyiminoacetamido]-3-[(1,3,4-thiadiazol-2-yl)thiomethyl]-Δ$^3$-O-2-isocephem-4-carboxylate (syn-isomer)

Under ice-cooling, hydrogen sulfide gas was introduced into a mixture of benzhydryl (6S,7S)-7-axido-3-[(1,3,4-thiadiazol-2-yl)thiomethyl]-Δ$^3$-O-2-isocephem-4-carboxylate (0.8 g, 1.58 mmol), triethylamine (0.34 ml, 2.44 mmol) and methylene chloride (100 ml). After confirming the disappearance of the spot of the starting compound by thin-layer chromatography 1 hour later, the reaction mixture was washed with saturated aqueous sodium hydrogen carbonate and saturated aqueous sodium chloride in that order and dried over anhydrous magnesium sulfate. The solvent was distilled off and the residue was dissolved in methylene chloride (100 ml), followed by addition of 2-(2-tritylaminothiazol-4-yl)-2-cyanomethoxyiminoacetic acid (syn-isomer) (1.04 g, 2.22 mmol). The mixture was stirred under ice-cooling and dicyclohexylcarbodiimide (DCC) (0.46 g, 2.23 mmol) was added thereto. The reaction was allowed to proceed overnight. The precipitate was filtered off and the filtrate was washed with water, dilute hydrochloric acid, aqueous sodium hydrogen carbonate and saturated aqueous sodium chloride in that order and dried over anhydrous magnesium sulfate. The solvent was distilled off under reduced pressure and the residue was subjected to silica gel column chromatography (eluent: chloroform) for separation and purification to give the title compound (0.85 g).

Light yellow powder
mp: 125°–127° C.
$[\alpha]_D^{22} = -17.0°$ (C=1, in chloroform).
NMR (CDCl$_3$) δ: 3.86–4.02 (2H, m), 4.35–4.80 (1H, m), 4.55 (2H, s), 4.89 (2H, s), 5.47 (1H, dd), 6.77 (1H, s), 6.89 (1H, s), 6.95–7.59 (10H, m), 7.30 (15H, s), 8.88 (1H, s).

EXAMPLE 62

(6S,7S)-7-[2-(2-Aminothiazol-4-yl)-2-cyanomethoxyiminoacetamido]-3-[(1,3,4-thiadiazol-2-yl)thiomethyl]-Δ$^3$-O-2-isocephem-4-carboxylic acid trifluoroacetate (syn-isomer)

To a solution of benzhydryl (6S,7S)-7-[2-(2-tritylaminothiazol-4-yl)-2-cyanomethoxyiminoacetamido]-3-[(1,3,4-thiadiazol-2-yl)thiomethyl]-Δ$^3$-O-2-isocephem-4-carboxylate (syn-isomer) (0.40 g, 0.43 mmol) and anisole (0.4 ml) was added trifluoroacetic acid (5 ml) under ice-cooling and the reaction was conducted for 10 minutes. Then, diethyl ether was added to the reaction mixture and the resulting crystals were collected by filtration, washed with diethyl ether and dried under reduced pressure to give the title compound (0.2 g).

Light yellow powder
m.p.: discoloration begins at 113° C.
$[\alpha]_D^{22} = +111°$ (C=1, in methanol).
NMR (DMSO-d6)δ: 3.57–4.20 (2H, m), 4.32–4.84 (1H, m), 4.56 (2H, s), 5.05 (2H, s), 5.75 (1H, dd), 6.95 (1H, s), 9.44 (1H, d), 9.56 (1H, s).

EXAMPLE 63

Benzhydryl (6S,7S)-7-[2-(2-tritylaminothiazol-4-yl)-2-cyclopropylmethyloxyiminoacetamido]-3-[(1,2,3-thiadiazol-5-yl)thiomethyl]-Δ$^3$-O-2-isocephem-4-carboxylate (syn-isomer)

Using Benzhydryl (6S,7S)-7-azido-3-[(1,2,3-thiadiazol-5-yl)thiomethyl]-Δ$^3$-O-2-isocephem-4-carboxylate (1.07 g, 2.17 mmol), the same reduction procedure as Example 61 was carried out to give benzhydryl (6S,7S)-7-amino-3-[(1,2,3-thiadiazol-5-yl) thiomethyl]-Δ$^3$-O-2-isocephem-4-carboxylate (1.04 g, 2.16 mmol). Using this product and 2-(2-tritylaminothiazol-4-yl)-2-cyclopropylmethyloxyiminoacetic acid (syn-isomer) (1.26 g, 2.59 mmol), the procedure of Example 51 was repeated to give the title compound (0.81 g).

mp: 107°–110° C.
$[\alpha]_D^{20} = -12°$ (C=1, in chloroform).
NMR (CDCl$_3$)δ: 0.11–0.7 (4H, m), 0.9–1.32 (1H, m), 3.87–4.20 (4H, m), 4.29 (2H, s), 4.65–4.81 (1H, m), 5.52 (1H, q, J=4 Hz, 3 Hz), 6.72 (1H, s), 6.92 (1H, s), 7.25–7.65 (25H, m), 8.49 (1H, s).

EXAMPLE 64

Benzhydryl (6S,7S)-7-[2-(2-aminothiazol-4-yl)-2-cyclopropylmethyloxyiminoacetamido]-3-[(1,2,3-thiadiazol-5-yl)thiomethyl]-Δ$^3$-O-2-isocephem-4-carboxylate (syn-isomer)

Using benzhydryl (6S,7S)-7-[2-(2-tritylaminothiazol-4-yl)-2-cyclopropylmethyloxyiminoacetamido]-3-[(1,2,3-thiadiazol-5-yl)thiomethyl]-Δ$^3$-O-2-isocephem-4-carboxylate (syn-isomer) (710 mg), the same procedure as Example 56 was carried out to give the title compound (350 mg).

Pale yellow powder.
mp: 137.5°–139° C.
$[\alpha]_D^{20} = -22.4°$ (C=1, in chloroform).
NMR (CDCl$_3$) δ: 0.15–0.70 (4H, m), 0.96–1.31 (1H, m), 3.80 (2H, m), 4.08 (2H, d), 4.28 (2H, s), 4.58–4.86 (1H, m), 5.59 (1H, q), 7.11 (1H, d), 7.18–7.57 (10H, m), 8.42 (1H, s).

EXAMPLE 65

(6S,7S)-7-[2-(2-Aminothiazol-4-yl)-2-cyclopropylmethyloxyiminoacetamido]-3-[(1,2,3-thiadiazol-5-yl)thiomethyl]-Δ$^3$-O-2-isocephem-4-carboxylic acid (syn-isomer)

Using benzhydryl (6S,7S)-7-[2-(2-aminothiazol-4-yl)-2-cyclopropylmethyloxyiminoacetamido]-3-[(1,2,3-thiadiazol-5-yl)thiomethyl]-Δ$^3$-O-2-isocephem-4-carboxylate (syn-isomer) (340 mg), the same procedure as Example 57 was carried out to give the title compound (120 mg).

Light pink powder.
mp: 118° C. (coloration).
$[\alpha]_D^{22} = -14.7°$ (C=0.1, in methanol).
NMR (DMSO-d6) δ: 0.15–0.67 (4H, m), 0.92–1.26 (1H, m), 3.63–4.08 (2H, m), 3.92 (2H, s), 4.25 (1H, d, J=14 Hz), 4.53 (1H, d, J=14 Hz), 4.52–4.69 (1H, m), 5.67 (1H, q, J=4 Hz, 8 Hz), 6.75 (1H, s), 7.17 (2H, bs), 8.85 (1H, s), 9.18 (1H, d, J=8 Hz).

EXAMPLE 66

Benzhydryl 7-[2-(2-tritylaminothiazol-4-yl)-2-methoxyiminoacetamido]-3-(pyridin-4-ylthiomethyl)-Δ$^3$-O-2-isocephem-4-carboxylate (syn-isomer)

In methylene chloride (50 ml) were dissolved 2-(2-tritylaminothiazol-4-yl)-2-methoxyiminoacetic acid (syn-isomer) (1.81 g, 4.07 mmol) and 1-hydroxybenztriazole (0.55 g, 4.07 mmol), and under ice-cooling, dicyclohexylcarbodiimide (DCC) (0.84 g, 4.07 mmol) was added thereto. The mixture was stirred for 1 hour, after which time a solution of benzhydryl 7-amino-3-(pyridin-4-ylthiomethyl)-Δ$^3$-O-2-isocophem-4-carboxylate (1.93 g, 4.07 mmol) in methylene chloride (30 ml) was added to the mixture. The mixture was stirred at room temperature for 18 hours. The reaction mixture was filtered and the filtrate was concentrated. The residue was purified by silica gel column chromatography

[eluent: chloroform-n-hexane=5:1(V/V)] and further reprecipitated from methylene chloride-n-hexane mixture to give the title compound (2.15 g) as white powder.

mp: 138°–139° C.

NMR (CDCl$_3$) δ: 3.8–4.15 (2H, m), 3.97 (3H, s), 4.27 (2H, dd), 4.60 (1H, dd), 5.45 (1H, dd), 6.56 (1H, s), 6.88 (1H, s), 6.9–7.6 (27H, m), 8.23 (2H, d).

EXAMPLE 67

Benzhydryl 7-[2-(2-aminothiazol-4-yl)-2-methoxyiminoacetamido]-3-(pyridin-4-ylthiomethyl)-Δ$^3$-O-2-isocephem-4-carboxylate (syn-isomer)

In a mixture of acetic acid (6 ml) and water (1 ml) was dissolved benzhydryl 7-[2-(2-tritylaminothiazol-4-yl)-2-methoxyiminoacetamido]-3-(pyridin-4-ylthiomethyl)-Δ$^3$-O-2-isocephem-4-carboxylate (syn-isomer) (0.20 g, 0.22 mmol) and the solution was warmed at 40° C. After 2 hours, the reaction mixture was concentrated to dryness and the residue dissolved in ethyl acetate. The solution was washed with 5% aqueous sodium hydrogen carbonate and, then, with saturated aqueous sodium chloride, followed by drying over anhydrous sodium sulfate. Finally, the solvent was distilled off to give the title compound (0.09 g).

NMR (DMSO-d6) δ: 3.83 (3H, s), 3.8–4.1 (2H, m), 4.1–4.5 (2H, m), 4.5–4.8 (1H, m), 5.78 (1H, dd), 6.77 (1H, s), 6.82 (1H, s), 7.0–7.7 (12H, m), 8.26 (2H, d), 9.12 (1H, d).

EXAMPLE 68

Benzhydryl 7-[2-(2-aminothiazol-4-yl)-2-methoxyiminoacetamido]-3-[(1-methyl-4-pyridinio)thiomethyl]-Δ$^3$-O-2-isocephem-4-carboxylate iodide salt (syn-isomer)

In methanol (2 ml) was dissolved benzhydryl 7-[2-(2-aminothiazol-4-yl)-2-methoxyiminoacetamido]-3-(pyridin-4-ylthiomethyl)-Δ$^3$-O-2-isocephem-4-carboxylate (syn-isomer) (0.09 g), followed by addition of iodomethane (2 ml). The mixture was stirred at room temperature for 20 hours. To the reaction mixture was added diethyl ether and the resulting product was collected by filtration to give the title compound (0.10 g) as pale yellow powder.

mp: 166°–175° C.

NMR (DMSO-d6) δ: 3.8–4.3 [8H, m; 3.84 (s) and 4.15 (s) are included], 4.4–4.8 (3H, m), 5.80 (1H, dd), 6.80 (1H, s), 6.81 (1H, s), 7.1–7.7 (10H, m), 7.88 (2H, d), 8.57 (2H, d), 9.15 (1H, d).

EXAMPLE 69

7-[2-(2-Aminothiazol-4-yl)-2-methoxyiminoacetamido]-3-[(1-methyl-4-pyridinio)thiomethyl]-Δ$^3$-O-2-isocephem-4-carboxylic acid trifluoroacetate (syn-isomer)

Benzhydryl 7-[2-(2-aminothiazol-4-yl)-2-methoxyiminoacetamido]-3-[(1-methyl-4-pyridinio)thiomethyl]-Δ$^3$-O-2-isocephem-4-carboxylate iodide salt (syn-isomer) (0.10 g) was treated with trifluoroacetic acid (1 ml) in the presence of anisole (0.1 ml) under ice-cooling for 8 minutes. Then, diethyl ether was added to the reaction mixture and the resulting powder was collected by filtration to give the title compound (0.06 g).

mp: 124° C.

NMR (DMSO-d6) δ: 3.8–4.1 (5H, m), 4.15 (3H, s), 4.4–4.8 (3H, m), 5.66 (1H, dd), 6.75 (1H, s), 7.95 (2H, d), 8.60 (2H, d), 9.11 (1H, d).

EXAMPLE 70

7-[2-(2-Aminothiazol-4-yl)-2-methoxyimino acetamido]-3-[(1-carboxymethyl-4-pyridinio)thiomethyl]-Δ$^3$-O-2-isocephem-4-carboxylate (syn-isomer)

Using the corresponding starting materials, the same procedure as Example 69 was followed to give the corresponding trifluoroacetate. This compound was dissolved in an aqueous solution of sodium hydrogen carbonate and the nonionic adsorbent resin Diaion HP-20 was added thereto to adsorb the desired compound. The system was adjusted to pH 4 to 5 and the resin was filtered off. The resin was packed into column and eluted with 5 to 20% solution of isopropyl alcohol in water. The eluate was concentrated under reduced pressure to give the title compound.

mp: 173° C.

EXAMPLE 71

7-[2-(2-Aminothiazol-4-yl)-2-cyanomethoxyiminoacetamido]-3-[(1-methyl-4-pyridinio)thiomethyl]-Δ$^3$-O-2-isocephem-4-carboxylic acid trifluoroacetate (syn-isomer)

In a manner analogous to Example 69, the title compound was produced from the corresponding starting compound.

mp: 134°–141° C. (decomposition).

EXAMPLE 72

7-[2-(2-Aminothiazol-4-yl)-2-cyanomethoxyiminoacetamido]-3-[(1-carboxymethyl-4-pyridinio)thiomethyl]-Δ$^3$-O-2-isocephem-4-carboxylate (syn-isomer)

In a manner analogous to Example 70, the title compound was produced from the corresponding starting compound.

mp: 168° C.

EXAMPLE 73

7-[2-(2-Aminothiazol-4-yl)-2-(2-carboxy-2-propoxyimino)acetamido]-3-[(1-methyl-4-pyridinio)thiomethyl]-Δ$^3$-O-2-isocephem-4-carboxylate (syn-isomer)

In a manner analogous to Example 70, the title compound was produced from the corresponding starting compound.

mp: 152° C.

EXAMPLE 74

7-[2-(2-Aminothiazol-4-yl)-2-methoxyiminoacetamido]-3-(pyridin-4-ylthiomethyl)-Δ$^3$-O-2-isocephem-4-carboxylic acid trifluoroacetate (syn-isomer)

In a manner analogous to Example 69, the title compound was produced from the corresponding starting compound.

mp: 138° C.

EXAMPLE 75

7-[2-(2-Aminothiazol-4-yl)2-cyanomethoxyacetamido]-3-(pyridin-4-ylthiomethyl)-Δ$^3$-O-2-isocephem-4-carboxylic acid trifluoroacetate (syn-isomer)

In a manner analogous to Example 69, the title compound was produced from the corresponding starting compound.

mp: 148°–152° C. (decomposition).

EXAMPLE 76

7-[2-(2-Aminothiazol-4-yl)-2-(2-carboxy-2-propoxyimino)acetamido]-3-(pyridin-4-ylthiomethyl)-$\Delta^3$-O-2-isocephem-4-carboxylic acid (syn-isomer)

In a manner analogous to Example 70, the title compound was produced from the corresponding starting compound.

mp: 162° C.

EXAMPLE 77

7-[2-(2-Aminothiazol-4-yl)-2-cyclopropylmethyloxyiminoacetamido]-3-(pyridin-4-ylthiomethyl)-$\Delta^3$-O-2-isocephem-4-carboxylic acid trifluoroacetate (syn-isomer)

In a manner analogous to Example 69, the title compound was produced from the corresponding starting compound.

mp: 146°–154° C. (decomposition).

EXAMPLE 78

Benzyl 7-[2-(2-benzyloxycarbonylaminothiazol-4-yl)-2-methoxyiminoacetamido]-3-[(1,3,4-triazol-2-yl)thiomethyl]-$\Delta^3$-O-2-isocephem-4-carboxylate (syn-isomer)

In methylene chloride (30 ml) was dissolved benzyl 7-amino-3-[(1,3,4-triazol-2-yl)thiomethyl]-$\Delta^3$-O-2-isocephem-4-carboxylate (270 mg, 0.72 mmol), followed by addition of 2-(2-benzyloxycarbonylaminothiazol-4-yl)-2-methoxyiminoacetic acid (syn-isomer) (240 mg, 0.72 mmol). Then, dicyclohexylcarbodiimide (DCC) (160 mg, 0.8 mmol) was added to the solution and the reaction was conducted at the same temperature overnight. The reaction mixture was filtered and the filtrate concentrated under reduced pressure. The residue was purified by silica gel column chromatography [eluent: n-hexane-ethyl acetate (1:9)] to give the title compound (230 mg).

mp: 198°–205° C. (decomposition).

NMR (CDCl$_3$) δ: 3.94 (3H, s), 3.7–4.1 (2H, m), 4.21 (1H, d), 4.43 (1H, d), 4.5–4.73 (1H, m), 5.23 (2H, s), 5.25 (2H, s), 5.70 (1H, dd), 7.25 (1H, s), 7.37 (10H, s), 8.11 (1H, s), 9.18 (1H, d).

EXAMPLE 79

7-[2-(2-Aminothiazol-4-yl)-2-methoxyiminoacetamido]-3-[(1,3,4-triazol-2-yl)thiomethyl]-$\Delta^3$-O-2-isocephem-4-carboxylic acid (syn-isomer)

In methylene chloride (6 ml) was suspended benzyl 7-[2-(2-benzyloxycarbonylaminothiazol-4-yl)-2-methoxyiminoacetamido]-3-[(1,3,4-triazol-2-yl)thiomethyl]-$\Delta^3$-O-2-isocephem-4-carboxylate (syn-isomer) (210 mg, 0.3 mmol), followed by addition of a solution of aluminum chloride (240 mg, 1.8 mmol) in nitromethane (3 ml). The reaction was conducted at room temperature for 4 hours. The reaction mixture was then poured into icewater (50 ml), and after addition of a 10-fold dilution of conc. hydrochloric acid (1 ml), the organic layer was separated and the aqueous layer was extracted with methylene chloride (20 ml). The aqueous layer was adjusted to pH 8 with saturated aqueous sodium hydrogen carbonate solution. The insoluble matter was filtered off with the aid of Celite. To the filtrate was added the nonionic adsorbent resin Diaion HP-20 (20 g) and after adjustment to pH 3.5 with a 10-fold dilution of conc. hydrochloric acid, the resin was washed with water (200 ml). Then, elution was carried out with 0 to 30% solution of isopropyl alcohol in water and the eluate was lyophilized to give the title compound (60 mg).

mp: 158° C. (discoloration), >300° C.

NMR (DMSO-d6) δ: 3.84 (3H, s), 3.6–4.02 (1H, m), 4.40–4.63 (1H, m), 4.21 (1H, d), 4.40 (1H, d), 5.64 (1H, dd), 6.78 (1H, s), 7.16 (1H, bs), 8.32 (1H, bs), 9.09 (1H, d).

EXAMPLE 80

7-[2-(2-Aminothiazol-4-yl)-2-methoxyiminoacetamido]-3-[(1-methyl-1,3,4-triazol-2-yl)thiomethyl]-$\Delta^3$-O-2-isocephem-4-carboxylic acid (syn-isomer)

In a manner analogous to Example 79, the title compound was produced from the corresponding starting compound.

mp: 155° C. (discoloration), >300° C.

EXAMPLE 81

7-[2-(2-Aminothiazol-4-yl)-2-methoxyiminoacetamido]-3-[(4-methyl-1,3,4-triazol-2-yl)thiomethyl]-$\Delta^3$-O-2-isocephem-4-carboxylic acid (syn-isomer)

In a manner analogous to Example 79, the title compound was produced from the corresponding starting compound.

mp: 152° C. (discoloration), >300° C.

EXAMPLE 82

7-[2-(2-Aminothiazol-4-yl)-2-methoxyiminoacetamido]-3-[(1-allyl-1H-tetrazol-5-yl)thiomethyl]-$\Delta^3$-O-2-isocephem-4-carboxylic acid (syn-isomer)

In a manner analogous to Example 79, the title compound was produced from the corresponding starting compound.

mp: 190° C. (carbonization).

EXAMPLE 83

7-[2-(2-Aminothiazol-4-yl)-2-methoxyimnoacetamido]-3-[(4-methyl-5-carboxymethylthiazol-2-yl)thiomethyl]-$\Delta^3$-O-2-isocephem-4-carboxylic acid (syn-isomer)

In a manner analogous to Example 79, the title compound was produced from the corresponding starting compound. mp: 160° C. (discoloration), >300° C.

EXAMPLE 84

7-[2-(2-Aminothiazol-4-yl)-2-methoxyiminoacetamido]-3-[(1-carboxymethyl-1H-tetrazol-5-yl)thiomethyl]-$\Delta^3$-O-2-isocephem-4-carboxylic acid (syn-isomer)

In a manner analogous to Example 79, the title compound was produced from the corresponding starting compound.

mp: 170° C. (carbonization).

EXAMPLE 85

7-[2-(2-Aminothiazol-4-yl)-2-methoxyiminoacetamido]-3-[[1-(2-hydroxyethyl)-1H-tetrazol-5-yl]thiomethyl]-$\Delta^3$-O-2-isocephem-4-carboxylic acid (syn-isomer)

In a manner analogous to Example 79, the title compound was produced from the corresponding starting compound.

mp: 158° C. (discoloration), >300° C.

EXAMPLE 86

7-[2-(2-Aminothiazol-4-yl)-2-methoxyiminoacetamido]-3-[(1,2,4-thiadiazol-5-yl)thiomethyl]-$\Delta^3$-O-2-isocephem-4-carboxylic acid (syn-isomer)

In a manner analogous to Example 79, the title compound was produced from the corresponding starting compound.

mp: 155° C. (carbonization).

EXAMPLE 87

7-[2-(2-Aminothiazol-4-yl)-2-cyclopentyloxyiminoacetamido]-3-[(1,3,4-thiadiazol-2-yl)thiomethyl]-$\Delta^3$-O-2-isocephem-4-carboxylic acid (syn-isomer)

In a manner analogous to Example 79, the title compound was produced from the corresponding starting compound.

mp: 156° C. (discoloration), >300° C.

EXAMPLE 88

7-[2-(2-Aminothiazol-4-yl)-2-cyclopentyloxyiminoacetamido]-3-[(1-methyl-1H-tetrazol-5-yl)thiomethyl]-$\Delta^3$-O-2-isocephem-4-carboxylic acid (syn-isomer)

In a manner analogous to Example 79, the title compound was produced from the corresponding starting compound.

mp: 140° C. (discoloration).

EXAMPLE 89

7-[2-(2-Aminothiazol-4-yl)-2-methoxyiminoacetamido]-3-[[1-[2-(4-methyl-1-piperazinyl)ethyl]-1H-tetrazol-5-yl]thiomethyl]-$\Delta^3$-O-2-isocephem-4carboxylic acid (syn-isomer)

In a manner analogous to Example 79, the title compound was produced from the corresponding starting compound.

mp: 111° C. (decomposition).

EXAMPLE 90

7-[2-(2-Aminothiazol-4-yl)-2-cyclopentyloxyiminoacetamido]-3-[(1,2,4-thiadiazol-5-yl)thiomethyl]-$\Delta^3$-O-2-isocephem-4-carboxylic acid (syn-isomer)

In a manner analogous to Example 79, the title compound was produced from the corresponding starting compound.

mp: 125° C. (discoloration), 170° C. (carbonization).

EXAMPLE 91

7-[2-(2-Aminothiazol-4-yl)-2-(4-thiazolylmethoxyimino)acetamido]-3-[(1,3,4-thiadiazol-2-yl)thiomethyl]-$\Delta^3$-O-2-isocephem-4-carboxylic acid (syn-isomer)

In a manner analogous to Example 79, the title compound was produced from the corresponding starting compound.

mp: 147° C. (decomposition).

EXAMPLE 92

7-[2-(2-Aminothiazol-4-yl)-2-cyclopentyloxyiminoacetamido]-3-[[1-(2-hydroxyethyl)-1H-tetrazol-5-yl]-thiomethyl]-$\Delta^3$-O-2-isocephem-4-carboxylic acid trifluoroacetate (syn-isomer)

In a manner analogous to Example 69, the title compound was produced from the corresponding starting compound.

mp: 130° C. (decomposition).

EXAMPLE 93

7-[2-(2-Aminothiazol-4-yl)-2-cyclopentyloxyiminoacetamido]-3-[(1,2,3-thiadiazol-5-yl)thiomethyl]-$\Delta^3$-O-2-isocephem-4-carboxylic acid (syn-isomer)

In a manner analogous to Example 79, the title compound was produced from the corresponding starting compound.

mp: 136° C. (discoloration).

EXAMPLE 94

7-[2-(2-Aminothiazol-4-yl)-2-cyclopentyloxyiminoacetamido]-3-[(pyridin-4-yl)thiomethyl]-$\Delta^3$-O-2-isocephem-4-carboxylic acid di-trifluoroacetate (syn-isomer)

In a manner analogous to Example 69, the title compound was produced from the corresponding starting compound.

mp: 158°–162° C. (decomposition).

EXAMPLE 95

7-[2-(2-Aminothiazol-4-yl)-2-cyclopentyloxyiminoacetamido]-3-[(1-carboxymethyl-4-pyridinio)thiomethyl]-$\Delta^3$-O-2-isocephem-4-carboxylate (syn-isomer)

In a manner analogous to Example 70, the title compound was produced from the corresponding starting compound.

mp: 167° C. (discoloration).

EXAMPLE 96

7-[2-(2-Aminothiazol-4-yl)-2-cyclopropylmethyloxyiminoacetamido]-3-[(1-carboxymethyl-4-pyridinio)thiomethyl]-$\Delta^3$-O-2-isocephem-4-carboxylic acid di-trifluoroacetate (syn-isomer)

In a manner analogous to Example 69, the title compound was produced from the corresponding starting compound.

mp: 144° C. (discoloration).

EXAMPLE 97

7-[2-(2-Aminothiazol-4-yl)-2-methoxyiminoacetamido]-3-[[1-methyl-6,7-dihydro-4-(5H-1-pyrindinio)]thiomethyl]-$\Delta^3$-O-2-isocephem-4-carboxylic acid di-trifluoroacetate (syn-isomer)

In a manner analogous to Example 69, the title compound was produced from the corresponding starting compound.

mp: 138° C. (discoloration).

EXAMPLE 98

7-[2-(2-Aminothiazol-4-yl)-2-methoxyiminoacetamido]-3-[(6,7-dihydro-5H-1-pyrindin-4-yl)thiomethyl]-$\Delta^3$-O-2-isocephem-4-carboxylic acid di-trifluoroacetate (syn-isomer)

In a manner analogous to Example 69, the title compound was produced from the corresponding starting compound.

mp: 156°–162° C. (decomposition).

EXAMPLE 99

7-[2-(2-Aminothiazol-4-yl)-2-methoxyiminoacetamido]-3-[[1-carboxymethyl-6,7-dihydro-4-(5H-1-pyrindinio)]-thiomethyl]-$\Delta^3$-O-2-isocephem-4-carboxylic acid di-trifluoroacetate (syn-isomer)

In a manner analogous to Example 69, the title compound was produced from the corresponding starting compound.

mp: 168° C. (discoloration).

EXAMPLE 100

7-[2-(2-Aminothiazol-4-yl)-2-cyanomethyloxyiminoacetamido]-3-[(6,7-dihydro-5H-1-pyrindin-4-yl)thiomethyl] -$\Delta^3$-O-2-isocephem-4-carboxylic acid di-trifluoroacetate (syn-isomer)

In a manner analogous to Example 69, the title compound was produced from the corresponding starting compound.

mp: 151° C. (discoloration).

EXAMPLE 101

7-[2-(2-Aminothiazol-4-yl)-2-cyanomethyloxyiminoacetamido]-3-[[1-carboxymethyl-6,7-dihydro-4-(5H-1-pyrindinio)]thiomethyl]-$\Delta^3$-O-2-isocephem-4-carboxylic acid di-trifluoroacetate (syn-isomer)

In a manner analogous to Example 69, the title compound was produced from the corresponding starting compound.

mp: 178° C. (discoloration).

EXAMPLE 102

7-[2-(2-Aminothiazol-4-yl)-2-(2-carboxy-2-propoxyimino)acetamido]-3-[[1-methyl-6,7-dihydro-4-(5H-1-pyrindinio)]thiomethyl]-$\Delta^3$-O-2-isocephem-4-carboxylate (syn-isomer)

In a manner analogous to Example 69, the title compound was produced from the corresponding starting compound.

mp: 183° C. (discoloration).

EXAMPLE 103

7-[2-(2-Aminothiazol-4-yl)-2-cyclopentyloxyiminoacetamido]-3-[[1-methyl-6,7-dihydro-4-(5H-1-pyrindinio)]thiomethyl]-$\Delta^3$-O-2-isocephem-4-carboxylic acid di-trifluoroacetate (syn-isomer)

In a manner analogous to Example 69, the title compound was produced from the corresponding starting compound.

mp: 122° C. (discoloration).

EXAMPLE 104

7-[2-(2-Aminothiazol-4-yl)-2-cyclopentyloxyiminoacetamido]-3-[(1-methyl-4-pyridinio)thiomethyl]-$\Delta^3$-O-2-isocephem-4-carboxylic acid di-trifluoroacetate (syn-isomer)

In a manner analogous to Example 69, the title compound was produced from the corresponding starting compound.

mp: 139° C. (discoloration).

EXAMPLE 105

(6S,7S)-7-[2-(2-Aminothiazol-4-yl)-2-cyclopentyloxyiminoacetamido]-3-[(1,3,4-thiadiazol-2-yl)thiomethyl]-$\Delta^3$-O-2-isocephem-4-carboxylic acid (syn-isomer)

In a manner analogous to Example 60, the title compound was produced from the corresponding starting compound.

$[\alpha]_D^{20} = -11.0°$ (C=0.73, in methanol).

mp: 150° C. (discoloration).

EXAMPLE 106

(6S,7S)-7-[2-(2-Aminothiazol-4-yl)-2-cyclopentyloxyiminoacetamido]-3-[(1,2,4-thiadiazol-5-yl)thiomethyl]-$\Delta^3$-O-2-isocephem-4-carboxylic acid (syn-isomer)

In a manner analogous to Example 60, the title compound was produced from the corresponding starting compound.

mp: 126° C. (discoloration).

$[\alpha]_D^{25} = -33.7°$ (C=0.42, in methanol).

EXAMPLE 107

(6S,7S)-7-[2-(2-Aminothiazol-4-yl)-2-cyclopentyloxyiminoacetamido]-3-[(1,2,3-thiadiazol-5-yl)thiomethyl]-$\Delta^3$-O-2-isocephem-4-carboxylic acid (syn-isomer)

In a manner analogous to Example 60, the title compound was produced from the corresponding starting compound.

mp: 128° C. (discoloration).

$[\alpha]_D^{25} = -11.1°$ (C=0.63, in methanol).

EXAMPLE 108

(6S,7S)-7-[2-(2-Aminothiazol-4-yl)-2-methoxyiminoacetamido]-3-[[1-methyl-6,7-dihydro-4-(5H-1-pyrindinio)]
thiomethyl]-$\Delta^3$-O-2-isocephem-4-carboxylic acid di-trifluoroacetate (syn-isomer)

In a manner analogous to Example 60, the title compound was produced from the corresponding starting compound.

mp: 138° C. (discoloration).

$[\alpha]_D^{25} = -3.0°$ (C=1.02, in methanol).

EXAMPLE 109

7-[2-(2-Aminothiazol-4-yl)-2-cyclopentyloxyiminoacetamido]-3-[(5-methyl-1,3,4-thiadiazol-2-yl)thiomethyl]-$\Delta^3$-O-2-isocephem-4-carboxylic acid (syn-isomer)

In a manner analogous to Example 79, the title compound was produced from the corresponding starting compound.

mp: 140° C. (discoloration).

EXAMPLE 110

7-[2-(2-Aminothiazol-4-yl)-2-cyclohexyloxyiminoacetamido]-3-[(1,3,4-thiadiazol-2-yl)thiomethyl]-$\Delta^3$-O-2-isocephem-4-carboxylic acid (syn-isomer)

In a manner analogous to Example 79, the title compound was produced from the corresponding starting compound.

mp: 160° C. (discoloration).

EXAMPLE 111

7-[2-(2-Aminothiazol-4-yl)-2-cyclopentyloxyiminoacetamido]-3-[(5-amino-1,3,4-thiadiazol-2-yl)thiomethyl]-$\Delta^3$-O-2-isocephem-4-carboxylic acid (syn-isomer)

In a manner analogous to Example 79, the title compound was produced from the corresponding starting compound.
mp: 174° C. (discoloration).

EXAMPLE 112

7-[2-(2-Aminothiazol-4-yl)-2-cyclopentyloxyiminoacetamido]-3-[[1-(2-dimethylaminoethyl)-1H-tetrazol-5-yl]thiomethyl]-$\Delta^3$-O-2-isocephem-4-carboxylic acid di-trifluoroacetate (syn-isomer)

In a manner analogous to Example 69, the title compound was produced from the corresponding starting compound.
mp: 120° C. (discoloration).

EXAMPLE 113

7-[2-(2-Aminothiazol-4-yl)-2-cyclopentyloxyiminoacetamido]-3-[[1-(2-piperidinoethyl)-1H-tetrazol-5-yl]thiomethyl]-$\Delta^3$-O-2-isocephem-4-carboxylic acid di-trifluoroacetate (syn-isomer)

In a manner analogous to Example 69, the title compound was produced from the corresponding starting compound.
mp: 122° C. (discoloration).

EXAMPLE 114

7-[2-(2-Aminothiazol-4-yl)-2-cyclopentyloxyiminoacetamido]-3-[[1-[2-(1-pyrrolidinyl)ethyl]-1H-tetrazol5-yl]thiomethyl]-$\Delta^3$-O-2-isocephem-4-carboxylic acid di-trifluoroacetate (syn-isomer)

In a manner analogous to Example 69, the title compound was produced from the corresponding starting compound.
mp: 118° C. (discoloration).

EXAMPLE 115

7-[2-(2-Aminothiazol-4-yl)-2-cyclopentyloxyiminoacetamido]-3-[(5-carbamoyl-1,3,4-thiadiazol-2-yl)thiomethyl]-$\Delta^3$-O-2-isocephem-4-carboxylic acid trifluoroacetate (syn-isomer)

In a manner analogous to Example 69, the title compound was produced from the corresponding starting compound.
mp: 140° C. (discoloration).

EXAMPLE 116

7-[2-(2-Aminothiazol-4-yl)-2-(tetrahydropyran-4-yl)oxyiminoacetamido]-3-[(1,3,4-thiadiazol-2-yl)thiomethyl]-$\Delta^3$-O-2-isocephem-4-carboxylic acid trifluoroacetate (syn-isomer)

In a manner analogous to Example 69, the title compound was produced from the corresponding starting compound.
mp: 140° C. (discoloration).

EXAMPLE 117

7-[2-(2-Aminothiazol-4-yl)-2-cyclopentyloxyiminoacetamido]-3-[(5-carboxymethyl-1,3,4-thiadiazol-2-yl)-thiomethyl]-$\Delta^3$-O-2-isocephem-4-carboxylic acid trifluoroacetate (syn-isomer)

In a manner analogous to Example 69, the title compound was produced from the corresponding starting compound.
mp: 150° C. (discoloration).

EXAMPLE 118

7-[2-(2-Aminothiazol-4-yl)-2-cyclopentyloxyiminoacetamido]-3-[(5-carboxymethyl-4-methylthiazol-2-yl)thiomethyl]-$\Delta^3$-O-2-isocephem-4-carboxylic acid trifluoroacetate (syn-isomer)

In a manner analogous to Example 69, the title compound was produced from the corresponding starting compound.
mp: 138° C. (discoloration).

EXAMPLE 119

7-[2-(2-Aminothiazol-4-yl)-2-cyclopentyloxyiminoacetamido]-3-[(5-hydroxymethyl-1,3,4-thiadiazol-2-yl)thiomethyl]-$\Delta^3$-O-2-isocephem-4-carboxylic acid trifluoroacetate (syn-isomer)

In a manner analogous to Example 69, the title compound was produced from the corresponding starting compound.
mp: 130° C. (discoloration).

EXAMPLE 120

7-[2-(2-Aminothiazol-4-yl)-2-isopropoxyiminoacetamido]-3-[(1,3,4-thiadiazol-2-yl)thiomethyl]-$\Delta^3$-O-2-isocephem-4-carboxylic acid trifluoroacetate (syn-isomer)

In a manner analogous to Example 99, the title compound was produced from the corresponding starting compound.
mp: 123° C. (discoloration).

EXAMPLE 121

7-[2-(2-Aminothiazol-4-yl)-2-cyclopentyloxyiminoacetamido]-3-[(5-cyano-1,3,4-thiadiazol-2-yl)thiomethyl]-$\Delta^3$-O-2-isocephem-4-carboxylic acid (syn-isomer)

In a manner analogous to Example 69, the title compound was produced from the corresponding starting compound.
mp: 137° C. (discoloration).

EXAMPLE 122

7-[2-(2-Aminothiazol-4-yl)-2-cyclopentyloxyiminoacetamido]-$\Delta^3$-O-2-isocephem-4-carboxylic acid (syn-isomer)

In a manner analogous to Example 70, the title compound was produced from the corresponding starting compound.
mp: 172° C. (discoloration).

EXAMPLE 123

Benzhydryl 7-[2-(2-tritylaminothiazol-4-yl)-2-(pyridin-4-ylmethoxyimino)acetamido]-3-[(1,3,4-thiadiazol-2-yl)thiomethyl]-$\Delta^3$-O-2-isocephem-4-carboxylate (syn-isomer)

In methylene chloride (100 ml) was dissolved benzhydryl 7-azido-3-[(1,3,4-thiadiazol-2-yl)thiomethyl]-$\Delta^3$-O-2-isocephem-4-carboxylate (1.71 g, 3.37 mmol), followed by addition of triethylamine (0.7 ml, 5.06 mmol). Then, under ice-cooling, hydrogen sulfide was introduced to the solution for 10 minutes. The reacation was further conducted at room temperature for 30 minutes, after which the reaction mixture was washed successively with saturated aqueous sodium hydrogen carbonate solution and saturated aqueous sodium chloride solution, drired over anhydrous magnesium sulfate, and concentrated to about 20 ml. (This solution is referred to as Solution A).

On the other hand, 2-(2-tritylaminothiazol-4-yl)-2-(pyridin-4-ylmethoxyimino)acetic acid (syn-isomer) (1.76 g, 3.37 mmol) and 1-hydroxybenzotriazole (0.45 g, 3.37 mmol) were dissolved in a mixture of methylene chloride (100 ml) and dimethylformamide (DMF) (10 ml), and, under ice-cooling, dicyclohexylcarbodiimide (DCC) (0.69 g, 3.37 mmol) was added thereto. The mixture was stirred for 30 minutes. To this mixture was added the above Solution A and the whole mixture was stirred at room temperature for 18 hours. The reaction mixture was filtered and the filtrate was concentrated. Finally, the residue was purified by silica gel column chromatography [eleuent: chloroform-methanol (80:1)]to give the tilte compound (1.10 g) as pale yellow amorphous powder.

mp: 138°-139° C.

NMR (CDCl$_3$) δ: 3.7–4.2 (2H, m), 4.3–4.7 (3H, m), 5.25 (2H, s), 5.50 (1H, dd), 6.62 (1H, s), 6.83 (1H, s), 7.1–7.5 (2H, m), 8.42 (2H, d), 8.78 (1H, s).

EXAMPLE 124

7-[2-(2-Aminothiazol-4-yl)-2-(pyridin-4-ylmethoxyimino)acetamido]-3-[(1,3,4-thiadiazol-2-yl)thiomethyl]-$\Delta^3$-O-2-isocephem-4-carboxylic acid di-trifluoroacetate (syn-isomer)

Benzhydryl 7-[2-(2-tritylaminothiazol-4-yl)-2-(pyridin-4-ylmethoxyimino)acetamido]-3-[(1,3,4-thiadiazol-2-yl)thiomethyl]-$\Delta^3$-O-2-isocephem-4-carboxylate (syn-isomer) (0.77 g, 0.78 mmol) was treated with a mixture of acetic acid (30 ml) and water (20 ml) at 40° C. for 2 hours. The reaction mixture was concentrated to dryness, diethyl ether was added to the residue, and the resulting powdery precipitate was collected by filtration to give the detrityl compound (0.51 g) as pale yellow powder. This powder (0.25 g) was treated with trifluoroacetic acid (3 ml) in the persence of anisole. The reaction was conducted under ice-cooling for 10 minutes, after which diethyl ether was added to the reaction mixture and the resulting powder was collected by filtration to give the title compound (0.26 g).

mp: 119° C. (discoloration), 136°-142° C. (decomposition).

NMR (DMSO-d6) δ: 3.6–4.2 (2H, m), 4.3–4.8 (3H, m), 5.38 (2H, s), 5.73 (1H, dd), 6.79 (1H, s), 7.1–7.5 (2H, m), 7.71 (2H, d), 8.69 (2H, d), 9.33 (1H, d), 9.44 (1H, s).

EXAMPLE 125

7-[2-(2-Aminothiazol-4-yl)-2-(1-methyl-4-pyridiniomethoxyimino)acetamido]-3-[(1,3,4-thiadiazol-2-yl)-thiomethyl]-$\Delta^3$-O-2-isocephem-4-carboxylic acid di-trifluoroacetate (syn-isomer)

In a mixture of methanol (3 ml) and methyl iodide (3 ml) was dissolved benzhydryl 7-[2-(2-tritylaminothiazol-4-yl)-2-(pyridin-4-ylmethoxyimino)acetamido]-3-[(1,3,4-thiadiazol-2-yl)thiomethyl]-$\Delta^3$-O-2-isocephem-4-carboxylate (syn-isomer) (0.30 g, 0.31 mmol) and the solution was allowed to stand at room temperature for 15 hours. The reaction mixture was then concentrated to dryness and the residue was treated with a mixture of acetic acid (12 ml) and water (8 ml) at 40° C. for 2 hours. The reaction mixture was then concentrated to dryness and treated with trifluoroacetic acid (5 ml) in the presence of anisole (0.5 ml). The reaction was carried out under ice-cooling for 10 minutcs, after which diethyl ether was added to the reaction mixture. The resulting pale yellow powder was collected by filtration to give the title compound (0.26 g).

mp: 106° C. (discoloration), 138°-142° C. (decomposition with foaming).

NMR (DMSO-d6) δ: 3.8-4.1 (2H, m), 4.30 (3H, s), 4.4–4.7 (3H, m), 5.47 (2H, s), 5.75 (1H, dd), 6.81 (1H, s), 7.92 (2H, d), 8.84 (2H, d), 9.37 (1H, d), 9.44 (1H, s).

EXAMPLE 126

Benzyl 7-[2-(2-tritylaminothiazol-4-yl)-2-(pyridin-3-ylmethoxyimino)acetamido]-3-[(1,3,4-thiadiazol-2-yl)thiomethyl]-$\Delta^3$-O-2-isocephem-4-carboxylate (syn-isomer)

In a manner analogous to Example 123, the title compound was produced from the corresponding starting compound.

mp: 128°-130° C.

EXAMPLE 127

Benzyl 7-[2-(2-aminothiazol-4-yl)-2-(pyridin-3-ylmethoxyimino)acetamido]-3-[(1,3,4-thiadiazol-2-yl)thiomethyl]-$\Delta^3$-O-2-isocephem-4-carboxylate acetate (syn-isomer)

Benzyl 7-[2-(2-tritylaminothiazol-4-yl)-2-(pyridin-3-ylmethoxyimino)acetamido]-3-[(1,3,4-thiadiazol-2-yl)thiomethyl]-$\Delta^3$-O-2-isocephem-4-carboxylate (syn-isomer) (0.67 g, 0.8 mmol) was treated with a mixture of acetic acid (30 ml) and water (20 ml) at 40° C. for 2 hours. The reaction mixture was concentrated under reduced pressure, diethyl ether was added to the residue, and the resulting powdery precipitate was collected by filtration to give the title compound (0.41 g) as pale yellow powder.

mp: 136°-139° C.

NMR (CDCl$_3$) δ: 2.05 (3H, s), 3.6–4.1 (2H, m), 4.3–4.75 (3H, m), 5.20 (2H, s), 5.30 (2H, bs), 5.64 (1H, dd), 6.80 (1H, s), 7.48 (5H, s), 7.38 (2H, d), 8.53 (2H, d), 9.15 (1H, s).

EXAMPLE 128

Benzyl 7-[2-(2chloroacetamidothiazol-4-yl)-2-(pyridin-4-ylmethoxyimino)acetamido]-3-[(1,2,3-thiadiazol-5-yl)thiomethyl]-$\Delta^3$-O-2-isocephem-4-carboxylate (syn-isomer)

In a manner analogous to Example 123, the title compound was produced from the corresponding starting compound.

mp: 147°–149° C.

EXAMPLE 129

7-[2-(2-Chloroacetamidothiazol-4-yl)-2-(pyridin-4-ylmethoxyimino)acetamido]-3-[(1,2,3-thiadiazol-5-yl)thiomethyl]-$\Delta^3$-O-2-isocephem-4-carboxylic acid (syn-isomer)

To benzyl 7-[2-(2-chloroacetamidothiazol-4-yl)-2-(pyridin-4-ylmethoxyimino)acetamido]-3-[(1,2,3-thiadiazol-5-yl)thiomethyl]-$\Delta^3$-O-2-isocephem-4-carboxylate (syn-isomer) (0.7 g, 0.95 mmol) were added methylene chloride (60 ml) and nitromethane (10 ml) to give the suspention. Then, a solutiuon of anhydrous aluminum chloride (1.73 g, 13 mmol) in nitromethane (10 ml) was added dropwise to the above suspension. The color of the reaction mixture changed from yellow to blackish brown. After 1 hour of reaction, the reaction mixture was poured into water (50 ml) and washed with ethyl acetate (100 ml). The aqueous layer was adjusted to pH 5 with a saturated aqueous solution of sodium hydrogen carbonate and extracted with ethyl acetate (100 ml). The ethyl acetate extract was washed with a saturated aqueous solution of sodium chloride, dried over anhydrous magnesium sulfate, filtered, and concentrated to give the title compound (0.2 g).

mp: 153° C. (discoloration).

NMR (DMSO-d6) $\delta$: 3.65–4.13 (2H, m), 4.32–4.75 (5H, m), 5.30 (2H, s), 5.63 (1H, dd), 7.38 (1H, s), 7.55 (2H, d), 8.48 (2H, d), 8.53 (1H, s).

EXAMPLE 130

7-[2-(2-trifluoroacetamidothiazol-4-yl)-2-(pyridin-3-ylmethoxyimino)acetamido]-3-[(1,4,5,6-tetrahydro-4-methyl-5,6-dioxo-1,2,4-triazin-3-yl)thiomethyl]-$\Delta^3$-O-2-isocephem-4-carboxylic acid (syn-isomer)

In a manner analogous to Example 123, the title compound was produced from the corresponding starting compounds.

mp: 142° C. (discoloration).

EXAMPLE 131

1-Acetoxyethyl 7-[2-(2-trifluoroacetamidothiazol-4-yl)-2-(pyridin-3-ylmethoxyimino)acetamido]-3-[(1,4,5,6-tetrahydro-4-methyl-5,6-dioxo-1,2,4-triazin-3-yl)thiomethyl]-$\Delta^3$-O-2-isocephem-4-carboxylate (syn-isomer)

7-[2-(2-trifluoroacetamidothiazol-4-yl)-2-(pyridin-3-ylmethoxyimino)acetamido]-3-[(1,4,5,6-tetrahydro-4-methyl-5,6-dioxo-1,2,4-triazin-3-yl)thiomethyl]-$\Delta^3$-O-2-isocephem-4-carboxylic acid (syn-isomer) (0.36 g, 0.5 mmol) was dissolved in aqueous sodium hydrogen carbonate in equimolar proportions, followed by lyophilizing to give the sodium salt. This sodium salt was dissolved in dimethylformamide (DMF)(6 ml) and, then, 1-acetoxybromoethane (0.1 g, 0.6 mmol) was added dropwise thereto under ice-cooling. The reaction was carried out for 3 hours, at the end of which time the reaction mixture was poured into water and extracted with ethyl acetate (50 ml). The ethyl acetate extract was successively washed with 5 % aqueous sodium hydrogen carbonate and saturated aqueous sodium chloride, dried over anhydrous sodium sulfate, and filtered. The filtrate was concentrated under reduced pressure to give the title compound (0.13 g).

mp: 129° C. (discoloration), 146° C. (decomposition).

NMR (CDCl$_3$) $\delta$: 1.30 (3H, d), 2.18 (3H, s), 3.36 (3H, s), 3.6–4.1 (2H, m), 4.3–4.7 (3H, m), 5.03 (1H, q), 5.30 (2H, s), 5.68 (1H, dd), 6.91 (1H, s), 7.1–7.8 (2H, m), 8.4–8.6 (2H, m).

EXAMPLE 132

Benzhydryl 7-[2-(2-benzyloxycarbonylaminothiazol-4-yl)-2-(pyridin-3-ylmethoxyimino)acetamido]-3-[(1-benzhydryloxycarbonylmethyl-4-pyridinio)thiomethyl]-$\Delta^3$-O-2-isocephem-4-carboxylate chloride (syn-isomer)

In a manner analogous to Example 123, the title compound was produced from the corresponding starting compounds.

mp: 113° C. (decomposition).

EXAMPLE 133

7-[2-(2-benzyloxycarbonylaminothiazol-4-yl)-2-(pyriding-3-ylmethoxyimino)acetamido]-3-[(1-carboxymethyl-4-pyridinio)thiomethyl]-$\Delta^3$-O-2-isocephem-4-carboxylic acid trifluoroacetate (syn-isomer)

In the presence of anisole (0.8 ml), benzhydryl 7-[-2-(2-benzyloxycarbonylaminothiazol-4-yl)-2-(pyridin-3-ylmethoxyimino)acetamido]-3-[(1-benzhydryloxycarbonylmethyl-4-pyridinio)thiomethyl]-$\Delta^3$-O-2-isocephem-4-carboxylate chloride (syn-isomer)(0.8 g) was reacted with trifluoroacetic acid (8 ml) under ice-cooling for 10 minutes. To the reaction mixture was added diethyl ether and the resulting powder was collected by filtration to give the title compound (0.23 g).

mp: 125° C. (discoloration).

EXAMPLE 134

7-[2-(2-Aminothiazol-4-yl)-2-(pyridin-3-ylmethoxyimino)acetamido]-3-[(1,3,4-thiadiazol-2-yl)thiomethyl]-$\Delta^3$-O-2-isocephem-4-carboxylic acid di-trifluoroacetate (syn-isomer)

In a manner analogous to Example 124, the title compound was produced from the corresponding starting compound.

mp: 112° C. (discoloration), 129°–135° C. (decomposition).

EXAMPLE 135

7-[2-(2-Formamidothiazol-4-yl)-2-(pyridin-4-ylmethoxyimino)acetamido]-3-[(1-methyl-4-pyridinio) thiomethyl]-$\Delta^3$-O-2-isocephem-4-carboxylic acid di-trifluoroacetate (syn-isomer)

In a manner analogous to Example 129, the title compound was produced from the corresponding starting compound.

mp: 121°–129° C. (decomposition).

EXAMPLE 136

Benzhydryl 7-[2-(2-tritylaminothiazol-4-yl)-2-(pyridin-3-ylmethoxyimino)acetamido]-3-[(1-methyl-4-pyridinio)thiomethyl]-$\Delta^3$-O-2-isocephem-4-carboxylate iodide (syn-isomer)

In a manner analogous to Example 123, the title compound was produced from the corresponding starting compound.

mp: 128°–132° C.

EXAMPLE 137

Benzyl 7-[2-(thiazol-4-yl)-2-(pyridin-4-ylmethoxyimino)acetamido]-3-[(pyridin-4-yl)thiomethyl]-$\Delta^3$-O-2-isocephem-4-carboxylate (syn-isomer)

In a manner analogous to Example 123, the title compound was produced from the corresponding starting compound.

mp: 136°–141° C.

EXAMPLE 138

1-Acetoxyethyl 7-[2-(2-trichloroacetamidothiazol-4-yl)-2-ylmetrhoxyimino)acetamido]-3-[(carbamoyloxy)methoxy]-$\Delta^3$-O-2-isocephem-4-carboxylate (syn-isomer)

In a manner analogous to Example 131, the title compound was produced from the corresponding starting compound.

mp: 112° C. (discoloration).

EXAMPLE 139

Benzyl 7-[2-(2-aminothiazol-4-yl)-2-(pyridin-3-ylmethoxyimino)acetamido]-3-[(1-methyl-1,3,4-triazol-2-yl)thiomethyl]-$\Delta^3$-O-2-isocephen-4-carboxylate (syn-isomer)

In manner analogous to Example 127, the title compound was produced from the corresponding starting compound.

mp: 127°–130° C.

EXAMPLE 140

7-[2-Trifluoroacetamidothiazol-4-yl)-2-(pyridin-2-ylmethoxyimino)acetamido]-3-[(1-allyl-1H-tetrazol-5-yl)thiomethyl]-$\Delta^3$-O-2-isocephem-4-carboxylic acid (syn-isomer)

In a manner analogous to Example 129, the title compound was produced from the corresponding starting compound.

mp: 146° C. (discoloration).

EXAMPLE 141

7-[2-(2-Benzyloxycarbonylaminothiazol-4-yl)-2-(pyridin-3-ylmethoxyimino)acetamido]-3-[(4-methyl-5-carboxymethylthiazol-2-yl)thiomethyl]-$\Delta^3$-O-2-isocephem-4-carboxylic acid trifluoroacetate (syn-isomer)

In a manner analogous to Example 133, the title compound was produced from the corresponding starting compound.

mp: 154° C. (discoloration).

EXAMPLE 142

Benzhydryl 7-[2-(2-chloroacetamidothiazol-4-yl)-2-(pyridin-4-ylmethoxyimino)acetamido]-3-[(1,2,4-thiadiazol-5yl)thiomethyl]-$\Delta^3$-O-2-isocephem-4-carboxylate (syn-isomer)

In a manner analogous to Example 123, the title compound was produced from the corresponding starting compound.

mp: 152° C. (discoloration).

EXAMPLE 143

7-[2-(2-Aminothiazol-4-yl)-2-(pyridin-4-ylmethoxyimino)acetamido]-3-[(1-methyl-1H-tetrazol-5-yl)-thiomethyl]-$\Delta^3$-O-2-isocephem-4-carboxylic acid ditrifluoroacetate (syn isomer)

In a manner analogous to Example 124, the title compound was produced from the corresponding starting compound.

mp: 126° C. (discoloration), 145°–148° C. (decomposition).

EXAMPLE 144

7-[2-(2-Aminothiazol-4-yl)-2-(pyridin-3-ylmethoxyimino)acetamido]-3-[[1-[2-(4-methyl-1-piperazinyl)ethyl]-1H-tetrazol-5-yl]thiomethyl]-$\Delta^3$-O-2-isocephem-4-carboxylic acid (syn-isomer)

In a manner analogous to Example 129, the title compound was produced from the corresponding starting compound.

mp: 117° C. (decomposition).

EXAMPLE 145

7-[2-(2-Benzyloxycarbonylaminothiazol-4-yl)-2-(pyridin-2-ylmethoxyimino)acetamido]-3-[[1-methyl-6,7-dihydro-4-(5H-1-pyrindinio)]thiomethyl]-$\Delta^3$-O-2-isocephem-4-carboxylic acid di-trifluoroacetate (syn-isomer)

In a manner analogous to Example 133, the title compound was produced from the corresponding starting compound.

mp: 121° C. (discoloration).

EXAMPLE 146

Benzyl 7-[2-(2-tritylaminothiazol-4-yl)-2-(pyridin-4-ylmethoxyimino)acetamido]-3-[(6,7-dihydro-5H-1-pyrindin-4-yl)thiomethyl]-$\Delta^3$-O-2-isocephem-4-carboxylate (syn-isomer)

In a manner analogous to Example 123, the title compound was produced from the corresponding starting compound.

mp: 132°–135° C.

EXAMPLE 147

7-[2-(2-Formamidothiazol-4-yl)-2-(pyridin-4-ylmethoxyimino)acetamido]-3-[[1-carboxymethyl-6,7-dihydro-4-(5H-1-pyrindinio)]thiomethyl]-$\Delta^3$-O-2-isocephem-4-carboxylic acid di-trifluoroacetate (syn-isomer)

In a manner analogous to Example 133, the title compound was produced from the corresponding starting compound.

mp: 133° C. (discoloration).

EXAMPLE 148

7-[2-(2-Trifluoroacetamidothiazol-4-yl)-2-(pyridin-4-ylmethoxyimino)acetamido]-3-[(5-methyl-1,3,4-thiadiazol-2-yl)thiomethyl]-$\Delta^3$-O-2-isocephem-4-carboxylic acid (syn-isomer)

In a manner analogous to Example 129, the title compound was produced from the corresponding starting compound.

mp: 147° C. (discoloration).

EXAMPLE 149

Benzyl 7-[2-(tritylaminothiazol-4-yl)-2-(pyridin-3-ylmethoxyimino)acetamido]-3-[(5-amino-1,3,4-thiadiazolyl)thiomethyl]-Δ³-O-2-isocephem-4-carboxylate (syn-isomer)

In a manner analogous to Example 123, the title compound was produced from the corresponding starting compound.

mp: 124°–129° C.

EXAMPLE 150

Benzyl 7-[2-(2-chloroacetamidothiazol-4-yl)-2-methoxyiminoacetamido]-3-[(carbamoyloxy)methyl]-Δ³-O-2-isocephem-4-carboxylate (syn-isomer)

To dichloromethane (20 ml) were added benzyl 7-[2-(2-aminothiazol-4-yl)-2-methoxyiminoacetamido]-3-[(carbamoyloxy)methyl]-Δ³-O-2-isocephem-4-carboxylate (syn-isomer) (0.53 g, 1 mmol) and triethylamine (0.15 g, 1.4 mmol), and under ice-cooling, a solution of monochloroacetic anhydride (0.20 g, 1.2 mmol) in dichloromethane (3 ml) was added dropwise. After completion of the dropwise addition, the mixture was stirred at the same temperature for 30 minutes and, then, at room temperature for 1 hour. The reaction mixture was poured into ice-water and the organic layer was separated. The organic layer was successively washed with a 20-fold dilution of concentrated hydrochloric acid, a 5% aqueous sodium hydrogen carbonate and saturated aqueous sodium chloride, dried over anhydrous magnesium sulfate, and filtered. The filtrate was concentrated to give the title compound (0.43 g) as light yellow powder.

mp: 161° C. (discoloration), >300° C.

EXAMPLE 151

Benzyl 7-[2-(2-aminothiazol-4yl)-2-cyclopentyloxyiminoacetamido]-3-[(1,3,4-thiadiazole-2-yl)thiomethyl]-Δ³-O-2-isocephem-4-carboxylate (syn-isomer)

(A) A solution of benzyl 7-amino-3-[(1,3,4-thiadiazol-2-yl)thiomethyl]-Δ³-O-2-isocephem-4-carboxylate (syn-isomer) (0.43 g, 1.05 mmol) and 3-oxo-4-bromo-2-cyclopentyloxyiminobutyric acid (0.36 g, 1.3 mmol) in a mixture of methylene chloride (10 ml) and dimethylformamide (2 ml) was stirred under ice-cooling. To this solution was added dicyclohexylcarbodiimide (DCC) (02.7 g, 1.3 mmol) all at once and the reaction was conducted overnight. The precipitate was filtered off and the filtrate was washed with water, dried over anhydrous magnesium sulfate, and filtered. The filtrate was concentrated and subjected to silica gel column chromatography [eluent: n-hexane-ethyl acetate (1:1) for separation and purification to give benzyl 7-(3-oxo-4-bromo-2-cyclopentyloxyiminobutyramido)-3-[(1,3,4-thiadiazol-2-yl)thiomethyl]-Δ³-O-2-isocephem-4-carboxylate (syn-isomer) (0.38 g).

NMR (CDCl₃) δ: 1.5–2.1 (8H, m), 3.6–4.2 (2H, m), 4.45 (2H, s), 4.50 (1H, m), 4.61 (1H, dd), 5.25 (2H, s), 5.75 (1H, dd), 6.60 (1H, s), 7.35 (5H, m), 8.2 (1H, d), 9.43 (1H, s).

(B) To benzyl 7-(3-oxo-4-bromo-2-cyclopentyloxyiminobutyramido)-3-[(1,3,4-thiadiazol-2-yl)thiomethyl]-Δ³-O-2-isocephem-4-carboxylate (syn-isomer) (6.64 g, 10 mmol), thiourea (0.76 g, 10 mmol), and soduim acetate (0.82 g, 10 mmol) were added methanol (10 ml) and water (10 ml), and the mixture was warmed at 60° C. for 1 hour. Thereafter, the reaction mixture was cooled and adjusted to pH 6.2 with saturated aqueous sodium hydrogen carbonate. The resulting crude crystals were collected by filtration, washed with diisopropyl ether and subjected to silica gel column chromatography [eluent: n-hexane-ethyl acetate (1:1)]for separation and purification to give the title compound (1.3 g).

NMR (CDCl₃) δ: 1.53–2.08 (8H, m), 3.60–4.21 (2H, m), 4.65 (1H, m), 5.05 (2H, dd), 5.28 (2H, s), 5.56 (2H, bs), 5.73 (1H, dd), 6.62 (1H, s), 7.40 (5H, m), 8.23 (1H, d), 9.45 (1H, s).

EXAMPLE 152

7-[2-(2-Aminothiazol-4-yl)-2-methoxyiminoacetamido]-3-[(1,3,4-thiadiazol-2-yl)thiomethyl]-Δ³-O-2-isocephem-4-carboxylic acid (syn-isomer)

In 0.2 M potassium phosphate buffer (100 ml) was dissolved 7-[2-(2-aminothiazol-4-yl)-2-methoxyiminoacetamido]-3-acetoxymethyl-Δ³-O-2-isocephem-4-carboxylic acid (syn-isomer) (4.4 g, 10 mmol), followed by addition of 2-mercapto-1,3,4-thiadiazole (1.8 g, 15 mmol). Then, the mixture was adjusted to pH 6.5 by dropwise addition of saturated aqueous sodium hydrogen carbonate. As this mixture was warmed to 65° C., there occurred an increase of pH. With the mixture being adjusted to pH 6.6 to 6.7 with a 10-fold dilution of concentrated hydrocholoric acid, the reaction was continued at that temperature for 6 hours. Then, the reaction mixture was adjusted to pH 4 with a 10-fold dilution of concentrated hydrochloric acid and the resulting precipitate was collected by filtration The precipitate was dissolved in a 7% aqueous solution of sodium hydrogen carbonate and the nonionic adsorbent resin Diaion HP-20 (100 g) was added thereto. The mixture was adjusted to pH 3.5 with a 10-fold dilution of concentrated hydrochloric acid. The Diaion HP-20 was collected by filtration and washed with water, followed by elution with 5%, 10% and 20% aqueous solutions of isopropyl alcohol. The eluate containing the desired product was concentrated under reduced 5 pressure to give the title compound (1.2 g).

mp: 146° C. (coloration), 158° C. (decomposition).

NMR (DMSO-d6) δ:3.60–5.13 (2H, m), 3.83 (3H, s), 5.67 (1H, dd), 6.75 (1H, s), 7.13 (2H, bs), 9.13 (1H, d), 9.49 (1H, s)

EXAMPLE 153

Benzyl 7-[2-(2-tert-butoxycarbonylaminothizol-4-yl)-2-methoxyiminoacetamido]-3-[(1,3,4-triazol-2-yl)-thiomethyl]-Δ³-O-2-isocephem-4-carboxylate (syn-isomer)

In a manner analogous to Example 1, the title compound was produced from the corresponding starting compound.

mp: 165–172 (decomposition).

NMR (CDCl₃) δ: 1.48 (9H, s), 3.95 (3H, s), 3.7–4.1 (2H, m), 4.21 (1H, d), 4.43 (1H, d), 4.5–4.8 (1H, m), 5.25 (2H, s), 5.70 (1H, dd), 7.27 (1H, s), 7.35 (5H, m), 8.10 (1H, s), 9.16 (1H, d).

EXAMPLE 154

7-[2-(2-Aminothiazol-4-yl)-2-methoxyiminoacetamido]-3-[(1-carbamoylmethyl-4-pyridinio)thiomethyl]-$\Delta^3$-O-2-isocephem-4-carboxylate (syn-isomer)

In a manner analogous to Example 70, the title compound was produced from the corresponding starting compound.
mp: 188° C. (discoloration).

EXAMPLE 155

7-[2-(2-Aminothiazol-4-yl)-2-cyanomethoxyiminoacetamido]-3-[(1-carbamoylmethyl-4-pyridinio)thiomethyl]-$\Delta^3$-O-2-isocephem-4-carboxylate (syn-isomer)

In a manner analogous to Example 70, the title compound was produced from the corresponding starting compound.
mp: 175° C. (discoloration).

EXAMPLE 156

7-[2-(2-Aminothiazol-4-yl)-2-methoxyiminoacetamido]-3-[(1-cyanomethyl-4-pyridinio)thiomethyl]-$\Delta^3$-O-2-isocephem-4-carboxylate (syn-isomer)

In a manner analogous to Example 70, the title compound was produced from the corresponding starting compound.
mp: 164° C. (discoloration).

EXAMPLE 157

7-[2-(2-Aminothiazol-4-yl)-2-cyanomethoxyiminoacetamido]-3-[(1-cyanomethyl-4-pyridinio)thiomethyl]-$\Delta^3$-O-2-isocephem-4-carboxylate (syn-isomer)

In a manner analogous to Example 70, the title compound was produced from the corresponding starting compound.
mp: 171° C. (discoloration).

EXAMPLE 158

7-[2-(2-Aminothiazol-4-yl)-b 2-methoxyiminoacetamido]-3-[[1-(2-hydroxyethyl)-4-pyridinio]thiomethyl]-$\Delta^3$O-2-isocephem-4-carboxylate (syn-isomer)

In a manner analogous to Example 70, the title compound was produced from the corresponding starting compound.
mp: 185° C. (discoloration).

EXAMPLE 159

7-[2-(2-Aminothiazol-4-yl)-2-methoxyiminoacetamido]-3-[(1-methylthiomethyl-4-pyridinio)thiomethyl]-$\Delta^{33}$-O-2-isocephem-4-carboxylate (syn-isomer)

In a manner analogous to Example 70, the title compound was produced from the corresponding starting compound.
mp: 126° C. (discoloration).

EXAMPLE 160

7-[2-(2-Aminothiazol-4-yl)-2-methoxyiminoacetamido]-3-[(1-sulfomethyl-4-pyridinio)thiomethyl]-$\Delta^3$-O-2-isocephem-4-carboxylate (syn-isomer)

In a manner analogous to Example 70, the title compound was produced from the corresponding starting compound.
mp: 136° C. (discoloration).

EXAMPLE 161

7-[2-(2-Aminothiazol-4-yl)-2-methoxyiminoacetamido]-3-[(5-carboxymethyl-1,3,4-thiadiazol-2-yl)thiomethyl]-$\Delta^3$-O-2-isocephem-4-carboxylic acid (syn isomer)

In a manner analogous to Example 79, the title compound was produced from the corresponding starting compound.
mp: 155° C. (discoloration).

EXAMPLE 162

(6S,7S)-7-[2-(2-Aminothiazol-4-yl)-2-cylopentyloxyiminoacetamido]-3-[(1-carbamoylmethyl-4-pyridinio)thiomethyl]-$\Delta^3$-O-2-isocephem-4-carboxylate (syn-isomer)

In a manner analogous to Example 69, the title compound was produced from the corresponding starting compound.
mp: 185° C. (discoloration).
NMR (DMSO-d6) δ: 1.3–2.0 (8H,m), 3.6–4.1 (2H, m), 4.1–5.7 (7H,m), 6.70 (1H,s), 7.15 (2H, s), 7.59(1H,s), 8.23(1H,s), 8.43 (2H, d), 8.63 (2H, d), 9.05 (1H,d).

EXAMPLE 163

(6S,7S)-7-[2-(2-Aminothiazol-4-yl)-2-cyclopentyloxyiminoacetamido]-3-[(1-methyl-4-pyridinio)thiomethyl]-$\Delta^3$-O-2-isocephem-4-carboxylate (syn-isomer)

In a manner analogous to Example 69, the title compound was produced from the corresponding starting compound.
mp: 168° C. (discoloration).
NMR (DMSO-d6) δ: 1.3–2.0(8H,m), 3.6–4.0(2H,m), 4.16 (3H,s), 4.2–5.3(4H,m), 5.45(1H,dd), 6.70 (1H,s), 7.16 (2H,s), 8.32(2H,d), 8.63(2H,d), 9.05(1H,d)

EXAMPLE 164

(6S,7S)-7-[2-(2-Aminothiazol-4-yl)-2-cyanomethoxyiminoacetamido]-3-[(1-carbamoylmethyl-4-pyridinio)thiomethyl]-$\Delta^3$-O -2-isocephem-4-carboxylate (syn-isomer)

In a manner analogous to Example 70, the title compound was produced from the corresponding starting compound.
mp: 165° C. (discoloration).

EXAMPLE 165

(6S,7S)-7-[2-(2-Aminothiazol-4-yl)-2-methoxyiminoacetamido]-3-[(1-methyl-4-pyridinio)thiomethyl]-$\Delta^3$-O-2-isocephem-4-carboxylate (syn-isomer)

In a manner analogous to Example 70, the title compound was produced from the corresponding starting compound.
mp: 160° C. (discoloration).

EXAMPLE 166

(6S,7S)-7-[2-(2-Aminothiazol-4-yl)-2-methoxyiminoacetamido]-3-[(1-carbamoylmethyl-4-pyridinio)thiomethy-1]-$\Delta^3$-O-2-isocephem-4-carboxylate (syn-isomer)

In a manner analogous to Example 70, the title compound was produced from the corresponding starting compound.
mp: 160° C. (discoloration)

EXAMPLE 167

(6S,7S)-7-[2-(2-Aminothiazol-4-yl)-2-cyclopentyloxyiminoacetamido]-3-[[1-(2-hydroxyethyl)-4-pyridinio]-thiomethyl]-$\Delta^3$-O-2-isocephem-4-carboxylate (syn-isomer)

In a manner analogous to Example 70, the title compound was produced from the corresponding starting compound.
mp: 166° C. (discoloration).

EXAMPLE 168

(6S,7S)-7-[2-(2-Aminothiazol-4-yl)-2-cyclopentyloxyiminoacetamido]-3-[(1-ethyl-4-pyridinio)thiomethyl-$\Delta^3$-O-2-isocephem-4-carboxylate (syn-isomer)

In a manner analogous to Example 70, the title compound was produced from the corresponding starting compound.
mp: 175° C. (discoloration).

EXAMPLE 169

(6S,7S)-7-[2-(2-Aminothiazol-4-yl)-2-methoxyiminoacetamido]-3-[(1-allyl-4-pyridinio)thiomethyl-$\Delta^3$-O-2-isocephem-4-carboxylate (syn-isomer)

In a manner analogous to Example 70, the title compound was produced from the corresponding starting compound.
NMR(DMSO-d6) δ; 3.83(3H,s), 3.65–4.05(2H,m), 4.3–4.75(3H,m), 4.95–5.15(2H,d), 5.2–5.4(1H,m), 6.75(1H,s), 7.05–7.25(2H,m), 7.46–7.61(1H,dd), 8.24–8.42 (2H,dd), 8.55–8.73(2H,dd), 9.0–9.18(1H,d).

EXAMPLE 170

(6S,7S)-7-[2-(2-Aminothiazol-4-yl)-2-methoxyiminoacetamido]-3-[[1-(2-hydroxyethyl)-4-pyridinio]-thiomethyl]-$\Delta^3$-O-2-isocephem-4-carboxylate (syn-isomer)

In a manner analogous to Example 70, the title compound was produced from the corresponding starting compound.
mp: 151° C. (discolored to a brown color)

EXAMPLE 171

(6S,7S)-7-[2-(2-Aminothiazol-4-1,1)-2-cyclopentyloxyiminoacetamido]-3-[(1-methyl-2-pyridinio)thiomethyl]-$\Delta^3$-O-2-isocephem-4-carboxylic acid sulfate (syn-isomer)

In a manner analogous to Example 69, the title compound was produced from the corresponding starting compound.
mp: 131° C. (discoloration).

EXAMPLE 172

(6S,7S)-7-[2-(2-Aminothiazol-4-yl)-2-cyclopentyloxyiminoacetamide]-3-[(1-allyl-4-pyridinio)thiomethyl]-$\Delta^3$-O-2-isocephem-4-carboxylate (syn-isomer)

In a manner analogous to Example 70, the title compound was produced from the corresponding starting compound.
NMR(DMSO-d6) δ; 1.35–2.0(8H,br), 3.70–3.95(2H,m), 4.25–4.46 (1H,m), 4.55–4.70(2H,dd), 5.0–5.15(1H,m), 5.20–5.40(1H,d), 5.48(2H,s), 6.72(1H,s), 7.10–7.25(2H,m), 7.50–7.64(1H,dd), 8.20–8.35 (2H,dd), 8.60–8.75(2H,dd), 9.0–9.15(1H,d)

EXAMPLE 173

(6S,7S)-7-[2-(2-Aminothiazol-4-yl)-2-cyanomethoxyiminoacetamido]-3-[(1-carboxymethyl-4-pyridinio)thiomethyl]-$\Delta^3$-O-2-isocephem-4-carboxylate (syn-isomer)

In a manner analogous to Example 70, the title compound was produced from the corresponding starting compound.
mp: 148° C. (discoloration).

EXAMPLE 174

(6S,7S)-7-[2-(2-Aminothiazol-4-yl)-2-methoxyiminoacetamido]-3-[(1-carboxymethyl-4-pyridinio)thiomethyl]-$\Delta^3$-O-2-isocephem-4-carboxylate (syn-isomer)

In a manner analogous to Example 70, the title compound was produced from the corresponding starting compound.
mp: 158° C. (discoloration).

EXAMPLE 175

(6S,7S)-7-[2-(2-Aminothiazol-4-yl)-2-carboxymethoxyiminoacetamido]-3-[(1-methyl-4-pyridinio)thiomethyl]-$\Delta^3$-O-2-isocephem-4-carboxylate (syn-isomer)

In a manner analogous to Example 70, the title compound was produced from the corresponding starting compound.
mp: 156° C. (discoloration).

EXAMPLE 176

(6S,7S)-7-[2-(2-Aminothiazol-4-yl)-2-(2-carboxy-2-propoxyimino)acetamido]-3-[(1-methyl-4-pyridinio)thiomethyl]-$\Delta^3$-O-2-isocephem-4-carboxylate (syn-isomer)

In a manner analogous to Example 70, the title compound was produced from the corresponding starting compound.
mp: 155° C. (discoloration).

EXAMPLE 177

(6S,7S)-7-[2-(2-Aminothiazol-4-yl)-2-cyclobutyloxyiminoacetamido]-3-[(1,3,4-thiadiazol-2-yl)thiomethyl]-$\Delta^3$-O-2-isocephem-4-carboxylic acid (syn-isomer)

In a manner analogous to Example 79, the title compound was produced from the corresponding starting compound.
mp: 167° C. (discoloration).

EXAMPLE 178

1-Acetoxyethyl (6S,7S)-7-[2-(2-aminothiazol-4-yl)-2-cyclopentyloxyiminoacetamido]-3-[(1,3,4-thiadiazol-2yl)thiomethyl]-$\Delta^3$-O-2-isocephem-4-carboxylate (syn-isomer)

In a manner analogous to Example 59, the title compound was produced from the corresponding starting compound.
mp: 126°–129° C.

EXAMPLE 179

1-Propionyloxyethyl (6S,7S)-7-[2-(2-aminothiazol-4-yl)-2-cyclopentyloxyiminoacetamido]-3-[(1,3,4thiadiazol-2-yl)thiomethyl]-$\Delta^3$-O-2-isocephem-4carboxylate (syn-isomer), In a manner analogous to Example 59, the title compound was produced from the corresponding starting compound.
mp: 124°–127° C.

EXAMPLE 180

(6S,7S)-7-[2-(2-Aminothiazol-4-yl)-2-methoxyiminoacetamido]-3-[(1-methyl-2-pyridinio)thiomethyl]-$\Delta^3$-O-2-isocephem-4-carboxylate (syn isomer)

In a manner analogous to Example 70, the title compound was produced from the corresponding starting compound.

mp: 154° C. (discoloration)

EXAMPLE 181

(6S,7S)-7-[2-(2-Aminothiazol-4-yl)-2-cyanomethoxyiminoacetamido]-3-[(1-methyl-4-pyridinio)thiomethyl]-$\Delta^3$-O-2-isocephem-4-carboxylate (syn-isomer)

In a manner analogous to Example 70, the title compound was produced from the corresponding starting compound.

mp: 155° C. (discoloration).

EXAMPLE 182

(6S,7S)-7-[2-(2-Aminothiazol-4-yl)-2-cyclopentyloxyiminoacetamido]-3-[(1-methylthiomethyl-4-pyridinio)thiomethyl]-$\Delta^3$-O-2-isocephem-4-carboxylate (syn-isomer)

In a manner analogous to Example 70, the title compound was produced from the corresponding starting compound.

NMR(DMSO-d6) δ: 1.3–1.9(8H, br), 2.14(3H, s), 3.70–3.90(2H, m), 4.27–4.75(3H, m), 4.8–4.95(1H, br), 5.14(2H, s), 5.45–5.70(1H, m), 6.70(1H, s) 8.15–8.35(2H, dd), 8.65–8.85(2H, dd), 8.95–9.10(1H, d)

EXAMPLE 183

Benzhydryl (6S,7S)-7-[2-(2-t-butoxycarbonylaminothiazol-4-yl)-2-methoxyiminoacetamido]-3-[(pyridin-4-yl)thiomethyl]-$\Delta^3$-O-2-isocephem-4-carboxylate (syn-isomer)

To a solution of benzhydryl (6S,7S)-7-azido-3-(pyridin-4-yl)thiomethyl]-$\Delta^3$-O-2-isocephem-4-carboxylate (13.60 g) in methylene chloride (150 ml) was added triethylamine (5.67 g) under ice-cooling, and hydrogen sulfide gas was bubbled into the mixture for 10 minutes. After stirring for 40 minutes at room temperature, the mixture was washed successively with a saturated aqueous solution of sodium hydrogencarbonate and a saturated aqueous solution of sodium chloride, dried over anhydrous magnesium sulfate and filtered to give a solution (hereinafter referred to as solution A).

On the other hand, to a suspension of 2-(2-t-butoxycarbonylaminothiazol-4-yl)-2-methoxyiminoacetic acid (syn-isomer) (9.0 g) in methylene chloride (150 ml) was added dicyclohexylcarbodiimide (6.16 g) under ice-cooling, and the mixture was stirred for 10 minutes at the same temperature. To this solution was added the solution A mentioned above, and the mixture was stirred for one hour under ice-cooling and 15 hours at room temperature. The reaction mixture was filtered off and the filtrate was evaporated in vacuo. The residue was purified by subjecting to silica gel column chromatography [eluent: chloroform-hexane (9:1)] to give the title compound (15.02 g).

Light yellow plate
mp: 140°–142° C.

| Pharmaceutical Example 1 | |
|---|---|
| 7-[2-(2-Aminothiazol-4-yl)-2-methoxyiminoacetamido]-3-[(carbamoyloxy)methyl]-$\Delta^3$-O—2-isocephem-4-carboxylic acid (syn-isomer) | 200 mg |
| Glucose | 250 mg |
| Distilled water for injection | q.s. |
| Total | 5 ml |

In distilled water for injection are dissolved 7-[2-(2-aminothiazol-4-yl)-2-methoxyiminoacetamido]-3-[(carbamoyloxy)methyl]-$\Delta^3$-O-2-isocephem-4-carboxylic acid (syn isomer) and glucose and the solution is filled into a 5 ml ampule. After nitrogen purging, sterilization is carried out by autoclaving at 121° C. for 15 minutes to give a parenteral product of the above composition.

| Pharmaceutical Example 2 | |
|---|---|
| 7-[2-(2-Aminothiazol-4-yl)-2-methoxyiminoacetamido]-3-[(1,3,4-thiadiazol-2-yl)thiomethyl]-$\Delta^3$-O—2-isocephem-4-carboxylic acid (syn-isomer) | 100 g |
| Avicel (trademark of Asahi Chemical Industry) | 40 g |
| Corn starch | 30 g |
| Magnesium stearate | 2 g |
| TC-5 (trademark of Shin-Etsu Chemical; hydroxypropylmethyl-cellulose) | 10 g |
| Polyethylene glycol 6000 | 3 g |
| Castor oil | 40 g |
| Ethanol | 40 g |

7-[2-(2-Aminothiazol-4-yl)-2-methoxyiminoacetamido]-3-[(1,3,4-trhiadiazol-2-yl)thiomethyl]-$\Delta^3$-O-2-isocephem-4-carboxylic acid (syn-isomer), Avicel, corn starch and magnesium stearate are milled together and tableted by means of an R 10 mm punch (for sugar-coated tablets). The resulting tablets were coated with a film coating composition consisting of TC-5, polyethylene 6000, castor oil and ethanol to give film-coated tablets of the above composition.

| Pharmaceutical Example 3 | |
|---|---|
| 7-[2-(2-Aminothiazol-4-yl)-2-allyloxyiminoacetamido]-3-[(1,3,4-thiadiazol-2-yl)thiomethyl]-$\Delta^3$-O—2-isocephem-4-carboxylic acid (syn-isomer) | 2 g |
| Purified lanolin | 5 g |
| White beeswax | 5 g |
| White petrolatum | 88 g |
| Total | 100 g |

White beeswax is melted by warming and, then, 7-[2-(2-aminothiazol-4-yl)-2-allyloxyiminoacetamido]-3-[(1,3,4-thiadiazol-2-yl)thiomethyl]-$\Delta^{33}$-O-2-isocephem-4-carboxylic acid (syn-isomer), purified lanolin and white petrolatum are added. The mixture is warmed until it forms a liquid and, then, stirred until it is solidified to give an ointment of the above composition.

[Antimicrobial activity test]

In order to investigate the in vitro activity of the under-mentioned compounds against various bacteria, the minimal inhibitory concentration (MIC) values were determined by the agar plate dilution method [see Chemotherapy, 22, 1126–1128 (1974)].

The results are shown in Table 1.

Each test inoculum was adjusted to $1 \times 10^6$ cells/ml (O.D., 600 mμ: 0.07–0.16).

Test compounds

No. 1: 7-[2-(2-Aminothiazol-4-yl)-2-methoxyiminoacetamido]-3-[(carbamoyloxy)methyl]-$\Delta^3$-O-2-isocephem-4-carboxylic acid (syn-isomer)

No. 2: 7-[2-(2-Aminothiazol-4-yl)-2-methoxyiminoacetamido]-3-[(1,3,4-thiadiazol-2-yl)thiomethyl]- $\Delta^{33}$-O-2-isocephem-4-carboxylic acid (syn-isomer)

No. 3: 7-[2-(2-Aminothiazol-4-yl)-2-allyloxyiminoacetamido]-3-[(1,3,4-thiadiazol-2-yl)thiomethyl]- $\Delta^3$-O-2-isocephem-4-carboxylic acid (syn-isomer)

No. 4: 7-[2-(2-Aminothiazol-4-yl)-2-methoxyiminoacetamido]-3-[(1,4,5,6-tetrahydro-4-methyl-5,6-dioxo-1,2,4-triazin-3-yl)thiomethyl]-$\Delta^3$-O-2-isocephem-4-carboxylic acid (syn-isomer)

No. 5: 7-[2-(2-Trifluoroacetamidothiazol-4-yl)-2-methoxyiminoacetamido]-3-[(carbamoyloxy)methyl]-$\Delta^3$-O-2-isocephem-4-carboxylic acid (syn-isomer)

No. 6: 7-[2-(Thiazol-4-yl)-2-carboxymethoxyiminoacetamido]-$\Delta^3$-O-2-isocephem-4-carboxylic acid (syn-isomer)

No. 7: 7-[2-(2-Aminothiazol-4-yl)-2-propargyloxyiminoacetamido]3-[(1,3,4-thiadiazol-2-yl)thiomethyl-66$^3$-O-b 2-isocephem-4-carboxylic acid trifluoroacetate (syn-isomer)

No. 8: 7-[2-(2-Aminothiazol-4-yl)-2-(pyrazol-3-yl)methoxyiminoacetamido]-3-[(1,3,4-thiadiazol-2-yl)thiomethyl]-$\Delta^3$-O-2-isocephem-4-carboxylic acid trifluoroacetate (syn-isomer)

No. 9: 7-[2-(2-Aminothiazol-4-yl)-2-(2-chloroethoxy)iminoacetamido]-3-[(1,3,4-thiadiazol-2-yl)thiomethyl]-$\Delta^3$-O-2-isocephem-4-carboxylic acid (syn-isomer)

No. 10: 7-[2-(2-Aminothiazol-4-yl)-2-cyclopropylmethyloxyiminoacetamido]-3-[(1,3,4-thiadiazol-2-yl)thiomethyl]-$\Delta^3$-O-2-isocephem-4-carboxylic acid trifluoroacetate (syn-isomer)

No. 11 7-[2-(2-Aminothiazol-4-yl)-2-cyanomethyloxyiminoacetamido]-3-[(1,3,4-thiadiazol-2-yl)thiomethyl]-$\Delta^3$-O-2-isocephem-4-carboxylic acid trifluoroacetate (syn-isomer)

No. 12: 7-[2-(2-Aminothiazol-4-yl)-2-methylthiomethoxyiminoacetamido]-3-[(1,3,4-thiadiazol-2-yl)thiomethyl]-$\Delta^3$-O-2-isocephem-4-carboxylic acid (syn-isomer)

No. 13: 7-[2-(2-Aminothiazol-4-yl)-2-benzyloxyiminoacetamido]-3-[(1,3,4-thiadiazol-2-yl)thiomethyl]-$\Delta^3$-O-2-isocephem-4-carboxylic acid trifluoroacetate (syn-isomer)

No. 14: 7-[2-(2-Aminothiazol-4-yl)-2-methoxyiminoacetamido]-3-[(1,2,3-thiadiazol-5-yl)thiomethyl]-$\Delta^3$-O-2-isocephem-4-carboxylic acid trifluoroacetate (syn-isomer)

No. 15: (6S,7S)-7-[2-(2-Aminothiazol-4-yl}-2methoxyiminoacetamido]-3-[(1,3,4-thiadiazol-2-yl)thiomethyl]-$\Delta^3$-O-2-isocephem-4-carboxylic acid trifluoroacetate (syn-isomer)

No. 16: (6S,7S)-7-[2-(2-Aminothiazol-4-yl)-2cyanomethoxyiminoacetamido]-3-[(1,3,4-thiadiazol-2-yl)thiomethyl]-$\Delta^3$-O-2-isocephem-4carboxylic acid trifluoroacetate (syn-isomer)

No. 17: 7-[2-(2-Aminothiazol-4-yl)-2-methoxyiminoacetamido]-3-[(1-methyl-4-pyridinio)thiomethyl]-$\Delta^3$-O-2-isocephem-4-carboxylic acid trifluoroacetate (syn-isomer)

No. 18: 7-[2-(2-Aminothiazol-4-yl)-2-methoxyiminoacetamido]-3-[(1-carboxymethyl-4-pyridinio)thiomethyl]-$\Delta^3$-O-2-isocephem-4-carboxylic acid trifluoroacetate (syn-isomer)

No. 19: 7-[2-(2-Aminothiazol-4-yl)-2-cyanomethoxyiminoacetamido]-3-[(1-methyl-4-pyridinio)thiomethyl]-$\Delta^3$-O-2-isocephem-4-carboxylic acid trifluoroacetate (syn-isomer)

No. 20: 7-[2-(2-Aminothiazol-4-yl)-2-methoxyiminoacetamido]-3-[(pyridin-4-yl)thiomethyl]-$\Delta^3$)O-2-isocephem-4-carboxylic acid trifluoroacetate (syn-isomer)

No. 21: 7-[2-(2-Aminothiazol-4-yl)-2-methoxyiminoacetamido]-3-[(1,3,4-triazol-2-yl)thiomethyl]-$\Delta^3$-O-2-isocephem-4-carboxylic acid (syn-isomer)

No. 22: 7-[2-(2-Aminothiazol-4-yl)-2-methoxyiminoacetamido]-3-[(1-allyl-1H-tetrazol-5-yl)thiomethyl]-$\Delta^3$-O-2-isocephem-4-carboxylic acid (syn-isomer)

No. 23: 7-[2-(2-Aminothiazol-4-yl)-2-methoxyiminoacetamido]-3-[(4-methyl-5-carboxymethylthiazol-2-yl)thiomethyl]-$\Delta^3$-O-2-isocephem-4-carboxylic acid (syn-isomer)

No. 24: 7-[2-(2-Aminothiazol-4-yl)-2-methoxyiminoacetamido]-3-[(1-carboxymethyl-1H-tetrazol-5-yl)thiomethyl]-$\Delta^3$-O-2-isocephem-4-carboxylic acid (syn-isomer)

No. 25: 7-[2-(2-Aminothiazol-4-yl)-2-methoxyiminoacetamido]-3-[[1-(2-hydroxyethyl)-1H-tetrazol-5-yl]thiomethyl]-$\Delta^3$-O-2-isocephem-4-carboxylic acid (syn-isomer)

No. 26: 7-[2-(2-Aminothiazol-4-yl)-2-methoxyiminoacetamido]-3-[(1,2,4-thiadiazol-5-yl)thiomethyl]-$\Delta^3$-O-2-isocephem-4-carboxylic acid (syn-isomer)

No. 27: 7-[2-(2-Aminothiazol-4-yl)-2-cyclopentyloxyiminoacetamido]-3-[(1,3,4-thiadiazol-2-yl)thiomethyl]-$\Delta^3$-O-2-isocephem-4-carboxylic acid (syn-isomer)

No. 28: 7-[2-(2-Aminothiazol-4-yl)-2-methoxyiminoacetamido]-3-[[1-[2-(4-methyl-1-piperazinyl)ethyl]-1H-tetrazol-5-yl]thiomethyl]-$\Delta^3$-O-2-isocephem-4-carboxylic acid (syn-isomer)

No. 29: 7-[2-(2-Aminothiazol-4-yl)-2-methoxyiminoacetamido]-3-[[1-methyl-6,7-dihydro-4-(5H-1pyrindinio)]thiomethyl]-$\Delta^3$-O-2-isocephem-4carboxylic acid di-trifluoroacetate (syn-isomer)

No. 30: 7-[2-(2-Aminothiazol-4-yl)-2-methoxyiminoacetamido]-3-[(6,7-dihydro-5H-1-pyrindin-4-yl)thiomethyl]-$\Delta^3$-O-2-isocephem-4-carboxylic acid di-trifluoroacetate (syn-isomer)

No. 31: 7-[2-(2-Aminothiazol-4-yl)-2-methoxyiminoacetamido]-3-[[1-carboxylmethyl-6,7-dihydro-4-(5H-1-pyrindinio)]thiomethyl]-$\Delta^3$-O-2-isocephem-4carboxylic acid di-trifluoroacetate (syn-isomer)

No. 32: 7-[2-(2-Aminothiazol-4-yl)-2-cyanomethyloxyiminoacetamido]-3-[[1-carboxymethyl-6,7-dihydro-4-(5H-1-pyrindinio)]thiomethyl]-$\Delta^3$-O-2-isocephem-4carboxylic acid di-trifluoroacetate (syn-isomer)

No. 33: 7-[2-(2-Aminothiazol-4-yl)-2-(2-carboxy-2propoxyimino)acetamido]-3-[[1-methyl-6,7-dihydro-4-(5H-1-pyrindinio)]thiomethyl]-$\Delta^3$-O-2-isocephem-4-carboxylate (syn-isomer)

No. 34: 7-[2-(2-Aminothiazol-4-yl)-2-cyclopentyloxyiminoacetamido]-3-[[1-methyl-6,7-dihydro-4-(5H-1pyrindinio)]thiomethyl]-$\Delta^3$-O-2-isocephem-4carboxylic acid di-trifluoroacetate (syn-isomer)

No. 35: (6S, 7S)-7-[2-(2-Aminothiazol-4-yl)-2-cyclopentyloxyiminoacetamido]-3-[(1,2,3-thiadiazol-5-yl)thiomethyl]-$\Delta^3$-O-2-isocephem-4-carboxylic acid (syn-isomer)

No. 36: (6S, 7S)-7-[2-(2-Aminothiazol-4-yl)-2-methoxyiminoacetamido]-3-[[1-methyl-6,7-dihydro-4-(5H-1-pyrindinio)]thiomethyl]-$\Delta^3$-O-2-isocephem-4carboxylic acid di-trifluoroacetate (syn-isomer)

No. 37: 7-[2-(2-Aminothiazol-4-yl)-2-(pyridin-4ylmethoxyimino)acetamido]-3-[(1,3,4-thiadiazol-2-yl)thiomethyl]-$\Delta^3$-O-2-isocephem-4-carboxylic acid di-trifluoroacetate (syn-isomer)

No. 38: 7-[2-(2-Aminothiazol-4-yl)-2-[(1-methyl-4pyridinio)methoxyimino]acetamido]-3-[1,3,4-thiadiazol-2-yl)thiomethyl]-$\Delta^3$-O-2-isocephem-4carboxylic acid di-trifluoroacetate (syn-isomer)

No. 39: Benzyl 7-[2-(2-aminothiazol-4-yl)-2-(pyridin-3-ylmethoxyimino)acetamido]-3-[(1-methyl-1,3,4-triazol-2-yl)thiomethyl]-$\Delta^3$-O-2-isocephem-4-carboxylate (syn-isomer)

No. 40: 7-[2-(2-Benzyloxycarbonylaminothiazol-4-yl)-2-(pyridin-2-ylmethoxyimino)acetamido]-3-[[1-methyl-6,7-dihydro-4-(5H-1-pyrindinio)]thiomethyl]-$\Delta^3$-O-2-isocphem-4-carboxylic acid di-trifluoroacetate (syn-isomer)

No. 41: 7-[2-(2-Aminothiazol-4-yl)-2-cyclopentyloxyiminoacetamido]-3-[(5-carbamoyl-1,3,4-thiadiazol-2yl)thiomethyl]-$\Delta^3$-O-2-isocephem-4-carboxylic acid trifluoroacetate (syn-isomer)

No. 42: 7-[2-(2-Aminothiazol-4-yl)-2-cyclopentyloxyiminoacetamido]-3-[(5-carboxymethyl-1,3,4-thiadiazol-2-yl)thiomethyl]-$\Delta^3$-O-2-isocephem-4-carboxylic acid trifluoroacetate (syn-isomer)

No. 43: 7-[2-(2-Aminothiazol-4-yl)-2-cyclopentyloxyiminoacetamido]-3-[(5-carboxymethyl-4-methyl-1,3-thiazol-2-yl)thiomethyl]-$\Delta^3$-O-2-isocephem-4carboxylic acid trifluoroacetate (syn-isomer)

No. 44: 7-[2-(2-Aminothiazol-4-yl)-2-cyclopentyloxyiminoacetamido]-3-[(5-hydroxymethyl-1,3,4-thiadiazol-2-yl)thiomethyl]-$\Delta^3$-O-2-isocephem-4carboxylic acid trifluoroacetate (syn-isomer)

No. 45: 7-[2-(2-Aminothiazol-4-yl)-2-cyclopentyloxyiminoacetamido]-3-[(5-cyano-1,3,4-thiadiazol-2-yl)thiomethyl]-$\Delta^3$-O-2-isocephem-4-carboxylic acid trifluoroacetate (syn-isomer)

No. 46: 7-[2-(2-Aminothiazol-4-yl)-2-methoxyiminoacetamido]-3-[(1-carbamoylmethyl-4-pyridinio)thiomethyl]-$\Delta^3$-O-2-isocephem-4-carboxylate (syn-isomer)

No. 47: 7-[2-(2-Aminothiazol-4-yl)-2-cyanomethoxyiminoacetamido]-3-[(1-carbamoylmethyl-4-pyridinio)thiomethyl]-$\Delta^3$-O-2-isocephem-4-carboxlate (syn-isomer)

No. 48: 7-[2-(2-Aminothiazol-4-yl)-2-methoxyiminoacetamido]-3-[(5-carboxymethyl-1,3,4-thiadiazol-2yl)thiomethyl]-$\Delta^3$-O-2-isocephem-4-carboxylic acid (syn-isomer)

No. 49: (6S,7S)-7-[2-(2-Aminothiazol-4-yl)-2-cyanomethoxyiminoacetamido]-3-[(1-carbamoylmethyl-4pyridinio)thiomethyl]-$\Delta^3$-O-2-isocephem-4-carboxylate (syn-isomer)

No. 50: (6S,7S)-7-[2-(2-Aminothiazol-4-yl)-2-methoxyiminoacetamido]-3-[(1-methyl-4-pyridinio)thiomethyl]-$\Delta^3$-O-2-isocephem-4-carboxylate (syn-isomer)

No. 51: (6S,7S)-7-[2-(2-Aminothiazol-4-yl)-2-methoxyiminoacetamido]-3-[(1-carbamoylmethyl-4-pyridinio)thiomethyl]-$\Delta^3$-O-2-isocephem-4-carboxylate (syn-isomer)

No. 52: (6S,7S)-7-[2-(2-Aminothiazol-4-yl)-2-cyclopentyloxyiminoacetamido]-3-[[1-(2-hydroxyethyl)-4-pyridinio]thiomethyl]-$\Delta^3$-O-2-isocephem-4-carboxylate (syn-isomer)

No. 53: (6S,7S)-7-[2-(2-Aminothiazol-4-yl)-2-cyclopentyloxyiminoacetamido]-3-[(1-ethyl-4-pyridinio)thiomethyl]-$\Delta^3$-O-2-isocephem-4-carboxylate (syn-isomer)

No. 54: (6S,7S)-7-[2-(2-Aminothiazol-4-yl)-2-methoxyiminoacetamido]-3-[(1-allyl-4-pyridinio)thiomethyl]-$\Delta^3$-O-2-isocephem-4-carboxylate (syn-isomer)

No. 55: (6S,7S)-7-[2-(2-Aminothiazol-4-yl)-2-methoxyiminoacetamido]-3-[[1-(2-hydroxyethyl)-4-pyridinio]thiomethyl]-$\Delta^3$-O-2-isocephem-4-carboxylate (syn-isomer)

No. 56: (6S,7S)-7-[2-(2-Aminothiazol-4-yl)-2-cyclopentyloxyiminoacetamido]-3-[(1-methyl-2-pyridinio)thiomethyl]-$\Delta^3$-O-2-isocephem-4-carboxylic acid sulfate (syn-isomer)

No. 57: (6S,7S)-7-[2-(2-Aminothiazol-4-yl)-2-cyclopentyloxyiminoacetamido]-3-[(1-allyl-4-pyridinio)thiomethyl]-$\Delta^3$-O-2-isocephem-4-carboxylate (syn-isomer)

No. 58: (6S,7S)-7-[2-(2-Aminothiazol-4-yl)-2-cyanomethoxyiminoacetamido]-3-[(1-carboxymethyl-4pyridinio)thiomethyl]-$\Delta^3$-O-2-isocephem-4-carboxylate (syn-isomer)

No. 59: (6S,7S)-7-[2-(2-Aminothiazol-4-yl)-2-methoxyiminoacetamido]-3-[(1-carboxymethyl-4-pyridinio)-thiomethyl]-$\Delta^3$-O-2-isocephem-4-carboxylate (syn-isomer)

No. 60: (6S,7S)-7-[2-(2-Aminothiazol-4-yl)-2-carboxymethoxyiminoacetamido]-3-[(1-methyl-4-pyridinio)-thiomethyl]-$\Delta^3$-O-2-isocephem-4-carboxylate (syn-isomer)

No. 61: (6S,7S)-7-[2-(2-Aminothiazol-4-yl)-2-(2-carboxy-2-propoxyimino)acetamido]-3-[(1-methyl-4-pyridinio)thiomethyl]-$\Delta^3$-O-2-isocephem-4-carboxylate (syn-isomer)

No. 62: (6S,7S)-7-[2-(2-Aminothiazol-4-yl)-2-cyclobutyloxyiminoacetamido]-3-[(1,3,4-thiadiazol-2-yl)thiomethyl]-$\Delta^3$-O-2-isocephem-4-carboxylic acid (syn-isomer)

No. 63: (6S,7S)-7-[2-(2-Aminothiazol-4-yl)-2-methoxyiminoacetamido]-3-[(1-methyl-2-pyridinio)thiomethyl]-$\Delta^3$-O-2-isocephem-4-carboxylate (syn-isomer)

No. 64: (6S,7S)-7-[2-(2-Aminothiazol-4-yl)-2-cyanomethoxyiminoacetamido]-3-[(1-methyl-4-pyridinio)thiomethyl]-$\Delta^3$-O-2-isocephem-4-carboxylate (syn-isomer)

No. 65: (6S,7S)-7-[2-(2-Aminothiazol-4-yl)-2-cyclopentyloxyiminoacetamido]-3-[(1-methylthiomethyl-4-pyridinio)thiomethyl]-$\Delta^3$-O-2-isocephem-4-carboxylate (syn-isomer)

TABLE 1

MIC (μg/ml) TEST COMPOUND

| Strain | No. 1 | No. 2 | No. 3 | No. 4 | No. 5 | No. 6 | No. 7 | No. 8 | No. 9 | No. 10 | No. 11 | No. 12 | No. 13 | No. 14 | No. 15 | No. 16 | No. 17 | No. 18 | No. 19 | No. 20 | No. 21 | No. 22 |
|---|---|---|---|---|---|---|---|---|---|---|---|---|---|---|---|---|---|---|---|---|---|---|
| S. aureus FDA-209-p | 6.25 | 0.78 | 0.39 | 0.78 | 3.13 | >100 | 0.78 | 0.78 | 0.78 | 0.39 | 0.78 | 1.56 | 0.39 | 0.2 | 0.39 | 0.78 | 0.2 | 0.78 | 0.39 | 0.39 | 3.13 | 1.56 |
| E. coli NIHJ | 0.05 | 0.1 | 0.2 | 0.05 | 0.2 | 0.78 | 0.1 | 0.1 | 0.2 | 0.2 | 0.1 | 0.39 | 0.39 | 0.05 | ≦0.025 | ≦0.025 | ≦0.025 | ≦0.025 | ≦0.025 | 0.05 | 0.1 | ≦0.025 |
| E. coli No. 29 | ≦0.025 | 0.05 | 0.2 | 0.05 | 0.1 | 0.78 | 0.1 | 0.2 | 0.39 | 0.39 | 0.05 | 0.78 | 0.39 | 0.05 | ≦0.025 | ≦0.025 | ≦0.025 | ≦0.025 | ≦0.025 | 0.1 | 0.1 | 0.1 |
| K. pneumoniae NCTC-9632 | ≦0.025 | 0.2 | 0.39 | 0.1 | ≦0.025 | 0.2 | 0.2 | 0.2 | 0.39 | 0.39 | 0.2 | 0.78 | 0.78 | 0.1 | 0.1 | 0.1 | ≦0.025 | ≦0.025 | ≦0.025 | 0.2 | 0.2 | 0.1 |
| P. mirabilis 1287 | ≦0.025 | ≦0.025 | ≦0.025 | ≦0.025 | ≦0.025 | 0.39 | ≦0.025 | 0.05 | 0.1 | 0.1 | ≦0.025 | 0.1 | 0.1 | ≦0.025 | ≦0.025 | ≦0.025 | ≦0.025 | ≦0.025 | ≦0.025 | ≦0.025 | ≦0.025 | ≦0.025 |
| M. morganii ATCC-25830 | ≦0.025 | ≦0.025 | ≦0.025 | 0.05 | 0.2 | ≦0.025 | 0.1 | 0.1 | 0.2 | ≦0.025 | 0.2 | 0.39 | ≦0.025 | ≦0.025 | ≦0.025 | ≦0.025 | ≦0.025 | ≦0.025 | 0.05 | 0.05 | 0.05 | |
| S. marcescens IFO-12648 | 0.1 | 0.2 | 0.39 | 0.2 | 0.2 | 0.39 | 0.39 | 0.39 | 0.78 | 0.39 | 0.2 | 0.78 | 0.78 | 0.1 | 0.1 | 0.2 | ≦0.025 | 0.2 | 0.05 | 0.2 | 0.39 | 0.2 |
| P. aeruginosa NCTC-10490 | 3.13 | 3.13 | 1.56 | 6.25 | 25 | 100 | 0.78 | 1.56 | 1.56 | 1.56 | 6.25 | 3.13 | 0.78 | 3.13 | 0.78 | 12.5 | 6.25 | 50 | 3.13 | 12.5 | 3.13 | 0.78 |

MIC (μg/ml) TEST COMPOUND

| Strain | No. 23 | No. 24 | No. 25 | No. 26 | No. 27 | No. 28 | No. 29 | No. 30 | No. 31 | No. 32 | No. 33 | No. 34 | No. 35 | No. 36 | No. 37 | No. 38 | No. 39 | No. 40 | No. 41 | No. 42 | No. 43 |
|---|---|---|---|---|---|---|---|---|---|---|---|---|---|---|---|---|---|---|---|---|---|
| S. aureus FDA-209-p | 6.25 | 12.5 | 1.56 | 0.2 | 0.1 | 0.78 | 0.05 | 0.1 | 0.39 | 0.39 | 1.56 | 0.05 | 0.2 | 0.05 | 0.78 | 0.39 | 1.56 | 6.25 | 0.39 | 0.78 | 1.56 |
| E. coli NIHJ | 0.1 | 0.2 | ≦0.025 | ≦0.025 | 0.10 | ≦0.025 | ≦0.025 | 0.05 | ≦0.025 | 0.05 | 0.1 | 0.1 | 0.2 | ≦0.025 | 0.05 | 0.05 | 0.05 | 1.56 | 0.39 | 0.39 | 0.39 |
| E. coli No. 29 | 0.2 | 0.39 | ≦0.025 | 0.05 | 0.1 | ≦0.025 | ≦0.025 | 0.1 | ≦0.025 | 0.1 | 0.2 | 0.2 | 0.2 | 0.05 | 0.2 | 0.1 | 0.2 | 3.13 | 0.2 | 0.2 | 0.39 |
| K. pneumoniae NCTC-9632 | 0.1 | 0.39 | 0.05 | 0.2 | 0.2 | 0.05 | 0.05 | 0.2 | 0.1 | 0.05 | 0.05 | 0.2 | 0.2 | 0.05 | 0.39 | 0.2 | 0.2 | 3.13 | 0.39 | 0.39 | 0.78 |
| P. mirabilis 1287 | ≦0.025 | ≦0.025 | ≦0.025 | 0.05 | 0.1 | ≦0.025 | ≦0.025 | 0.2 | ≦0.025 | 0.05 | 0.2 | 0.39 | 0.2 | ≦0.025 | 0.2 | 0.2 | 0.2 | 6.25 | 0.2 | 0.05 | 0.1 |
| M. morganii ATCC-25830 | 0.1 | 0.1 | ≦0.025 | 0.05 | 0.1 | ≦0.025 | ≦0.025 | 0.39 | 0.05 | 0.1 | 0.2 | 0.78 | 0.39 | ≦0.025 | 0.78 | 0.39 | 0.39 | 3.13 | 0.78 | 0.1 | 1.56 |
| S. marcescens IFO-12648 | 0.39 | 0.39 | 0.2 | 0.39 | 0.2 | 0.2 | 0.2 | 0.39 | 0.39 | 0.78 | 0.78 | 0.78 | 0.39 | 0.05 | 1.56 | 0.78 | 0.78 | 12.5 | 1.56 | 1.56 | 6.25 |
| P. aeruginosa NCTC-10490 | 12.5 | 12.5 | 0.78 | 6.25 | 0.2 | 1.56 | 6.25 | 25 | 25 | 12.5 | 1.56 | 0.78 | 0.78 | 3.13 | 1.56 | 1.56 | 1.56 | 25 | 0.78 | 1.56 | 50 |

MIC (μg/ml) TEST COMPOUND

| Strain | No. 44 | No. 45 | No. 46 | No. 47 | No. 48 | No. 49 | No. 50 | No. 51 | No. 52 | No. 53 | No. 54 | No. 55 | No. 56 | No. 57 | No. 58 | No. 59 | No. 60 | No. 61 | No. 62 | No. 63 | No. 64 | No. 65 |
|---|---|---|---|---|---|---|---|---|---|---|---|---|---|---|---|---|---|---|---|---|---|---|
| S. aureus FDA-209-p | 0.39 | 0.39 | 0.2 | 0.2 | 0.78 | 0.1 | 0.1 | 0.1 | 0.05 | 0.05 | 0.1 | 0.2 | 0.05 | 0.1 | 0.39 | 0.39 | 1.56 | 1.56 | 0.39 | 0.1 | 0.1 | 0.1 |
| E. coli NIHJ | 0.39 | 0.39 | ≦0.025 | ≦0.025 | 0.05 | ≦0.025 | ≦0.025 | ≦0.025 | 0.2 | 0.1 | ≦0.025 | ≦0.025 | 0.2 | 0.2 | ≦0.025 | ≦0.025 | ≦0.025 | 0.1 | 0.39 | ≦0.025 | ≦0.025 | 0.2 |
| E. coli No. 29 | 0.2 | 0.39 | ≦0.025 | ≦0.025 | 0.39 | ≦0.025 | ≦0.025 | ≦0.025 | 0.1 | 0.05 | 0.1 | 0.1 | 0.1 | 0.1 | ≦0.025 | ≦0.025 | ≦0.025 | 0.05 | 0.2 | 0.1 | ≦0.025 | 0.1 |

TABLE 1-continued

| | | | | | | | | | | | | | | | | | | | | |
|---|---|---|---|---|---|---|---|---|---|---|---|---|---|---|---|---|---|---|---|---|
| K. pneumoniae NCTC-9632 | 0.39 | 0.39 | 0.05 | ≤0.025 | 0.2 | ≤0.025 | ≤0.025 | ≤0.025 | 0.2 | 0.2 | ≤0.025 | ≤0.025 | 0.39 | ≤0.025 | ≤0.025 | 0.05 | 0.39 | ≤0.025 | ≤0.025 | 0.39 |
| P. mirabilis 1287 | 0.2 | 0.2 | ≤0.025 | ≤0.025 | ≤0.025 | ≤0.025 | ≤0.025 | ≤0.025 | 0.1 | 0.1 | ≤0.025 | ≤0.025 | 0.1 | ≤0.025 | ≤0.025 | ≤0.025 | 0.1 | ≤0.025 | ≤0.025 | 0.2 |
| M. morganii ATCC-25830 | 0.78 | 0.39 | ≤0.025 | ≤0.025 | ≤0.025 | ≤0.025 | ≤0.025 | ≤0.025 | 0.05 | 0.05 | ≤0.025 | ≤0.025 | 0.05 | ≤0.025 | ≤0.025 | ≤0.025 | 0.05 | ≤0.025 | ≤0.025 | 0.05 |
| S. marcescens IFO-12648 | 1.56 | 0.78 | 0.1 | 0.1 | 0.39 | 0.1 | 0.1 | 0.1 | 0.78 | 0.78 | 0.39 | 0.2 | 0.78 | 0.39 | 0.2 | 0.78 | 0.78 | 0.05 | 0.05 | 0.78 |
| P. aeruginosa NCTC-10490 | 3.13 | 6.25 | 3.13 | 3.13 | 6.25 | 1.56 | 1.56 | 0.78 | 0.39 | 0.39 | 25 | 1.56 | 0.78 | 25 | 1.56 | 3.13 | 0.39 | 0.78 | 1.56 | 0.78 |

What we claim is:

1. A 2-oxa-isocephem compound of the formula (1):

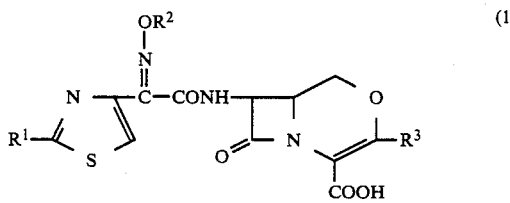

wherein $R^1$ is a hydrogen atom, an amino group, a lower alkanoylamino group, a halogen-substituted lower alkanoylamino group, a phenyl-substituted lower alkylamino group having 1 to 3 phenyl groups, a phenyl-lower alkoxycarbonylamino group or a lower alkoxycarbonylamino group; $R^2$ is a hydrogen atom, a lower alkyl group, a lower alkenyl group, a lower alkynyl group, a cycloalkyl group, a tetrahydropyranyl group or a group of the formula:

—A—$R^4$ (wherein A is a lower alkylene group, $R^4$ is a cyano group, a carboxy group, a lower alkoxycarbonyl group, a halogen-substituted lower alkyl group, a lower alkylthio group, a thiazolyl group, an imidazolyl group, a cycloalkyl group, a phenyl group, a tetrahydrofuranyl group, an oxazolyl group, a 4-lower alkyl-2,3-dioxo-1-piperazinylcarbonyl group, a trityl-substituted or unsubstituted pyrazolyl group or a lower alkyl-substituted or unsubstituted pyridyl group); $R^3$ is a hydrogen atom, a methyl group, a lower alkanoyloxymethyl group, a carbamoyloxymethyl group, a lower alkoxymethyl group, or an unsaturated heterocycle-thiomethyl group containing 1 to 4 hetero atoms selected from the group consisting of nitrogen and sulfur atoms; in which the heterocyclic moiety of said heterocycle-thiomethyl group may optionally have 1 to 3 substituents selected from the group consisting of lower alkyl, lower alkenyl, lower alkoxycarbonyl, carboxy, phenyl-lower alkoxycarbonyl-lower alkyl having 1 to 3 phenyl groups, carboxy-lower alkyl, hydroxy-lower alkyl, hydroxy, oxo, amino, carbamoyl, cyano, lower alkyl-substituted amino-lower alkyl, piperidinyl-lower alkyl, pyrrolidinyl-lower alkyl, carbamoyl-lower alkyl, and cyano-lower alkyl groups, or a 4-lower alkyl-1-piperazinyl-lower alkyl group; provided that when $R^1$ is an amino group, a lower alkanoylamino group, a halogen-substituted lower alkanoylamino group, a phenyl-substituted lower alkyl amino group having 1 to 3 phenyl groups, a phenyl-lower alkoxycarbonylamino group or a lower alkoxycarbonylamino group and $R^3$ is a hydrogen atom, a methyl group or a lower alkanoyloxymethyl group, $R^2$ means a cyclo-lower alkyl group or a tetrahydropyranyl group or $R^4$ means a cyano group, a cycloalkyl group, a tetrahydrofuranyl group or a 4-lower alkyl-2,3-dioxo-1-piperazinylcarbonyl group; and pharmaceutically acceptable salts thereof, esters of the carboxy group in the 4-position thereof and quaternary ammonium salts thereof.

2. A 2-oxa-isocephem compound as claimed in claim 1, wherein $R^1$ is a hydrogen atom.

3. A 2-oxa-isocephem compound as claimed in claim 1, wherein $R^1$ is an amino group.

4. A 2-oxa-isocephem compound as claimed in claim 1, wherein $R^1$ is a lower alkanoylamino group, a halogen-substituted lower alkanoylamino group, a phenyl-substituted lower alkylamino group having 1 to 3 phenyl groups, a phenyl-lower alkoxycarbonylamino group or a lower alkoxycarbonylamino group.

5. A 2-oxa-isocephem compound as claimed in claim 3, wherein $R^3$ is a hydrogen atom, a methyl group, a lower alkanoyloxymethyl group, a carbamoyloxymethyl group or a lower alkoxymethyl group.

6. A 2-oxa-isocephem compound as claimed in claim 3, wherein $R^3$ is an unsaturated heterocycle-thiomethyl group containing 1 to 4 hetero atoms selected from the group consisting of nitrogen and sulfur atoms; in which the heterocyclic moiety of said heterocycle-thiomethyl methyl group may optionally have 1 to 3 substituents selected from the group consisting of lower alkyl, lower alkenyl, lower alkoxycarbonyl, carboxy, phenyl-lower alkoxycarbonyl-lower alkyl having 1 to 3 phenyl groups, carboxy-lower alkyl, hydroxy-lower alkyl, hydroxy, oxo, amino, carbamoyl, cyano, lower alkyl-substituted amino-lower alkyl, piperidinyl-lower alkyl, pyrrolidinyl-lower alkyl, carbamoyl-lower alkyl, and cyano-lower alkyl groups, or a 4-lower alkyl-1-piperazinyl-lower alkyl group.

7. A 2-oxa-isocephem compound as claimed in claim 6, wherein $R^2$ is a lower alkyl group or a group of the formula: —A—$R^4$, in which A has the same meaning as defined above, and $R^4$ is a cyano group, a carboxy group or a lower alkoxycarbonyl group.

8. A 2-oxa-isocephem compound as claimed in claim 7, wherein the heterocyclic moiety of the heterocycle-thiomethyl group for $R^3$ is a heterocyclic group selected from the group consisting of a 1,3,4-thiadiazolyl group, a 1,2,3-thiadiazolyl group, a 1,2,4-thiadiazolyl group, a 1,2,4-triazolyl group, a 1,3,4-triazolyl group, a 1,2,3-triazolyl group, a tetrazolyl group, a pyridyl group, a 1,2-thiazolyl group, a 1,3-thiazolyl group, an imidazolyl group, a 1,2,4-triazinyl group, a 5,6,7,8-tetrahydroquinolyl group, an $\alpha,\beta$-ethylenepyridyl group or a 6,7-dihydro-5H-pyrindinyl group, in which these heterocyclic groups may optionally have substituent(s) as defined in claim 6.

9. A 2-oxa-isocephem compound as claimed in claim 8, wherein the heterocyclic group is a pyridyl group, a 5,6,7,8-tetrahydroquinolyl group, an $\alpha,\beta$-ethylenepyridyl group or a 6,7-dihydro-5H-pyrindinyl group, in which these heterocyclic groups may optionally have substituent(s) as defined in claim 6.

10. A 2-oxa-isocephem compound as claimed in claim 8, wherein the heterocyclic group is a 1,3,4-thiadiazolyl group, a 1,2,3-thiadiazolyl group, a 1,2,4-thiadiazolyl group, a 1,2,4-triazinyl group or a tetrazolyl group, in which these heterocyclic groups may optionally have substituent(s) as defined in claim 6.

11. A 2-oxa-isocephem compound as claimed in claim 8, wherein the heterocyclic group is a 1,2,4-triazolyl group, a 1,3,4-triazolyl group, a 1,2,3-triazolyl group, a 1,2-thiazolyl group, a 1,3-thiazolyl group or an imidazolyl group, in which these heterocyclic groups may optionally have substituent(s) as defined in claim 6.

12. A 2-oxa-isocephem compound as claimed in claim 9, wherein the heterocyclic group is a pyridyl group optionally having substituent(s) as defined in claim 6.

13. A 2-oxa-isocephem compound as claimed in claim 9, wherein the heterocyclic group is a 6,7-dihydro-5H-pyrindinyl group optionally having substituent(s) as defined in claim 6.

14. A 2-oxa-isocephem compound as claimed in claim 12, wherein the pyridyl group is a pyridyl group substituted, at the N atom thereof, with a lower alkyl group, a carboxy-lower alkyl group or a carbamoyl-lower alkyl group.

15. A 2-oxa-isocephem compound as claimed in claim 13, wherein the 6,7-dihydro-5H-pyrindinyl group is a 6,7-dihydro-5H-pyrindinyl group optionally substituted, at the N atom thereof, with a lower alkyl group or a carboxy-lower alkyl group.

16. 7-[2-(2-Aminothiazol-4-yl)-2-methoxyiminoacetamido]-3-[(1-methyl-4-pyridinio)thiomethyl]-$\Delta^3$-O-2-isocephem-4-carboxylate (syn-isomer), 7-[2-(2-aminothiazol-4-yl)-2-methoxyiminoacetamido]-3-[(1-carboxymethyl-4-pyridinio)thiomethyl]-$\Delta^3$-O-2-isocephem-4-carboxylate (syn-isomer), 7-[2-(2-aminothiazol-4-yl)-2cyanomethoxyiminoacetamido]-3-[(1-methyl-4-pyridinio)thiomethyl]-$\Delta^3$-O-2-isocephem-4-carboxylate (syn-isomer), 7-[2-(2-aminothiazol-4-yl)-2-cyanomethoxyiminoacetamido]-3-[(1-carboxymethyl-4-pyridinio)thiomethyl]-$\Delta^3$-O-2-isocephem-b 4-carboxylate (syn-isomer), 7-[2-(2-aminothiazol-4-yl)-2-methoxyiminoacetamido]-3-[(1-carbamoylmethyl-4-pyridinio)thiomethyl]-$\Delta^3$-O-2-isocephem-4carboxylate (syn-isomer) or 7-[2-(2-aminothiazol-4-yl)-2-cyanomethoxyiminoacetamido]-3-[(1-carbamoylmethyl-4pyridinio)thiomethyl]-$\Delta^3$-O-2-isocephem-4-carboxylate (syn-isomer), or optically active compounds thereof, or pharmaceutically acceptable salts thereof according to claim 14.

17. 7-[2-(2-Aminothiazol-4-yl)-2-methoxyiminoacetamido]-3-[[1-methyl-6,7-dihydro-4-(5H-1pyrindinio)]thiomethyl]-$\Delta^3$-O-2-isocephem-4-carboxylate (syn-isomer), 7-[2-(2-aminothiazol-4-yl)-2-methoxyiminoacetamido]-3-[(6,7-dihydro-5H-1-pyrindino-4-yl)thiomethyl]-$\Delta^3$-O-2-isocephem-4-carboxylic acid (syn-isomer), 7-[2-(2-aminothiazol-4-yl)-2-methoxyiminoacetamido]-3[[1-carboxymethyl-6,7-dihydro-4-(5H-1-pyrindino)]thiomethyl]-$\Delta^3$-O-2-isocephem-4-carboxylate (syn-isomer), 7-[2-(2-aminothiazol-4-yl)-2-cyanomethyloxyiminoacetamido]-3-[(6,7-dihydro-5H-1-pyrindin-4-yl)thiomethyl]-$\Delta^3$-O-2-isocephem-4-carboxylic acid (syn-isomer) or 7-[2-(2-aminothiazol-4-yl)-2-(2-carboxy-2-propoxyimino)acetamido]-3-[[1-methyl-6,7-dihydro-4-(5H-1pyrindino)]thiomethyl]-$\Delta^3$-O-2-isocephem-4-carboxylate (syn-isomer), or optically active compounds thereof, or pharmaceutically acceptable salts thereof according to claim 15.

18. 7-[2-(2-Aminothiazol-4-yl)-2-methoxyiminoacetamido]-3-[(1,3,4-thiadiazol-2-yl)thiomethyl]-$\Delta^3$-O-2-isocephem-4-carboxylic acid (syn-isomer), 7-[2-(2-aminothiazol-4-yl)-2-methoxyiminoacetamido]-3[(1,4,5,6-tetrahydro-4-methyl-5,6-dioxo-1,2,4-triazin-3-yl)thiomethyl-$\Delta^3$-O-2-isocephem-4-carboxylic acid (synisomer), 7-[2-(2-aminothiazol-4-yl)-2-methoxyiminoacetamido]-3-[[1-[2-(4-methyl-1-piperazinyl)ethyl]-1H-tetrazol-5-yl]thiomethyl]-$\Delta^3$-O-2-isocephem-4-carboxylic acid (syn-isomer), or optically active compounds thereof, or pharmaceutically acceptable salts thereof according to claim 10.

19. A 2-oxa-isocephem compound as claimed in claim 6, wherein $R^2$ is a cycloalkyl group or a group of the formula: —A—$R^4$, in which A has the same meaning as defined above and $R^4$ is a cycloalkyl group.

20. A 2-oxa-isocephem compound as claimed in claim 19, wherein the heterocyclic moiety of the heterocycle-thiomethyl group for $R^3$ is a heterocyclic group selected from the group consisting of a 1,3,4-thiadiazolyl group, a 1,2,3-thiadiazolyl group, a 1,2,4-thiadiazolyl group, a 1,2,4-triazolyl group, a 1,3,4-triazolyl group, a 1,2,3-triazolyl group, a tetrazolyl group, a pyridyl group, a 1,2-thiazolyl group, a 1,3-thiazolyl group, an imidazolyl group, a 1,2,4-triazinyl group, a 5,6,7,8-tetrahydroquinolyl group, an $\alpha,\beta$-ethylenepyridyl group or a 6,7-dihydro-5H-pyrindinyl group, in which these heterocyclic groups may optionally have substituent(s) as defined in claim 6.

21. A 2-oxa-isocephem compound as claimed in claim 20, wherein the heterocyclic group is a pyridyl group, a 5,6,7,8-tetrahydroquinolyl group, an $\alpha,\beta$-ethylenepyridyl group or a 6,7-dihydro-5H-pyrindinyl group, in which these heterocyclic groups may optionally have substituent(s) as defined in claim 6.

22. A 2-oxa-isocephem compound as claimed in claim 20, wherein the heterocyclic group is a 1,2-thiazolyl group or a 1,3-thiazolyl group, in which these heterocyclic groups may optionally have substituent(s) as defined in claim 6.

23. A 2-oxa-isocephem compound as claimed in claim 20, wherein the heterocyclic group is a 1,3,4-thiadiazolyl group, a 1,2,3-thiadiazolyl group or a 1,2,4-thiadiazolyl group, in which these heterocyclic groups may optionally have substituent(s) as defined in claim 6.

24. A 2-oxa-isocephem compound as claimed in claim 20, wherein the heterocyclic group is a 1,3,4-triazolyl group, a 1,2,3-triazolyl group, a 1,2,4-triazolyl group, a tetrazolyl group, an imidazolyl group or a 1,2,4-triazinyl group, in which these heterocyclic groups may optionally have substituent(s) as defined in claim 6.

25. A 2-oxa-isocephem compound as claimed in claim 21, wherein the heterocyclic group is a pyridyl group optionally having substituent(s) as defined in claim 6.

26. A 2-oxa-isocephem compound as claimed in claim 21, wherein the heterocyclic group is a 6,7-dihydro-5H-pyrindinyl group optionally having substituent(s) as defined in claim 6.

27. A 2-oxa-isocephem compound as claimed in claim 22, wherein said thiazolyl groups are thiazolyl groups substituted with a lower alkyl group or a carboxy-lower alkyl group.

28. A 2-oxa-isocephem compound as claimed in claim 23, wherein said thiadiazolyl groups are thiadiazolyl groups optionally substituted with a carbamoyl group, a carboxy-lower alkyl group, a hydroxylower alkyl group, a cyano group or an amino group.

29. A 2-oxa-isocephem compound as claimed in claim 25, wherein the pyridyl group is pyridyl group substituted, at the N atom thereof, with a lower alkyl group or a carboxy-lower alkyl group.

30. A 2-oxa-isocephem compound as claimed in claim 26, wherein the 6,7-dihydro-5H-pyrindinyl group is a 6,7-dihydro-5H-pyrindinyl group substituted, at the N atom thereof, with a lower alkyl group.

31. 7-[2-(2-Aminothiazol-4-yl)-2-cyclopropylmethyloxyiminoacetamido]-3-[(1-carboxymethyl-4-pyridinio)thiomethyl]-$\Delta^3$-O-2-isocephem-4-carboxylate (syn-isomer) or 7-[2-(2-aminothiazol-4-yl)-2-cyclopentyloxyiminoacetamido]-3-[(1-methyl-4-pyridinio)thiomethyl]-$\Delta^3$-O-2-isocephem-4-carboxylate (syn-isomer), or optically active compounds thereof, or pharmaceutically acceptable salts thereof according to claim 29.

32. 7-[2-(2-Aminothiazol-4-yl)-2-cyclopentyloxyiminoacetamido]-3-[[1-methyl-6,7-dihydro-4-(5H-1pyrindinio)thiomethyl]-$\Delta^3$-O-2-isocephem-4-carboxylate (syn-isomer) or its optically active compound, or a pharmaceutically acceptable salt thereof according to claim 30.

33. 7-[2-(2-Aminothiazol-4-yl)-2-cyclopentyloxyiminoacetamido]-3-[5-(carboxymethyl-4-methyl-1,3-thiazol-2-yl)thiomethyl]-Δ³-O-2-isocephem-4-carboxylic acid (syn-isomer) or its optically active compound or a pharmaceutically acceptable salt thereof according to claim 27.

34. 7-[2-(2-Aminothiazol-4-yl)-2-cyclopropylmethyloxyiminoacetamido]-3-[(1,3,4-thiadiazol-2-yl)thiomethyl]-Δ³O-2-isocephem-4-carboxylic acid (syn-isomer), 7-[2-(2-aminothiazol-4-yl)-2-cyclopentyloxyiminoacetamido]-3-[(1,3,4-thiadiazol-2-yl)thiomethyl]-Δ³-O-2-isocephem-4-carboxylic acid (syn-isomer), 7-[2-(2-aminothiazol-4-yl)2-cyclohexyloxyiminoacetamido]-3[(1,3,4-thiadiazol-2-yl)-thiomethyl]-Δ⁻ᴼ-2-isocephem-4carboxylic acid (syn-isomer), 7-[2-(2-aminothiazol-4-yl)-2-cyclopentyloxy-iminoacetamido]-3-[(5-carbamoyl-1,3,4-thiadiazol-2-yl)thiomethyl]-Δ³-O-2-isocephem-4-carboxylic acid (syn-isomer), 7-[2-(2-aminothiazol-4-yl)-2-cyclopentyloxy-iminoacetamido]-3-[(5-carboxymethyl-1,3,4-thiadiazol-2-yl)thiomethyl]-Δ³-O-2-isocephem-4-carboxylic acid (syn-isomer), 7-[2-(2-aminothiazol-4-yl)-2-cyclopentyloxy-iminoacetamido]-3-[(5-amino-1,3,4-thiadiazol-2-yl)-thiomethyl]-Δ³-O-2-isocephem-4carboxylic acid (syn-isomer), 7-[2-(2-aminothiazol-4-yl)-2-cyclopentyloxyiminoacetamido]-3-[(5-hydroxymethyl-1,3,4-thiadiazol-2-yl)thiomethyl]-Δ³-O-2-isocephem-4-carboxylic acid (syn-isomer) or 7-[2-(2-aminothiazol-4-yl)-2-cyclopentyloxyiminoacetamido]-3-[(5-cyano-1,3,4-thiadiazol-2-yl)thiomethyl]-Δ³-O-2-isocephem-4-carboxylic acid (syn-isomer), or optically active compounds thereof, or pharmaceutically acceptable salts thereof according to claim 28.

35. A 2-oxa-isocephem compound as claimed in claim 6, wherein $R^2$ is a lower alkenyl group or a lower alkynyl group.

36. A 2-oxa-isocephem compound as claimed in claim 35, wherein the heterocyclic moiety of the heterocyclethiomethyl group for $R^3$ is a heterocyclic group selected from the group consisting of a 1,3,4-thiadiazolyl group, a 1,2,3-thiadiazolyl group, a 1,2,4-thiadiazolyl group, a 1,2,4-triazolyl group, a 1,3,4-triazolyl group, a 1,2,3-triazolyl group, a tetrazolyl group, a pyridyl group, a 1,2-thiazolyl group, a 1,3-thiazolyl group, an imidazolyl group, a 1,2,4-triazinyl group, a 5,6,7,8-tetrahydroquinolyl group, an α,β-ethylenepyridyl group or a 6,7-dihydro-5H-pyrindinyl group, in which these heterocyclic groups may optionally have substituent(s) as defined in claim 6.

37. A 2-oxa-isocephem compound as claimed in claim 36, wherein the heterocyclic group is a 5,6,7,8-tetrahydroquinolyl group, an α,β-ethylenepyridyl group or a 6,7-dihydro-5H-pyrindinyl group, in which these heterocyclic groups may optionally have substituent(s) as defined in claim 6.

38. A 2-oxa-isocephem compound as claimed in claim 36, wherein the heterocyclic group is a 1,3,4-thiadiazolyl group, a 1,2,3-thiadiazolyl group or a 1,2,4-thiadiazolyl group, in which these heterocyclic groups may optionally have substituent(s) as defined in claim 6.

39. A 2-oxa-isocephem compound as claimed in claim 36, wherein the heterocyclic group is a 1,2-thiazolyl group, a 1,3-thiazolyl group or a tetrazolyl group, in which these heterocyclic groups may optionally have substituent(s) as defined in claim 6.

40. A 2-oxa-isocephem compound as claimed in claim 36, wherein the heterocyclic group is a 1,3,4-triazolyl group, a 1,2,3-triazolyl group, a 1,2,4-triazolyl, a pyridyl group, an imidazolyl group or a 1,2,4-triazinyl group, in which these heterocyclic groups may optionally have substituent(s) as defined in claim 6.

41. 7-[2-(2-Aminothiazol-4-yl)-2-allyloxyiminoacetamido]-3-[(1,3,4-thiadiazol-2-yl)thiomethyl]-Δ³-O-2-isocephem-4-carboxylic acid (syn-isomer) or its optionally active active compound, or a pharmaceutically acceptable salt thereof according to claim 38.

42. A 2-oxa-isocephem compound as claimed in claim 6, wherein R2 is a hydrogen atom, a tetrahydropyranyl group or a group of the formula: —A—$R^4$, in which A has the same meaning as defined above, and $R^4$ is a halogen-substituted lower alkyl group, a lower alkylthio group, a thiazoly group, an imidazolyl group, a phenyl group, a tetrahydrofuranyl group, an oxazolyl group, a 4-lower alkyl-2,3-dioxo-1-piperazinylcarbonyl group, a trityl-substituted or unsubstituted pyrazolyl group, or a lower alkyl-substituted or unsubstituted pyridyl group; and the heterocyclic moiety of the heterocycle-thiomethyl group for $R^3$ is a heterocyclic group selected from the group consisting of a 1,3,4-thiadiazolyl group, a 1,2,3-thiadiazolyl group, a 1,2,4-thiadiazolyl group, a 1,2,4-triazolyl group, a 1,3,4-triazolyl group, a 1,2,3-triazolyl group, a tetrazolyl group, a pyridyl group, a 1,2-thiazolyl group, a 1,3-thiazolyl group, an imidazolyl group, a 1,2,4-triazinyl group, a 5,6,7,8-tetrahydroquinolyl group, an α,β-ethylenepyridyl group or a 6,7-dihydro-5H-pyrindinyl group, in which these heterocyclic groups may optionally have substituent(s) as defined in claim 6.

43. A 2-oxa-isocephem compound as claimed in claim 14, wherein the pyridyl group is a pyridyl group substituted, at the N atom thereof, with a carbamoyl-lower alkyl group, and $R^2$ is an isopropyl group.

44. A 2-oxa-isocephem compound as claimed in claim 43, wherein the carbamoyl-lower alkyl group is a carbamoylmethyl group.

45. A 2-oxa-isocephem compound as claimed in claim 14, wherein the pyridyl group is a pyridyl group substituted, at the N atom thereof, with a lower alkyl group, and $R^4$ is a carboxy group.

46. A 2-oxa-isocephem compound as claimed claim 45, wherein A is a methylmethylene group or an ethylene group.

47. (6S,7S)-7-[2-(2-Aminothiazal-4-yl)-2-cyclopentyloxyaminoacetamido]-3-[[1-(2-hydroxyethyl)-4-pyridinio]thiomethyl]-Δ³-O-2-isocephem-4-carboxylate(syn-isomer) or a pharmaceutically acceptable salt thereof according to claim 25.

48. An antimicrobial composition comprising a antimicrobial composition comprising a antimicrobially effective amount of a 2-oxa-isocephem compound of the formula (1):

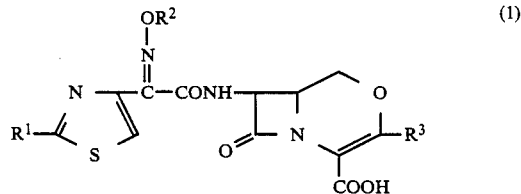

wherein $R^1$ is a hydrogen atom, an amino group, a lower alkanoylamino group, a halogen-substituted lower alkanoylamino group, a phenyl-substituted lower alkyl-amino group having 1 to 3 phenyl groups, a phenyl-lower alkoxycarbonylamino group or a lower alkoxycarbonylamino group; $R^2$ is a hydrogen atom, a lower alkyl group, a lower alkenyl group, a lower alkynyl group, a cycloalkyl group, a tetrahydropyranyl group or a group of the formula:

$$-A-R^4$$

(wherein A is a lower alkylene group, $R^4$ is a cyano group, a carboxy group, a lower alkoxycarbonyl group, a halogen-substituted lower alkyl group, a lower alkylthio group, a thiazolyl group, an imidazolyl group, a cycloalkyl group, a phenyl group, a tetrahydrofuranyl group, an oxazolyl group, a 4-lower alkyl-2,3-dioxo-1-piperazinylcarbonyl group, a trityl-substituted or unsubstituted pyrazolyl group or a lower alkyl-substituted or unsubstituted pyridyl group); $R^3$ is a hydrogen atom, a methyl group, a lower alkanoyloxymethyl group, a carbamoyloxymethyl group, a lower alkoxymethyl group, or an unsaturated heterocycle-thiomethyl group containing 1 to 4 hetero atoms selected from the group consisting of nitrogen and sulfur atoms; in which the heterocyclic moiety of said heterocycle-thiomethyl group may optionally have 1 to 3 substituents selected from the group consisting of lower alkyl, lower alkenyl, lower alkoxycarbonyl, carboxy, phenyl-lower alkoxycarbonyllower alkyl having 1 to 3 phenyl groups, carboxy-lower alkyl, hydroxy-lower alkyl, hydroxy, oxo, amino, carbamoyl, cyano, lower alkyl-substituted amino-lower alkyl, piperidinyl-lower alkyl, pyrrolidinyl-lower alkyl, carbamoyl-lower alkyl, and cyano-lower alkyl groups, or a 4-lower alkyl-1-piperazinyl-lower alkyl group; provided that when $R^1$ is an amino group, a lower alkanoylamino group, a halogen-substituted lower alkanoylamino group, a phenyl-substituted lower alkyl amino group having 1 to 3 phenyl groups, a phenyl-lower alkoxycarbonylamino group or a lower alkoxycarbonylamino group and $R^3$ is a hydrogen atom, a methyl group or a lower alkanoyloxymethyl group, $R^2$ means a cyclo-lower alkyl group or a tetrahydropyranyl group or $R^4$ means a cyano group, a cycloalkyl group, a tetrahydrofuranyl group or a 4-lower alkyl-2,3-dioxo-1-piperazinylcarbonyl group; pharmaceutically acceptable salts thereof, esters of the carboxy group in the 4-position thereof and quaternary ammonium salts thereof, and a pharmaceutically acceptable carrier.

49. A method for treatment of diseases caused by pathogenic bacteria which comprises administering a 2-oxa-isocephem compound of claim 1 to human being and animals.

* * * * *